(12) United States Patent
Anderson et al.

(10) Patent No.: US 10,844,122 B2
(45) Date of Patent: Nov. 24, 2020

(54) PROSTATE SPECIFIC MEMBRANE ANTIGEN (PSMA) BISPECIFIC BINDING AGENTS AND USES THEREOF

(71) Applicant: Janssen Biotech, Inc., Horsham, PA (US)

(72) Inventors: Glenn Anderson, Spring House, PA (US); Rosa Cardoso, Spring House, PA (US); Michael Diem, Spring House, PA (US); Francois Gaudet, Spring House, PA (US); Shalom Goldberg, Spring House, PA (US); Benjamin Harman, Spring House, PA (US); Linus Hyun, Spring House, PA (US); Steven Jacobs, Spring House, PA (US); Donna Klein, Spring House, PA (US); Yingzhe Li, Spring House, PA (US); Jinquan Luo, Spring House, PA (US); Ronan McDaid, Spring House, PA (US); Jill Mooney, San Diego, CA (US); Jennifer Nemeth-Seay, Spring House, PA (US); Karyn O'Neil, Spring House, PA (US); Steven Pomerantz, Spring House, PA (US); Galla Chandra Rao, Spring House, PA (US); Tracy Spinka-Doms, Spring House, PA (US); Alexey Teplyakov, Spring House, PA (US); Leopoldo Luistro, Spring House, PA (US); Sheng-Jiun Wu, Spring House, PA (US)

(73) Assignee: Janssen Biotech, Inc., Horsham, PA (US)

( * ) Notice: Subject to any disclaimer, the term of this patent is extended or adjusted under 35 U.S.C. 154(b) by 49 days.

(21) Appl. No.: 15/148,371

(22) Filed: May 6, 2016

(65) Prior Publication Data

US 2016/0347840 A1 Dec. 1, 2016

Related U.S. Application Data

(60) Provisional application No. 62/157,789, filed on May 6, 2015.

(51) Int. Cl.
| | |
|---|---|
| *A61K 38/00* | (2006.01) |
| *C07K 16/28* | (2006.01) |
| *A61K 49/00* | (2006.01) |
| *A61K 47/68* | (2017.01) |
| *A61K 45/06* | (2006.01) |
| *C07K 14/78* | (2006.01) |
| *C07K 16/30* | (2006.01) |
| *A61K 39/00* | (2006.01) |
| *A61K 39/395* | (2006.01) |

(52) U.S. Cl.
CPC .......... *C07K 16/2809* (2013.01); *A61K 45/06* (2013.01); *A61K 47/6803* (2017.08); *A61K 47/6869* (2017.08); *A61K 49/0045* (2013.01); *A61K 49/0058* (2013.01); *C07K 14/78* (2013.01); *C07K 16/3069* (2013.01); *C12Y 304/17021* (2013.01); *A61K 38/00* (2013.01); *A61K 39/39558* (2013.01); *A61K 2039/505* (2013.01); *C07K 2317/24* (2013.01); *C07K 2317/31* (2013.01); *C07K 2317/524* (2013.01); *C07K 2317/53* (2013.01); *C07K 2317/55* (2013.01); *C07K 2317/70* (2013.01); *C07K 2317/73* (2013.01); *C07K 2317/92* (2013.01); *C07K 2317/94* (2013.01); *C07K 2318/20* (2013.01); *C07K 2319/30* (2013.01)

(58) Field of Classification Search
CPC ........ A61K 2039/505; A61K 39/39558; A61K 38/00
See application file for complete search history.

(56) References Cited

U.S. PATENT DOCUMENTS

| | | | |
|---|---|---|---|
| RE30,985 E | 6/1982 | Cartaya | |
| 4,560,655 A | 12/1985 | Baker | |
| 4,657,866 A | 4/1987 | Kumar | |
| 4,767,704 A | 8/1988 | Cleveland et al. | |
| 4,816,397 A | 3/1989 | Boss et al. | |
| 4,816,567 A | 3/1989 | Cabilly et al. | |

(Continued)

FOREIGN PATENT DOCUMENTS

| | | |
|---|---|---|
| EP | 0 239 400 B1 | 9/1987 |
| EP | 0 519 596 B1 | 12/1992 |

(Continued)

OTHER PUBLICATIONS

Natarajan et al. (Clin Cancer Res. Dec. 15, 2013; 19 (24): 6820-9; pp. 1-11).*
Friedrich et al. (Mol. Cancer Ther. Dec. 2012; 11 (12): 2664-73).*
Bowie et al. (Science 1990; 257: 1306-1310).*
Abhinandan, et al., "Analysis and improvements to kabat and structurally correct numbering of antibody variable domains," Molecular Immunology, 45: 3832-3839 (2008).

(Continued)

*Primary Examiner* — Stephen L Rawlings
(74) *Attorney, Agent, or Firm* — Eric Dichter

(57) ABSTRACT

Provided herein are isolated CD3×PSMA-bispecific antigen-binding molecules or bispecific antigen-binding fragment thereof wherein a FN3 domain specifically binds human prostate specific membrane antigen (PSMA) and a second antigen-binding site immunospecifically binds CD3. Also described are fusion proteins and related polynucleotides capable of encoding the provided fusion proteins and, cells expressing the provided fusion proteins. In addition, methods of using the provided isolated CD3×PSMA-bispecific antigen-binding molecules or bispecific antigen-binding fragment thereof are described.

8 Claims, 26 Drawing Sheets

Specification includes a Sequence Listing.

(56) References Cited

U.S. PATENT DOCUMENTS

| | | |
|---|---|---|
| 4,927,762 A | 5/1990 | Darfler |
| 4,946,778 A | 8/1990 | Ladner et al. |
| 5,112,946 A | 5/1992 | Malone |
| 5,122,469 A | 6/1992 | Mather et al. |
| 5,194,594 A | 3/1993 | Khawli et al. |
| 5,223,409 A | 6/1993 | Ladner et al. |
| 5,255,539 A | 10/1993 | Zimmer |
| 5,258,498 A | 11/1993 | Huston et al. |
| 5,260,203 A | 11/1993 | Ladner et al. |
| 5,336,603 A | 8/1994 | Capon et al. |
| 5,349,053 A | 9/1994 | Landolfi |
| 5,359,046 A | 10/1994 | Capon et al. |
| 5,403,484 A | 4/1995 | Ladner et al. |
| 5,427,908 A | 6/1995 | Dower et al. |
| 5,447,851 A | 9/1995 | Beutler et al. |
| 5,455,030 A | 10/1995 | Ladner et al. |
| 5,516,637 A | 5/1996 | Huang et al. |
| 5,530,101 A | 6/1996 | Queen et al. |
| 5,534,411 A | 7/1996 | Weltzin |
| 5,565,332 A | 10/1996 | Hoogenboom et al. |
| 5,571,698 A | 11/1996 | Ladner et al. |
| 5,580,717 A | 12/1996 | Dower et al. |
| 5,585,089 A | 12/1996 | Queen et al. |
| 5,622,929 A | 4/1997 | Willner et al. |
| 5,658,727 A | 8/1997 | Barbas et al. |
| 5,698,426 A | 12/1997 | Huse |
| 5,723,125 A | 3/1998 | Chang et al. |
| 5,733,743 A | 3/1998 | Johnson et al. |
| 5,747,654 A | 5/1998 | Pastan et al. |
| 5,750,753 A | 5/1998 | Kimae et al. |
| 5,780,225 A | 7/1998 | Wigler et al. |
| 5,783,181 A | 7/1998 | Browne et al. |
| 5,807,715 A | 9/1998 | Morrison et al. |
| 5,821,047 A | 10/1998 | Garrard et al. |
| 5,844,096 A | 12/1998 | Hinrichs et al. |
| 5,856,456 A | 1/1999 | Whitlow et al. |
| 5,908,626 A | 6/1999 | Chang et al. |
| 5,939,598 A | 8/1999 | Kucherlapati et al. |
| 5,969,108 A | 10/1999 | McCafferty et al. |
| 7,955,590 B2 | 6/2011 | Gillies et al. |
| 2004/0024188 A1 | 2/2004 | Murphy et al. |
| 2009/0252683 A1 | 10/2009 | Kischel et al. |
| 2010/0144601 A1 | 6/2010 | Jacobs et al. |
| 2011/0026439 A1 | 10/2011 | Kufer, et al. |
| 2013/0079280 A1 | 3/2013 | Baca et al. |
| 2013/0247236 A1 | 9/2013 | McWhirter et al. |
| 2014/0072958 A1 | 3/2014 | Nabel et al. |
| 2014/0086835 A1 | 3/2014 | Liu |
| 2014/0099318 A1 | 4/2014 | Huang et al. |
| 2014/0199294 A1* | 7/2014 | Mimoto ............... C07K 16/00 424/133.1 |

FOREIGN PATENT DOCUMENTS

| | | |
|---|---|---|
| EP | 0 592 106 B1 | 4/1994 |
| WO | WO 87/00195 A1 | 1/1987 |
| WO | WO 90/02809 A1 | 3/1990 |
| WO | WO 90/03430 A1 | 4/1990 |
| WO | WO 91/09967 A1 | 7/1991 |
| WO | WO 91/10737 A1 | 7/1991 |
| WO | WO 92/01047 A1 | 1/1992 |
| WO | WO 92/18619 A1 | 10/1992 |
| WO | WO 92/22324 A1 | 12/1992 |
| WO | WO 93/11236 A1 | 6/1993 |
| WO | WO 94/11026 A2 | 5/1994 |
| WO | WO 94/13804 A1 | 6/1994 |
| WO | WO 95/15982 A2 | 6/1995 |
| WO | WO 95/20401 A1 | 8/1995 |
| WO | WO0232925 A2 * | 4/2002 |
| WO | WO 03/011161 A1 | 2/2003 |
| WO | WO 2009/133208 A1 | 11/2009 |
| WO | WO 2010/080538 A1 | 7/2010 |
| WO | WO 2013/049275 A1 | 4/2013 |
| WO | WO 2014/081944 A2 | 5/2014 |

OTHER PUBLICATIONS

Baccala, et al., "Expression of Prostate-Specific Membrane Antigen in tumor-Associated Neovasculature of Renal Neoplasms," Urology, 70: 385-390 (2007).

Baum, et al., "Antitumor activities of PDSMxCD3 diabodies by redirected T-cell lysis of prostate cancer cells," Immunotherapy, 5 (1): 27-38 (2013).

Binz, et al., "High-affinity binders selected from designed ankyrin repeat protein libraries," Nature Biotechnology, 22(5): 575-582 (2004).

Birtalan, et al., The Intrinsic Contributions of Tyrosine, Serine, Glycine and Arginine to the Affinity and Specificity of Antibodies, Journal of Molecular Biology, 377: 1518-1528 (2008).

Bork, et al., "Proposed acquisition of an animal protein domain by bacteria," Proceedings of The National Academy of Science USA, 89: 8990-8994 (1992).

Boyton, et al., "Natural killer cells, killer immunoglobulin-like receptors and human leucocyte antigen class 1 in disease," Clinical and Experimental Immunology, 149: 1-8 (2007).

Michael Brinkley, "A Brief Survey of Methods for Preparing Protein Conjugates with Dyes, Haptens, and Cross-Linking Reagents," Bioconjugate Chemistry, 3: 2-13 (1992).

Bühler, et al., "Target-dependent T-cell Activation by Coligation with a PSMAxCD3 Diabody Induces Lysis of Prostate Cancer Cells," Journal of Immunotherapy, 32 (6): 565-573 (2009).

Chen, et al., "A general strategy for the evolution of bond-forming enzymes using yeast display," Proceedings of the National Academy of Science, 108(28): 11399-11404 (2011).

Martin J. Cline, "Perspectives for Gene Therapy: Inserting New Genetic Information Into Mammalian Cells by Physical Techniques and Viral Vectors," Pharmaceutical Therapy, 29: 69-92 (1985).

Emsley, et al., "Coot: model building tools for molecular graphics," ACTA Crystallographica, D60: 2126-2132 (2004).

Fortmüller, et al., "Effective targeting of prostate cancer by lymphocytes redirected by a PMSA * CD3 bispecific single-chain diabody," Prostate, 71 (6): 588-596 (2011).

Fransson, et al., "Human Framework Adaptation of a Mouse Anti-Human IL-13 Antibody,"Journal of Molecular Biology, 398: 214-231 (2010).

Friedrich, et al., "Regression of human prostate cancer xenografts in mice by AMG212/BAY2010112, a novel PSMA/CD3-Bispecific BiTE antibody cross-reactive with non-human primate antigens," Molecular Cancer Therapeutics, 11 (12): 2664-2673 (2012).

Gadi, et al., "In vivo sensitization of ovarian tumors to chemotherapy by expression of E. coli purine nucleoside phosphorylase in a small fraction of cells," Gene Therapy, 7: 1738-1743 (2000).

Holliger, et al., "'Diabodies': Small bivalent and bispecific antibody fragments," Proceedings of the National Academy of Science USA, 90: 6444-6448 (1993).

Holt, et al., "Domain antibodies: proteins for therapy," TRENDs in Biotechnology, 21(11): 484-490 (2003).

Jacobs, et al., "Design of novel FN3 domains with high stability by a consensus sequence approach," Protein Engineering, Design & Selection, 25(3): 107-117 (2012).

Johnson, et al., "Relationships between drug activity in Nci preclinical in vitro and in vivo models and early clinical trials," British Journal of Cancer, 84(10): 1424-1431 (2001).

Volker, et al., "Antitumor activities of PSMA*CD3 diabodies by redirected T-cell lysis of prostate cancer cells," Immunotherapy, 5 (1): 27-38 (2013).

Koide, et al., "High-affinity single-domain binding proteins with a binary-code interface,"Proceedings of the National Academy of Science USA, 104 (16): 6632-6637 (2007).

Liu, et al., "Monoclonal Antibodies to the Extracellular Domain of Prostate-specific M Antigen Also React with Tumor Vascular Endothelium," Cancer Research, 57: 3629-3634 (1997).

Ljunggren, et al., "Prospects for the use of NK cells in immunotherapy of human cancer,"Nature Reviews, 7: 329-339 (2007).

Meinke, et al., "Cellulose-Binding Polypeptides from Cellulomonas fimi: Endoglucanase D (CenD), a Family A β1,4-Glucanase," Journal of Bacteriology, 175 (7): 1910-1918 (1993).

(56) References Cited

OTHER PUBLICATIONS

Milowsky, et al., "Vascular Targeted Therapy With Anti-Prostate-Specific Membrane Antigen Monoclonal Antibody J591 in Advanced Solid Tumors," Journal of Clinical Oncology,.

Myers, et al., "Optimal alignments in linear space," Cabios, 4 (1): 11-17 (1988).

Needleman, et al., "A General Method Applicable to the Search for Similarities in the Amino Acid Sequence of Two Proteins," Journal of Molecular Biology, 48: 443-453 (1970).

Odegrip, et al., "CID display: *In vitro* selection of peptides from libraries of protein-CND complexes," Proceedings of the National Academy of Science USA, 101 (9): 2806-2810 (2004).

Olson, et al., "Design, expression, and stability of a diverse protein library based on the human fibronectin type III domain," Protein Science, 16: 476-484 (2007).

Revets, et al., "Nanobodies as novel agents for cancer therapy," Expert Opinion on Biological Therapy, 5 (10: 111-124 (2005)

SwissProt Accession no. N04234, created Mar. 20, 1987.
SwissProt Accession No. P07766, created Aug. 1, 1988.
SwissProt Accession No. P09693, created Jul. 1, 1989.

Therasse, et al., "New Guidelines to Evaluate the Response to Treatment in Solid Tumors," Journal of the National Cancer Institute, 92 (3): 205-216 (2000).

Ton-That, et al., "Purification and characterization of sortase, the transpeptidase that cleaves surface proteins of *Staphylococcus aureus* at the LPXTG motif," Proceedings of the National Academy of Science USA, 96 (22): 12424-12429 (1999).

Ward, et al., "Binding activities of a repertoire of single immunoglobulin variable domains secreted from *Escherichia coli*," Nature, 341: 544-546 (1989).

Watanabe, et al., "Gene Cloning of Chitinase A1 from *Bacillus circulans* WL-12 Revealed Its Evolutionary Relationship to Serratia Chitinase and to the Type III Homology Units of Fibronectin," The Journal of Biological Chemistry, 265 (26): 15659-15665 (1990).

\* cited by examiner

Figure 4A.

```
h    KSSNEATNITPKHNMKAFLDELKAENIKKFLYNFTQIPHLAGTEQNFQLA
c    KSSSEATNITPKHNMKAFLDELKAENIKKFLHNFTQIPHLAGTEQNFQLA h    KQIQSQWKEFGLDSVELAHYDVLLSYPNKTHPNYISIINEDGNEIFNTSL
c    KQIQSQWKEFGLDSVELTHYDVLLSYPNKTHPNYISIINEDGNEIFNTSL h    FEPPPEGYENVSDIVPPFSAFSPQGMPEGDLVYVNYARTEDFFKLERDMK
c    FEPPPAGYENVSDIVPPFSAFSPQGMPEGDLVYVNYARTEDFFKLERDMK h    INCSGKIVIARYGKVFRGNKVKNAQLAGAKGVILYSDPADYFAPGVKSYP
c    INCSGKIVIARYGKVFRGNKVKNAQLAGATGVILYSDPDDYFAPGVKSYP h    DGWNLPGGGVQRGNILNLNGAGDPLTPGYPANEYAYRRGIAEAVGLPSIP
c    DGWNLPGGGVQRGNILNLNGAGDPLTPGYPANEYAYRRGMAEAVGLPSIP h    VHPIGYYDAQKLLEKMGGSAPPDSSWRGSLKVPYNVGPGFTGNFSTQKVK
c    VHPIGYYDAQKLLEKMGGSASPDSSWRGSLKVPYNVGPGFTGNFSTQKVK h    MHIHSTNEVTRIYNVIGTLRGAVEPDRYVILGGHRDSWVFGGIDPQSGAA
c    MHIHSTSEVTRIYNVIGTLRGAVEPDRYVILGGHRDSWVFGGIDPQSGAA h    VVHEIVRSFGILKKEGWRPRRTILFASWDAEEFGLLGSTEWAEENSRLLQ
c    VVHEIVRSFGMLKKEGWRPRRTILFASWDAEEFGLLGSTEWAEENSRLLQ h    ERGVAYINADSSIEGNYTLRVDCTPLMYSLVHNLTKELKSPDEGFEGKSL
c    ERGVAYINADSSIEGNYTLRVDCTPLMYSLVYNLTKELESPDEGFEGKSL h    YESWTKKSPSPEFSGMPRISKLGSGNDFEVFFQRLGIASGRARYTKNWET
c    YESWTKKSPSPEFSGMPRISKLGSGNDFEVFFQRLGIASGRARYTKNWET h    NKFSGYPLYHSVYETYELVEKFYDPMFKYHLTVAQVRGGMVFELANSIVL
c    NKFSSYPLYHSVYETYELVEKFYDPMFKYHLTVAQVRGGMVFELANSVVL h    PFDCRDYAVVLRKYADKIYSISMKHPQEMKTYSVSFDSLFSAVKNFTEIA
c    PFDCRDYAVVLRKYADKIYNISMKHPQEMKTYSVSFDSLFSAVKNFTEIA h    SKFSERLQDFDKSNPIVLRMMNDQLMFLERAFIDPLGLPDRPFYRHVIYA
c    SKFSERLRDFDKSNPILLRMMNDQLMFLERAFIDPLGLPDRPFYRHVIYA h    PSSHNKYAGESFPGIYDALFDIESKVDPSKAWGEVKRQIYVAAFTVQAAA
c    PSSHNKYAGESFPGIYDALFDIESKVDPSQAWGEVKRQISIATFTVQAAA h    ETLSEVA
c    ETLSEVA
```

Figure 4B.

```
1                                                  50
LPAPKNLVVSRVTEDSARLSWTAPDAAFDSF<u>AI</u>GY<u>WEWDDD</u>G<u>EA</u>I<u>V</u>LTVP 51                                       89
GSERSYDLTGLKP<u>G</u>TEY<u>PVY</u>IA<u>G</u>VKGGQ<u>WSFP</u>LS<u>AI</u>FTT
```

A. LNCaP (High PSMA+ Cell line)

Figure 8

CDRs in AbM definition are underlined [Abhinandan KR, Martin AC. 2008. *Mol. Immunol.* 45, 3832-3839.]. Ser230 is the last HC residue present in papain-cleaved Fab. Residues 231-455 are from IGHG3_MOUSE (mouse IgG3, isoform 2).

```
Light Chain (SEQ ID NO:160)
         10        20        30        40        50        60
    .     |    .    |    .    |    .    |    .    |    .    |
    QAVVTQESALTTSPGETVTLTCRSSTGAVTTSNYANWVQEKPDHLFTGLIGGTNKRAPGV 70        80        90       100       110       120
    .     |    .    |    .    |    .    |    .    |    .    |
    PARFSGSLIGDKAALTITGAQTEDEAIYFCALWYSNLWVFGGGTKLTVLGQPKSSPSVTL 130       140       150       160       170       180
    .     |    .    |    .    |    .    |    .    |    .    |
    FPPSSEELETNKATLVCTITDFYPGVVTVDWKVDGTPVTQGMETTQPSKQSNNKYMASSY 190       200       210
    .     |    .    |    .    |    .
    LTLTARAWERHSSYSCQVTHEGHTVEKSLSRADCS Heavy Chain (SEQ ID NO:161)
         10        20        30        40        50        60
    .     |    .    |    .    |    .    |    .    |    .    |
    EVKLLESGGGLVQPKGSLKLSCAASGFTFNTYAMNWVRQAPGKGLEWVARIRSKYNNYAT 70        80        90       100       110       120
    .     |    .    |    .    |    .    |    .    |    .    |
    YYADSVKDRFTISRDDSQSILYLQMNNLKTEDTAMYYCVRHGNFGNSYVSWFAYWGQGTL 130       140       150       160       170       180
    .     |    .    |    .    |    .    |    .    |    .    |
    VTVSAATTTAPSVYPLVPGCSDTSGSSVTLGCLVKGYFPEPVTVKWNYGALSSGVRTVSS 190       200       210       220       230       240
    .     |    .    |    .    |    .    |    .    |    .    |
    VLQSAFYSLSSLVTVPSSTWPSQTVICNVAHPASKTELIKRIEPRIPKPSTPPGSSCPPG 250       260       270       280       290       300
    .     |    .    |    .    |    .    |    .    |    .    |
    NILGGPSVFIFPPKPKDALMISLTPKVTCVVVDVSEDDPDVHVSWFVDNKEVHTAWTQPR 310       320       330       340       350       360
    .     |    .    |    .    |    .    |    .    |    .    |
    EAQYNSTFRVVSALPIQHQDWMRGKEFKCKVNNKALPAPIERTISKPKGRAQTPQVYTIP 370       380       390       400       410       420
    .     |    .    |    .    |    .    |    .    |    .    |
    PPREQMSKKKVSLTCLVTNFFSEAISVEWERNGELEQDYKNTPPILDSDGTYFLYSKLTV 430       440       450
    .     |    .    |    .    |    .
    DTDSWLQGEIFTCSVVHEALHNHHTQKNLSRSPGK
```

Figure 10

```
VH              10        20        30        40        50        60
                 .    |    .    |    .    |    .    |    .    |    .    |
sp34     EVKLLESGGGLVQPKGSLKLSCAASGFTFNTYAMNWVRQAPGKGLEWVARIRSKYNNYATY
CD3H141  EVQLVESGGGLVQPGGSLRLSCAASGFTFNTYAMNWVRQAPGKGLEWVARIRSKYNNYATY
CD3H142  EVQLLESGGGLVQPGGSLRLSCAASGFTFNTYAMNWVRQAPGKGLEWVARIRSKYNNYATY
CD3H143  EVQLLESGGGLVQPGGSLRLSCAASGFTFNTYAMNWVRQAPGKGLEWVARIRSKYNNYATY
CD3H144  EVQLVESGGGLVQPGGSLKLSCAASGFTFNTYAMNWVRQASGKGLEWVGRIRSKYNGYATY 70        80        90       100       110       120
                 .    |    .    |    .    |    .    |    .    |    .    |
sp34     YADSVKDRFTISRDDSQSILYLQMNNLKTEDTAMYYCVRHGNFGNSYVSWFAYWGQGTLVTVSA
CD3H141  YAASVKGRFTISRDDSKNSLYLQMNSLKTEDTAVYYCARHGNFGNSYVSWFAYWGQGTLVTVSS
CD3H142  YADSVKGRFTISRDNSKNTLYLQMNSLRAEDTAVYYCAKHGNFGNSYVSWFAYWGQGTLVTVSS
CD3H143  YADSVKGRFTISRDNSKNTLYLQMNSLRAEDTAVYYCVKHGNFGNSYVSWFAYWGQGTLVTVSS
CD3H144  YAASVKGRFTISRDDSKNTAYLQMNSLKTEDTAVYYCTRHGNFGNSYVSWFAYWGQGTLVTVSS

VL              10        20        30        40        50        60
                 .    |    .    |    .    |    .    |    .    |    .    |
sp34     QAVVTQES-ALTTSPGETVTLTCRSSTGAVTTSNYANWVQEKPDHLFTGLIGGTNKRAPGV
CD3L63   QAVVTQEP-SLTVSPGGTVTLTCRSSTGAVTTSNYANWVQQKPGQAPRGLIGGTNKRAPGT
CD3L64   QSVLTQPP-SVSAAPGQKVTISCRSSTGAVTTSNYANWVQQLPGTAPKGLIGGTNKRAPGI
CD3L66   QTVVTQEP-SLTVSPGGTVTLTCRSSTGAVTTSNYANWVQQKPGQAPRGLIGGTNKRAPGT 70        80        90       100       110
                 .    |    .    |    .    |    .    |    .    |
sp34     PARFSGSLIGDKAALTITGAQTEDEAIYFCALWYSNLWVFGGGTKLTVL
CD3L63   PARFSGSLLGGKAALTLSGAQPEDEAEYYCALWYSNLWVFGGGTKLTVL...
CD3L64   PDRFSGSKSGTSATLGITGLQTGDEADYYCALWYSNLWVFGGGTKLTVL...
CD3L66   PARFSGSLLGGKAALTLSGVQPEDEAEYYCALWYSNLWVFGGGTKLTVL...
```

Binding of SP34 HFA variants to primary Human T cells.

Primary antibodies were used at 12.5 µg/mL.

Binding of SP34 HFA variants to primary Cynomolgous primary T cells

SP34 HFA variants Activate primary Human T cells *in vitro*.

Negative and positive controls are shown in white and black, respectively.

SP34 HFA variants Activate primary Cynomolgous T cells *in vitro*.

Negative and positive controls are shown in gray and green, respectively.

Figure 15
Correlation of binding and activation by SP34 HFA variants.
Average binding and CD69 MFI values for human (a) and cynomolgus (b) were plotted against each other.
a) Human
b) Cynomolgous monkey
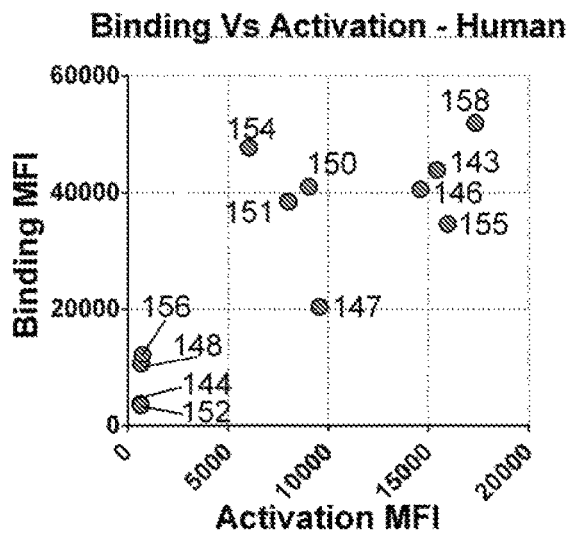
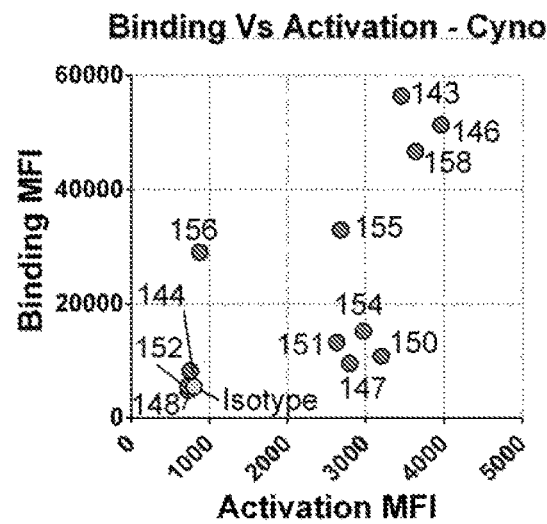

Design of CD3 X PSMA multispecific antigen-binding molecule constructs.

T-cell mediated cytotoxicity assay

PROSTATE SPECIFIC MEMBRANE ANTIGEN (PSMA) BISPECIFIC BINDING AGENTS AND USES THEREOF

CROSS-REFERENCE TO RELATED APPLICATION

This application claims the benefit of U.S. Provisional Application Ser. No. 62/157,789, filed 6 May 2015, the entire contents of which are incorporated herein by reference in its entirety.

SEQUENCE LISTING

The instant application contains a Sequence Listing which has been submitted electronically in ASCII format and is hereby incorporated by reference in its entirety.

TECHNICAL FIELD

The disclosure provided herein relates to multispecific agents that specifically bind human prostate specific membrane antigen (PSMA) and immunospecifically bind cluster determinant 3 (CD3), and methods of producing and using the described agents.

BACKGROUND

Prostate specific membrane antigen (PSMA), also known as glutamate carboxypeptidase II or N-acetylated alpha-linked acidic dipeptidase 1, is a dimeric type 2 transmembrane glycoprotein. PSMA cleaves several substrates, including folate and N-acetyl-L-aspartyl-L-glutamate, and is expressed in a number of tissues with highest expression in prostate, and to a lesser extent in the small intestine, central and peripheral nervous system, kidney and lung. PSMA is constitutively internalized through clathrin coated pits.

PSMA is a prostate-cancer related cell membrane antigen frequently overexpressed in prostatic intraepithelial neoplasia (PIN), a condition in which some prostate cells have begun to look and behave abnormally; primary and metastatic prostate cancers; and the neovasculature of other solid tumors (e.g. breast, lung, bladder, kidney). PSMA expression correlates with disease progression and Gleason score. PSMA expression is increased in metastatic disease, hormone refractory cases, and higher-grade lesions, and it is further upregulated in androgen-insensitive tumors Prostate cancer is the leading cause of cancer among males, and the 2$^{nd}$ leading cause of cancer-induced death. Globally, there are approximately 1,100,000 new cases and 300,000 mortalities every year, translationg to about 4% of all cancer deaths. It is estimated that 1 in every 6 men will be diagnosed with the disease. In the U.S., more than 90% of prostate cancers are found in local or regional stages. At these early stages, the 5-year survival rate is close to 100%. When the cancer has metastasized, however, the 5-year survival rate is reduced to about 28%.

Current treatments for prostate cancer include surgery, radiation, hormone and antibody-drug conjugate (ADC) therapies. However, tumor cells often become androgen insensitive, and, when this occurs, limited treatment options remain. Typically, the cancer vaccine sipuleucel-T, a radio-pharmaceutical agent (such as radium-223 chloride), secondary hormone therapies (such as abiraterone or enzalutamide), and/or chemotherapies (docetaxel and cabazitaxel) are added to the hormonal therapy in sequence.

While each of these treatments can delay growth of the cancer for several months and palliate symptoms produced by the disease, the disease ultimately becomes resistant to them.

Therefore, there remains a need for additional and improved therapeutics to treat prostate cancer and other cancers overexpressing PSMA.

SUMMARY

Described herein are isolated multispecific antigen-binding molecules that bind the antigens CD3 and PSMA ("CD3×PSMA multispecific molecules") or multispecific antigen-binding fragments thereof. In one embodiment, an isolated multispecific molecule or multispecific antigen-binding fragment thereof that binds specifically to PSMA is provided. In one embodiment, the PSMA that is bound comprises the amino acid sequence of SEQ ID NO: 144.

FN3 Domain

In some embodiments, the PSMA-specific domain of the multispecific antigen-binding molecule or multispecific antigen-binding fragment thereof binds human PSMA. In some embodiments, the PSMA-specific domain of the multispecific or multispecific antigen-binding fragment thereof cross reacts with *Macaca fascicularis* PSMA or with Pan troglodytes PSMA. In preferred embodiments, the CD3×PSMA-multispecific antigen-binding molecule or multispecific antigen-binding fragment thereof is a CD3×PSMA-bispecific antigen-binding molecule or bispecific antigen-binding fragment thereof. In some embodiments, an isolated antigen-binding molecule or multispecific antigen-binding fragment thereof comprises: a) a FN3 domain; b) a light chain (LC); and c) a heavy chain (HC), wherein the FN3 domain forms a first antigen-binding site that specifically binds human prostate specific membrane antigen (PSMA), and the HC and the LC pair to form a second antigen-binding site that immunospecifically binds CD3, or a PSMA-binding FN3 domain×CD3 bispecific antigen-binding fragment thereof is provided. In another embodiment, an isolated cell expressing the CD3×PSMA-multispecific antigen-binding molecule or bispecific antigen-binding fragment thereof is provided. In some embodiments, the FN3 domain (or "PSMA-specific arm") of the CD3×PSMA-bispecific antigen-binding molecule or bispecific antigen-binding fragment thereof thereof is derived from a TENCON™ sequence of SEQ ID NO: 1 or TENCON™27 of SEQ ID NO: 4, the SEQ ID NO: 1 or SEQ ID NO: 4 optionally having substitutions at residue positions 11, 14, 17, 37, 46, 73, and/or 86; or the FN3 domain is isolated from a library comprising the sequence of SEQ ID NOs: 2, 3, 5, 6, 7, or 8 described herein. Examples of FN3 domains having these sequences are listed in Table 1).

TABLE 1

| Clone ID | SEQ ID NO: | Sequence |
|---|---|---|
| P229CR5P819_H11 | 40 | LPAPKNLVVSRVTEDSARLSWDIDEQRDWFDSFL IQYQESEKVGEAIVLTVPGSERSYDLTGLKPGTE YTVSIYGVYHVYRSSNPLSAIFTT |
| P258AR6P1071_G03 | 35 | LPAPKNLVVSRVTEDSARLSWDIDEQRDWFDSFL IQYQESEKVGEAIVLTVPGSERSYDLTGLKPGTE YTVSIYGVYHVYRSNPLSAIFTT |
| P258AR6P1070_A05 | 36 | LPAPKNLVVSRVTEDSARLSWTIDEQRDWFDSFL IQYQESEKVGEAIVLTVPGSERSYDLTGLKPGTE YTVSIYGVYHVYRSNPLSAIFTT |
| P258AR6P1071_F04 | 37 | LPAPKNLVVSRVTEDSARLSWVIDEQRDWFDSFL IQYQESEKVGEAIVLTVPGSERSYDLTGLKPGTE YTVSIYGVYHVYRSNPLSAIFTT |
| P258AR6P1070_F09 | 38 | LPAPKNLVVSRVTEDSARLSWTIDEQRDWFESFL IQYQESEKVGEAIVLTVPGSERSYDLTGLKPGTE YTVSIYGVYHVYRSNPLSAIFTT |
| P258AR6P1071_D02 | 39 | LPAPKNLVVSRVTEDSARLSWAIDEQRDWFESFL IQYQESEKVGEAIVLTVPGSERSYDLTGLKPGTE YTVSIYGVYHVYRSNPLSAIFTT |
| P234CR9_H01 | 46 | LPAPKNLVVSRVTEDSARLSWEWWVIPGDFDSFL IQYQESEKVGEAIVLTVPGSERSYDLTGLKPGTE YTVSIYGVVNSGQWNDTSNPLSAIFTT |
| P234CR9_A7 | 45 | LPAPKNLVVSRVTEDSARLSWGEQFTIFDSFLIQ YQESEKVGEAIVLTVPGSERSYDLTGLKPGTEYT VSIYGASGYEWFHAFGSSNPLSAIFTT |
| P233FR9_H10 | 41 | LPAPKNLVVSRVTEDSARLSWTAPDAAFDSFAIG YWEWDDDGEAIVLTVPGSERSYDLTGLKPGTEYP VYIAGVKGGQWSFPLSAIFTT |
| P233FR9P1001_D9 | 44 | LPAPKNLVVSRVTEDSARLSWTAPDAAFDSFPIG YWEWDDDGEAIVLTVPGSERSYDLTGLKPGTEYW VYIAGVKGGQWSFPLSAIFTT |
| P233FR9P1001_B5-5 | 42 | LPAPKNLVVSRVTEDSARLSWTAPDAAFDSFTIG YWEWDDDGEAIVLTVPGSERSYDLTGLKPGTEYP VYIAGVKGGQWSFPLSAIFTT |
| P233FR9P1001_H3-1 | 43 | LPAPKNLVVSRVTEDSARLSWTAPDAAFDSFPIG YWEWDDDGEAIVLTVPGSERSYDLTGLKPGTEYH VYIAGVKGGQWSFPLSAIFTT |

In another embodiment, the FN3 domain of the isolated CD3×PSMA-bispecific antigen-binding molecule or bispecific antigen-binding fragments thereof may be selected from the sequences listed in Table 2.

TABLE 2

| Clone ID | SEQ ID NO: | Sequence |
|---|---|---|
| P258AR6P1071_D02_v1 | 75 | LPAPKNLVVSRVTEDSARLSWAADEQRDWFE SFLIQYQESEKVGEAIVLTVPGSCRSYDLTG LKPGTEYTVSIYGVYHVYRSNPLSAIFTT |
| P258AR6P1071_D02_v2 | 76 | LPAPKNLVVSRVTEDSARLSWAIAEQRDWFE SFLIQYQESEKVGEAIVLTVPGSCRSYDLTG LKPGTEYTVSIYGVYHVYRSNPLSAIFTT |
| P258AR6P1071_D02_v3 | 77 | LPAPKNLVVSRVTEDSARLSWAIDAQRDWFE SFLIQYQESEKVGEAIVLTVPGSCRSYDLTG LKPGTEYTVSIYGVYHVYRSNPLSAIFTT |
| P258AR6P1071_D02_v4 | 78 | LPAPKNLVVSRVTEDSARLSWAIDEARDWFE SFLIQYQESEKVGEAIVLTVPGSCRSYDLTG LKPGTEYTVSIYGVYHVYRSNPLSAIFTT |

TABLE 2-continued

| Clone ID | SEQ ID NO: | Sequence |
| --- | --- | --- |
| P258AR6P1071_D02_v5 | 79 | LPAPKNLVVSRVTEDSARLSWAIDEQADWFE SFLIQYQESEKVGEAIVLTVPGSCRSYDLTG LKPGTEYTVSIYGVYHVYRSNPLSAIFTT |
| P258AR6P1071_D02_v6 | 80 | LPAPKNLVVSRVTEDSARLSWAIDEQRAWFE SFLIQYQESEKVGEAIVLTVPGSCRSYDLTG LKPGTEYTVSIYGVYHVYRSNPLSAIFTT |
| P258AR6P1071_D02_v7 | 81 | LPAPKNLVVSRVTEDSARLSWAIDEQRDAFE SFLIQYQESEKVGEAIVLTVPGSCRSYDLTG LKPGTEYTVSIYGVYHVYRSNPLSAIFTT |
| P258AR6P1071_D02_v8 | 82 | LPAPKNLVVSRVTEDSARLSWAIDEQRDWFE SFLIQYQESEKVGEAIVLTVPGSCRSYDLTG LKPGTEYTVSIYGVAHVYRSNPLSAIFTT |
| P258AR6P1071_D02_v9 | 83 | LPAPKNLVVSRVTEDSARLSWAIDEQRDWFE SFLIQYQESEKVGEAIVLTVPGSCRSYDLTG LKPGTEYTVSIYGVYAVYRSNPLSAIFTT |
| P258AR6P1071_D02_v10 | 84 | LPAPKNLVVSRVTEDSARLSWAIDEQRDWFE SFLIQYQESEKVGEAIVLTVPGSCRSYDLTG LKPGTEYTVSIYGVYHAYRSNPLSAIFTT |
| P258AR6P1071_D02_v11 | 85 | LPAPKNLVVSRVTEDSARLSWAIDEQRDWFE SFLIQYQESEKVGEAIVLTVPGSCRSYDLTG LKPGTEYTVSIYGVYHVARSNPLSAIFTT |
| P258AR6P1071_D02_v12 | 86 | LPAPKNLVVSRVTEDSARLSWAIDEQRDWFE SFLIQYQESEKVGEAIVLTVPGSCRSYDLTG LKPGTEYTVSIYGVYHVYASNPLSAIFTT |
| P258AR6P1071_D02_v13 | 87 | LPAPKNLVVSRVTEDSARLSWAIDEQRDWFA SFLIQYQESEKVGEAIVLTVPGSCRSYDLTG LKPGTEYTVSIYGVYHVYRSNPLSAIFTT |
| P258AR6P1071_D02_v14 | 88 | LPAPKNLVVSRVTEDSARLSWDIDEQRDWFE SFLIQYQESEKVGEAIVLTVPGSCRSYDLTG LKPGTEYTVSIYGVYHVYRSNPLSAIFTT |
| P258AR6P1071_D02_v15 | 89 | LPAPKNLVVSRVTEDSARLSWAIDEQRDWFD SFLIQYQESEKVGEAIVLTVPGSCRSYDLTG LKPGTEYTVSIYGVYHVYRSNPLSAIFTT |
| P258AR6P1071_D02_v16 | 90 | LPAPKNLVVSRVTEDSARLSWAIDEQRDWFE SFLIQYQESEKVGEAIVLTVPGSCRSYDLTG LKPGTEYTVSIYGVYHVYRSSNPLSAIFTT |
| P258AR6P1071_D02_v17 | 91 | LPAPKNLVVSRVTEDSARLSWDIDEQRDWFD SFLIQYQESEKVGEAIVLTVPGSCRSYDLTG LKPGTEYTVSIYGVYHVYRSNPLSAIFTT |
| P258AR6P1071_D02_v18 | 92 | LPAPKNLVVSRVTEDSARLSWDIDEQRDWFE SFLIQYQESEKVGEAIVLTVPGSCRSYDLTG LKPGTEYTVSIYGVYHVYRSSNPLSAIFTT |
| P258AR6P1071_D02_v19 | 93 | LPAPKNLVVSRVTEDSARLSWAIDEQRDWFD SFLIQYQESEKVGEAIVLTVPGSCRSYDLTG LKPGTEYTVSIYGVYHVYRSSNPLSAIFTT |
| P233FR9_H10_v1 | 94 | LPAPKNLVVSRVTEDSARLSWTAPDAAFDSF AIGYWEWDDDGEAIVLTVPGSCRSYDLTGLK PGTEYRVYIAGVKGGQWSFPLSAIFTT |
| P233FR9_H10_v2 | 95 | LPAPKNLVVSRVTEDSARLSWTAPDAAFDSF AIGYWEWDDDGEAIVLTVPGSCRSYDLTGLK PGTEYKVYIAGVKGGQWSFPLSAIFTT |
| P233FR9_H10_v3 | 96 | LPAPKNLVVSRVTEDSARLSWTAPDAAFDSF AIGYWEWDDDGEAIVLTVPGSCRSYDLTGLK PGTEYEVYIAGVKGGQWSFPLSAIFTT |
| P233FR9_H10_v4 | 97 | LPAPKNLVVSRVTEDSARLSWTAPDAAFDSF AIGYWEWDDDGEAIVLTVPGSCRSYDLTGLK PGTEYHVYIAGVKGGQWSFPLSAIFTT |

TABLE 2-continued

| Clone ID | SEQ ID NO: | Sequence |
|---|---|---|
| P233FR9_H10_v5 | 98 | LPAPKNLVVSRVTEDSARLSWTAPDAAFDSF AIGYWEWDDDGEAIVLTVPGSCRSYDLTGLK PGTEYDVYIAGVKGGQWSFPLSAIFTT |
| P233FR9_H10_v6 | 99 | LPAPKNLVVSRVTEDSARLSWTAPDAAFDSF AIGYWEWDDDGEAIVLTVPGSCRSYDLTGLK PGTEYAVYIAGVKGGQWSFPLSAIFTT |
| P233FR9_H10_v7 | 100 | LPAPKNLVVSRVTEDSARLSWTAPDAAFDSF AIGYWEWDDDGEAIVLTVPGSCRSYDLTGLK PGTEYGVYIAGVKGGQWSFPLSAIFTT |
| P233FR9_H10_v8 | 101 | LPAPKNLVVSRVTEDSARLSWTAPDAAFDSF AIGYWEWDDDGEAIVLTVPGSCRSYDLTGLK PGTEYVVYIAGVKGGQWSFPLSAIFTT |
| P233FR9_H10_v9 | 102 | LPAPKNLVVSRVTEDSARLSWTAPDAAFDSF AIGYWEWDDDGEAIVLTVPGSCRSYDLTGLK PGTEYLVYIAGVKGGQWSFPLSAIFTT |
| P233FR9_H10_v10 | 103 | LPAPKNLVVSRVTEDSARLSWTAPDAAFDSF AIGYWEWDDDGEAIVLTVPGSCRSYDLTGLK PGTEYIVYIAGVKGGQWSFPLSAIFTT |
| P233FR9_H10_v11 | 104 | LPAPKNLVVSRVTEDSARLSWTAPDAAFDSF AIGYWEWDDDGEAIVLTVPGSCRSYDLTGLK PGTEYFVYIAGVKGGQWSFPLSAIFTT |
| P233FR9_H10_v12 | 105 | LPAPKNLVVSRVTEDSARLSWTAPDAAFDSF AIGYWEWDDDGEAIVLTVPGSCRSYDLTGLK PGTEYWVYIAGVKGGQWSFPLSAIFTT |
| P233FR9_H10_v13 | 106 | LPAPKNLVVSRVTEDSARLSWTAPDAAFDSF AIGYWEWDDDGEAIVLTVPGSCRSYDLTGLK PGTEYNVYIAGVKGGQWSFPLSAIFTT |
| P233FR9_H10_v14 | 107 | LPAPKNLVVSRVTEDSARLSWTAPDAAFDSF AIGYWEWDDDGEAIVLTVPGSCRSYDLTGLK PGTEYQVYIAGVKGGQWSFPLSAIFTT |
| P233FR9_H10_v15 | 108 | LPAPKNLVVSRVTEDSARLSWTAPDAAFDSF AIGYWEWDDDGEAIVLTVPGSCRSYDLTGLK PGTEYSVYIAGVKGGQWSFPLSAIFTT |
| P233FR9_H10_v16 | 109 | LPAPKNLVVSRVTEDSARLSWTAPDAAFDSF AIGYWEWDDDGEAIVLTVPGSCRSYDLTGLK PGTEYTVYIAGVKGGQWSFPLSAIFTT |
| P233FR9_H10_v17 | 110 | LPAPKNLVVSRVTEDSARLSWTAPDAAFDSF AIGYWEWDDDGEAIVLTVPGSCRSYDLTGLK PGTEYYVYIAGVKGGQWSFPLSAIFTT |
| P233FR9_H10_v18 | 111 | LPAPKNLVVSRVTEDSARLSWTAPDAAFDSF AIAYWEWDDDGEAIVLTVPGSCRSYDLTGLK PGTEYPVYIAGVKGGQWSFPLSAIFTT |
| P233FR9_H10_v19 | 112 | LPAPKNLVVSRVTEDSARLSWTAPDAAFDSF AISYWEWDDDGEAIVLTVPGSCRSYDLTGLK PGTEYPVYIAGVKGGQWSFPLSAIFTT |
| P233FR9_H10_v20 | 113 | LPAPKNLVVSRVTEDSARLSWTAPDAAFDSF AIGYWEWDTDGEAIVLTVPGSCRSYDLTGLK PGTEYPVYIAGVKGGQWSFPLSAIFTT |
| P233FR9_H10_v21 | 114 | LPAPKNLVVSRVTEDSARLSWTAPDAAFDSF AIGYWEWDSDGEAIVLTVPGSCRSYDLTGLK PGTEYPVYIAGVKGGQWSFPLSAIFTT |
| P233FR9_H10_v22 | 115 | LPAPKNLVVSRVTEDSARLSWTAPDAAFDSF AIGYYEWDDDGEAIVLTVPGSCRSYDLTGLK PGTEYPVYIAGVKGGQWSFPLSAIFTT |
| P233FR9_H10_v23 | 116 | LPAPKNLVVSRVTEDSARLSWTAPDAAFDSF AIGYFEWDDDGEAIVLTVPGSCRSYDLTGLK PGTEYPVYIAGVKGGQWSFPLSAIFTT |

TABLE 2-continued

| Clone ID | SEQ ID NO: | Sequence |
|---|---|---|
| P233FR9_H10_v24 | 117 | LPAPKNLVVSRVTEDSARLSWTAPDAAFDSFAIGYLEWDDDGEAIVLTVPGSCRSYDLTGLKPGTEYPVYIAGVKGGQWSFPLSAIFTT |
| P233FR9_H10_v25 | 118 | LPAPKNLVVSRVTEDSARLSWTAPDAAFDSFAIGYWEYDDDGEAIVLTVPGSCRSYDLTGLKPGTEYPVYIAGVKGGQWSFPLSAIFTT |
| P233FR9_H10_v26 | 119 | LPAPKNLVVSRVTEDSARLSWTAPDAAFDSFAIGYWEFDDDGEAIVLTVPGSCRSYDLTGLKPGTEYPVYIAGVKGGQWSFPLSAIFTT |
| P233FR9_H10_v27 | 120 | LPAPKNLVVSRVTEDSARLSWTAPDAAFDSFAIGYWELDDDGEAIVLTVPGSCRSYDLTGLKPGTEYPVYIAGVKGGQWSFPLSAIFTT |
| P233FR9_H10_v28 | 121 | LPAPKNLVVSRVTEDSARLSWTAPDAAFDSFAIGYWEWDDDGEAIVLTVPGSCRSYDLTGLKPGTEYPVYIAGVKGGQYSFPLSAIFTT |
| P233FR9_H10_v29 | 122 | LPAPKNLVVSRVTEDSARLSWTAPDAAFDSFAIGYWEWDDDGEAIVLTVPGSCRSYDLTGLKPGTEYPVYIAGVKGGQFSFPLSAIFTT |
| P233FR9_H10_v30 | 123 | LPAPKNLVVSRVTEDSARLSWTAPDAAFDSFAIGYWEWDDDGEAIVLTVPGSCRSYDLTGLKPGTEYPVYIAGVKGGQLSFPLSAIFTT |
| P233FR9P1001-H3-1_v1 | 124 | LPAPKNLVVSRVTEDSARLSWTAPDAAFDSFRIGYWEWDDDGEAIVLTVPGSCRSYDLTGLKPGTEYHVYIAGVKGGQWSFPLSAIFTT |
| P233FR9P1001-H3-1_v2 | 125 | LPAPKNLVVSRVTEDSARLSWTAPDAAFDSFKIGYWEWDDDGEAIVLTVPGSCRSYDLTGLKPGTEYHVYIAGVKGGQWSFPLSAIFTT |
| P233FR9P1001-H3-1_v3 | 126 | LPAPKNLVVSRVTEDSARLSWTAPDAAFDSFEIGYWEWDDDGEAIVLTVPGSCRSYDLTGLKPGTEYHVYIAGVKGGQWSFPLSAIFTT |
| P233FR9P1001-H3-1_v4 | 127 | LPAPKNLVVSRVTEDSARLSWTAPDAAFDSFHIGYWEWDDDGEAIVLTVPGSCRSYDLTGLKPGTEYHVYIAGVKGGQWSFPLSAIFTT |
| P233FR9P1001-H3-1_v5 | 128 | LPAPKNLVVSRVTEDSARLSWTAPDAAFDSFDIGYWEWDDDGEAIVLTVPGSCRSYDLTGLKPGTEYHVYIAGVKGGQWSFPLSAIFTT |
| P233FR9P1001-H3-1_v6 | 129 | LPAPKNLVVSRVTEDSARLSWTAPDAAFDSFAIGYWEWDDDGEAIVLTVPGSCRSYDLTGLKPGTEYHVYIAGVKGGQWSFPLSAIFTT |
| P233FR9P1001-H3-1_v7 | 130 | LPAPKNLVVSRVTEDSARLSWTAPDAAFDSFGIGYWEWDDDGEAIVLTVPGSCRSYDLTGLKPGTEYHVYIAGVKGGQWSFPLSAIFTT |
| P233FR9P1001-H3-1_v8 | 131 | LPAPKNLVVSRVTEDSARLSWTAPDAAFDSFVIGYWEWDDDGEAIVLTVPGSCRSYDLTGLKPGTEYHVYIAGVKGGQWSFPLSAIFTT |
| P233FR9P1001-H3-1_v9 | 132 | LPAPKNLVVSRVTEDSARLSWTAPDAAFDSFLIGYWEWDDDGEAIVLTVPGSCRSYDLTGLKPGTEYHVYIAGVKGGQWSFPLSAIFTT |
| P233FR9P1001-H3-1_v10 | 133 | LPAPKNLVVSRVTEDSARLSWTAPDAAFDSFIIGYWEWDDDGEAIVLTVPGSCRSYDLTGLKPGTEYHVYIAGVKGGQWSFPLSAIFTT |
| P233FR9P1001-H3-1_v11 | 134 | LPAPKNLVVSRVTEDSARLSWTAPDAAFDSFFIGYWEWDDDGEAIVLTVPGSCRSYDLTGLKPGTEYHVYIAGVKGGQWSFPLSAIFTT |
| P233FR9P1001-H3-1_v12 | 135 | LPAPKNLVVSRVTEDSARLSWTAPDAAFDSFWIGYWEWDDDGEAIVLTVPGSCRSYDLTGLKPGTEYHVYIAGVKGGQWSFPLSAIFTT |

TABLE 2-continued

| Clone ID | SEQ ID NO: | Sequence |
|---|---|---|
| P233FR9P1001-H3-1_v13 | 136 | LPAPKNLVVSRVTEDSARLSWTAPDAAFDSF NIGYWEWDDDGEAIVLTVPGSCRSYDLTGLK PGTEYHVYIAGVKGGQWSFPLSAIFTT |
| P233FR9P1001-H3-1_v14 | 137 | LPAPKNLVVSRVTEDSARLSWTAPDAAFDSF QIGYWEWDDDGEAIVLTVPGSCRSYDLTGLK PGTEYHVYIAGVKGGQWSFPLSAIFTT |
| P233FR9P1001-H3-1_v15 | 138 | LPAPKNLVVSRVTEDSARLSWTAPDAAFDSF SIGYWEWDDDGEAIVLTVPGSCRSYDLTGLK PGTEYHVYIAGVKGGQWSFPLSAIFTT |
| P233FR9P1001-H3-1_v16 | 139 | LPAPKNLVVSRVTEDSARLSWTAPDAAFDSF TIGYWEWDDDGEAIVLTVPGSCRSYDLTGLK PGTEYHVYIAGVKGGQWSFPLSAIFTT |
| P233FR9P1001-H3-1_v17 | 140 | LPAPKNLVVSRVTEDSARLSWTAPDAAFDSF YIGYWEWDDDGEAIVLTVPGSCRSYDLTGLK PGTEYHVYIAGVKGGQWSFPLSAIFTT |

In another embodiment, the isolated FN3 domain of the isolated CD3×PSMA-bispecific antigen-binding molecule or bispecific antigen-binding fragments thereof that specifically binds human PSMA of SEQ ID NO: 144 comprises an amino acid sequence that is 89% identical to the amino acid sequence of SEQ ID NO: 41, or that has 1, 2, 3, 4, 5, 6, 7, 8, 9, 10 or 11 substitutions when compared to the amino acid sequence of SEQ ID NO: 41.

In another embodiment, the FN3 domain of the CD3×PSMA-bispecific antigen-binding molecule or bispecific antigen-binding fragments thereof that specifically binds human PSMA of SEQ ID NO: 144 comprises the amino acid sequence of SEQ ID NO: 35, 36, 37, 38, 39, 40, 41, 42, 43, 44, 45, 46, 47, 48, 49, 50, 51, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139 or 140.

Fusion Proteins

Another embodiment of the invention is a fusion protein comprising: a heavy chain; a FN3 domain; and a linker. The heavy chain Fc region can be IgG4 PAA. Another embodiment of the invention is a fusion protein comprising: a Fc region; a FN3 domain; and a linker. The linker and FN3 domain may be attached to the amino-terminus or the the carboxyl-terminus of the Fc region. The linker can comprise the amino acid sequence of SEQ ID NO: 175 (GGGGSGGGGS). Another embodiment of the invention is an isolated polynucleotide encoding a fusion protein comprising: a heavy chain; an FN3 domain; and a linker. The heavy chain Fc region can be IgG4 PAA. Another embodiment of the invention is an isolated polynucleotide encoding a fusion protein comprising: an Fc region; an FN3 domain; and a linker. The linker and FN3 domain may be attached to the amino-terminus or the the carboxyl-terminus of the Fc region. The linker can comprise the amino acid sequence of SEQ ID NO: 175 (GGGGSGGGGS). Another embodiment of the invention is a vector comprising the polynucleotide of the invention. Another embodiment of the invention is a host cell comprising the vector of the invention.

CD3-Binding Arm

In some embodiments, the CD3-binding arm (or "CD3-specific arm") of the CD3×PSMA-bispecific antigen-binding molecule or bispecific antigen-binding fragments thereof is derived from the mouse monoclonal antibody SP34, a mouse IgG3/lambda isotype. (K. R. Abhinandan and A. C. Martin, 2008. Mol. Immunol. 45, 3832-3839). In some embodiments, the CD3-binding arm of the CD3×PSMA-bispecific antigen-binding molecule or bispecific antigen-binding fragments thereof comprises one VH domain and one VL domain selected from Table 3. Table 3 provides a summary of examples of some the heavy chains and light chains of the CD3-specific antibodies and antigen-binding fragments.

TABLE 3

The VH and VL sequences of the antibodies are shown below:

| mAb | HC | VH Amino Acid sequence | SEQ ID NO: | LC | VL Amino Acid sequence | SEQ ID NO: |
|---|---|---|---|---|---|---|
| CD3B143 | CD3H141 | EVQLVESGGGLVQPGGSLRLSCAASGFTFNTYAMNWVRQAPGKGLEWVARIRSKYNNYATYYAASVKGRFTISRDDSKNSLYLQMNSLKTEDTAVYYCARHGNFGNSYVSWFAYWGQGTLVTVSS | 163 | CD3L63 | QAVVTQEPSLTVSPGGTVTLTCRSSTGAVTTSNYANWVQQKPGQAPRGLIGGTNKRAPGTPARFSGSLLGGKAALTLSGAQPEDEAEYYCALWYSNLWVFGGGTKLTVL | 167 |
| CD3B144 | CD3H141 | EVQLVESGGGLVQPGGSLRLSCAASGFTFNTYAMNWVRQAPGKGL | 163 | CD3L64 | QSVLTQPPSVSAAPGQKVTISCRSSTGAVTTSNYANWVQQLP | 168 |

TABLE 3-continued

The VH and VL sequences of the antibodies are shown below:

| mAb | HC | VH Amino Acid sequence | SEQ ID NO: | LC | VL Amino Acid sequence | SEQ ID NO: |
|---|---|---|---|---|---|---|
| | | EWVARIRSKYNNYAT YYAASVKGRFTISRD DSKNSLYLQMNSLKT EDTAVYYCARHGNFG NSYVSWFAYWGQGTL VTVSS | | | GTAPKGLIGGTNKR APGIPDRFSGSKSG TSATLGITGLQTGD EADYYCALWYSNLW VFGGGTKLTVL | |
| CD3B146 | CD3H141 | EVQLVESGGGLVQPG GSLRLSCAASGFTFN TYAMNWVRQAPGKGL EWVARIRSKYNNYAT YYAASVKGRFTISRD DSKNSLYLQMNSLKT EDTAVYYCARHGNFG NSYVSWFAYWGQGTL VTVSS | 163 | CD3L66 | QTVVTQEPSLTVSP GGTVTLTCRSSTGA VTTSNYANWVQQKP GQAPRGLIGGTNKR APGTPARFSGSLLG GKAALTLSGVQPED EAEYYCALWYSNLW VFGGGTKLTVL | 169 |
| CD3B147 | CD3H142 | EVQLLESGGGLVQPG GSLRLSCAASGFTFN TYAMNWVRQAPGKGL EWVARIRSKYNNYAT YYADSVKGRFTISRD NSKNTLYLQMNSLRA EDTAVYYCAKHGNFG NSYVSWFAYWGQGTL VTVSS | 164 | CD3L63 | QAVVTQEPSLTVSP GGTVTLTCRSSTGA VTTSNYANWVQQKP GQAPRGLIGGTNKR APGTPARFSGSLLG GKAALTLSGAQPED EAEYYCALWYSNLW VFGGGTKLTVL | 167 |
| CD3B148 | CD3H142 | EVQLLESGGGLVQPG GSLRLSCAASGFTFN TYAMNWVRQAPGKGL EWVARIRSKYNNYAT YYADSVKGRFTISRD NSKNTLYLQMNSLRA EDTAVYYCAKHGNFG NSYVSWFAYWGQGTL VTVSS | 164 | CD3L64 | QSVLTQPPSVSAAP GQKVTISCRSSTGA VTTSNYANWVQQLP GTAPKGLIGGTNKR APGIPDRFSGSKSG TSATLGITGLQTGD EADYYCALWYSNLW VFGGGTKLTVL | 168 |
| CD3B150 | CD3H142 | EVQLLESGGGLVQPG GSLRLSCAASGFTFN TYAMNWVRQAPGKGL EWVARIRSKYNNYAT YYADSVKGRFTISRD NSKNTLYLQMNSLRA EDTAVYYCAKHGNFG NSYVSWFAYWGQGTL VTVSS | 164 | CD3L66 | QTVVTQEPSLTVSP GGTVTLTCRSSTGA VTTSNYANWVQQKP GQAPRGLIGGTNKR APGTPARFSGSLLG GKAALTLSGVQPED EAEYYCALWYSNLW VFGGGTKLTVL | 169 |
| CD3B151 | CD3H143 | EVQLLESGGGLVQPG GSLRLSCAASGFTFN TYAMNWVRQAPGKGL EWVARIRSKYNNYAT YYADSVKGRFTISRD NSKNTLYLQMNSLRA EDTAVYYCVKHGNFG NSYVSWFAYWGQGTL VTVSS | 165 | CD3L63 | QAVVTQEPSLTVSP GGTVTLTCRSSTGA VTTSNYANWVQQKP GQAPRGLIGGTNKR APGTPARFSGSLLG GKAALTLSGAQPED EAEYYCALWYSNLW VFGGGTKLTVL | 167 |
| CD3B152 | CD3H143 | EVQLLESGGGLVQPG GSLRLSCAASGFTFN TYANNWVRQAPGKGL EWVARIRSKYNNYAT YYADSVKGRFTISRD NSKNTLYLQMNSLRA EDTAVYYCVKHGNFG NSYVSWFAYWGQGTL VTVSS | 165 | CD3L64 | QSVLTQPPSVSAAP GQKVTISCRSSTGA VTTSNYANWVQQLP GTAPKGLIGGTNKR APGIPDRFSGSKSG TSATLGITGLQTGD EADYYCALWYSNLW VFGGGTKLTVL | 168 |
| CD3B154 | CD3H143 | EVQLLESGGGLVQPG GSLRLSCAASGFTFN TYAMNWVRQAPGKGL EWVARIRSKYNNYAT YYADSVKGRFTISRD NSKNTLYLQMNSLRA | 165 | CD3L66 | QTVVTQEPSLTVSP GGTVTLTCRSSTGA VTTSNYANWVQQKP GQAPRGLIGGTNKR APGTPARFSGSLLG GKAALTLSGVQPED | 169 |

TABLE 3-continued

The VH and VL sequences of the antibodies are shown below:

| mAb | HC | VH Amino Acid sequence | SEQ ID NO: | LC | VL Amino Acid sequence | SEQ ID NO: |
|---|---|---|---|---|---|---|
| | | EDTAVYYCVKHGNFG NSYVSWFAYWGQGTL VTVSS | | | EAEYYCALWYSNLW VFGGGTKLTVL | |
| CD3B155 | CD3H144 | EVQLVESGGGLVQPG GSLKLSCAASGFTFN TYAMNWVRQASGKGL EWVGRIRSKYNGYAT YYAASVKGRFTISRD DSKNTAYLQMNSLKT EDTAVYYCTRHGNFG NSYVSWFAYWGQGTL VTVSS | 166 | CD3L63 | QTVVTQEPSLTVSP GGTVTLTCRSSTGA VTTSNYANWVQQKP GQAPRGLIGGTNKR APGTPARFSGSLLG GKAALTLSGAQPED EAEYYCALWYSNLW VFGGGTKLTVL | 167 |
| CD3B156 | CD3H144 | EVQLVESGGGLVQPG GSLKLSCAASGFTFN TYAMNWVRQASGKGL EWVGRIRSKYNGYAT YYAASVKGRFTISRD DSKNTAYLQMNSLKT EDTAVYYCTRHGNFG NSYVSWFAYWGQGTL VTVSS | 166 | CD3L64 | QSVLTQPPSVSAAP GQKVTISCRSSTGA VTTSNYANWVQQLP GTAPKGLIGGTNKR APGIPDRFSGSKSG TSATLGITGLQTGD EADYYCALWYSNLW VFGGGTKLTVL | 168 |
| CD3B158 | CD3H144 | EVQLVESGGGLVQPG GSLKLSCAASGFTFN TYAMNWVRQASGKGL EWVGRIRSKYNGYAT YYAASVKGRFTISRD DSKNTAYLQMNSLKT EDTAVYYCTRHGNFG NSYVSWFAYWGQGTL VTVSS | 166 | CD3L66 | QTVVTQEPSLTVSP GGTVTLTCRSSTGA VTTSNYANWVQQKP GQAPRGLIGGTNKR APGTPARFSGSLLG GKAALTLSGVQPED EAEYYCALWYSNLW VFGGGTKLTVL | 169 |

In some embodiments, the CD3-specific antibodies and antigen-binding fragments comprise a heavy chain from Table 4 and a light chain from Table 4. Table 4 provides a summary of the matrix of the heavy chains and light chains of the CD3-specific antibodies and antigen-binding fragments.

TABLE 4

The antibodies created by combining the heavy and light chains.

| | Light chain | | |
|---|---|---|---|
| Heavy chain | CD3L63 (LV746/W59G) | CD3L64 (LV1-51) | CD3L66 (LV743/W59G) |
| CD3H141 | CD3B143 | CD3B144 | CD3B146 |
| CD3H142 (HV3-23 + S49A) | CD3B147 | CD3B148 | CDB150 |
| CD3H143 (HV3-23 + S49A, A99V) | CD3B151 | CD3B152 | CD3B154 |
| CD3H144 (VH3-73 with G49) | CD3B155 | CD3B156 | CD3B158 |

The IgG class is divided in four isotypes: IgG1, IgG2, IgG3 and IgG4 in humans. They share more than 95% homology in the amino acid sequences of the Fc regions but show major differences in the amino acid composition and structure of the hinge region. The Fc region mediates effector functions, such as antibody-dependent cellular cytotoxicity (ADCC) and complement-dependent cytotoxicity (CDC). In ADCC, the Fc region of an antibody binds to Fc receptors (FcgRs) on the surface of immune effector cells such as natural killers and macrophages, leading to the phagocytosis or lysis of the targeted cells. In CDC, the antibodies kill the targeted cells by triggering the complement cascade at the cell surface.

For many applications of therapeutic antibodies, Fc-mediated effector functions are not part of the mechanism of action. These Fc-mediated effector functions can be detrimental and potentially pose a safety risk by causing off-mechanism toxicity. Modifying effector functions can be achieved by engineering the Fc regions to reduce their binding to FcgRs or the complement factors. The binding of IgG to the activating (FcgRI, FcgRIIa, FcgRIIIa and FcgRIIIb) and inhibitory (FcgRIIb) FcgRs or the first component of complement (Clq) depends on residues located in the hinge region and the CH2 domain. In some cases, mutations have been introduced in IgG1, IgG2 and IgG4 to reduce or silence Fc functionalities.

In one embodiment, the antibody comprises an Fc region with one or more of the following properties: (a) reduced effector function when compared to the parent Fc; (b) reduced affinity to Fcg RI, Fcg RIIa, Fcg RIIb, Fcg RIIIb and/or Fcg RIIIa, (c) reduced affinity to FcgRI (d) reduced affinity to FcgRIIa (e) reduced affinity to FcgRIIb, (f) reduced affinity to Fcg RIIIb or (g) reduced affinity to FcgRIIIa.

In some embodiments, the CD3-specific antibody or antigen-binding fragment from which the CD3-specific arm of the multispecific antibody is derived is IgG, or a derivative thereof. In some embodiments, the CD3-specific antibody or antigen-binding fragment from which the CD3-specific arm of the multispecific antibody is derived is IgG1, or a derivative thereof. In some embodiments, for example, the Fc region of the CD3-specific IgG1 antibody from which the CD3-binding arm is derived comprises L234A, L235A, and F405L substitutions in its Fc region. In some embodiments, the CD3-specific antibody or antigen-binding fragment from which the CD3-specific arm of the multispecific antibody is derived is IgG4, or a derivative thereof. In some embodiments, for example, the Fc region of the CD3-specific IgG4 antibody from which the CD3-binding arm is derived comprises S228P, L234A, L235A, F405L, and R409K substitutions in its Fc region. In some embodiments, for example, the Fc region of the CD3-specific IgG4 antibody from which the CD3-binding arm is derived comprises S228P, L234A, L235A, and F405L substitutions in its Fc region. In some embodiments, the CD3-specific antibody or antigen-binding fragment from which the CD3-specific arm of the multispecific antibody is derived is IgG-AA Fc. In some embodiments, the CD3-specific antibody or antigen-binding fragment from which the CD3-specific arm of the multispecific antibody is derived is IgG-AA Fc-L234A, L235A, and F405L (where L234A, L235A, and F405L are mutations). In some embodiments, the CD3-specific antibody or antigen-binding fragment from which the CD3-specific arm of the multispecific antibody is derived binds CD3ε on primary human T cells and/or primary cynomolgus T cells. In some embodiments, the CD3-specific antibody or antigen-binding fragment from which the CD3-specific arm of the multispecific antibody is derived activates primary human CD4+ T cells and/or primary cynomolgus CD4+ T cells.

Further provided herein, are pharmaceutical compositions comprising the CD3×PSMA-bispecific antigen-binding molecule or bispecific antigen-binding fragments thereof and a pharmaceutically acceptable carrier.

In some embodiments, the CD3×PSMA-bispecific antigen-binding molecule comprises the amino acid sequence of SEQ ID NO: 171, the light chain comprises the amino acid sequence of SEQ ID NO; 170, and the FN3 domain comprises the amino acid sequence of SEQ ID NO: 172.

In some embodiments, the CD3×PSMA-bispecific antigen-binding molecule comprises the amino acid sequence of SEQ ID NO: 171, the light chain comprises the amino acid sequence of SEQ ID NO; 170, and the FN3 domain comprises the amino acid sequence of SEQ ID NO: 173.

In some embodiments, the CD3×PSMA-bispecific antigen-binding molecule comprises the amino acid sequence of SEQ ID NO: 174, the light chain comprises the amino acid sequence of SEQ ID NO; 170, and the FN3 domain comprises the amino acid sequence of SEQ ID NO: 173.

Methods of Using CD3×PSMA-Bispecific Antigen-Binding Molecule or Bispecific Antigen-Binding Fragments Thereof Methods of using the described CD3×PSMA-bispecific antigen-binding molecules or bispecific antigen-binding fragments thereof are also disclosed. For example, the CD3×PSMA-bispecific antigen-binding molecules or bispecific antigen-binding fragments thereof may be useful in the treatment of a PSMA-overexpressing disease in a subject in need thereof. In some embodiments, the disease is cancer, preferably a PSMA-overexpressing cancer. In some embodiments, the PSMA-overexpressing disease is a prostatic intraepithelial neoplasia (PIN), a condition in which some prostate cells have begun to look and behave abnormally. In some embodiments, the cancers are primary and metastatic prostate cancers and other solid tumors, (e.g. breast, lung, bladder, kidney). In some embodiments, the cancers are prostate cancer, colorectal cancer, gastric cancer, clear cell renal carcinoma, bladder cancer, lung cancer, endometrial cancer or kidney cancer. In some embodiments, the PSMA-overexpressing cancer is associated with angiogenesis or vasculature of the cancer such as squamous cell carcinoma of the oral cavity, gliomas and breast cancer.

In some embodiments, the cancer is a neovascular disorder such as, for example, a cancer characterized by solid tumor growth. Exemplary cancers with tumor vasculatures characterized by PSMA overexpression and amenable to treatment in accordance with the present invention include, for example, clear cell renal carcinoma (CCRCC), colorectal cancer, breast cancer, bladder cancer, lung cancer, and pancreatic cancer (see, e.g., Baccala et al., Urology 70:385.390, 2007 (expression of PSMA in CCRCC); Liu et al., Cancer Res. 57:3629-3634, 1997 (expression of PSMA in various non-prostate cancers, including renal, urothelial, lung, colon, breast, and adenocarcinaoma to the liver); and Milowsky et al., J. Clin. Oncol. 25:540-547, 2007.

The described methods of treating PSMA-overexpressing disorders in a subject in need thereof include administering to the subject a therapeutically effective amount of a described CD3×PSMA-bispecific antigen-binding molecule or bispecific antigen-binding fragments thereof. In some embodiments, the subject is a mammal, preferably a human. Preferred embodiments are provided of methods for treating a subject having PSMA-overexpressing cancer by administering a therapeutically effective amount of the CD3×PSMA-bispecific antigen-binding molecule or bispecific antigen-binding fragments thereof to a patient in need thereof for a time sufficient to treat the cancer.

Further provided herein are methods for inhibiting growth or proliferation of cancer cells by administering a therapeutically effective amount of the CD3×PSMA-bispecific antigen-binding molecule or bispecific antigen-binding fragments thereof to inhibit the growth or proliferation of cancer cells.

Also provided herein are methods of redirecting a T cell to a PSMA-expressing cancer cell by administering a therapeutically effective amount of the CD3×PSMA-bispecific antigen-binding molecule or bispecific antigen-binding fragments thereof to redirect a T cell to a cancer.

CD3×PSMA-Bispecific Antigen-Binding Molecule or Bispecific Antigen-Binding Fragments Thereof Kits Described herein are kits including the disclosed CD3×PSMA-bispecific antigen-binding molecule or bispecific antigen-binding fragments thereof or bispecific antigen-binding fragments thereof. The described kits may be used to carry out the methods of using the CD3×PSMA-bispecific antigen-binding molecule or bispecific antigen-binding fragments thereof provided herein, or other methods known to those skilled in the art. In some embodiments the described kits may include the CD3×PSMA-bispecific antigen-binding molecule or bispecific antigen-binding fragments thereof described herein and reagents for use in treating a PSMA expressing cancer. Accordingly, the described kits may include one or more of the CD3×PSMA-bispecific antigen-binding molecule or bispecific antigen-binding fragments thereof, described herein, and a vessel for containing the CD3×PSMA-bispecific antigen-binding molecule or bispecific antigen-binding fragments thereof when not in use, and/or instructions for use of the isolated CD3×PSMA-bispecific antigen-binding molecule or bispecific antigen-binding fragments thereof.

BRIEF DESCRIPTION OF THE DRAWINGS

FIG. 1 shows biodistribution of untargeted $^{89}$Zr-labeled FN3 domain following intravenous injection in male NSG mice.

FIG. 2A shows the overall crystal structure of the P233FR9_H10 PSMA binding FN3 domain (H10) in complex with cynomolgous PSMA dimer, showing that H10 binds to the region near the PSMA active site. The zinc atoms (Zn) indicate the location of the PSMA active site. The N- and C-terminus of PSMA and H10 molecules are indicated for one of the complexes. The approximate location of the cell membrane is indicated. FIG. 2B shows the crystal structure of the H10 FN3 domain in complex with cynomolgous PSMA. The A, B, C, D, E, F and G beta strands in the H10 FN3 domain are shown. The negatively charged residues in the CD loop of H10 (residues W38, D39, D40, D41 and E43) that inserts into the positively charged entrance of the PSMA active site are shown. H10 residue numbering according to SEQ ID NO: 41. FIG. 2C shows the crystal structure of the H10 FN3 domain in complex with cynomolgous PSMA. The H10 contact residues W38, D39, D40, D41 and E43 are shown in the Figure. Some of the cyno PSMA residues that contact H10 (R511, K514 and K545), coordinate the zinc atoms (H377, D387, E424, E425, D453, and H553) or compose the active site cavity (R536 and R534) are shown. H10 beta strands C, D, F and G are marked in the Figure. H10 and cynomolgous PSMA residue numbering is according to SEQ ID NO: 41 and 141, respectively.

FIG. 3A shows a close view of the crystal structure combining site between the H10 FN3 domain and cynomolgous PSMA. The H10 FN3 domain contact residues A32, W36, W38-D41, E43, A44, V46, G64, P68, Y70, A72, W79, F81, P82, A85, and I86 are shown. The cyno PSMA contact residues Y460, K499-P502, P504, R511, K514, N540, W541, K545, F546, F488, K610, N613, and I614 are shown. H10 and cynomolgous PSMA residue numbering is according to SEQ ID NO: 41 and 141, respectively. FIG. 3B shows an interaction map between the H10 FN3 domain and cynomolgous PSMA contact residues. A distance cut-off of 4 Å was used to define the contact residues. FN3 domain and cyno PSMA residues are shown in gray and white boxes, respectively, van der Waals interactions are shown as dashed lines, and H-bonds are solid lines with arrows indicating backbone H bonds and pointing to the backbone atoms. Residue numbering is according to SEQ ID NO: 41 (H10) and SEQ ID NO: 141 (cyno PSMA).

FIGS. 4A and 4B. FIG. 4A shows the amino acid sequence alignment between human (h) and cynomolgous (c) PSMA extracellular domains. The H10 contact residues are underlined and in bold. The residues that differ between human and cynomolgus PSMA are shaded. All cyno PSMA residues interacting with H10 are conserved in human PSMA except for N613. Human PSMA ECD; SEQ ID NO: 143. Cyno PSMA ECD: SEQ ID NO: 32. FIG. 4B shows the H10 FN3 domain residues in contact with cynomolgous PSMA. The contact residues are underlined and in bold. H10 amino acid sequence is shown in SEQ ID NO: 41.

FIG. 5 shows the location of H10 FN3 domain residue N6, R11, T22, D25, A26, S52, E53, K62, and the N- and C-terminus, which are possible sites for chemical conjugation, in the crystal structure of H10 bound to cynomolgous PSMA. The FN3 domain/PSMA contacting regions are shown in black. H10 beta strands C, D, F and G are marked in the Figure. Residue numbering is according to SEQ ID NO: 41 (H10).

FIG. 6 shows the comparison of mean fluorescence intensity (MFI) of different tumor cell lines stained with anti PSMA PE-conjugated FN3 domain (black) and anti PSMA antibody-PE (white).

FIGS. 7A-7D show a series of the CellTracks Analyzer II browser images with different tumor cells stained with DAPI, anti cytokeratin-FITC, anti-CD45-APC and anti-PSMA FN3 domain-PE. The thumbnail images show, from right to left, PSMA-PE staining, CD45-APC signal, DAPI stained nuclei, Cytokeratin-FITC reactivity, and finally an overlay of the Cytokeratin-FITC & DAPI staining. A cell must have a nucleus, express cytokeratin and be negative for CD45 to be counted as a Circulating Tumor Cells (CTC). The CTC must have a positive signal for PSMA to be scored as PSMA positive CTC. FIG. 7A shows the expression of PSMA on LNCaP cells (100% of cells are positive for PSMA). FIG. 7B shows the expression of PSMA on 22Rv1 cells (26% of cells are positive for PSMA). FIG. 7C shows the expression of PSMA on PC3 cells (0% of cells are positive for PSMA). FIG. 7D shows the expression of PSMA on SKBR3 cells (0% of cells are positive for PSMA).

FIG. 8. FIG. 8 shows the amino acid sequence of SP34 with sequential numbering. CDRs in AbM definition are underlined. Ser230 is the last HC residue present in papain-cleaved Fab. Residues 231-455 are from IGHG3_MOUSE (mouse IgG3, isoform 2).

FIG. 9 shows the variable domain of SP34 with key residues at VL/VH interface shown. Residues 38, 48, and 51 in VL (labeled) are in contact with CDR-H3.

FIG. 10. FIG. 10 shows the Human Framework Adaptation ("HFA") variants for VH (SEQ ID NOS 233 and 184-187, respectively, in order of appearance) and VL (SEQ ID NOS 234 and 188-190, respectively, in order of appearance). The numbering is sequential; CDRs in the AbM definition are underlined; residues that differ from SP34 are highlighted in bold; back mutations in HFA variants are bold and underlined.

FIG. 11 shows binding of SP34 HFA variants to primary Human T cells.

FIG. 12 shows binding of SP34 HFA variants to Cynomolgus primary T cells.

FIG. 13 shows that SP34 HFA variants activate primary human T cells in vitro. Negative controls are shown in white and positive controls are shown in black.

FIG. 14 shows that SP34 HFA variants activate primary cynomolgus T cells in vitro. Negative controls are shown in white and positive controls are shown in black.

FIG. 15. FIG. 15 shows the correlation of binding and activation by SP34 HFA variants. Average binding and CD69 Mean Fluorescence Intensity ("MFI") values for human (FIG. 15A) and cynomolgus (FIG. 15B) were plotted against each other.

FIG. 16 shows the design of CD3×PSMA-multispecific antigen-binding molecule constructs.

FIG. 17 shows the results of the T-cell mediated cytotoxicity assay for the CD3×PSMA-multispecific antigen-binding molecules on PSMA+LNCAP cells.

FIG. 18 shows prevention of tumorigenesis of HEK293-PSMA xenografts treated with B219xCW6 Mabtyrin in PBMC humanized NSG mice. PBMC humanized mice bearing HEK293-PSMA cells were iv dosed with 0.004 mg/kg, 0.04 mg/kg and 0.4 mg/kg B219xCW6 (dosing indicated by arrows). Sc tumors were measured twice weekly and the results presented as the average tumor volume, expressed in mm3±standard error of the mean (SEM), of each group.

FIG. 19 shows Body weight of PBMC-humanized NSG mice bearing HEK293-PSMA xenografts treated with B219xCW6 Mabtyrin. PBMC humanized NSG mice bearing HEK293-PSMA cells were iv dosed with 0.004 mg/kg, 0.04 mg/kg and 0.4 mg/kg B219xCW6 (dosing indicated by arrows). Body weights are presented as group means, expressed in g±standard error of the mean (SEM).

DETAILED DESCRIPTION OF ILLUSTRATIVE EMBODIMENTS

Definitions

Figure 1:
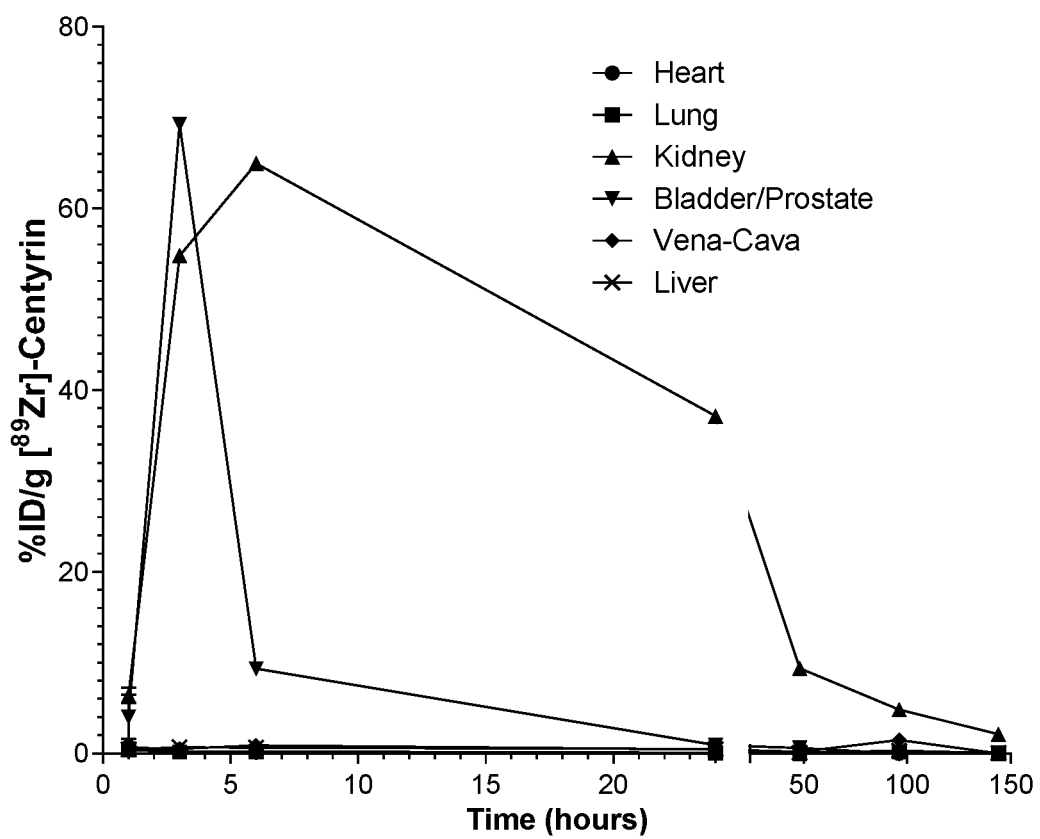
FIG. 1.

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of up to +10% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

"Isolated" means a biological component (such as a nucleic acid, peptide or protein) has been substantially separated, produced apart from, or purified from other biological components of the organism in which the component naturally occurs, i.e., other chromosomal and extrachromosomal DNA and RNA, and proteins. Nucleic acids, peptides and proteins that have been "isolated" thus include nucleic acids and proteins purified by standard purification methods. "Isolated" nucleic acids, peptides and proteins can be part of a composition and still be isolated if such composition is not part of the native environment of the nucleic acid, peptide, or protein. The term also embraces nucleic acids, peptides and proteins prepared by recombinant expression in a host cell as well as chemically synthesized nucleic acids. An "isolated" CD3×PSMA-bispecific antigen-binding molecule or bispecific antigen-binding fragments thereof as used herein, is intended to refer to an isolated CD3×PSMA-bispecific antigen-binding molecule or bispecific antigen-binding fragments thereof which is substantially free of other CD3×PSMA-bispecific antigen-binding molecule or bispecific antigen-binding fragments thereof having different antigenic specificities.

"Polynucleotide," synonymously referred to as "nucleic acid molecule," "nucleotides" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

The meaning of "substantially the same" can differ depending on the context in which the term is used. Because of the natural sequence variation likely to exist among heavy and light chains and the genes encoding them, one would expect to find some level of variation within the amino acid sequences or the genes encoding the antibodies or antigen-binding fragments described herein, with little or no impact on their unique binding properties (e.g., specificity and affinity). Such an expectation is due in part to the degeneracy of the genetic code, as well as to the evolutionary success of conservative amino acid sequence variations, which do not appreciably alter the nature of the encoded protein. Accordingly, in the context of nucleic acid sequences, "substantially the same" means at least 65% identity between two or more sequences. Preferably, the term refers to at least 70% identity between two or more sequences, more preferably at least 75% identity, more preferably at least 80% identity, more preferably at least 85% identity, more preferably at least 90% identity, more preferably at least 91% identity, more preferably at least 92% identity, more preferably at least 93% identity, more preferably at least 94% identity, more preferably at least 95% identity, more preferably at least 96% identity, more preferably at least 97% identity, more preferably at least 98% identity, and more preferably at least 99% or greater identity. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The percent identity between two nucleotide or amino acid sequences may e.g. be determined using the algorithm of E. Meyers and W. Miller, Comput. Appl. Biosci 4, 11-17 (1988) which has been incorporated into the ALIGN program (version 2.0), using a PAM120 weight residue table, a gap length penalty of 12 and a gap penalty of 4. In addition, the percent identity between two amino acid sequences may be determined using the Needleman and Wunsch, J. Mol. Biol. 48, 444-453 (1970) algorithm.

The degree of variation that may occur within the amino acid sequence of a protein without having a substantial effect on protein function is much lower than that of a nucleic acid sequence, since the same degeneracy principles do not apply to amino acid sequences. Accordingly, in the context of an antibody or antigen-binding fragment, "substantially the same" means antibodies or antigen-binding fragments having 90%, 91%, 92%, 93%, 94%, 95%, 96%, 97%, 98%, or 99% identity to the antibodies or antigen-binding fragments described.

A "vector" is a replicon, such as plasmid, phage, cosmid, or virus in which another nucleic acid segment may be operably inserted so as to bring about the replication or expression of the segment.

A "clone" is a population of cells derived from a single cell or common ancestor by mitosis. A "cell line" is a clone of a primary cell that is capable of stable growth in vitro for many generations. In some examples provided herein, cells are transformed by transfecting the cells with DNA.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression or production of an antibody or antigen-binding fragment thereof may be within the cytoplasm of the cell, or into the extracellular milieu such as the growth medium of a cell culture.

The term "treating" or "treatment" refers to any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, neurological examination, or psychiatric evaluations.

An "effective amount" or "therapeutically effective amount" refers to an amount effective, at dosages and for periods of time necessary, to achieve a desired therapeutic result. A therapeutically effective amount of a CD3×PSMA-multispecific antigen-binding molecule or multispecific antigen-binding fragments thereof may vary according to factors such as the disease state, age, sex, and weight of the individual, and the ability of the antibody to elicit a desired response in the individual. A therapeutically effective amount is also one in which any toxic or detrimental effects of the antibody or antibody portion are outweighed by the therapeutically beneficial effects.

"Antibody" refers to all isotypes of immunoglobulins (IgG, IgA, IgE, IgM, IgD, and IgY) including various monomeric, polymeric and chimeric forms, unless otherwise specified. Specifically encompassed by the term "antibody" are polyclonal antibodies, monoclonal antibodies (mAbs), and antibody-like polypeptides, such as chimeric antibodies and humanized antibodies.

Antigen-binding fragments are any proteinaceous structure that may exhibit binding affinity for a particular antigen. Antigen-binding fragments include those provided by any known technique, such as enzymatic cleavage, peptide synthesis, and recombinant techniques. Some antigen-binding fragments are composed of portions of intact antibodies that retain antigen-binding specificity of the parent antibody molecule. For example, antigen-binding fragments may comprise at least one variable region (either a heavy chain or light chain variable region) or one or more CDRs of an antibody known to bind a particular antigen. Examples of suitable antigen-binding fragments include, without limitation diabodies and single-chain molecules as well as Fab, F(ab')2, Fc, Fabc, and Fv molecules, single chain (Sc) antibodies, individual antibody light chains, individual antibody heavy chains, chimeric fusions between antibody chains or CDRs and other proteins, protein scaffolds, heavy chain monomers or dimers, light chain monomers or dimers, dimers consisting of one heavy and one light chain, a monovalent fragment consisting of the VL, VH, CL and CH1 domains, or a monovalent antibody as described in WO2007059782, bivalent fragments comprising two Fab fragments linked by a disulfide bridge at the hinge region, a Fd fragment consisting essentially of the $V_H$ and $C_H1$ domains; a Fv fragment consisting essentially of the VL and VH domains of a single arm of an antibody, a dAb fragment (Ward et al., Nature 341, 544-546 (1989)), which consists essentially of a VH domain and also called domain antibodies (Holt et al; Trends Biotechnol. 2003 November; 21(11): 484-90); camelid or nanobodies (Revets et al; Expert Opin Biol Ther. 2005 January; 5(1):111-24); an isolated complementarity determining region (CDR), and the like. All antibody isotypes may be used to produce antigen-binding fragments. Additionally, antigen-binding fragments may include non-antibody proteinaceous frameworks that may successfully incorporate polypeptide segments in an orientation that confers affinity for a given antigen of interest, such as protein scaffolds. Antigen-binding fragments may be recombinantly produced or produced by enzymatic or chemical cleavage of intact antibodies. The phrase "an antibody or antigen-binding fragment thereof" may be used to denote that a given antigen-binding fragment incorporates one or more amino acid segments of the antibody referred to in the phrase. When used herein in the context of two or more antibodies or antigen-binding fragments, the term "competes with" or "cross-competes with" indicates that the two or more antibodies or antigen-binding fragments compete for binding. For some pairs of antibodies or antigen-binding fragments, competition or blocking in the assay of the Examples is only observed when one antibody is coated on the plate and the other is used to compete, and not vice versa. Unless otherwise defined or negated by context, the terms "competes with" or "cross-competes with" when used herein is also intended to cover such pairs of antibodies or antigen-binding fragments.

The term "epitope" means a protein determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The epitope may comprise amino acid residues directly involved in the binding and other amino acid residues, which are not directly involved in the binding, such as amino acid residues which are effectively blocked or covered by the specifically antigen binding peptide (in other words, the amino acid residue is within the footprint of the specifically antigen binding peptide).

"Immunospecific binding" or derivatives thereof when used in the context of antibodies, or antibody fragments, represents binding via domains encoded by immunoglobulin genes or fragments of immunoglobulin genes to one or more epitopes of a protein of interest, without preferentially binding other molecules in a sample containing a mixed population of molecules. Typically, an antibody binds to a cognate antigen with a $K_d$ of less than about $1\times10^{-8}$M, as measured by a surface plasmon resonance assay or a cell binding assay. Phrases such as "[antigen]-specific" antibody (e.g., CD3-specific antibody) are meant to convey that the recited antibody specifically binds the recited antigen.

The term "fibronectin type III (FN3) domain" (FN3 domain) as used herein refers to a domain occurring frequently in proteins including fibronectins, tenascin, intracellular cytoskeletal proteins, cytokine receptors and prokaryotic enzymes (Bork and Doolittle, Proc Nat Acad Sci USA 89:8990-8994, 1992; Meinke et al., J Bacteriol 175:1910-1918, 1993; Watanabe et al., J Biol Chem 265:15659-15665, 1990). Exemplary FN3 domains are the 15 different FN3 domains present in human tenascin C, the 15 different FN3 domains present in human fibronectin (FN), and non-natural synthetic FN3 domains as described for example in U.S. Pat. No. 8,278,419. Individual FN3 domains are referred to by domain number and protein name, e.g., the $3^{rd}$ FN3 domain of tenascin (TN3), or the $10^{th}$ FN3 domain of fibronectin (FN10).

"CENTYRIN™" as used herein refers to a FN3 domain that is based on the consensus sequence of the 15 different FN3 domains present in human tenascin C.

The term "substituting" or "substituted" or "mutating" or "mutated" as used herein refers to altering, deleting, or inserting one or more amino acids or nucleotides in a polypeptide or polynucleotide sequence to generate a variant of that sequence.

The term "randomizing" or "randomized" or "diversified" or "diversifying" as used herein refers to making at least one substitution, insertion or deletion in a polynucleotide or polypeptide sequence.

"Variant" as used herein refers to a polypeptide or a polynucleotide that differs from a reference polypeptide or a reference polynucleotide by one or more modifications for example, substitutions, insertions or deletions.

The term "specifically binds" or "specific binding" as used herein refers to the ability of the FN3 domain of the invention to bind to a predetermined antigen with a dissociation constant ($K_D$) of about $1\times10^{-6}$ M or less, for example about $1\times10^{-7}$ M or less, about $1\times10^{-8}$ M or less, about $1\times10^{-9}$ M or less, about $1\times10^{-10}$ M or less, about $1\times10^{-11}$ M or less, about $1\times10^{-12}$ M or less, or about $1\times10^{-13}$ M or less. Typically the FN3 domain of the invention binds to a predetermined antigen (i.e. human PSMA) with a $K_D$ that is at least ten fold less than its $K_D$ for a nonspecific antigen (for example BSA or casein) as measured by surface plasmon resonance using for example a Proteon Instrument (BioRad). The isolated FN3 domain of the invention that specifically binds to human PSMA may, however, have cross-reactivity to other related antigens, for example to the same predetermined antigen from other species (homologs), such as *Macaca Fascicularis* (cynomolgous monkey, cyno) or *Pan troglodytes* (chimpanzee).

The term "library" refers to a collection of variants. The library may be composed of polypeptide or polynucleotide variants.

The term "stability" as used herein refers to the ability of a molecule to maintain a folded state under physiological conditions such that it retains at least one of its normal functional activities, for example, binding to a predetermined antigen such as human PSMA.

Human PSMA as used herein refers to the well-known type II glycoprotein of about 100 kD with a short intracellular domain (residues 1-18), a transmembrane domain (residues 19-43) and an extracellular domain (residues 44-750). The amino acid sequence of the mature human PSMA is shown in SEQ ID NO: 144.

"Overexpress", "overexpressed" and "overexpressing" as used herein interchangeably refer to a cancer or malignant cell that has measurably higher levels of PSMA on the surface compared to a normal cell of the same tissue type. Such overexpression may be caused by gene amplification or by increased transcription or translation. PSMA overexpression can be measured using well known assays, for example ELISA, immunofluorescence, flow cytometry or radioimmunoassay on live or lysed cells. Alternatively, or additionally, levels of PSMA nucleic acid molecules may be measured in the cell for example using fluorescent in situ hybridization, Southern blotting, or PCR techniques. PSMA is overexpressed when the level of PSMA on the surface of the cell is at least 1.5-fold higher when compared to the normal cell.

"TENCON™" as used herein refers to the synthetic fibronectin type III (FN3) domain having the sequence shown in SEQ ID NO: 1 and described in U.S. Pat. Publ. No. US2010/0216708.

A "cancer cell" or a "tumor cell" as used herein refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is exemplified by, e.g., morphological changes, immortalization of cells, aberrant growth control, foci formation, proliferation, malignancy, tumor specific markers levels, invasiveness, tumor growth or suppression in suitable animal hosts such as nude mice, and the like, in vitro, in vivo, and ex vivo (Freshney, Culture of Animal Cells: A Manual of Basic Technique (3rd ed. 1994)).

"Inhibits growth" (e.g. referring to cells, such as tumor cells) refers to a measurable decrease in the cell growth in vitro or in vivo when contacted with a therapeutic or a combination of therapeutics or drugs when compared to the growth of the same cells grown in appropriate control conditions well known to the skilled in the art. Inhibition of growth of a cell in vitro or in vivo may be at least about 10%, 20%, 30%, 40%, 50%, 60%, 70%, 80%, 90%, 99%, or 100%. Inhibition of cell growth may occur by a variety of mechanisms, for example by apoptosis, necrosis, or by inhibition of cell proliferation, or lysis of cells.

The term "vector" means a polynucleotide capable of being duplicated within a biological system or that can be moved between such systems. Vector polynucleotides typically contain elements, such as origins of replication, polyadenylation signal or selection markers that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

The term "expression vector" means a vector that can be utilized in a biological system or in a reconstituted biological system to direct the translation of a polypeptide encoded by a polynucleotide sequence present in the expression vector.

The term "polypeptide" or "protein" means a molecule that comprises at least two amino acid residues linked by a peptide bond to form a polypeptide. Small polypeptides of less than about 50 amino acids may be referred to as "peptides".

"Valent" as used herein refers to the presence of a specified number of binding sites specific for an antigen in a molecule. As such, the terms "monovalent", "bivalent", "tetravalent", and "hexavalent" refer to the presence of one, two, four and six binding sites, respectively, specific for an antigen in a molecule.

The term "in combination with" as used herein means that two or more therapeutics can be administered to a subject together in a mixture, concurrently as single agents or sequentially as single agents in any order.

"Synergy", "synergism" or "synergistic" means more than the expected additive effect of a combination.

The term "$k_d$" ($sec^{-1}$), as used herein, refers to the dissociation rate constant of a particular antibody-antigen interaction. Said value is also referred to as the $k_{off}$ value.

The term "$k_a$" ($M^{-1}$ $sec^{-1}$), as used herein, refers to the association rate constant of a particular antibody-antigen interaction.

The term "$K_D$" (M), as used herein, refers to the dissociation equilibrium constant of a particular antibody-antigen interaction.

The term "$K_A$" ($M^{-1}$), as used herein, refers to the association equilibrium constant of a particular antibody-antigen interaction and is obtained by dividing the $k_a$ by the $k_d$.

The term "subject" refers to human and non-human animals, including all vertebrates, e.g., mammals and non-mammals, such as non-human primates, mice, rabbits, sheep, dogs, cats, horses, cows, chickens, amphibians, and reptiles. In many embodiments of the described methods, the subject is a human.

The term "sample" as used herein refers to a collection of similar fluids, cells, or tissues (e.g., surgically resected tumor tissue, biopsies, including fine needle aspiration), isolated from a subject, as well as fluids, cells, or tissues present within a subject. In some embodiments the sample is a biological fluid. Biological fluids are typically liquids at physiological temperatures and may include naturally occurring fluids present in, withdrawn from, expressed or otherwise extracted from a subject or biological source. Certain biological fluids derive from particular tissues, organs or localized regions and certain other biological fluids may be more globally or systemically situated in a subject or biological source. Examples of biological fluids include blood, serum and serosal fluids, plasma, lymph, urine, saliva, cystic fluid, tear drops, feces, sputum, mucosal secretions of the secretory tissues and organs, vaginal secretions, ascites fluids such as those associated with non-solid tumors, fluids of the pleural, pericardial, peritoneal, abdominal and other body cavities, fluids collected by bronchial lavage and the like. Biological fluids may also include liquid solutions contacted with a subject or biological source, for example, cell and organ culture medium including cell or organ conditioned medium, lavage fluids and the like. The term "sample," as used herein, encompasses materials removed from a subject or materials present in a subject.

The term "CD3" refers to the human CD3 protein multi-subunit complex. The CD3 protein multi-subunit complex is composed of 6 distinctive polypeptide chains. These include a CD3γ chain (SwissProt P09693), a CD3δ chain (SwissProt P04234), two CD3ε chains (SwissProt P07766), and one CD3 ζ chain homodimer (SwissProt 20963), and which is associated with the T cell receptor α and β chain. The term "CD3" includes any CD3 variant, isoform and species homolog which is naturally expressed by cells (including T cells) or can be expressed on cells transfected with genes or cDNA encoding those polypeptides, unless noted.

A "CD3×PSMA-multispecific antigen-binding molecule or multispecific antigen-binding fragments thereof" is a multispecific molecule, optionally a CD3×PSMA-bispecific antigen comprising: a FN3 domain; a light chain (LC); and a heavy chain (HC), wherein the FN3 domain forms a first antigen-binding site that specifically binds human prostate specific membrane antigen (PSMA), and the HC and the LC pair to form a second antigen-binding site that immunospecifically binds CD3, or a bispecific antigen-binding fragment thereof.

CD3×PSMA-bispecific antigen-binding molecule or bispecific antigen-binding fragments thereof, comprise two different antigen-binding regions, one of which binds specifically to the antigen PMSA and one of which binds specifically to CD3. A multispecific antibody can be a bispecific antibody, diabody, or similar molecule (see for instance PNAS USA 90(14), 6444-8 (1993) for a description of diabodies).

A "reference sample" is a sample that may be compared against another sample, such as a test sample, to allow for characterization of the compared sample. The reference sample will have some characterized property that serves as the basis for comparison with the test sample. For instance, a reference sample may be used as a benchmark for PSMA levels that are indicative of a subject having cancer. The reference sample does not necessarily have to be analyzed in parallel with the test sample, thus in some instances the reference sample may be a numerical value or range previously determined to characterize a given condition, such as PSMA levels that are indicative of cancer in a subject. The term also includes samples used for comparative purposes that are known to be associated with a physiologic state or disease condition, such as PSMA-expressing cancer, but that have an unknown amount of PSMA.

The term "progression," as used in the context of progression of PSMA-expressing cancer, includes the change of a cancer from a less severe to a more severe state. This may include an increase in the number or severity of tumors, the degree of metastasis, the speed with which the cancer is growing or spreading, and the like. For example, "the progression of colon cancer" includes the progression of such a cancer from a less severe to a more severe state, such as the progression from stage I to stage II, from stage II to stage III, etc.

The term "regression," as used in the context of regression of PSMA-expressing cancer, includes the change of a cancer from a more severe to a less severe state. This could include a decrease in the number or severity of tumors, the degree of metastasis, the speed with which the cancer is growing or spreading, and the like. For example, "the regression of colon cancer" includes the regression of such a cancer from a more severe to a less severe state, such as the progression from stage III to stage II, from stage II to stage I, etc.

The term "stable" as used in the context of stable PSMA-expressing cancer, is intended to describe a disease condition that is not, or has not, changed significantly enough over a clinically relevant period of time to be considered a progressing cancer or a regressing cancer.

The embodiments described herein are not limited to particular methods, reagents, compounds, compositions or biological systems, which can, of course, vary.

In some embodiments, the antibodies or antigen-binding fragments are IgG, or derivatives thereof, e.g., IgG1, IgG2, IgG3, and IgG4 isotypes. In some embodiments wherein the antibody has an IgG1 isotype, the antibody contains L234A, L235A, and K409R substitution(s) in its Fc region. In some embodiments wherein the antibody has an IgG4 isotype, the antibody contains S228P, L234A, and L235A substitutions in its Fc region.

Polynucleotides encoding recombinant antigen-binding proteins also are within the scope of the disclosure. In some embodiments, the polynucleotides described (and the peptides they encode) include a leader sequence. Any leader sequence known in the art may be employed. The leader sequence may include, but is not limited to, a restriction site or a translation start site.

PSMA Binding Molecules

The FN3 domain of the invention may bind human, *Macaca Fascicularis* and/or Pan troglodytes PSMA with a dissociation constant ($K_D$) of less than about $1\times10^{-7}$ M, for example less than about $1\times10^{-8}$ M, less than about $1\times10^{-9}$ M, less than about $1\times10^{-10}$ M, less than about $1\times10^{-11}$ M, less than about $1\times10^{-12}$ M, or less than about $1\times10^{-13}$ M as determined by surface plasmon resonance or the Kinexa method, as practiced by those of skill in the art. The measured affinity of a particular FN3 domain-antigen interaction can vary if measured under different conditions (e.g., osmolarity, pH). Thus, measurements of affinity and other antigen-binding parameters (e.g., $K_D$, $K_{on}$, $K_{off}$) are made with standardized solutions of protein scaffold and antigen, and a standardized buffer, such as the buffer described herein.

In another embodiment of the invention, the FN3 domain specifically binds human PSMA, wherein the FN3 domain inhibits human PSMA enzymatic activity. PSMA enzymatic activity may be measured using standard methods. For example, hydrolysis of a detectable or labeled PSMA substrate of PSMA may be used. Exemplary PSMA substrates that may be used are N-Acetyl Aspartyl Glutamate (NAAG), folate polyglutamate, methotrexate tri-gamma glutamate, methotrexate di-gamma glutamate, pteroylpentaglutamate and derivatives thereof.

In some embodiments of the invention described herein, the FN3 domain comprises an amino acid sequence that is at least 89%, 90%, 91%, 92%, 93%, 94%, 95%, 96%, 97%, 98%, or 99% identical to the amino acid sequence of SEQ ID NO: 41.

In some embodiments of the invention described herein, the FN3 domain comprises an amino acid sequence that has 1, 2, 3, 4, 5, 6, 7, 8, 9, 10 or 11 substitutions when compared to the amino acid sequence of SEQ ID NO: 41.

In some embodiments of the invention described herein, the FN3 domain that specifically binds human PSMA comprises a cysteine residue in at least one residue position corresponding to residue positions 6, 11, 22, 25, 26, 52, 53, 61 of SEQ ID NO 1, or at a C-terminus.

In some embodiments, the FN3 domain specifically competes for binding to human PSMA with the FN3 domain of SEQ ID NO: 41.

In some embodiments, the FN3 domain specifically binds to the region KKSPSPEFSGMPRISK (SEQ ID NO: 159) and NWETNKF (SEQ ID NO: 160) of human PSMA.

The human PSMA epitope bound by the FN3 domain of the invention includes some or all of the residues within the amino sequences shown in SEQ ID NO: 159 or SEQ ID NO: 160. In some embodiments disclosed herein, the epitope bound by the FN3 domain of the invention comprises at least one amino acid in the region KKSPSPEFSGMPRISK (SEQ ID NO: 159) and NWETNKF (SEQ ID NO: 160) of human PSMA (SEQ ID NO: 144). In some embodiments disclosed herein, the epitope bound by the FN3 domain of the invention comprises at least two, three, four, five, six or seven amino acids in the region KKSPSPEFSGMPRISK (SEQ ID NO: 159) and at least two, three, four, five or six amino acids in the region NWETNKF (SEQ ID NO: 160) of human PSMA (SEQ ID NO: 144).

In some embodiments disclosed herein, the FN3 domain of the invention binds human PSMA at residues K499, K500, S501, P502, P504, R511, K514, N540, W541, E542, N544, K545 and F546 (residue numbering according to SEQ ID NO: 144).

In some embodiments disclosed herein, the FN3 domain of the invention further binds human PSMA at residues R181, Y460, F488, K610 and/or 1614.

The crystal structure of the FN3 domain P233FR9_H10 was solved in complex with cynoPSMA. As the contact residues between human and cyno PSMA are identical except for one residue, it is expected that P233FR9_H10 will bind human PSMA at the same epitope residues than what it binds cyno PSMA.

Methods of Treatment

The subjects for administration of the CD3×PSMA-multispecific antigen-binding molecule or multispecific antigen-binding fragments thereof, as described herein, include patients at high risk for developing a particular disorder characterized by PSMA overexpression as well as patients presenting with an existing such disorder. Typically, the subject has been diagnosed as having the disorder for which treatment is sought. Further, subjects can be monitored during the course of treatment for any change in the disorder (e.g., for an increase or decrease in clinical symptoms of the disorder).

In prophylactic applications, pharmaceutical compositions or medicants are administered to a patient susceptible to, or otherwise at risk of, a particular disorder in an amount sufficient to eliminate or reduce the risk or delay the onset of the disorder. In therapeutic applications, compositions or medicants are administered to a patient suspected of, or already suffering from such a disorder in an amount sufficient to cure, or at least partially arrest, the symptoms of the disorder and its complications. An amount adequate to accomplish this is referred to as a therapeutically effective dose or amount. In both prophylactic and therapeutic regimes, agents are usually administered in several dosages until a sufficient response (e.g., inhibition of inappropriate angiogenesis activity) has been achieved. Typically, the response is monitored and repeated dosages are given if the desired response starts to fade.

To identify subject patients for treatment according to the methods of the invention, accepted screening methods may be employed to determine risk factors associated with specific disorders or to determine the status of an existing disorder identified in a subject. Such methods can include, for example, determining whether an individual has relatives who have been diagnosed with a particular disorder. Screening methods may also include, for example, conventional work-ups to determine familial status for a particular disorder known to have a heritable component. For example, various cancers are also known to have certain inheritable components. Inheritable components of cancers include, for example, mutations in multiple genes that are transforming (e.g., Ras, Raf, EGFR, cMet, and others), the presence or absence of certain HLA and killer inhibitory receptor (KIR) molecules, or mechanisms by which cancer cells are able to modulate immune suppression of cells like NK cells and T cells, either directly or indirectly (see, e.g., Ljunggren and Malmberg, *Nature Rev. Immunol.* 7:329-339, 2007; Boyton and Altmann, *Clin. Exp. Immunol.* 149:1-8, 2007). Toward this end, nucleotide probes can be routinely employed to identify individuals carrying genetic markers associated with a particular disorder of interest. In addition, a wide variety of immunological methods are known in the art that are useful to identify markers for specific disorder. For example, various ELISA immunoassay methods are available and well-known in the art that employ monoclonal antibody probes to detect antigens associated with specific tumors. Screening can be implemented as indicated by known patient symptomology, age factors, related risk factors, etc. These methods allow the clinician to routinely select patients in need of the methods described herein for treatment. In accordance with these methods, targeting pathological, PSMA-expressing cells can be implemented as an independent treatment program or as a follow-up, adjunct, or coordinate treatment regimen to other treatments.

In some methods described herein, the CD3×PSMA-multispecific antigen-binding molecule or multispecific antigen-binding fragments thereof of the invention may be used to treat a subject with prostate cancer in combination with a second therapeutic.

In some methods described herein, the CD3×PSMA-multispecific antigen-binding molecule or multispecific antigen-binding fragments thereof may be used to treat a subject who is resistant or has acquired resistance to a treatment with a second therapeutic.

The second therapeutic may be an approved drug for the treatment of prostate cancer, such as Abiraterone Acetate (ZYTIGA™), Bicalutamide, Cabazitaxel, CASODEX™ (Bicalutamide), Degarelix, Docetaxel, Enzalutamide, Goserelin Acetate, JEVTANA™ (Cabazitaxel), Leuprolide Acetate, LUPRON™ (Leuprolide Acetate), LUPRON DEPOT™ (Leuprolide Acetate), LUPRON DEPOT™-3 Month (Leuprolide Acetate), LUPRON DEPOT™-4 Month (Leuprolide Acetate), LUPRON DEPOT™-Ped (Leuprolide Acetate), Mitoxantrone Hydrochloride, Prednisone, PROVENGE™ (Sipuleucel-T), RADIUM™ 223 Dichloride, Sipuleucel-T, TAXOTERE™ (Docetaxel), VIADUR™ (Leuprolide Acetate), XOFIGO™ (Radium 223 Dichloride), XTANDI™ (Enzalutamide) or ZOLADEX™ (Goserelin Acetate) (source: National Cancer Institute).

Various qualitative and/or quantitative methods may be used to determine if a subject is resistant, has developed or is susceptible to developing a resistance to treatment. Symptoms that may be associated with resistance include, for example, a decline or plateau of the well-being of the patient, an increase in the size of a tumor, arrested or slowed decline in growth of a tumor, and/or the spread of cancerous cells in the body from one location to other organs, tissues or cells. Re-establishment or worsening of various symptoms associated with cancer may also be an indication that a subject has developed or is susceptible to developing resistance to treatment, such as anorexia, cognitive dysfunction, depression, dyspnea, fatigue, hormonal disturbances, neutropenia, pain, peripheral neuropathy, and sexual dysfunction. The symptoms associated with cancer may vary according to the type of cancer. For example, symptoms associated with prostate cancer may include trouble passing or frequent urge to pass urine, painful urination, blood in the urine or semen, nagging pain in the pelvis, back and/or hips. Symptoms associated with lung cancer may include persistent cough, coughing up blood, shortness of breath, wheezing chest pain, loss of appetite, losing weight without trying and fatigue. One skilled in oncology may readily identify symptoms associated with a particular cancer type.

Administration/Pharmaceutical Compositions

The invention provides for pharmaceutical compositions of the CD3×PSMA-multispecific antigen-binding molecule or multispecific antigen-binding fragments thereof, and a pharmaceutically acceptable carrier. For therapeutic use, the CD3×PSMA-multispecific antigen-binding molecule or multispecific antigen-binding fragments thereof may be prepared as pharmaceutical compositions containing an effective amount of the domain or molecule as an active ingredient in a pharmaceutically acceptable carrier. The term "carrier" refers to a diluent, adjuvant, excipient, or vehicle with which the active compound is administered. Such vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the molecules of the invention in such pharmaceutical formulation can vary widely, i.e., from less than about 0.5%, usually at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, See especially pp. 958-989.

Thus the mode of administration for therapeutic use of the CD3×PSMA-multispecific antigen-binding molecule or multispecific antigen-binding fragments thereof of the invention may be any suitable route that delivers the agent to the host, such as parenteral administration, e.g., intradermal, intramuscular, intraperitoneal, intravenous or subcutaneous, pulmonary; transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

Thus, a pharmaceutical composition of the invention for intramuscular injection could be prepared to contain 1 ml sterile buffered water, and between about 1 ng to about 100 mg, e.g. about 50 ng to about 30 mg or more preferably, about 5 mg to about 25 mg, of the CD3×PSMA-multispecific antigen-binding molecule or multispecific antigen-binding fragments thereof.

CD3×PSMA-multispecific antigen-binding molecule or multispecific antigen-binding fragments thereof of the invention may be administered to a patient by any suitable route, for example parentally by intravenous (IV) infusion or bolus injection, intramuscularly or subcutaneously or intraperitoneally. IV infusion can be given over as little as 15 minutes, but more often for 30 minutes, 60 minutes, 90 minutes or even 2 or 3 hours. The isolated CD3×PSMA-bispecific antigen-binding molecule or bispecific antigen-binding fragments thereof of the invention may also be injected directly into the site of disease. The dose given to a patient having a cancer is sufficient to alleviate or at least partially arrest the disease being treated ("therapeutically effective amount") and may be sometimes 0.1 to 10 mg/kg body weight, for example 1, 2, 3, 4, 5, 6, 7, 8, 9 or 10 mg/kg, but may even higher, for example 15, 20, 30, 40, 50, 60, 70, 80, 90 or 100 mg/kg. A fixed unit dose may also be given, for example, 50, 100, 200, 500 or 1000 mg, or the dose may be based on the patient's surface area, e.g., 400, 300, 250, 200, or 100 mg/m$^2$. Usually between 1 and 8 doses, (e.g., 1, 2, 3, 4, 5, 6, 7 or 8) may be administered to treat cancer, but 10, 12, 20 or more doses may be given. Administration of the CD3×PSMA-multispecific antigen-binding molecule or multispecific antigen-binding fragments thereof of the invention may be repeated after one day, two days, three days, four days, five days, six days, one week, two weeks, three weeks, one month, five weeks, six weeks, seven weeks, two months, three months, four months, five months, six months or longer. Repeated courses of treatment are also possible, as is chronic administration. The repeated administration may be at the same dose or at a different dose.

For example, a pharmaceutical composition of the isolated CD3×PSMA-bispecific antigen-binding molecule or bispecific antigen-binding fragments thereof for intravenous infusion may be made up to contain about 200 ml of sterile Ringer's solution, and about 8 mg to about 2400 mg, about 400 mg to about 1600 mg, or about 400 mg to about 800 mg of the PSMA binding FN3 domains for administration to a 80 kg patient. Methods for preparing parenterally administrable compositions are well known and are described in more detail in, for example, "Remington's Pharmaceutical Science", 15th ed., Mack Publishing Company, Easton, Pa.

The isolated CD3×PSMA-bispecific antigen-binding molecule or bispecific antigen-binding fragments thereof of the invention may be lyophilized for storage and reconstituted in a suitable carrier prior to use. This technique has been shown to be effective with conventional protein preparations and art-known lyophilization and reconstitution techniques can be employed.

The isolated CD3×PSMA-bispecific antigen-binding molecule or bispecific antigen-binding fragments thereof of the invention may be administered to a subject in a single dose or the administration may be repeated, e.g. after one day, two days, three days, four days, five days, six days, one week, two weeks, three weeks, one month, five weeks, six weeks, seven weeks, two months or three months. The repeated administration can be at the same dose or at a different dose. The administration can be repeated once, twice, three times, four times, five times, six times, seven times, eight times, nine times, ten times, or more.

The isolated CD3×PSMA-bispecific antigen-binding molecule or bispecific antigen-binding fragments thereof of the invention may be administered in combination with a second therapeutic agent as described above simultaneously, sequentially or separately.

The isolated CD3×PSMA-bispecific antigen-binding molecule or bispecific antigen-binding fragments thereof of the invention, optionally in combination with the second therapeutic agent may be administered together with any form of radiation therapy including external beam radiation, intensity modulated radiation therapy (IMRT) and any form of radiosurgery including GAMMA KNIFE™, CYBERKNIFE™, LINAC™, and interstitial radiation (e.g. implanted radioactive seeds, GLIASITE™ balloon), and/or with surgery.

With particular regard to treatment of solid tumors, protocols for assessing endpoints and anti-tumor activity are well-known in the art. While each protocol may define tumor response assessments differently, the RECIST (Response evaluation Criteria in solid tumors) criteria is currently considered to be the recommended guidelines for assessment of tumor response by the National Cancer Institute (see Therasse et al., *J. Natl. Cancer Inst.* 92:205-216, 2000). According to the RECIST criteria tumor response means a reduction or elimination of all measurable lesions or metastases. Disease is generally considered measurable if it comprises lesions that can be accurately measured in at least one dimension as ≥20 mm with conventional techniques or ≥10 mm with spiral CT scan with clearly defined margins by medical photograph or X-ray, computerized axial tomography (CT), magnetic resonance imaging (MRI), or clinical examination (if lesions are superficial). Non-measurable disease means the disease comprises of lesions <20 mm with conventional techniques or <10 mm with spiral CT scan, and truly non-measurable lesions (too small to accurately measure). Non-measurable disease includes pleural effusions, ascites, and disease documented by indirect evidence.

The criteria for objective status are required for protocols to assess solid tumor response. Representative criteria include the following: (1) Complete Response (CR), defined as complete disappearance of all measurable disease; no new lesions; no disease related symptoms; no evidence of non-measurable disease; (2) Partial Response (PR) defined as 30% decrease in the sum of the longest diameter of target lesions (3) Progressive Disease (PD), defined as 20% increase in the sum of the longest diameter of target lesions or appearance of any new lesion; (4) Stable or No Response, defined as not qualifying for CR, PR, or Progressive Disease. (See Therasse et al., supra.)

Additional endpoints that are accepted within the oncology art include overall survival (OS), disease-free survival (DFS), objective response rate (ORR), time to progression (TTP), and progression-free survival (PFS) (see *Guidance for Industry: Clinical Trial Endpoints for the Approval of Cancer Drugs and Biologics*, April 2005, Center for Drug Evaluation and Research, FDA, Rockville, Md.)

Pharmaceutical compositions can be supplied as a kit comprising a container that comprises the pharmaceutical composition as described herein. A pharmaceutical composition can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a pharmaceutical composition. Such a kit can further comprise written information on indications and usage of the pharmaceutical composition.

In some embodiments, expression of the fusion protein is placed under control of a powerful constitutive promoter, such as the promoters for the following genes: hypoxanthine phosphoribosyl transferase (HPRT), adenosine deaminase, pyruvate kinase, beta-actin, human myosin, human hemoglobin, human muscle creatine, and others. In addition, many viral promoters function constitutively in eukaryotic cells and are suitable for use with the described embodiments. Such viral promoters include without limitation, Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus.

Vectors described herein may contain one or more Internal Ribosome Entry Site(s) (IRES). Inclusion of an IRES sequence into fusion vectors may be beneficial for enhancing expression of some proteins. In some embodiments the vector system will include one or more polyadenylation sites (e.g., SV40), which may be upstream or downstream of any of the aforementioned nucleic acid sequences. Vector components may be contiguously linked, or arranged in a manner that provides optimal spacing for expressing the gene products (i.e., by the introduction of "spacer" nucleotides between the ORFs), or positioned in another way. Regulatory elements, such as the IRES motif, may also be arranged to provide optimal spacing for expression.

The vectors may comprise selection markers, which are well known in the art. Selection markers include positive and negative selection markers, for example, antibiotic resistance genes (e.g., neomycin resistance gene, a hygromycin resistance gene, a kanamycin resistance gene, a tetracycline resistance gene, a penicillin resistance gene), glutamate synthase genes, HSV-TK, HSV-TK derivatives for ganciclovir selection, or bacterial purine nucleoside phosphorylase gene for 6-methylpurine selection (Gadi et al., 7 Gene Ther. 1738-1743 (2000)). A nucleic acid sequence encoding a selection marker or the cloning site may be upstream or downstream of a nucleic acid sequence encoding a polypeptide of interest or cloning site.

The vectors described herein may be used to transform various cells with the genes encoding the described antibodies or antigen-binding fragments. For example, the vectors may be used to generate fusion protein-producing cells. Thus, another aspect features host cells transformed with vectors comprising a nucleic acid sequence encoding fusion proteins, such as the fusion proteins described and exemplified herein.

Numerous techniques are known in the art for the introduction of foreign genes into cells and may be used to construct the recombinant cells for purposes of carrying out the described methods, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline, 29 Pharmac. Ther. 69-92 (1985)). Calcium phosphate precipitation and polyethylene glycol (PEG)-induced fusion of bacterial protoplasts with mammalian cells may also be used to transform cells.

Cells suitable for use in the expression of the fusion proteins described herein are preferably eukaryotic cells, more preferably cells of plant, rodent, or human origin, for example but not limited to NSO, CHO, CHOK1, perC.6, Tk-tsl3, BHK, HEK293 cells, COS-7, T98G, CV-1/EBNA, L cells, C127, 3T3, HeLa, NS1, Sp2/0 myeloma cells, and BHK cell lines, among others. In addition, expression of antibodies may be accomplished using hybridoma cells. Methods for producing hybridomas are well established in the art.

Cells transformed with expression vectors described herein may be selected or screened for recombinant expression of the antibodies or antigen-binding fragments described herein. Recombinant-positive cells are expanded and screened for subclones exhibiting a desired phenotype, such as high level expression, enhanced growth properties, or the ability to yield proteins with desired biochemical characteristics, for example, due to protein modification or altered post-translational modifications. These phenotypes may be due to inherent properties of a given subclone or to mutation. Mutations may be effected through the use of chemicals, UV-wavelength light, radiation, viruses, insertional mutagens, inhibition of DNA mismatch repair, or a combination of such methods.

Multispecific Isolated CD3×PSMA-Bispecific Antigen-Binding Molecule or Bispecific Antigen-Binding Fragments Thereof.

Preferred isolated CD3×PSMA-bispecific antigen-binding molecules or bispecific antigen-binding fragments thereof are provided in Table 21.

Different formats of bispecific antibodies have been described and were recently reviewed by Chames and Baty (2009) Curr Opin Drug Disc Dev 12: 276.

In some embodiments, the bispecific antibody of the present invention is a diabody, a cross-body, or a bispecific antibody obtained via a controlled Fab arm exchange as those described in the present invention.

In some embodiments, the bispecific antibodies include IgG-like molecules with complementary CH3 domains to force heterodimerisation; recombinant IgG-like dual targeting molecules, wherein the two sides of the molecule each contain the Fab fragment or part of the Fab fragment of at least two different antibodies; IgG fusion molecules, wherein full length IgG antibodies are fused to an extra Fab fragment or parts of Fab fragment; Fc fusion molecules, wherein single chain Fv molecules or stabilized diabodies are fused to heavy-chain constant-domains, Fc-regions or parts thereof; Fab fusion molecules, wherein different Fab-fragments are fused together; ScFv- and diabody-based and heavy chain antibodies (e.g., domain antibodies, nanobodies) wherein different single chain Fv molecules or different diabodies or different heavy-chain antibodies (e.g. domain antibodies, nanobodies) are fused to each other or to another protein or carrier molecule.

In some embodiments, IgG-like molecules with complementary CH3 domains molecules include the Triomab/Quadroma (Trion Pharma/Fresenius Biotech), the Knobs-into-Holes (Genentech), CrossMAbs (Roche) and the electrostatically-matched (Amgen), the LUZ-Y (Genentech), the Strand Exchange Engineered Domain body (SEEDbody)(EMD Serono), the BIOCLONIC™ (Merus) and the DUOBODY™ (Genmab A/S).

In some embodiments, recombinant IgG-like dual targeting molecules include Dual Targeting (DT)-Ig (GSK/Domantis), Two-in-one Antibody (Genentech), Cross-linked Mabs (Karmanos Cancer Center), mAb2 (F-Star) and CovX-body (CovX/Pfizer).

In some embodiments, IgG fusion molecules include Dual Variable Domain (DVD)-Ig (Abbott), IgG-like Bispecific (InnClone/Eli Lilly), Ts2Ab (MedImmune/AZ) and BsAb (Zymogenetics), HERCULES™ (Biogen Idec) and TVAB™ (Roche).

In some embodiments, Fc fusion molecules include to ScFv/Fc Fusions (Academic Institution), SCORPION™ (Emergent BioSolutions/Trubion, Zymogenetics/BMS), Dual Affinity Retargeting Technology (Fc-DART) (Macro-Genics) and Dual(ScFv). sub.2-Fab (National Research Center for Antibody Medicine—China).

In some embodiments, Fab fusion bispecific antibodies include F(ab)2 (Medarex/AMGEN), Dual-Action or Bis-Fab (Genentech), DOCK-AND-LOCK™ (DNL) (Immuno-Medics), Bivalent Bispecific (Biotecnol) and Fab-Fv (UCB-Celltech). ScFv-, diabody-based and domain antibodies include but are not limited to Bispecific T Cell Engager (BITE) (Micromet, Tandem Diabody (Tandab) (Affimed), Dual Affinity Retargeting Technology (DART) (MacroGenics), Single-chain Diabody (Academic), TCR-like Antibodies (AIT, ReceptorLogics), Human Serum Albumin ScFv Fusion (Merrimack) and COMBODY™ (Epigen Biotech), dual targeting nanobodies (Ablynx), dual targeting heavy chain only domain antibodies.

Full length bispecific antibodies of the invention may be generated for example using Fab arm exchange (or half molecule exchange) between two mono specific bivalent antibodies by introducing substitutions at the heavy chain CH3 interface in each half molecule to favor heterodimer formation of two antibody half molecules having distinct specificity either in vitro in cell-free environment or using co-expression. The Fab arm exchange reaction is the result of a disulfide-bond isomerization reaction and dissociation-association of CH3 domains. The heavy-chain disulfide bonds in the hinge regions of the parent mono specific antibodies are reduced. The resulting free cysteines of one of the parent monospecific antibodies form an inter heavy-chain disulfide bond with cysteine residues of a second parent mono specific antibody molecule and simultaneously CH3 domains of the parent antibodies release and reform by dissociation-association. The CH3 domains of the Fab arms may be engineered to favor heterodimerization over homodimerization. The resulting product is an isolated CD3×PSMA-bispecific antigen-binding molecule or bispecific antigen-binding fragments thereof having two Fab arms or half molecules which each bind a distinct epitope, i.e. an epitope on PSMA and an epitope on CD3.

"Homodimerization" as used herein refers to an interaction of two heavy chains having identical CH3 amin acid sequences. "Homodimer" as used herein refers to an antibody having two heavy chains with identical CH3 amino acid sequences.

"Heterodimerization" as used herein refers to an interaction of two heavy chains having non-identical CH3 amino acid sequences. "Heterodimer" as used herein refers to an antibody having two heavy chains with non-identical CH3 amino acid sequences.

The "knob-in-hole" strategy (see, e.g., PCT Inti. Publ. No. WO 2006/028936) may be used to generate full length bispecific antibodies. Briefly, selected amino acids forming the interface of the CH3 domains in human IgG can be mutated at positions affecting CH3 domain interactions to promote heterodimer formation. An amino acid with a small side chain (hole) is introduced into a heavy chain of an antibody specifically binding a first antigen and an amino acid with a large side chain (knob) is introduced into a heavy chain of an antibody specifically binding a second antigen. After co-expression of the two antibodies, a heterodimer is formed as a result of the preferential interaction of the heavy chain with a "hole" with the heavy chain with a "knob". Exemplary CH3 substitution pairs forming a knob and a hole are (expressed as modified position in the first CH3 domain of the first heavy chain/modified position in the second CH3 domain of the second heavy chain): T366Y/F405A, T366W/F405W, F405W/Y407A, T394W/Y407T, T394S/Y407A, T366W/T394S, F405W/T394S and T366W/T366S_L368A_Y407V.

Other strategies such as promoting heavy chain heterodimerization using electrostatic interactions by substituting positively charged residues at one CH3 surface and negatively charged residues at a second CH3 surface may be used, as described in US Pat. Publ. No. US2010/0015133; US Pat. Publ. No. US2009/0182127; US Pat. Publ. No. US2010/028637 or US Pat. Publ. No. US2011/0123532. In other strategies, heterodimerization may be promoted by the following substitutions (expressed as modified position in the first CH3 domain of the first heavy chain/modified position in the second CH3 domain of the second heavy chain): L351Y_F405AY407V/T394W, T366I_K392M_T394W/F405A_Y407V, T366L_K392M_T394W/F405A_Y407V, L351Y_Y407A/T366A_K409F, L351Y_Y407A/T366V_K409F Y407A/T366A_K409F, or T350V_L351Y_F405A Y407V/T350V_T366L_K392L_T394W as described in U.S. Pat. Publ. No. US2012/0149876 or U.S. Pat. Publ. No. US2013/0195849.

In addition to methods described above, isolated CD3× PSMA-bispecific antigen-binding molecule or bispecific antigen-binding fragments thereof of the invention may be generated in vitro in a cell-free environment by introducing asymmetrical mutations in the CH3 regions of two mono specific homodimeric antibodies and forming the bispecific heterodimeric antibody from two parent monospecific homodimeric antibodies in reducing conditions to allow disulfide bond isomerization according to methods described in Inti. Pat. Publ. No. WO2011/131746. In the methods, the first monospecific FN3 domain and a monospecific bivalent antibody (e.g., anti-CD3 antibody) are engineered to have certain substitutions at the CH3 domain that promotes heterodimer stability; the antibodies are incubated together under reducing conditions sufficient to allow the cysteines in the hinge region to undergo disulfide bond isomerization; thereby generating the bispecific antibody by Fab arm exchange. The incubation conditions may optimally be restored to non-reducing conditions. Exemplary reducing agents that may be used are 2-mercaptoethylamine (2-MEA), dithiothreitol (DTT), dithioerythritol (DTE), glutathione, tris (2-carboxyethyl)phosphine (TCEP), L-cysteine and beta-mercaptoethanol, preferably a reducing agent selected from the group consisting of: 2-mercaptoethylamine, dithiothreitol and tris (2-carboxyethyl)phosphine. For example, incubation for at least 90 min at a temperature of at least 20° C. in the presence of at least 25 mM 2-MEA or in the presence of at least 0.5 mM dithiothreitol at a pH from 5-8, for example at pH of 7.0 or at pH of 7.4 may be used.

Also provided herein are methods for killing a PMSA-expressing cell by administering to a patient in need thereof a multispecific antibody which binds said PMSA and is able to recruit T cells to kill said PMSA-expressing cell (i.e., T cell redirection). Any of the isolated CD3×PSMA-bispecific antigen-binding molecule or bispecific antigen-binding fragments thereof of the invention may be used therapeutically.

In a preferred embodiment, isolated CD3×PSMA-bispecific antigen-binding molecule or bispecific antigen-binding fragments thereof of the invention are used for the treatment of a hyperproliferative disorder in a mammal. In a more preferred embodiment, one of the pharmaceutical compositions disclosed above, and which contains a multispecific antibody or antibody fragment of the invention, is used for the treatment of a hyperproliferative disorder in a mammal. In one embodiment, the disorder is a cancer.

Similarly, further provided herein is a method for inhibiting the growth of selected cell populations comprising contacting PMSA-expressing target cells, or tissue containing such target cells, with an effective amount of a isolated CD3×PSMA-bispecific antigen-binding molecule or bispecific antigen-binding fragments thereof of the present invention, either alone or in combination with other cytotoxic or therapeutic agents. In preferred embodiments, the multispecific antigen-binding molecule is an isolated CD3×PSMA-bispecific antigen-binding molecule or bispecific antigen-binding fragments thereof. The method for inhibiting the growth of selected cell populations can be practiced in vitro, in vivo, or ex vivo. Kits Also provided herein are includes kits, e.g., comprising a described multispecific antibody or antigen-binding fragment thereof and instructions for the use of the isolated CD3×PSMA-bispecific antigen-binding molecule or bispecific antigen-binding fragments thereof for killing of particular cell types. In preferred embodiments, the multispecific isolated CD3×PSMA-multispecific antigen-binding molecule or multispecific antigen-binding fragments thereof as described herein, and more preferably isolated CD3× PSMA-bispecific antigen-binding molecule or bispecific antigen-binding fragments thereof. The instructions may include directions for using the multispecific antibody or antigen-binding fragment thereof in vitro, in vivo or ex vivo.

Typically, the kit will have a compartment containing the isolated CD3×PSMA-multispecific antigen-binding molecule or multispecific antigen-binding fragment thereof. The multispecific antibody or antigen-binding fragment thereof may be in a lyophilized form, liquid form, or other form amendable to being included in a kit. The kit may also contain additional elements needed to practice the method described on the instructions in the kit, such a sterilized solution for reconstituting a lyophilized powder, additional agents for combining with the multispecific antibody or antigen-binding fragment thereof prior to administering to a patient, and tools that aid in administering the multispecific antibody or antigen-binding fragment thereof to a patient.

EXAMPLES

The following examples are provided to supplement the prior disclosure and to provide a better understanding of the subject matter described herein. These examples should not be considered to limit the described subject matter. It is understood that the examples and embodiments described herein are for illustrative purposes only and that various modifications or changes in light thereof will be apparent to persons skilled in the art and are to be included within, and can be made without departing from, the true scope of the invention.

Reagents and Constructs:

The extracellular domains of cynomolgus (cyno monkey protein database ref #EHH56646.1, SEQ ID NO: 32) and chimpanzee (Uniprot, Ref #H2Q3K5, SEQ ID NO: 33) PSMA were cloned into the pUnder expression vector along with a 6His and Avi tag. Proteins were transiently expressed in 293HEK-expi cells. Supernatants were harvested and clarified by centrifugation. The proteins were purified using a two-step purification process: 1) IMAC purification with a HisTrap HP column and 2) size exclusion purification (Superdex 200) where the elution buffer is DPBS containing $Mg^{2+}$, $Ca^{2+}$, and 0.5 mM ZnC12 to stabilize PSMA dimerization. Fractions containing the protein of interest were pooled and protein concentration was determined by A280.

The gene encoding S. aureus sortase A was produced by DNA2.0 and subcloned into pJexpress401 vector (DNA2.0) for expression under the T5 promoter. The sortase construct for soluble expression is lacking the N-terminal domain of the natural protein consisting of 25 amino acids since this domain is membrane associated (Ton-That et al., Proc Natl Acad Sci USA 96: 12424-12429, 1999). The sortase was expressed as N-terminal His6-tag (HHHHHH, SEQ ID NO:34) followed by a TEV protease site for tag removal (ENLYFQS, SEQ ID NO: 54), resulting in the sortase having the amino acid sequence of SEQ ID NO: 52. The sortase protein used also includes 5 mutations sequence that are reported to increase the catalytic efficiency of the enzyme when compared to the wild type proteins (SEQ ID NO: 53) (Chen et al., Proc Natl Acad Sci USA 108: 11399-11404, 2011). The plasmid was transformed into E. coli BL21 Gold cells (Agilent) for expression. A single colony was picked and grown in Luria Broth (Teknova) supplemented with kanamycin and incubated 18 h at 37° C. 250 RPM. 250 mL of Terrific Broth (Teknova), supplemented with kanamycin, was inoculated from these subcultures and grown at 37° C. for ~4 h while shaking. Protein expression was induced with 1 mM IPTG, and the protein was expressed for 18 h at 30° C. Cells were harvested by centrifugation at 6000 g and stored at −20° C. until purification. The frozen cell pellet was thawed for 30 min at room temperature and suspended in BugBusterHT protein extraction reagent (EMD Millipore) supplemented with 1 uL per 30 mL of recombinant lysozyme (EMD Millipore) at 5 ml per gram of cell paste and incubated for 30 minutes on a shaker at room temperature. The lysate was clarified by centrifugation at 74,600 g for 30 min.

The supernatant was applied onto a gravity column packed with 3 mL of QIAGEN® Superflow Ni-NTA resin pre-equilibrated with buffer A (50 mM sodium phosphate buffer, pH 7.0 containing 0.5 M NaCl and 10 mM imidazole). After loading, the column was washed with 100 mL of Buffer A. The protein was eluted with Buffer A supplemented with 250 mM imidazole and loaded on a preparative gel-filtration column, TSK Gel G3000SW 21.5×600 mm (Tosoh) equilibrated in PBS (Gibco). The gel-filtration chromatography was performed at room temperature in PBS at flow rate 10 ml/min using an AKTA-AVANT™ chromatography system. Purified sortase was then digested with TEV protease to remove the His6 tag. 28 mgs of sortase was incubated in 10 mLs with 3000 units of AcTEV protease (Invitrogen) in the supplied buffer supplemented with 1 mM DTT for 2 hours at 30° C. The tagless sortase was purified with Ni-NTA resin. The reaction was exchanged into TBS buffer (50 mM Tris pH 7.5, 150 mM NaCl) using PD-10 columns (GE Healthcare) and applied onto a gravity column packed with 0.5 mL of Qiagen Superflow Ni-NTA resin pre-equilibrated with buffer A. The flowthrough was collected and the resin was washed with 3 mL of buffer A which was added to the flowthrough. This flowthrough was concentrated to ~0.5 mL in an Amicon 15 concentrator with 10 kDa cutoff (EMD Millipore). Additional TBS buffer was added and the sample was concentrated again (repeated twice) to exchange the buffer to TBS. ⅓rd volume of 40% glycerol was added (final concentration of 10% glycerol), and the sortase was stored at −20° C. for short term use or −80° C. for long term.

Example 1. Construction of TENCON™ Libraries with Randomized Loops

TENCON™ (SEQ ID NO: 1) is an immunoglobulin-like scaffold, fibronectin type III (FN3) domain, designed from a consensus sequence of fifteen FN3 domains from human tenascin-C (Jacobs et al., Protein Engineering, Design, and Selection, 25:107-117, 2012; U.S. Pat. No. 8,278,419). The crystal structure of TENCON™ shows six surface-exposed loops that connect seven beta-strands. These loops, or selected residues within each loop, can be randomized in order to construct libraries of fibronectin type III (FN3) domains that can be used to select novel molecules that bind to specific targets.

TENCON™: Lpapknlvvsevtedslrlswtapdaafdsfliqyqese-kvgeainltvpgsersydltglkpgteytvsiygvkgghrsnplsaeftt (SEQ ID NO 1):

Various libraries were generated using the TENCON™ scaffold and various design strategies. In general, libraries TCL1 and TCL2 produced good binders. Generation of TCL1 and TCL2 libraries are described in detail in Int. Pat. Publ. No. WO2014081944A2.

Construction of TCL1 Library

A library designed to randomize only the FG loop of TENCON™ (SEQ ID NO: 1), TCL1, was constructed for use with the cis-display system (Jacobs et al., Protein Engineering, Design, and Selection, 25:107-117, 2012). In this system, a single-strand DNA incorporating sequences for a Tac promoter, TENCON™ library coding sequence, RepA coding sequence, cis-element, and ori element is produced. Upon expression in an in vitro transcription/translation system, a complex is produced of the TENCON™-RepA fusion protein bound in cis to the DNA from which it is encoded. Complexes that bind to a target molecule are then isolated and amplified by polymerase chain reaction (PCR), as described below.

Construction of the TCL1 library for use with cis-display was achieved by successive rounds of PCR to produce the final linear, double-stranded DNA molecules in two halves; the 5' fragment contains the promoter and TENCON™ sequences, while the 3' fragment contains the repA gene and the cis- and ori elements. These two halves are combined by restriction digest in order to produce the entire construct. The TCL1 library was designed to incorporate random amino acids only in the FG loop of TENCON™, KGGHRSN (SEQ ID NO: 55). NNS codons were used in the construction of this library, resulting in the possible incorporation of all 20 amino acids and one stop codon into the FG loop. The TCL1 library contains six separate sub-libraries, each having a different randomized FG loop length, from 7 to 12 residues, in order to further increase diversity.

TCL1 library (SEQ ID NO: 2) LPAPKNLVVSEVTED-SLRLSWTAPDAAFDSFLIQYQESEKVGEAINLTVPG-SERSYDLTG LKPGTEYTVSIYGVX$_{7-12}$PLSAEFTT; wherein X$_1$, X$_2$, X$_3$, X$_4$, X$_5$, X$_6$, X$_7$ is any amino acid; and X$_8$, X$_9$, X$_{10}$, X$_{11}$ and X$_{12}$ are any amino acid or deleted.

Construction of TCL2 Library

TCL2 library was constructed in which both the BC and the FG loops of TENCON™ were randomized and the distribution of amino acids at each position was strictly controlled. Table 6 shows the amino acid distribution at desired loop positions in the TCL2 library. The designed amino acid distribution had two aims. First, the library was biased toward residues that were predicted to be structurally important for TENCON™ folding and stability based on analysis of the TENCON™ crystal structure and/or from homology modeling. For example, position 29 was fixed to be only a subset of hydrophobic amino acids, as this residue was buried in the hydrophobic core of the TENCON™ fold. A second layer of design included biasing the amino acid distribution toward that of residues preferentially found in the heavy chain HCDR3 of antibodies, to efficiently produce high-affinity binders (Birtalan et al., J Mol Biol 377:1518-28, 2008; Olson et al., Protein Sci 16:476-84, 2007). Towards this goal, the "designed distribution" in Table 5 refers to the distribution as follows: 6% alanine, 6% arginine, 3.9% asparagine, 7.5% aspartic acid, 2.5% glutamic acid, 1.5% glutamine, 15% glycine, 2.3% histidine, 2.5% isoleucine, 5% leucine, 1.5% lysine, 2.5% phenylalanine, 4% proline, 10% serine, 4.5% threonine, 4% tryptophan, 17.3% tyrosine, and 4% valine. This distribution is devoid of methionine, cysteine, and STOP codons.

TCL2 library (SEQ ID NO: 3) LPAPKNLVVSEV-TEDSLRLSWX$_1$X$_2$X$_3$X$_4$X$_5$X$_6$X$_7$X$_8$SFLIQYQESEKVGE-AINLTVPGSERSYDLTGLKPGTEYTVSIYGVX$_9$X$_{10}$ X$_{11}$ X$_{12}$X$_{13}$SX$_{14}$X$_{15}$LSAEFTT; wherein X$_1$ is Ala, Arg, Asn, Asp, Glu, Gln, Gly, His, Ile, Leu, Lys, Phe, Pro, Ser, Thr, Trp, Tyr or Val; X$_2$ is Ala, Arg, Asn, Asp, Glu, Gln, Gly, His, Ile, Leu, Lys, Phe, Pro, Ser, Thr, Trp, Tyr or Val; X$_3$ Ala, Arg, Asn, Asp, Glu, Gln, Gly, His, Ile, Leu, Lys, Phe, Pro, Ser, Thr, Trp, Tyr or Val; X$_4$ is Ala, Arg, Asn, Asp, Glu, Gln, Gly, His, Ile, Leu, Lys, Phe, Pro, Ser, Thr, Trp, Tyr or Val; X$_5$ is Ala, Arg, Asn, Asp, Glu, Gln, Gly, His, Ile, Leu, Lys, Phe, Pro, Ser, Thr, Trp, Tyr or Val; X$_6$ is Ala, Arg, Asn, Asp, Glu, Gln, Gly, His, Ile, Leu, Lys, Phe, Pro, Ser, Thr, Trp, Tyr or Val; X$_7$ is Phe, Ile, Leu, Val or Tyr; X$_8$ is Asp, Glu or Thr; X$_9$ is Ala, Arg, Asn, Asp, Glu, Gln, Gly, His, Ile, Leu, Lys, Phe, Pro, Ser, Thr, Trp, Tyr or Val; X$_{10}$ is Ala, Arg, Asn, Asp, Glu, Gln, Gly, His, Ile, Leu, Lys, Phe, Pro, Ser, Thr, Trp, Tyr or Val; X$_{11}$ is Ala, Arg, Asn, Asp, Glu, Gln, Gly, His, Ile, Leu, Lys, Phe, Pro, Ser, Thr, Trp, Tyr or Val; X$_{12}$ is Ala, Arg, Asn, Asp, Glu, Gln, Gly, His, Ile, Leu, Lys, Phe, Pro, Ser, Thr, Trp, Tyr or Val; X$_{13}$ is Ala, Arg, Asn, Asp, Glu, Gln, Gly, His, Ile, Leu, Lys, Phe, Pro, Ser, Thr, Trp, Tyr or Val; X$_{14}$ is Ala, Arg, Asn, Asp, Glu, Gln, Gly, His, Ile, Leu, Lys, Phe, Pro, Ser, Thr, Trp, Tyr or Val; and X$_{15}$ is Ala, Arg, Asn, Asp, Glu, Gln, Gly, His, Ile, Leu, Lys, Phe, Pro, Ser, Thr, Trp, Tyr or Val.

TABLE 5

| Residue Position* | WT residues | Distribution in the TCL2 library |
| --- | --- | --- |
| 22 | T | designed distribution |
| 23 | A | designed distribution |
| 24 | P | 50% P + designed distribution |
| 25 | D | designed distribution |
| 26 | A | 20% A + 20% G + designed distribution |
| 27 | A | designed distribution |
| 28 | F | 20% F, 20% I, 20% L, 20% V, 20% Y |
| 29 | D | 33% D, 33% E, 33% T |
| 75 | K | designed distribution |
| 76 | G | designed distribution |
| 77 | G | designed distribution |
| 78 | H | designed distribution |
| 79 | R | designed distribution |
| 80 | S | 100% S |
| 81 | N | designed distribution |
| 82 | P | 50% P + designed distribution |

*residue numbering is based on Tencon sequence of SEQ ID NO: 1

Subsequently, these libraries were improved by various ways, including building of the libraries on a stabilized TENCON™ framework (U.S. Pat. No. 8,569,227) that incorporates substitutions E11R/L17A/N46V/E86I (TENCON™27; SEQ ID NO: 4) when compared to the wild type TENCON™ as well as altering of the positions randomized in the BC and FG loops. TENCON™27 is described in Int. Pat. Appl. No. WO2013049275. From this, new libraries designed to randomize only the FG loop of TENCON™ (library TCL9), or a combination of the BC and FG loops (library TCL7) were generated. These libraries were constructed for use with the cis-display system (Odegrip et al., Proc Natl Acad Sci USA 101: 2806-2810, 2004). The details of this design are shown below:

Stabilized TENCON™ (TENCON™27) (SEQ ID NO: 4)

LPAPKNLVVSRVTEDSARLSWTAPDAAFDSFLIQYQESEKVGEAIVLTV
PGSERSYDLTGLKPGTEYTVSIYGVKGGHRSNPLSAIFTT

TCL7 (randomized FG and BC loops) (SEQ ID NO: 5) LPAPKNLVVSRVTEDSARLSWX$_1$X$_2$X$_3$X$_4$X$_5$X$_6$X$_7$X$_8$X$_9$FDSFLIQYQESEKVGEAIVLTVPGSERSYDLTGLK PG-TEYTVSIYGVX$_{10}$X$_{11}$X$_{12}$X$_{13}$X$_{14}$X$_{15}$X$_{16}$X$_{17}$X$_{18}$X$_{19}$SNP-LSAIFTT; wherein X$_1$, X$_2$, X$_3$, X$_4$, X$_5$, X$_6$, X$_{10}$, X$_{11}$, X$_{12}$, X$_{13}$, X$_{14}$, X$_{15}$ and X$_{16}$ is A, D, E, F, G, H, I, K, L, N, P, Q, R, S, T, V, W or Y; and X$_7$, X$_8$, X$_9$, X$_{17}$, X$_{18}$ and X$_{19}$, is A, D, E, F, G, H, I, K, L, N, P, Q, R, S, T, V, W, Y or deleted.

TCL9 (randomized FG loop) (SEQ ID NO: 6) LPAPKN-LVVSRVTEDSARLSWTAPDAAFDSFLIQYQESEK-VGEAIVLTVPGSERSYDLTG LKPGTEYTVSIYGV X$_1$X$_2$X$_3$X$_4$X$_5$X$_6$X$_7$X$_8$X$_9$ X$_{10}$X$_{11}$X$_{12}$SNPLSAIFTT; X$_1$, X$_2$, X$_3$, X$_4$, X$_5$, X$_6$ and X$_7$, is A, D, E, F, G, H, I, K, L, N, P, Q, R, S, T, V, W or Y; and X$_8$, X$_9$, X$_{10}$, X$_{11}$ and X$_{12}$ is A, D, E, F, G, H, I, K, L, N, P, Q, R, S, T, V, W, Y or deleted.

For library construction, DNA fragments encoding randomized BC loops (lengths 6-9 positions) or FG loops (lengths 7-12 positions) were synthesized using Slonomics technology (Sloning Biotechnology GmbH) so as to control the amino acid distribution of the library and to eliminate stop codons. Two different sets of DNA molecules randomizing either the BC loop or the FG loops were synthesized independently and later combined using PCR to produce the full library product.

Construction of FG Loop Libraries (TCL9)

A set of synthetic DNA molecules consisting of a 5' Tac promoter followed by the complete gene sequence of Tencon with the exception of randomized codons in the FG loop was produced (SEQ ID NOs: 26-31). For FG loop randomization, all amino acids except cysteine and methionine were encoded at equal percentages. The lengths of the diversified portion are such that they encode for 7, 8, 9, 10, 11, or 12 amino acids in the FG loop. Sub-libraries of each length variation were synthesized individually at a scale of 2 ug and then amplified by PCR using oligos Sloning-FOR (SEQ ID NO: 9) and Sloning-Rev (SEQ ID NO: 10).

The 3' fragment of the library is a constant DNA sequence containing elements for display, including a PspOMI restriction site, the coding region of the repA gene, and the cis- and ori elements. PCR reactions were performed to amplify this fragment using a plasmid (pCR4Blunt) (Invitrogen) as a template with M13 Forward and M13 Reverse primers. The resulting PCR products were digested by PspOMI overnight and gel-purified. To ligate the 5' portion of library DNA to the 3' DNA containing repA gene, 2 pmol (~540 ng to 560 ng) of 5' DNA was ligated to an equal molar (~1.25 μg) of 3' repA DNA in the presence of NotI and PspOMI enzyme and T4 ligase at 37° C. overnight. The ligated library product was amplified by using 12 cycles of PCR with oligos POP2250 (SEQ ID NO: 11) and DigLigRev (SEQ ID NO: 12). For each sub-library, the resulting DNA from 12 PCR reactions were combined and purified by QIAGEN® spin column. The yield for each sub-library of TCL9 ranged from 32-34 μg.

Construction of FG/BC Loop libraries (TCL7)

The TCL7 library provides for a library with randomized Tencon BC and FG loops. In this library, BC loops of lengths 6-9 amino acids were mixed combinatorially with randomized FG loops of 7-12 amino acids in length. Synthetic Tencon fragments BC6, BC7, BC8, and BC9 (SEQ ID No. 13-16) were produced to include the Tencon gene encoding for the N-terminal portion of the protein up to and including residue VX such that the BC loop is replaced with either 6, 7, 8, or 9 randomized amino acids. These fragments were synthesized prior to the discovery of L17A, N46V and E83I mutations (CEN5243) but these mutations were introduced in the molecular biology steps described below. In order to combine this fragment with fragments encoding for randomized FG loops, the following steps were taken.

First, a DNA fragment encoding the Tac promoter and the 5' sequence of Tencon up to the nucleotide endoding for amino acid A17 (130mer-L17A, SEQ ID No. 17) was produced by PCR using oligos POP2222ext (SEQ ID No. 18) and LS1114 (SEQ ID No. 19). This was done to include the L17A mutation in the library (CEN5243). Next, DNA fragments encoding for Tencon residues R18-V75 including randomized BC loops were amplified by PCR using BC6, BC7, BC8, or BC9 as a templates and oligos LS1115 (SEQ ID No. 20) and LS1117 (SEQ ID No. 21). This PCR step introduced a BsaI site at the 3' end. These DNA fragments were subsequently joined by overlapping PCR using oligos POP2222ext and LS1117 as primers. The resulting PCR product of 240 bp was pooled and purified by QIAGEN® PCR purification kit. The purified DNA was digested with BsaI-HF and gel purified.

Fragments encoding the FG loop were amplified by PCR using FG7, FG8, FG9, FG10, FG11, and FG12 (SEQ ID No. 26-31) as templates with oligonucleotides SDG10 (SEQ ID No. 22) and SDG24 (SEQ ID No. 23) to incorporate a BsaI restriction site and N46V and E86I variations (CEN5243).

The digested BC fragments and FG fragments were ligated together in a single step using a 3-way ligation. Four ligation reactions in the 16 possible combinations were set up, with each ligation reaction combining two BC loop lengths with 2 FG loop lengths. Each ligation contained ~300 ng of total BC fragment and 300 ng of the FG fragment. These 4 ligation pools were then amplified by PCR using oligos POP2222 (SEQ ID No. 24) and SDG28 SEQ ID No. 25). 7.5 μg of each reaction product were then digested with NotI and cleaned up with a QIAGEN® PCR purification column. 5.2 μg of this DNA, was ligated to an equal molar amount of RepA DNA fragment (~14 μg) digested with PspOMI and the product amplified by PCR using oligos POP2222.

Example 2: Generation of Tencon Libraries Having Alternative Binding Surfaces

The choice of residues to be randomized in a particular library design governs the overall shape of the interaction surface created. X-ray crystallographic analysis of an FN3 domain containing scaffold protein selected to bind maltose binding protein (MBP) from a library in which the BC, DE, and FG loops were randomized was shown to have a largely curved interface that fits into the active site of MBP (Koide et al., Proc Natl Acad Sci USA 104: 6632-6637, 2007). In contrast, an ankyrin repeat scaffold protein that was selected to bind to MBP was found to have a much more planar interaction surface and to bind to the outer surface of MBP distant from the active (Binz et al., Nat Biotechnol 22: 575-582, 2004). These results suggest that the shape of the binding surface of a scaffold molecule (curved vs. flat) may dictate what target proteins or specific epitopes on those target proteins are able to be bound effectively by the scaffold. Published efforts around engineering protein scaffolds containing FN3 domains for protein binding has relied on engineering adjacent loops for target binding, thus producing curved binding surfaces. This approach may limit the number of targets and epitopes accessible by such scaffolds.

Tencon and other FN3 domains contain two sets of CDR-like loops lying on the opposite faces of the molecule, the first set formed by the BC, DE, and FG loops, and the second set formed by the AB, CD, and EF loops. The two sets of loops are separated by the beta-strands that form the center of the FN3 structure. If the image of the Tencon is rotated by 90 degrees, an alternative surface can be visualized. This slightly concave surface is formed by the CD and FG loops and two antiparallel beta-strands, the C and the F beta-strands, and is herein called the C-CD-F-FG surface. The C-CD-F-FG surface can be used as a template to design libraries of protein scaffold interaction surfaces by randomizing a subset of residues that form the surface. Beta-strands have a repeating structure with the side chain of every other residue exposed to the surface of the protein. Thus, a library can be made by randomizing some or all surface exposed residues in the beta strands. By choosing the appropriate residues in the beta-strands, the inherent stability of the Tencon scaffold should be minimally compromised while providing a unique scaffold surface for interaction with other proteins.

Library TCL14 (SEQ ID NO: 7), was designed into Tencon27 scaffold (SEQ ID NO: 4).

A full description of the methods used to construct this library is described in US. Pat. Publ. No. US2013/0226834.

TCL14 library (SEQ ID NO: 7): LPAPKNLVVSRVTEDSARLSWTAPDAAFDSFX$_1$IX$_2$YX$_3$EX$_4$X$_5$X$_6$X$_7$GEAIVLTVPGSERSY DLTGLKPGTEYX$_8$VX$_9$IX$_{10}$ GVKGGX$_{11}$X$_{12}$SX$_{13}$PLSAIFTT; wherein X$_1$, X$_2$, X$_3$, X$_4$, X$_5$, X$_6$, X$_{10}$, X$_{11}$, X$_{12}$ and X$_{13}$ are A, D, E, F, G, H, I, K, L, N, P, Q, R, S, T, V, W, Y, C or M.

The two beta strands forming the C-CD-F-FG surface in Tencon27 have a total of 9 surface exposed residues that could be randomized; C-strand: S30, L32, Q34, Q36; F-strand: E66, T68, S70, Y72, and V74, while the CD loop has 6 potential residues: S38, E39, K40, V41, G42, and E43 and the FG loop has 7 potential residues: K75, G76, G77, H78, R79, S80, and N81. Select residues were chosen for inclusion in the TCL14 design due to the larger theoretical size of the library if all 22 residues were randomized.

Thirteen positions in Tencon were chosen for randomizing: L32, Q34 and Q36 in C-strand, S38, E39, K40 and V41 in CD-loop, T68, S70 and Y72 in F-strand, H78, R79, and N81 in FG-loop. In the C and F strands S30 and E66 were not randomized as they lie just beyond the CD and FG loops and do not appear to be as apparently a part of the C-CD-F-FG surface. For the CD loop, G42 and E43 were not randomized as glycine, providing flexibility, can be valuable in loop regions, and E43 lies at the junction of the surface. The FG loop had K75, G76, G77, and S80 excluded. The glycines were excluded for the reasons above while careful inspection of the crystal structures revealed S80 making key contacts with the core to help form the stable FG loop. K75 faces away from the surface of the C-CD-F-FG surface and was a less appealing candidate for randomization. Although the above-mentioned residues were not randomized in the original TCL14 design, they could be included in subsequent library designs to provide additional diversity for de novo selection or for example for an affinity maturation library on a select TCL14 target specific hit.

Subsequent to the production of TCL14, 3 additional Tencon libraries of similar design were produced. These two libraries, TCL19, TCL21 and TCL23, are randomized at the same positions as TCL14 (see above) however the distribution of amino acids occurring at these positions is altered (Table 6). TCL19 and TCL21 were designed to include an equal distribution of 18 natural amino acids at every position (5.55% of each), excluding only cysteine and methionine. TCL23 was designed such that each randomized position approximates the amino acid distribution found in the HCDR3 loops of functional antibodies (Birtalan et al., J Mol Biol 377: 1518-1528, 2008) as described in Table 6. As with the TCL21 library, cysteine and methionine were excluded.

A third additional library was built to expand potential target binding surface of the other libraries library. In this library, TCL24, 4 additional Tencon positions were randomized as compared to libraries TCL14, TCL19, TCL21, and TCL23. These positions include N46 and T48 from the D strand and S84 and I86 from the G strand. Positions 46, 48, 84, and 86 were chosen in particular as the side chains of these residues are surface exposed from beta-strands D and G and lie structurally adjacent to the randomized portions of the C and F strand, thus increasing the surface area accessible for binding to target proteins. The amino acid distribution used at each position for TCL24 is identical to that described for TCL19 and TCL21 in Table 6.

TCL24 Library (SEQ ID NO: 8) LPAPKNLVVSRVTEDSARLSWTAPDAAFDSFX$_1$X$_2$YX$_3$EX$_4$X$_5$X$_6$X$_7$GEAIX$_8$LX$_9$VPGSERS YDLTGLKPGTEYX$_{10}$VX$_{11}$IX$_{12}$GVKGGX$_{13}$X$_{14}$SX$_{15}$PLX$_{16}$AX$_{17}$FTT; wherein X$_1$, X$_2$, X$_3$, X$_4$, X$_5$, X$_6$, X$_{10}$, X$_{11}$ X$_{12}$, X$_{13}$, X$_{14}$, X$_{15}$, X$_{16}$ and X$_{17}$ are A, D, E, F, G, H, I, K, L, N, P, Q, R, S, T, V Y or W.

Table 6. Amino acid frequency (%) at each randomized position for TCL21, TCL23, and TCL24.

TABLE 6

| Amino Acid | TCL19 | TCL21 | TCL23 | TCL24 |
|---|---|---|---|---|
| Ala | 5.6 | 5.6 | 6.0 | 5.6 |
| Arg | 5.6 | 5.6 | 6.0 | 5.6 |
| Asn | 5.6 | 5.6 | 3.9 | 5.6 |
| Asp | 5.6 | 5.6 | 7.5 | 5.6 |
| Cys | 0.0 | 0.0 | 0.0 | 0.0 |
| Gln | 5.6 | 5.6 | 1.5 | 5.6 |
| Glu | 5.6 | 5.6 | 2.5 | 5.6 |
| Gly | 5.6 | 5.6 | 15.0 | 5.6 |
| His | 5.6 | 5.6 | 2.3 | 5.6 |
| Ile | 5.6 | 5.6 | 2.5 | 5.6 |
| Leu | 5.6 | 5.6 | 5.0 | 5.6 |
| Lys | 5.6 | 5.6 | 1.5 | 5.6 |
| Met | 0.0 | 0.0 | 0.0 | 0.0 |
| Phe | 5.6 | 5.6 | 2.5 | 5.6 |
| Pro | 5.6 | 5.6 | 4.0 | 5.6 |
| Ser | 5.6 | 5.6 | 10.0 | 5.6 |
| Thr | 5.6 | 5.6 | 4.5 | 5.6 |
| Trp | 5.6 | 5.6 | 4.0 | 5.6 |
| Tyr | 5.6 | 5.6 | 17.3 | 5.6 |
| Val | 5.6 | 5.6 | 4.0 | 5.6 |

Generation of TCL21, TCL23, and TCL24 Libraries

The TCL21 library was generated using Colibra library technology (Isogenica) in order to control amino acid distributions. TCL19, TCL23, and TCL24 gene fragments were generated using Slonomics technology (Morphosys) to control amino acid distributions. PCR was used to amplify each library following initial synthesis followed by ligation to the gene for RepA in order to be used in selections using the CIS-display system (Odegrip et al., Proc Natl Acad Sci USA 101: 2806-2810, 2004) as described above for the loop libraries.

Example 3: Selection of Fibronectin Type III (FN3) Domains that Bind PSMA

Plate-Based Selections

CIS-display was used to select PSMA binding FN3 domains from the TCL7, TCL9, TCL19, and TCL21 libraries. For in vitro transcription and translation (ITT), 3 µg of library DNA were incubated at 30° C. with 0.1 mM complete amino acids, 1×S30 premix components, and 15 µL of S30 extract (Promega) in a total volume of 50 µL. After 1 hour, 375 µL of blocking solution (lx TBS pH 7.4, 0.01% I-block (Life Technologies, #T2015), 100 ug/ml herring sperm DNA) was added and reactions were incubated on ice for 15 minutes. ITT reactions were incubated with recombinant proteins, chimpanzee (pan 229) or cynomolgus monkey PSMA (pan 230), or cynomolgus monkey PSMA-Fc fusion (pan 231), which were immobilized on anti-human PSMA antibody (Lifespan Bioscience, catalog # LC-C150527) coated 96-well Maxisorb plates. Unbound library members were removed by successive washes with TBST and TBS. After washing, DNA was eluted from the target protein by heating to 85° C. for 10 minutes and amplified by PCR for further rounds of panning. High affinity binders were isolated by successively lowering the concentration of target PSMA during each round from 400 nM to 100 nM and increasing the washing stringency.

Following panning, selected FN3 domains were amplified by PCR, subcloned into a pET vector modified to include a ligase independent cloning site, and transformed into BL21-GOLD (DE3) (Stratagene) cells for soluble expression in *E. coli* using standard molecular biology techniques. A gene sequence encoding a C-terminal poly-histidine tag was added to each FN3 domain to enable purification and detection. Cultures were grown to an optical density of 0.6-0.8 in TB medium supplemented with 100 µg/mL carbenicillin in 1-mL 96-well blocks at 37° C. before the addition of IPTG to 1 mM, at which point the temperature was reduced to 30° C. Cells were harvested approximately 16 hours later by centrifugation and frozen at −20° C. Cell lysis was achieved by incubating each pellet in 0.6 mL of BugBuster® HT lysis buffer (Novagen EMD Biosciences) with shaking at room temperature for 45 minutes.

Bead-Based Selections

FN3 domains were also selected using a bead-based capture setup. ITT reactions were prepared as described above and then incubated with biotinylated recombinant proteins, chimpanzee or cynomolgus monkey PSMA. The biotinylated recombinant proteins and the bound library members were captured on neutravidin or streptavidin coated magnetic beads. Unbound library members were removed by successive washes with TBST and TBS. After washing, DNA was eluted from the target protein by heating to 85° C. for 10 minutes and amplified by PCR for further rounds of panning. High affinity binders were isolated by successively lowering the concentration of target PSMA during each round from 400 nM to 100 nM and increasing the washing stringency.

Off-Rate Selections

Outputs from the fifth round of bead-based selection were subjected to four rounds of off-rate selection. After the ITT reactions were incubated with biotinylated recombinant chimpanzee or cynomolgus monkey proteins, the proteins and the bound library members were captured on neutravidin or streptavidin coated magnetic beads, and washed in TBST extensively, the bound complexes were washed in 5 µM cold recombinant PSMA proteins for 1 hour. Then the ITT bound to beads were washed extensively in TBST and TBS before being eluted. The biotinylated target antigen concentration was stepped down from 25 nM in rounds 6 and 7 to 2.5 nM in rounds 8 and 9. Selection outputs from rounds 7 and 9 were subcloned into the modified pET15 vector for expression and screening.

Affinity Maturation Library Selection

An affinity maturation library (TCL25) based on the sequence of clone P229CR9P819-H11 (SEQ ID NO: 40) was generated using Slonomics technology at Morphosys (Munich, Germany) in which positions 23-30 from the BC loop and positions 78-83 from the FG loop were randomized. Maintenance of target binding in the library was achieved by doping nucleotides encoding the parent amino acid (from P229CR9P819-H11) at a target frequency of 65% at each randomized position. The remaining 35% of nucleotides were designed to contain a mixture of codons encoding for an equal probability of all other 20 natural amino acids, with the exception of cysteine and methionine which were not included. Table 7 shows the design of the TCL25 maturation library. In the table, numbers in parenthesis represent the percentage of molecules in the library designed to contain the corresponding amino acid at each position. This doping scheme (65% parent at 14 positions) generates a theoretical distribution of molecules containing mostly 3, 4, 5, 6, or 7 changes as compared to the parent molecule.

TABLE 7

| Position | Parent Amino Acid | Amino Acid Distribution (%) |
|---|---|---|
| 23 | Asp | (2.05), arg (2.05), asn (2.05), asp (65), gln (2.05), glu (2.05), gly (2.05), his (2.05), ile (2.05), leu (2.05), lys (2.05), phe (2.05), pro (2.05), ser (2.05), thr (2.05), tyr(2.05), trp (2.05), val (2.05) |
| 24 | Ile | ala (2.05), arg (2.05), asn (2.05), asp (2.05), gln (2.05), glu (2.05), gly (2.05), his (2.05), ile (65), leu (2.05), lys (2.05), phe (2.05), pro (2.05), ser (2.05), thr (2.05), tyr(2.05), trp (2.05), val (2.05) |
| 25 | Asp | ala (2.05), arg (2.05), asn (2.05), asp (65), gln (2.05), glu (2.05), gly (2.05), his (2.05), ile (2.05), leu (2.05), lys (2.05), phe (2.05), pro (2.05), ser (2.05), thr (2.05), tyr(2.05), trp (2.05), val (2.05) |
| 26 | Glu | ala (2.05), arg (2.05), asn (2.05), asp (2.05), gln (2.05), glu (65), gly (2.05), his (2.05), ile (2.05), leu (2.05), lys (2.05), phe (2.05), pro (2.05), ser (2.05), thr (2.05), tyr(2.05), trp (2.05), val (2.05) |
| | | ala (2.05), arg (2.05), asn (2.05), asp (2.05), gln (65), glu (2.05), gly |

TABLE 7-continued

| Position | Parent Amino Acid | Amino Acid Distribution (%) |
|---|---|---|
| 27 | Gln | (2.05), his (2.05), ile (2.05), leu (2.05), lys (2.05), phe (2.05), pro (2.05), ser (2.05), thr (2.05), tyr(2.05), trp (2.05), val (2.05) |
| 28 | Arg | ala (2.05), arg (65), asn (2.05), asp (2.05), gln (2.05), glu (2.05), gly (2.05), his (2.05), ile (2.05), leu (2.05), lys (2.05), phe (2.05), pro (2.05), ser (2.05), thr (2.05), tyr(2.05), trp (2.05), val (2.05) |
| 29 | Asp | ala (2.05), arg (2.05), asn (2.05), asp (65), gln (2.05), glu (2.05), gly (2.05), his (2.05), ile (2.05), leu (2.05), lys (2.05), phe (2.05), pro (2.05), ser (2.05), thr (2.05), tyr(2.05), trp (2.05), val (2.05) |
| 30 | Trp | ala (2.05), arg (2.05), asn (2.05), asp (2.05), gln (2.05), glu (2.05), gly (2.05), his (2.05), ile (2.05), leu (2.05), lys (2.05), phe (2.05), pro (2.05), ser (2.05), thr (2.05), tyr(2.05), trp (65), val (2.05) |
| 78 | Tyr | ala (2.05), arg (2.05), asn (2.05), asp (2.05), gln (2.05), glu (2.05), gly (2.05), his (2.05), ile (2.05), leu (2.05), lys (2.05), phe (2.05), pro (2.05), ser (2.05), thr (2.05), tyr(65), trp (2.05), val (2.05) |
| 79 | His | ala (2.05), arg (2.05), asn (2.05), asp (2.05), gln (2.05), glu (2.05), gly (2.05), his (65), ile (2.05), leu (2.05), lys (2.05), phe (2.05), pro (2.05), ser (2.05), thr (2.05), tyr(2.05), trp (2.05), val (2.05) |
| 80 | Val | ala (2.05), arg (2.05), asn (2.05), asp (2.05), gln (2.05), glu (2.05), gly (2.05), his (2.05), ile (2.05), leu (2.05), lys (2.05), phe (2.05), pro (2.05), ser (2.05), thr (2.05), tyr(2.05), trp (2.05), val (65) |
| 81 | Tyr | ala (2.05), arg (2.05), asn (2.05), asp (2.05), gln (2.05), glu (2.05), gly (2.05), his (2.05), ile (2.05), leu (2.05), lys (2.05), phe (2.05), pro (2.05), ser (2.05), thr (2.05), tyr(65), trp (2.05), val (2.05) |
| 82 | Arg | ala (2.05), arg (65), asn (2.05), asp (2.05), gln (2.05), glu (2.05), gly (2.05), his (2.05), ile (2.05), leu (2.05), lys (2.05), phe (2.05), pro (2.05), ser (2.05), thr (2.05), tyr(2.05), trp (2.05), val (2.05) |
| 83 | Ser | ala (2.05), arg (2.05), asn (2.05), asp (2.05), gln (2.05), glu (2.05), gly (2.05), his (2.05), ile (2.05), leu (2.05), lys (2.05), phe (2.05), pro (2.05), ser (65), thr (2.05), tyr(2.05), trp (2.05), val (2.05) |

CIS-display was used to select PSMA binding FN3 domains from TCL25 library. The ITT reactions were incubated with biotinylated recombinant proteins, chimpanzee or cyno monkey PSMA. The biotinylated recombinant proteins and the bound library members were captured on neutravidin or streptavidin coated magnetic beads. Unbound library members were removed by successive washes with TBST and TBS. After washing, DNA was eluted from the target protein by heating to 85° C. for 10 minutes and amplified by PCR for further rounds of panning. FN3 domain binders were isolated by successively lowering the concentration of target PSMA during each round from 400 nM to 100 nM and increasing the washing stringency.

Outputs from the second round selection were subjected to four rounds of off-rate selection. After the ITT reactions were incubated biotinylated recombinant PSMA proteins, the proteins and the bound library members were captured on neutravidin or streptavidin coated magnetic beads, and washed in TBST extensively, the bound complexes were washed in 5 µM cold recombinant PSMA proteins for 1 hour. Then the ITT bound to beads were washed extensively in TBST and TBS before being eluted. The biotinylated target antigen concentration was stepped down from 25 nM in rounds 3 and 4 to 2.5 nM in rounds 5 and 6. Selection outputs from rounds 7 and 9 were subcloned into the modified pET15 vector for expression and screening.

Biochemical Screening for FN3 Domains that Bind PSMA

Neutravidin-coated plates were blocked for 1 h in Starting Block T20 (Pierce) and then coated with biotinylated PSMA (using same antigen as in panning) or negative control for 1 h. Plates were rinsed with TBST and diluted lysate was applied to plates for 1 h. Following additional rinses, wells were treated with HRP-conjugated anti-FN3 domain antibody (PAB25) for 1 h and then assayed with POD (Roche). FN3 domains with signals at least 10-fold above background were selected for further analysis.

Size Exclusion Chromatography Analysis

Size exclusion chromatography was used to determine the aggregation state of PSMA binding FN3 domains. Aliquots (10 µL) of each purified FN3 domain were injected onto a SUPERDEX® 75 5/150 column (GE Healthcare) at a flow rate of 0.3 mL/min in a mobile phase of PBS pH 7.4. Elution from the column was monitored by absorbance at 280 nm. Wild type TENCON™ was included in each run as a control. AGILENT® ChemStation software (Rev. B. 04.02) was used to analyse the elution profiles. Only those proteins with elution profiles similar to that of wild type protein in the same run were considered for further characterization.

High-Throughput Expression, Conjugation and Purification of FN3 Domains

Isolated clones from unique hits identified by biochemical binding ELISA were combined into a single hit plate for growth in 96-well block plates; clones grew in 1 mL cultures (LB media supplemented with kanamycin for selection) at 37° C. overnight with shaking. For protein expression in 96-block plates, 1 mL TB media supplemented with kanamycin was inoculated with 50 uL of the overnight culture and grown at 37° C. with continual shaking at 300 rpm until OD600=0.6-1. Once the target OD was reached, protein expression was induced with addition of IPTG to 1 mM; plates were transferred to 30° C. (300 rpm) for overnight growth. Overnight cultures were centrifuged to harvest the cells; bacterial pellets were stored at −80° C. until ready for use. Both positive and negative controls were included in replicate on every plate.

For conjugation to the sortase tag, bacterial pellets were thawed, resuspended and lysed in BUGBUSTER® HT (EMD Catalog #70922) supplemented with recombinant human lysozyme (EMD, Catalog #71110). Lysis proceeded at room temperature with gentle agitation, after which the plate was transferred to a 42° C. to precipitate host proteins. Debris was pelleted by centrifugation, and supernatants were transferred to a new block plate for sortase-catalyzed labeling. A master mix containing Gly3-vc-MMAF (Concortis), tagless SortaseA, and sortase buffer (Tris, sodium chloride, and calcium chloride) was prepared at a 2× concentration and added in equal volume to the lysate supernatants. The labeling reaction proceeded for two hours at room temperature, after which proteins were purified using a Ni-NTA multi-trap HP plate (GE Catalog #28-4009-89). Protein conjugates were recovered by step elution with imidazole-containing elution buffer (50 mM Tris pH7.5, 500 mM NaCl, 250 mM imidazole), filter sterilized and used directly for cell based cytotoxicity assays.

High-Throughput Cytotoxicity Assay of FN3 Domain-Drug Conjugates 96-well black tissue culture-coated plates (BD/Corning Catalog #353219) were seeded with LNCaP FGC cells (ATCC, Catalog #CRL-1740) at a density of 10,000 cells/well in assay media (phenol red-free RPMI (Life Technologies Catalog #11835-030) supplemented with 5% fetal bovine serum). Seeded plates were incubated overnight at 37° C. with 5% CO2 to allow for cell attachment. Twenty-four hours later, CDCs were diluted in assay media (1:100, 1:300, 1:1000, or 1:3000) and applied directly to LNCaP cells. LNCaP cells then incubated at 37° C., 5% CO2 for 66-72 h. Cell toxicity was assessed using CellTiter-Glo reagent (Promega, Catalog #G7571); 100 μL prepared reagent was added directly to treated wells and incubated for ten minutes with gentle shaking, protected from light. Luminescence was measured using a SpectraMax M5 plate reader. Values were normalized to untreated controls and selected for further analysis if more than 50% toxicity was achieved.

Example 4: Characterization of Anti-PSMA FN3 Domains

Large-Scale Expression and Purification

Gene sequences encoding FN3 Domain mutants were discovered through panning and cloned into the pET15b vector for expression under the T7 promoter or produced by DNA2.0 and subcloned into pJexpress401 vector (DNA2.0) for expression under the T5 promoter. The resulting plasmids were transformed into E. coli BL21 Gold (Agilent) or BL21DE3 Gold (Agilent) for expression. A single colony was picked and grown in Luria Broth (Teknova) supplemented with kanamycin and incubated 18 h at 37° C. 250 RPM. One liter Terrific Broth (TEKNOVA™), supplemented with kanamycin, was inoculated from these subcultures and grown at 37° C. for 4 h while shaking. Protein expression was induced with 1 mM IPTG, once the optical density at the absorption of 600 nm reached 1.0. The protein was expressed for 4 h at 37° C. or 18 h at 30° C. Cells were harvested by centrifugation at 6000 g and stored at −20 C until purification. The frozen cell pellet (~15-25 g) was thawed for 30 min at room temperature and suspended in BUGBUSTER® HT protein extraction reagent (EMD Millipore) supplemented with 0.2 mg/ml recombinant lysozyme (Sigma) at 5 ml per gram of cell paste and incubated for 1 h on a shaker at room temperature. The lysate was clarified by centrifugation at 74 600 g for 25 min. The supernatant was applied onto a 5 ml Qiagen Ni-NTA cartridge immersed in ice at a flow rate of 4 ml/min using an AKTA™ AVANT chromatography system. All other Ni-NTA chromatography steps were performed at flow rate 5 ml/min. The Ni-NTA column was equilibrated in 25.0 ml of 50 mM Tris-HCl buffer, pH 7.0 containing 0.5 M NaCl and 10 mM imidazole (Buffer A). After loading, the column was washed with 100 ml of Buffer A, followed by 100 ml of 50 mM Tris-HCl buffer, pH7.0 containing 10 mM imidazole, 1% CHAPS and 1% n-octyl-β-D-glucopyranoside detergents, and 100 ml Buffer A. The protein was eluted with Buffer A supplemented with 250 mM imidazole and loaded on a preparative gel-filtration column, TSK Gel G3000SW 21.5×600 mm (Tosoh) equilibrated in PBS (Gibco). The gel-filtration chromatography was performed at room temperature in PBS at flow rate 10 ml/min using an AKTA-AVANT chromatography system.

Determination of Thermal Stability

Thermal stability was measured by capillary DSC. Each sample was diluted in PBS pH 7.4 to a concentration of 1 mg/ml. Melting temperatures were measured for these samples using a VP-DSC instrument equipped with an autosampler (MicroCal, LLC). Samples were heated from 10 to 95° C. or 100° C. at a rate of 1° C. per minute. A buffer only scan was completed between each sample scan in order to calculate a baseline for integration. Data were fit to a two-state unfolding model following subtraction of the buffer only signal. Reversibility of thermal denaturation was determined by repeating the scan for each sample without removing it from the cell.

Selective Cytotoxicity of Anti-PSMA FN3 Domain Drug Conjugates on PSMA+Cells

FN3 domains were conjugated to vc-MMAF through either cysteine-maleimide chemistry (Brinkley, Bioconjugate Chemistry 3: 2-13, 1992) or using the sortase reaction described above. Cytotoxicity of FN3 domain-vcMMAF conjugates was assessed in LNCaP, VCAP, MDA-PC-2B, and PC3 cells in vitro. Cells were plated in 96 well black plates for 24 h and then treated with variable doses of FN3 domain-vcMMAF conjugates. Cells were allowed to incubate with FN3 domain drug conjugates (FDDCs) for 66-72 h. CellTiterGlo was used to assess toxicity, as described above. Luminescence values were imported into Excel, from which they were copied and pasted into Prism for graphical analysis. Data were transformed using X=Log(x), then analyzed using nonlinear regression, applying a 3-parameter model to determine $IC_{50}$.

Table 8 summarizes the unique hits identified through panning, spanning multiple sequence families. FN3 domains exhibited thermal stabilities between 55° to 85° C. and were cytotoxic to LNCaP cells when conjugated to vcMMAF, with $IC_{50}$ values from 22.6-0.38 nM. Table 9, 10 and 11 shows the BC, C, CD, F and FG loop amino acid sequences of select clones. Table 12 shows the amino acid sequences of the clines.

TABLE 8

| Clone ID | SEQ ID NO: | Antigen species | LNCaP $IC_{50}$ (nM) | Tm (°C) |
|---|---|---|---|---|
| P229CR5P819_H11 | 40 | Chimp | 20.7 | 78.1 |
| P258AR6P1071_G03 | 35 | Cyno | 5.8 | 83.1 |
| P258AR6P1070_A05 | 36 | Cyno | 4.6 | 83 |
| P258AR6P1071_F04 | 37 | Cyno | 5.4 | 80.8 |
| P258AR6P1070_F09 | 38 | Cyno | 0.9 | 79.8 |
| P258AR6P1071_D02 | 39 | Cyno | 0.8 | 78.5 |
| P234CR9_H01 | 46 | Cyno | 22.6 | 74.1 |
| P234CR9_A7 | 45 | Cyno | 8.8 | ND |
| P233FR9_H10 | 41 | Chimp | 0.4 | 65.5 |
| P233FR9P1001_D9 | 44 | Chimp | 1.4 | 58.1 |
| P233FR9P1001_B5-5 | 42 | Chimp | 0.5 | 65 |
| P233FR9P1001_H3-1 | 43 | Chimp | 0.4 | 64.5 |

TABLE 9

| Clone ID | BC loop SEQ ID NO: | Sequence | C loop SEQ ID NO: | Sequence | SEQ ID NO: |
|---|---|---|---|---|---|
| P229CR5P819_H11 | 40 | DIDEQRDW | 56 | FDSFLIQYQE | 63 |
| P258AR6P1071_G03 | 35 | DIDEQRDW | 56 | FDSFLIQYQE | 63 |
| P258AR6P1070_A05 | 36 | TIDEQRDW | 57 | FDSFLIQYQE | 63 |
| P258AR6P1071_F04 | 37 | VIDEQRDW | 58 | FDSFLIQYQE | 63 |
| P258AR6P1070_F09 | 38 | TIDEQRDW | 57 | FESFLIQYQE | 64 |
| P258AR6P1071_D02 | 39 | AIDEQRDW | 59 | FESFLIQYQE | 64 |
| P234CR9_H01 | 46 | EWWVIPGD | 60 | FDSFLIQYQE | 63 |
| P234CR9_A7 | 45 | GEQFTI | 61 | FDSFLIQYQE | 63 |
| P233FR9_H10 | 41 | TAPDAA | 62 | FDSFAIGYWE | 65 |
| P233FR9P1001_D9 | 44 | TAPDAA | 62 | FDSFPIGYWE | 66 |
| P233FR9P1001_B5-5 | 42 | TAPDAA | 62 | FDSFTIGYWE | 67 |
| P233FR9P1001_H3-1 | 43 | TAPDAA | 62 | FDSFPIGYWE | 66 |

TABLE 10

| Clone ID | CD loop SEQ ID NO: | Sequence | F loop SEQ ID NO: | Sequence | SEQ ID NO: |
|---|---|---|---|---|---|
| P229CR5P819_H11 | 40 | SEKVGE | 68 | TEYTVSIYGV | 70 |
| P258AR6P1071_G03 | 35 | SEKVGE | 68 | TEYTVSIYGV | 70 |
| P258AR6P1070_A05 | 36 | SEKVGE | 68 | TEYTVSIYGV | 70 |
| P258AR6P1071_F04 | 37 | SEKVGE | 68 | TEYTVSIYGV | 70 |
| P258AR6P1070_F09 | 38 | SEKVGE | 68 | TEYTVSIYGV | 70 |
| P258AR6P1071_D02 | 39 | SEKVGE | 68 | TEYTVSIYGV | 70 |
| P234CR9_H01 | 46 | SEKVGE | 68 | TEYTVSIYGV | 70 |
| P234CR9_A7 | 45 | SEKVGE | 68 | TEYTVSIYG | 71 |
| P233FR9_H10 | 41 | WDDDGE | 69 | TEYPVYIAGV | 72 |
| P233FR9P1001_D9 | 44 | WDDDGE | 69 | TEYWVYIAGV | 73 |
| P233FR9P1001_B5-5 | 42 | WDDDGE | 69 | TEYPVYIAGV | 72 |
| P233FR9P1001_H3-1 | 43 | WDDDGE | 69 | TEYHVYIAGV | 74 |

TABLE 11

| Clone ID | SEQ ID NO: | FG loop Sequence | SEQ ID NO: |
|---|---|---|---|
| P229CR5P819_H11 | 40 | YHVYRSSN | 75 |
| P258AR6P1071_G03 | 35 | YHVYRSN | 76 |
| P258AR6P1070_A05 | 36 | YHVYRSN | 76 |
| P258AR6P1071_F04 | 37 | YHVYRSN | 76 |
| P258AR6P1070_F09 | 38 | YHVYRSN | 76 |
| P258AR6P1071_D02 | 39 | YHVYRSN | 76 |
| P234CR9_H01 | 46 | VNSGQWNDTSN | 77 |
| P234CR9_A7 | 45 | ASGYEWFHAFGSSN | 78 |
| P233FR9_H10 | 41 | KGGQWSF | 79 |
| P233FR9P1001_D9 | 44 | KGGQWSF | 79 |
| P233FR9P1001_B5-5 | 42 | KGGQWSF | 79 |
| P233FR9P1001_H3-1 | 43 | KGGQWSF | 79 |

TABLE 12

| Clone ID | SEQ ID NO: | Clone Sequence |
|---|---|---|
| P229CR5P819_H11 | 40 | LPAPKNLVVSRVTEDSARLSWDIDEQRDWFDSFLIQYQESEKVGEAIVLTVPGSERSYDLTGLKPGTEYTVSIYGVYHVYRSSNPLSAIFTT |
| P258AR6P1071_G03 | 35 | LPAPKNLVVSRVTEDSARLSWDIDEQRDWFDSFLIQYQESEKVGEAIVLTVPGSERSYDLTGLKPGTEYTVSIYGVYHVYRSNPLSAIFTT |
| P258AR6P1070_A05 | 36 | LPAPKNLVVSRVTEDSARLSWTIDEQRDWFDSFLIQYQESEKVGEAIVLTVPGSERSYDLTGLKPGTEYTVSIYGVYHVYRSNPLSAIFTT |
| P258AR6P1071_F04 | 37 | LPAPKNLVVSRVTEDSARLSWVIDEQRDWFDSFLIQYQESEKVGEAIVLTVPGSERSYDLTGLKPGTEYTVSIYGVYHVYRSNPLSAIFTT |
| P258AR6P1070_F09 | 38 | LPAPKNLVVSRVTEDSARLSWTIDEQRDWFESFLIQYQESEKVGEAIVLTVPGSERSYDLTGLKPGTEYTVSIYGVYHVYRSNPLSAIFTT |

TABLE 12-continued

| Clone ID | SEQ ID NO: | Sequence |
|---|---|---|
| P258AR6P1071_D02 | 39 | LPAPKNLVVSRVTEDSARLSWAIDEQRDWFESFL IQYQESEKVGEAIVLTVPGSERSYDLTGLKPGTE YTVSIYGVYHVYRSNPLSAIFTT |
| P234CR9_H01 | 46 | LPAPKNLVVSRVTEDSARLSWEWWVIPGDFDSFL IQYQESEKVGEAIVLTVPGSERSYDLTGLKPGTE YTVSIYGVVNSGQWNDTSNPLSAIFTT |
| P234CR9_A7 | 45 | LPAPKNLVVSRVTEDSARLSWGEQFTIFDSFLIQ YQESEKVGEAIVLTVPGSERSYDLTGLKPGTEYT VSIYGASGYEWPHAFGSSNPLSAIFTT |
| P233FR9_H10 | 41 | LPAPKNLVVSRVTEDSARLSWTAPDAAFDSFAIG YWEWDDDGEAIVLTVPGSERSYDLTGLKPGTEYP VYIAGVKGGQWSFPLSAIFTT |
| P233FR9P1001_D9 | 44 | LPAPKNLVVSRVTEDSARLSWTAPDAAFDSFPIG YWEWDDDGEAIVLTVPGSERSYDLTGLKPGTEYW VYIAGVKGGQWSFPLSAIFTT |
| P233FR9P1001_B5-5 | 42 | LPAPKNLVVSRVTEDSARLSWTAPDAAFDSFTIG YWEWDDDGEAIVLTVPGSERSYDLTGLKPGTEYP VYIAGVKGGQWSFPLSAIFTT |
| P233FR9P1001_H3-1 | 43 | LPAPKNLVVSRVTEDSARLSWTAPDAAFDSFPIG YWEWDDDGEAIVLTVPGSERSYDLTGLKPGTEYH VYIAGVKGGQWSFPLSAIFTT |

Select drug conjugates were tested across a panel of cell lines. Table 13 shows the $IC_{50}$ values for several FN3 domains conjugated to vcMMAF. Data represent averages between one and nine curve fits. Data are presented as average±SEM. CDCs were most potent in LNCaP cells, a line known to express high levels of PSMA. CDCs were also active in MDA-PCA-2B and VCAP cells, prostate cancer lines with lower levels of PSMA. No activity was observed in PC3 cells, a PSMA negative cell line, demonstrating selectivity.

TABLE 13

Cytotoxicity Assays of FN3 domain-Drug-Conjugates

| Clone | SEQ ID NO: | LNCaP cells $IC_{50}$ (nM) | MDA-PCA-2B cells $IC_{50}$ (nM) | VCAP cells $IC_{50}$ (nM) | PC3 cells $IC_{50}$ (nM) |
|---|---|---|---|---|---|
| P233FR9P1001-H3-1 | 43 | 0.4 | 4.6 ± 1.2 | 15.2 ± 1.0 | >500 |
| P234CR9_H01 | 46 | 22.6 | 150.8 ± 4.4 | 401.0 ± 130.0 | >500 |
| P233FR9_H10 | 41 | 0.5 ± 0.1 | 5.8 ± 2.3 | 25.9 ± 15.0 | >500 |
| P229CR5P819_H11 | 40 | 9.3 ± 1.9 | 106.8 ± 13.6 | 231.0 ± 38.0 | >500 |

Example 5: Engineering of Anti-PSMA FN3 Domains Cysteine Scan

Genes encoding anti-PSMA FN3 Domain, P233FR9_10 with cysteine residues introduced at various positions in the protein were obtained from DNA2.0 and used to express and purify proteins as described above. The resulting FN3 domains were evaluated for thermal stability (with and without vcMMAF conjugate) and LNCaP cytotoxicity, as described above. Results are summarized in Table 14.

TABLE 14

| Clone ID | SEQ ID NO: | Cysteine location* | Thermal stability (NEM capped) | Thermal Stability (vcMMAF conjugated) | LNCaP cytotoxicity ($IC_{50}$; nM) |
|---|---|---|---|---|---|
| P233FR9_H10 (c-term) | 47 | c-terminal | TBD | TBD | ND |
| P233FR9_H10 (K62C) | 51 | K62 | 56.91 | 54.03 | 0.69 |
| P233FR9_H10 (R11C) | 50 | R11 | 65.72 | 63.58 | 0.40 |
| P233FR9_H10 (E53C) | 49 | E53 | 66.75 | 65.98 | 0.66 |

*Residue numbering according to SEQ ID NO: 41

Example 6: Imaging Biodistribution of Untargeted FN3 Domains

A FN3 domain with no specific binding to a target antigen engineered to contain a cysteine at position 62 was conjugated to DOTA and then a zirconium-89 radioisotope at IsoTherapeutics Group, LLC (Angleton, Tex.). Castrated male NSG mice were (Jackson laboratories) were anesthetized with 1.5% isoflurane and imaged in a Siemens Inveon microPET/CT. Mice were administered approximately 0.2 mCi [89Zr] FN3 Domain (SEQ ID 51) via tail vein injection (made up to a 1 mg/kg dose with cold FN3 domain) and imaged continuously for the first 60 minutes, and then at 3, 6 and 24 hrs post injection of the FN3 domain.

Three-dimensional PET images were reconstructed using a 2D ordered-subsets expectation maximization algorithm (Siemens Healthcare, Knoxville, Tenn.) into a 768×768×512 tomographic volume, with voxel size 0.107 mm×0.107 mm×0.107 mm. Images were processed and analyzed using PMOD v3.0 software (PMOD Technologies, Zurich, Switzerland). A cylinder of known activity was scanned in the PET scanner to provide a cross-calibration between injected dose measured by the dose calibrator, and counts per voxel in the PET images. Each PET image was co-registered to the CT image, to provide anatomical reference, using PMOD image fusion software. Regions of interest (ROI) were drawn around every 4th section for each tissue being analyzed. Mean counts per voxel were derived, and converted percentage injected dose per gram of body weight, and using the correction factor derived from the calibration cylinder of known activity. All measures of radioactivity were corrected for decay, using the known half-life of Zr-89 (78.41 hours).

FIG. 1 shows the tissue distribution of radiolabeled FN3 domain over time. Rapid accumulation in the kidney and bladder is observed, with only limited accumulation in the liver, suggesting that FN3 domains are cleared through the kidneys.

Example 7: Crystal Structure of Anti-PSMA P233FR9-H10 in Complex with Cyno PSMA The His-tagged P233FR9-H10 FN3 domain (called herein as H10 FN3 domain) was expressed in *E. coli* and purified using affinity and size-exclusion chromatography. The FN3 domain was received in dPBS, pH 7.2.

The cynomolgus PSMA extracellular domain as a C-terminal fusion to the huIgG1 Fc domain was expressed in GnTI⁻ cells and purified by affinity and size-exclusion chromatography. The fusion protein was received in dPBS, 0.5 mM ZnC12, pH 7.2. Then, the Fc domain was removed with a Prescission protease treatment followed by affinity and size-exclusion chromatography. The isolated cynomolgus PSMA (cynoPSMA) extracellular domain was stored in dPBS, 0.5 mM ZnC12, pH 7.2.

The H10 FN3 Domain/cynoPSMA complex was prepared by mixing cynoPSMA with H10 FN3 domain at a molar ratio of 1:3 (excess FN3 domain) while dialyzing for 48 h at 4° C. against 20 mM Hepes pH 7.0, 0.5 mM ZnC12. The complex was then eluted from a monoS column with a gradient of 48-68 mM NaCl, 20 mM Hepes pH 7.5, 10% glycerol and concentrated to 3.4 mg/mL. Crystals suitable for X-diffraction were obtained from 25% PEG 3 kDa, 0.2 M NH$_4$Cl, 0.1 M Na Acetate pH 4.5 using the sitting drop vapor-diffusion method at 20° C.

For X-ray data collection, the crystal was soaked for a few seconds in a cryo-protectant solution containing mother liquor supplemented with 20% glycerol, and then frozen in liquid nitrogen. X-ray diffraction data were collected with a Dectris Pilatus 6M Pixel Array detector at the beamline 17-ID of the Advanced Photon Source (APS) at Argonne National Laboratory. Diffraction data were processed with the program HKL2000 (Otwinowski & Minor, 1997). X-ray data statistics are given in Table 15.

The structure was solved by molecular replacement (MR) with Phaser (Read, 2001). The search models for MR were the crystal structures of human PSMA (PDB code 2C6G) and the structure of P114AR7P94-A3 W33A FN3 domain. The structures were refined with PHENIX (Adams et al, 2004) and model adjustments were carried out using COOT (Emsley & Cowtan, 2004). All other crystallographic calculations were performed with the CCP4 suite of programs (CCP4, 1994). All molecular graphics were generated with PyMol (DeLano, 2002). The structure refinement statistics are given in Table 15.

TABLE 15

|  | PS42 |
| --- | --- |
| Crystal data | |
| Crystallization solution | |
| 0.1 M Buffer | Acetate pH 4.5 |
| Precipitant | 25% PEG 3 kDa |
| Additive | 0.2 M NH$_4$Cl |
| Space group | P2$_1$2$_1$2 |
| Complex/asym.unit | 2 |
| Unit cell | |
| a (Å) | 84.0 |
| b (Å) | 109.9 |
| c (Å) | 261.6 |
| V$_m$ (Å$^3$/Da) | 3.32 |
| Solvent content (%) | 63 |
| X-ray data* | |
| Resolution (Å) | 50.00-2.80 |
| High Resolution Shell (Å) | (2.85-2.80) |
| Measured reflections | 335,467 |
| Unique reflections | 57,166 |
| Completeness (%) | 93.2 (69.3) |
| Redundancy | 5.9 (4.4) |
| Rsym (%) | 25.1 (64.1) |
| <I/σ> | 6.4 (1.6) |
| Refinement | |
| Resolution (Å) | 40.0-2.8 |
| Number of reflections | 57,063 |
| Number of all atoms | 12,330 |
| Number of waters | 8 |
| Rfactor (%) | 25.14 |
| Rfree (%) | 31.28 |
| RMSD | |
| bond lengths (Å) | 0.003 |
| bond angles (°) | 0.998 |
| Average B-factor (Å$^2$) | 78.9 |
| Ramachandran Plot | |
| favored region (%) | 94.9 |
| allowed region (%) | 4.8 |
| outliers (%) | 0.3 |

*Values for high resolution shell are in parenthesis.

The structure of the homodimeric cynoPSMA includes residues 57-750, corresponding to the protease (residues 57-116 and 352-590), apical (residues 117-351) and helical (residues 591-750) domains, and eight of eleven possible N-linked glycans (in Asn-76, -121, -140, -195, -459, -476, -613, and -638) per dimer subunit. The cynoPSMA active site is located at the interface between the three domains and it contains two zinc atoms coordinated by histidine (H377 and H553) and glutamate/aspartate (D387, catalytic E424, E425, and D453) residues and a water molecule. The H10 FN3 domain (SEQ ID NO: 41) structure contains residues 2-92. H10 residues are numbered sequentially according to SEQ ID NO: 41. cynoPSMA residues are numbered according to the full length cyno PSMA sequence of SEQ ID NO: 141. The mature cynoPSMA (without signal peptide) starts at residue 44 of SEQ ID NO: 141.

Figure 2A:
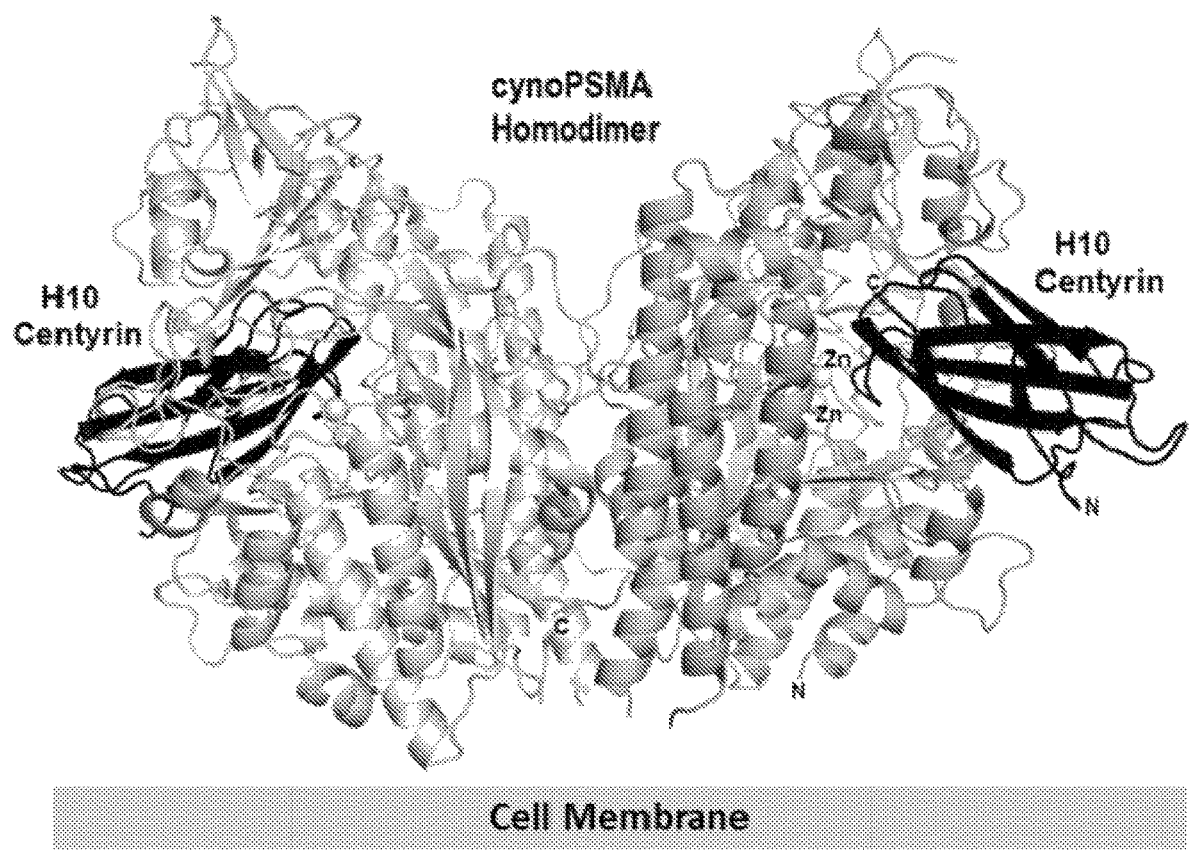
FIGS. 2A, 2B and 2C.

There is one cynoPSMA homodimer in the asymmetric unit with one H10 FN3 domain bound to each PSMA subunit (FIG. 2A). The two FN3 domain/PSMA complexes are structurally very similar as indicated by the root mean square deviation (r.m.s.d.) of 0.72 Å for the superposition of all equivalent atoms in the PSMA subunits. Also, there is a high degree of structural similarity between human and cynomolgus PSMA and absence of large conformational changes induced by the FN3 domain binding, as indicated by a r.m.s.d of 0.5 Å for the Cα atom superposition between the cynoPSMA molecule in the FN3 domain complex and unbound human PSMA (PDB code 2OOT, structure at 1.6 Å resolution). An interesting feature is that the loop region 541-547 is visible only in the cynomolgus protein due to stabilization of the loop conformation through interactions with the FN3 domain.

The FN3 domain/PSMA combining site is well defined by the $2F_{obs}$-$F_{calc}$ electron density map, which allows reliable positioning of the binding residues. Only the interactions between the B and C chains (PSMA and FN3 domain chains, respectively) are described in the next section.

The H10 FN3 domain binds to a region near the PSMA active site (FIG. 2A) and covers a cynoPSMA area of about 1,170 Å$^2$. Specifically, the FN3 domain recognizes cynoPSMA residues in the protease (Y460, F488, K499-P502, P504, R511, K514, N540-E542, and N544-F546), apical (residue R181), and helical (residues K610, N613, and I614) domains as shown in FIGS. 3 and 4.

Figure 2B:
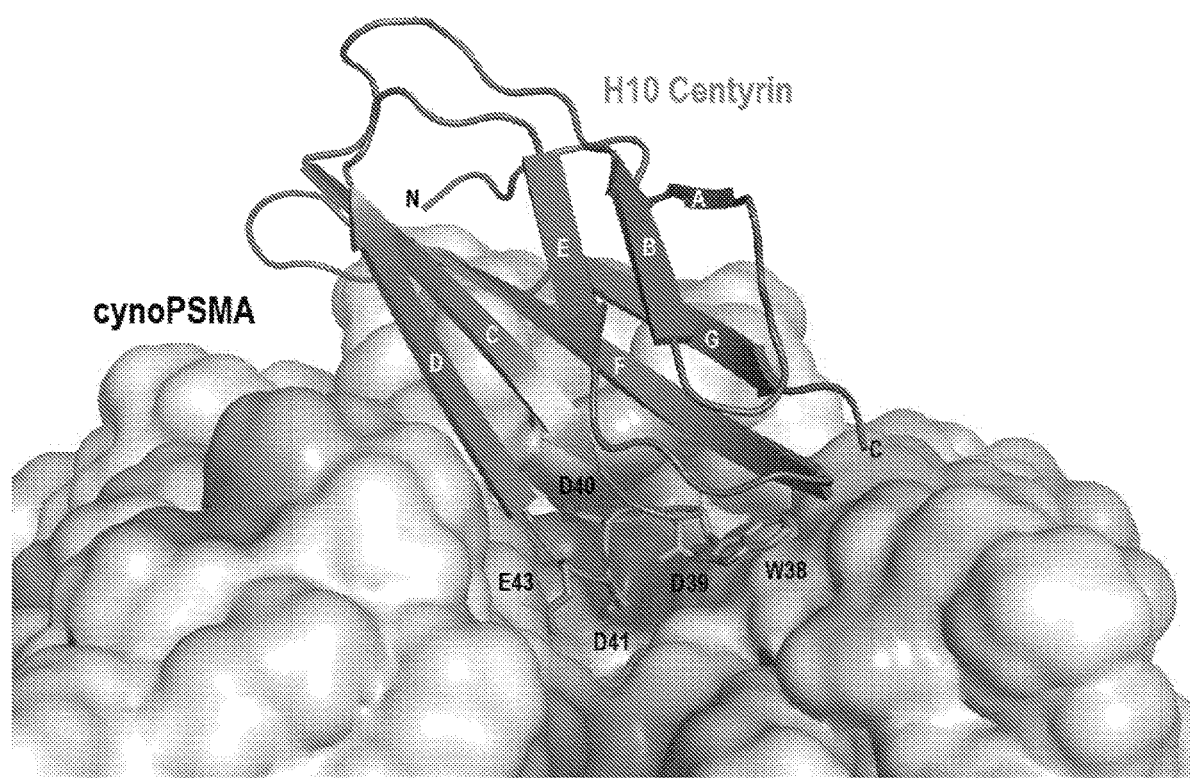
Figure 2C:
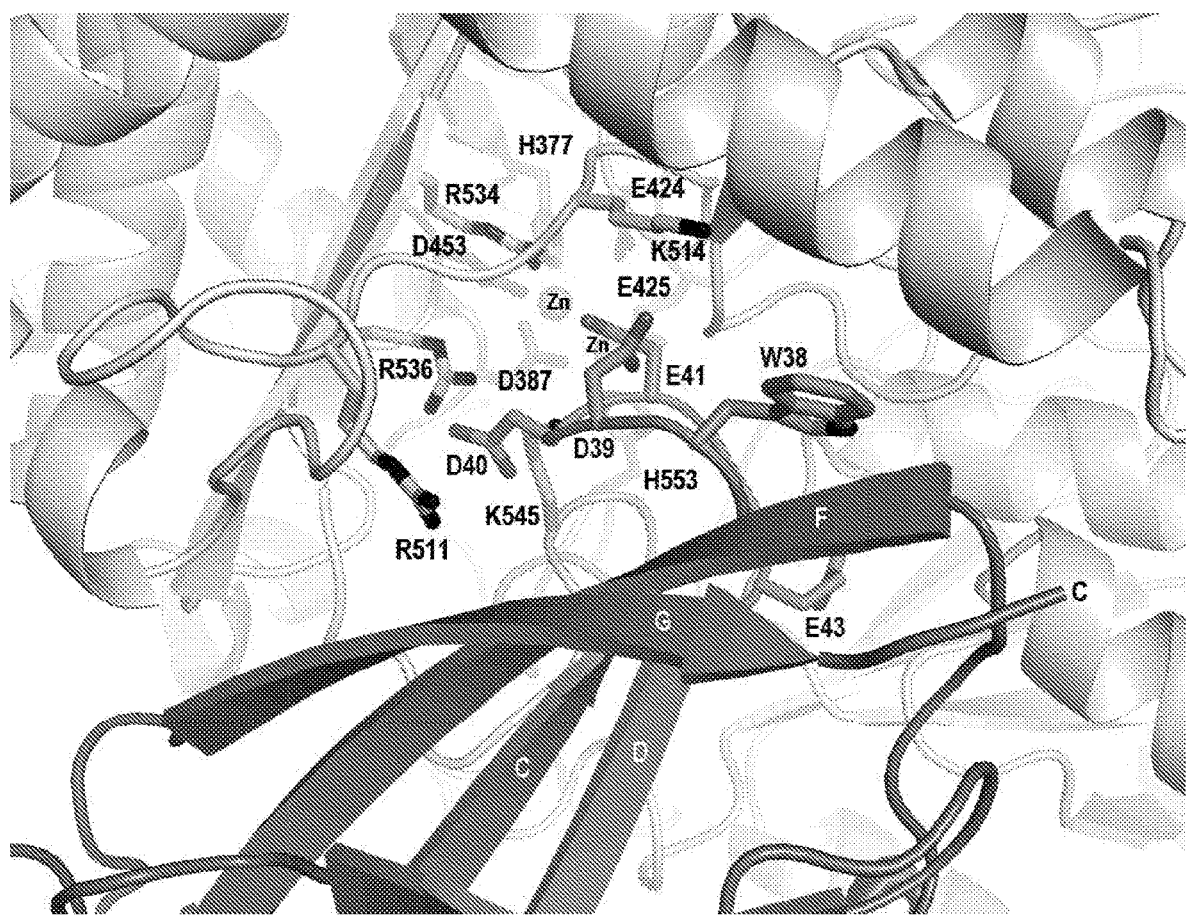

The face of the FN3 domain four-stranded β-sheet packs onto the PSMA surface with the CD loop deeply inserted into the active site entrance (FIGS. 2B and 2C). Specifically, the H10 FN3 domain residues involved in PSMA binding are located in the C (A32 and G34), D (V46), F (G64, P68, Y70, and A72), and G (S84-I86) β-strands and the CD (W36, W38-D41, E43, and A44) and FG loops (W79, F81, and P82). Residues D39, D40, D41, and E43 confer a negative charge to the FN3 domain CD loop and these residues are inserted into the ~20 Å deep, positively charged, funnel that leads to the zinc ions in the active site, likely blocking substrate entrance into the funnel and PSMA enzymatic activity (FIGS. 2B and 2C). However, the FN3 domain does not interact directly with the zinc ions or their coordinating residues.

Figure 3A:
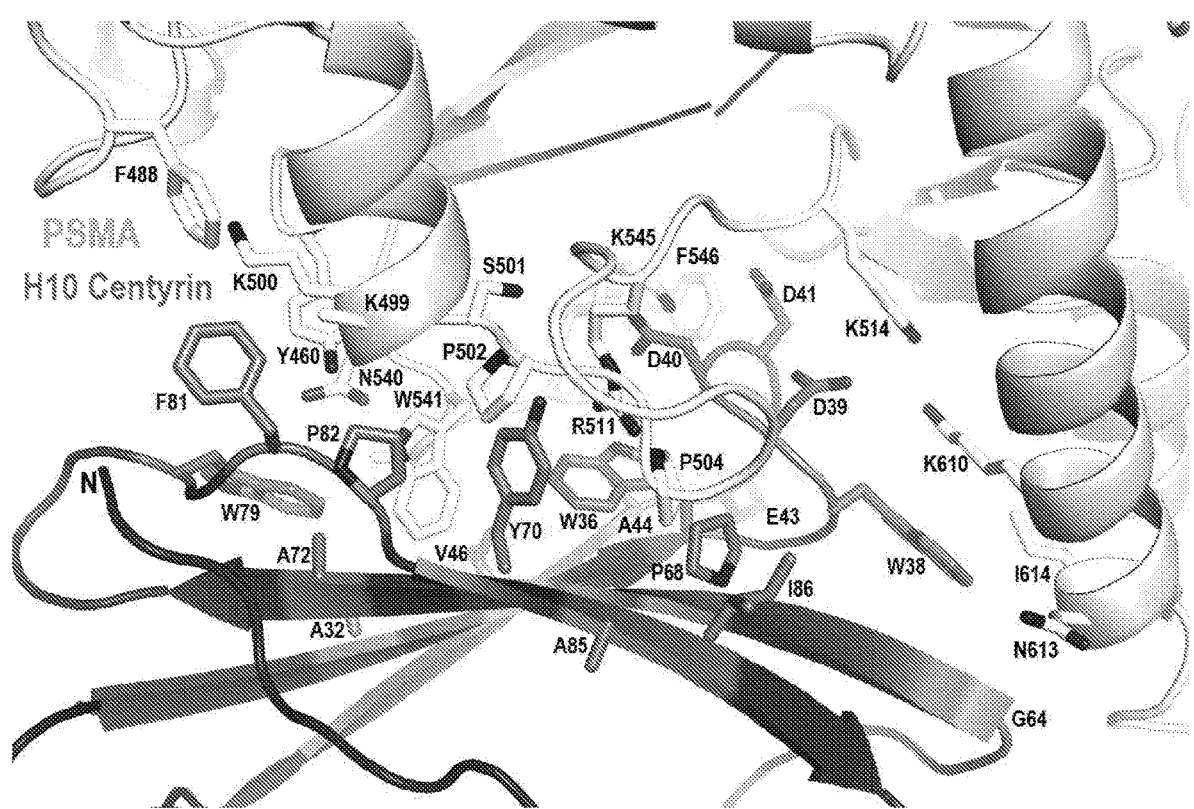
FIGS. 3A and 3B.
Figure 3B:
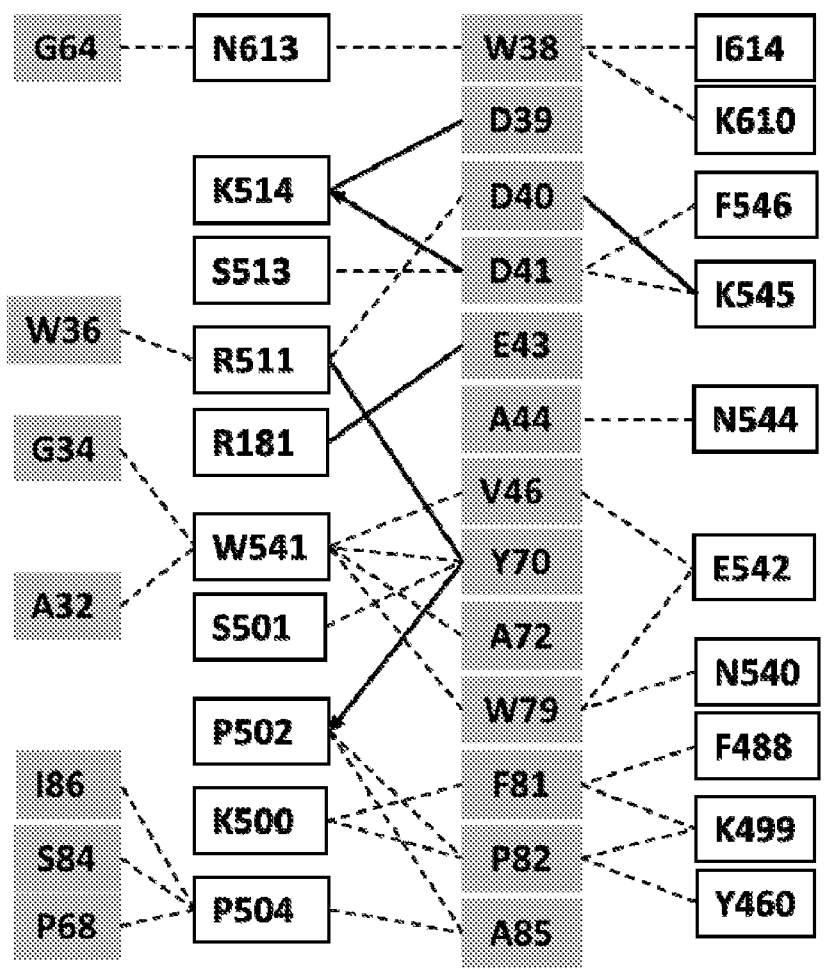

Conserved PSMA residues W541, Y460, F488, P502 and P504 form an aromatic cluster across the combing site with FN3 domain residues W36, P68, Y70, W79, F81, and P82 (FIG. 3A). Conserved R511 is in a central location of the combining site and H bonds Y70, a central residue of the FN3 domain four-stranded β-sheet. FIG. 3B shows a cartoon of the paratope and epitope residues.

Human and cynomolgus PSMA are 97% identical, and, except for a S613N change, all residues interacting with H10 are conserved between the two species (FIG. 4). The S613N change results in N613 glycosylation in cynoPSMA and the gain of van der Waals contacts between the carbohydrate and FN3 domain residues E66, I86, T88 (F and G β-strands) that will not be present in the human enzyme.

FN3 Domain Residues for Conjugation

Figure 5:
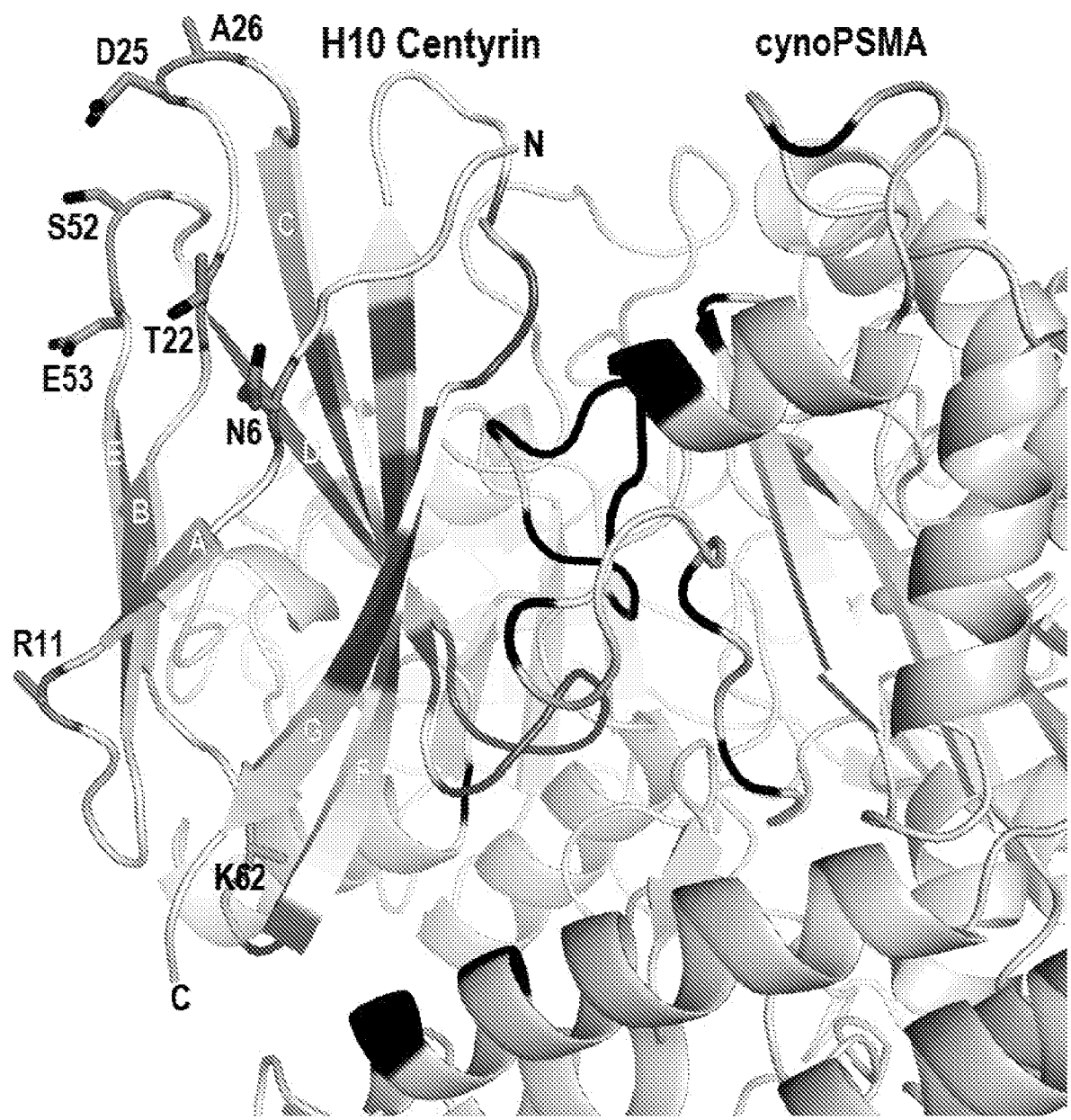
FIG. 5.

Various H10 FN3 domain residues outside the combining site can be modified for conjugation of small molecules (toxic payloads) without disrupting PSMA binding or FN3 domain fold. Cysteines were already placed and conjugated to payloads at the C-terminus (after the His-tag) and at positions R11, E53, and K62 and all of these variants demonstrated similarly potent cytotoxicity. In addition, residues T22, D25, and A26 in the BC loop, terminal residue N6, and S52 in the DE loop are potentially good sites for mutagenesis followed by chemical conjugation (FIG. 5). These solvent exposed residues are away from the FN3 domain/PSMA interface and located in structurally flexible regions.

Furthermore, both N- and C-terminal regions are free for fusions with other protein domains. The N-terminus is oriented towards the PSMA protease domain and reachable with a fusion linker, while the also accessible C-terminus goes towards the PSMA helical domain. The optimal linker length to the FN3 domain fusion partner will depend on the structure of the fusion partner and location of its binding site on the target molecule.

Mechanism of Action

The H10 FN3 domain is a candidate for targeted delivery of payloads (toxic small molecules, nucleic acid, etc.) into prostate cancer cells due to internalization of the FN3 domain/PSMA complex. Furthermore, the H10 FN3 domain is a candidate for redirection of immune cells to prostate cancer cells when in a multispecific format.

H10 FN3 domain is likely to also inhibit the enzymatic activity of PSMA, which may contribute to decreased cell fitness and survival. The FN3 domain/cynoPSMA structure shows the FN3 domain bound to the entrance of the active site, which might prevent substrate interaction with PSMA through steric occlusion and direct competition for the binding site.

Example 8: Generation of Additional Anti-PSMA FN3 Domain Variants

Select anti-PSMA FN3 domain were further engineered to improve properties of the parental FN3 domain. Which, FN3 domains binding to PSMA were generated using libraries described above, and tested for their binding to PSMA.

Table 16 shows the amino acid sequences of the generated molecules.

TABLE 16

| Clone ID | SEQ ID NO: | Sequence |
| --- | --- | --- |
| P258AR6P1071_D02_v1 | 75 | LPAPKNLVVSRVTEDSARLSWAADEQRDWFE SFLIQYQESEKVGEAIVLTVPGSCRSYDLTG LKPGTEYTVSIYGVYHVYRSNPLSAIFTT |
| P258AR6P1071_D02_v2 | 76 | LPAPKNLVVSRVTEDSARLSWAIAEQRDWFE SFLIQYQESEKVGEAIVLTVPGSCRSYDLTG LKPGTEYTVSIYGVYHVYRSNPLSAIFTT |

TABLE 16-continued

| Clone ID | SEQ ID NO: | Sequence |
|---|---|---|
| P258AR6P1071_D02_v3 | 77 | LPAPKNLVVSRVTEDSARLSWAIDAQRDWFE SFLIQYQESEKVGEAIVLTVPGSCRSYDLTG LKPGTEYTVSIYGVYHVYRSNPLSAIFTT |
| P258AR6P1071_D02_v4 | 78 | LPAPKNLVVSRVTEDSARLSWAIDEARDWFE SFLIQYQESEKVGEAIVLTVPGSCRSYDLTG LKPGTEYTVSIYGVYHVYRSNPLSAIFTT |
| P258AR6P1071_D02_v5 | 79 | LPAPKNLVVSRVTEDSARLSWAIDEQADWFE SFLIQYQESEKVGEAIVLTVPGSCRSYDLTG LKPGTEYTVSIYGVYHVYRSNPLSAIFTT |
| P258AR6P1071_D02_v6 | 80 | LPAPKNLVVSRVTEDSARLSWAIDEQRAWFE SFLIQYQESEKVGEAIVLTVPGSCRSYDLTG LKPGTEYTVSIYGVYHVYRSNPLSAIFTT |
| P258AR6P1071_D02_v7 | 81 | LPAPKNLVVSRVTEDSARLSWAIDEQRDAFE SFLIQYQESEKVGEAIVLTVPGSCRSYDLTG LKPGTEYTVSIYGVYHVYRSNPLSAIFTT |
| P258AR6P1071_D02_v8 | 82 | LPAPKNLVVSRVTEDSARLSWAIDEQRDWFE SFLIQYQESEKVGEAIVLTVPGSCRSYDLTG LKPGTEYTVSIYGVAHVYRSNPLSAIFTT |
| P258AR6P1071_D02_v9 | 83 | LPAPKNLVVSRVTEDSARLSWAIDEQRDWFE SFLIQYQESEKVGEAIVLTVPGSCRSYDLTG LKPGTEYTVSIYGVYAVYRSNPLSAIFTT |
| P258AR6P1071_D02_v10 | 84 | LPAPKNLVVSRVTEDSARLSWAIDEQRDWFE SFLIQYQESEKVGEAIVLTVPGSCRSYDLTG LKPGTEYTVSIYGVYHAYRSNPLSAIFTT |
| P258AR6P1071_D02_v11 | 85 | LPAPKNLVVSRVTEDSARLSWAIDEQRDWFE SFLIQYQESEKVGEAIVLTVPGSCRSYDLTG LKPGTEYTVSIYGVYHVARSNPLSAIFTT |
| P258AR6P1071_D02_v12 | 86 | LPAPKNLVVSRVTEDSARLSWAIDEQRDWFE SFLIQYQESEKVGEAIVLTVPGSCRSYDLTG LKPGTEYTVSIYGVYHVYASNPLSAIFTT |
| P258AR6P1071_D02_v13 | 87 | LPAPKNLVVSRVTEDSARLSWAIDEQRDWFA SFLIQYQESEKVGEAIVLTVPGSCRSYDLTG LKPGTEYTVSIYGVYHVYRSNPLSAIFTT |
| P258AR6P1071_D02_v14 | 88 | LPAPKNLVVSRVTEDSARLSWDIDEQRDWFE SFLIQYQESEKVGEAIVLTVPGSCRSYDLTG LKPGTEYTVSIYGVYHVYRSNPLSAIFTT |
| P258AR6P1071_D02_v15 | 89 | LPAPKNLVVSRVTEDSARLSWAIDEQRDWFD SFLIQYQESEKVGEAIVLTVPGSCRSYDLTG LKPGTEYTVSIYGVYHVYRSNPLSAIFTT |
| P258AR6P1071_D02_v16 | 90 | LPAPKNLVVSRVTEDSARLSWAIDEQRDWFE SFLIQYQESEKVGEAIVLTVPGSCRSYDLTG LKPGTEYTVSIYGVYHVYRSSNPLSAIFTT |
| P258AR6P1071_D02_v17 | 91 | LPAPKNLVVSRVTEDSARLSWDIDEQRDWFD SFLIQYQESEKVGEAIVLTVPGSCRSYDLTG LKPGTEYTVSIYGVYHVYRSNPLSAIFTT |
| P258AR6P1071_D02_v18 | 92 | LPAPKNLVVSRVTEDSARLSWDIDEQRDWFE SFLIQYQESEKVGEAIVLTVPGSCRSYDLTG LKPGTEYTVSIYGVYHVYRSSNPLSAIFTT |
| P258AR6P1071_D02_v19 | 93 | LPAPKNLVVSRVTEDSARLSWAIDEQRDWFD SFLIQYQESEKVGEAIVLTVPGSCRSYDLTG LKPGTEYTVSIYGVYHVYRSSNPLSAIFTT |
| P233FR9_H10_v1 | 94 | LPAPKNLVVSRVTEDSARLSWTAPDAAFDSF AIGYWEWDDDGEAIVLTVPGSCRSYDLTGLK PGTEYRVYIAGVKGGQWSFPLSAIFTT |
| P233FR9_H10_v2 | 95 | LPAPKNLVVSRVTEDSARLSWTAPDAAFDSF AIGYWEWDDDGEAIVLTVPGSCRSYDLTGLK PGTEYKVYIAGVKGGQWSFPLSAIFTT |

TABLE 16-continued

| Clone ID | SEQ ID NO: | Sequence |
| --- | --- | --- |
| P233FR9_H10_v3 | 96 | LPAPKNLVVSRVTEDSARLSWTAPDAAFDSF<br>AIGYWEWDDDGEAIVLTVPGSCRSYDLTGLK<br>PGTEYEVYIAGVKGGQWSFPLSAIFTT |
| P233FR9_H10_v4 | 97 | LPAPKNLVVSRVTEDSARLSWTAPDAAFDSF<br>AIGYWEWDDDGEAIVLTVPGSCRSYDLTGLK<br>PGTEYHVYIAGVKGGQWSFPLSAIFTT |
| P233FR9_H10_v5 | 98 | LPAPKNLVVSRVTEDSARLSWTAPDAAFDSF<br>AIGYWEWDDDGEAIVLTVPGSCRSYDLTGLK<br>PGTEYDVYIAGVKGGQWSFPLSAIFTT |
| P233FR9_H10_v6 | 99 | LPAPKNLVVSRVTEDSARLSWTAPDAAFDSF<br>AIGYWEWDDDGEAIVLTVPGSCRSYDLTGLK<br>PGTEYAVYIAGVKGGQWSFPLSAIFTT |
| P233FR9_H10_v7 | 100 | LPAPKNLVVSRVTEDSARLSWTAPDAAFDSF<br>AIGYWEWDDDGEAIVLTVPGSCRSYDLTGLK<br>PGTEYGVYIAGVKGGQWSFPLSAIFTT |
| P233FR9_H10_v8 | 101 | LPAPKNLVVSRVTEDSARLSWTAPDAAFDSF<br>AIGYWEWDDDGEAIVLTVPGSCRSYDLTGLK<br>PGTEYVVYIAGVKGGQWSFPLSAIFTT |
| P233FR9_H10_v9 | 102 | LPAPKNLVVSRVTEDSARLSWTAPDAAFDSF<br>AIGYWEWDDDGEAIVLTVPGSCRSYDLTGLK<br>PGTEYLVYIAGVKGGQWSFPLSAIFTT |
| P233FR9_H10_v10 | 103 | LPAPKNLVVSRVTEDSARLSWTAPDAAFDSF<br>AIGYWEWDDDGEAIVLTVPGSCRSYDLTGLK<br>PGTEYIVYIAGVKGGQWSFPLSAIFTT |
| P233FR9_H10_v11 | 104 | LPAPKNLVVSRVTEDSARLSWTAPDAAFDSF<br>AIGYWEWDDDGEAIVLTVPGSCRSYDLTGLK<br>PGTEYFVYIAGVKGGQWSFPLSAIFTT |
| P233FR9_H10_v12 | 105 | LPAPKNLVVSRVTEDSARLSWTAPDAAFDSF<br>AIGYWEWDDDGEAIVLTVPGSCRSYDLTGLK<br>PGTEYWVYIAGVKGGQWSFPLSAIFTT |
| P233FR9_H10_v13 | 106 | LPAPKNLVVSRVTEDSARLSWTAPDAAFDSF<br>AIGYWEWDDDGEAIVLTVPGSCRSYDLTGLK<br>PGTEYNVYIAGVKGGQWSFPLSAIFTT |
| P233FR9_H10_v14 | 107 | LPAPKNLVVSRVTEDSARLSWTAPDAAFDSF<br>AIGYWEWDDDGEAIVLTVPGSCRSYDLTGLK<br>PGTEYQVYIAGVKGGQWSFPLSAIFTT |
| P233FR9_H10_v15 | 108 | LPAPKNLVVSRVTEDSARLSWTAPDAAFDSF<br>AIGYWEWDDDGEAIVLTVPGSCRSYDLTGLK<br>PGTEYSVYIAGVKGGQWSFPLSAIFTT |
| P233FR9_H10_v16 | 109 | LPAPKNLVVSRVTEDSARLSWTAPDAAFDSF<br>AIGYWEWDDDGEAIVLTVPGSCRSYDLTGLK<br>PGTEYTVYIAGVKGGQWSFPLSAIFTT |
| P233FR9_H10_v17 | 110 | LPAPKNLVVSRVTEDSARLSWTAPDAAFDSF<br>AIGYWEWDDDGEAIVLTVPGSCRSYDLTGLK<br>PGTEYYVYIAGVKGGQWSFPLSAIFTT |
| P233FR9_H10_v18 | 111 | LPAPKNLVVSRVTEDSARLSWTAPDAAFDSF<br>AIAYWEWDDDGEAIVLTVPGSCRSYDLTGLK<br>PGTEYPVYIAGVKGGQWSFPLSAIFTT |
| P233FR9_H10_v19 | 112 | LPAPKNLVVSRVTEDSARLSWTAPDAAFDSF<br>AISYWEWDDDGEAIVLTVPGSCRSYDLTGLK<br>PGTEYPVYIAGVKGGQWSFPLSAIFTT |
| P233FR9_H10_v20 | 113 | LPAPKNLVVSRVTEDSARLSWTAPDAAFDSF<br>AIGYWEWDTDGEAIVLTVPGSCRSYDLTGLK<br>PGTEYPVYIAGVKGGQWSFPLSAIFTT |
| P233FR9_H10_v21 | 114 | LPAPKNLVVSRVTEDSARLSWTAPDAAFDSF<br>AIGYWEWDSDGEAIVLTVPGSCRSYDLTGLK<br>PGTEYPVYIAGVKGGQWSFPLSAIFTT |

TABLE 16-continued

| Clone ID | SEQ ID NO: | Sequence |
|---|---|---|
| P233FR9_H10_v22 | 115 | LPAPKNLVVSRVTEDSARLSWTAPDAAFDSF<br>AIGYYEWDDDGEAIVLTVPGSCRSYDLTGLK<br>PGTEYPVYIAGVKGGQWSFPLSAIFTT |
| P233FR9_H10_v23 | 116 | LPAPKNLVVSRVTEDSARLSWTAPDAAFDSF<br>AIGYFEWDDDGEAIVLTVPGSCRSYDLTGLK<br>PGTEYPVYIAGVKGGQWSFPLSAIFTT |
| P233FR9_H10_v24 | 117 | LPAPKNLVVSRVTEDSARLSWTAPDAAFDSF<br>AIGYLEWDDDGEAIVLTVPGSCRSYDLTGLK<br>PGTEYPVYIAGVKGGQWSFPLSAIFTT |
| P233FR9_H10_v25 | 118 | LPAPKNLVVSRVTEDSARLSWTAPDAAFDSF<br>AIGYWEYDDDGEAIVLTVPGSCRSYDLTGLK<br>PGTEYPVYIAGVKGGQWSFPLSAIFTT |
| P233FR9_H10_v26 | 119 | LPAPKNLVVSRVTEDSARLSWTAPDAAFDSF<br>AIGYWEFDDDGEAIVLTVPGSCRSYDLTGLK<br>PGTEYPVYIAGVKGGQWSFPLSAIFTT |
| P233FR9_H10_v27 | 120 | LPAPKNLVVSRVTEDSARLSWTAPDAAFDSF<br>AIGYWELDDDGEAIVLTVPGSCRSYDLTGLK<br>PGTEYPVYIAGVKGGQWSFPLSAIFTT |
| P233FR9_H10_v28 | 121 | LPAPKNLVVSRVTEDSARLSWTAPDAAFDSF<br>AIGYWEWDDDGEAIVLTVPGSCRSYDLTGLK<br>PGTEYPVYIAGVKGGQYSFPLSAIFTT |
| P233FR9_H10_v29 | 122 | LPAPKNLVVSRVTEDSARLSWTAPDAAFDSF<br>AIGYWEWDDDGEAIVLTVPGSCRSYDLTGLK<br>PGTEYPVYIAGVKGGQFSFPLSAIFTT |
| P233FR9_H10_v30 | 123 | LPAPKNLVVSRVTEDSARLSWTAPDAAFDSF<br>AIGYWEWDDDGEAIVLTVPGSCRSYDLTGLK<br>PGTEYPVYIAGVKGGQLSFPLSAIFTT |
| P233FR9P1001-H3-1_v1 | 124 | LPAPKNLVVSRVTEDSARLSWTAPDAAFDSF<br>RIGYWEWDDDGEAIVLTVPGSCRSYDLTGLK<br>PGTEYHVYIAGVKGGQWSFPLSAIFTT |
| P233FR9P1001-H3-1_v2 | 125 | LPAPKNLVVSRVTEDSARLSWTAPDAAFDSF<br>KIGYWEWDDDGEAIVLTVPGSCRSYDLTGLK<br>PGTEYHVYIAGVKGGQWSFPLSAIFTT |
| P233FR9P1001-H3-1_v3 | 126 | LPAPKNLVVSRVTEDSARLSWTAPDAAFDSF<br>EIGYWEWDDDGEAIVLTVPGSCRSYDLTGLK<br>PGTEYHVYIAGVKGGQWSFPLSAIFTT |
| P233FR9P1001-H3-1_v4 | 127 | LPAPKNLVVSRVTEDSARLSWTAPDAAFDSF<br>HIGYWEWDDDGEAIVLTVPGSCRSYDLTGLK<br>PGTEYHVYIAGVKGGQWSFPLSAIFTT |
| P233FR9P1001-H3-1_v5 | 128 | LPAPKNLVVSRVTEDSARLSWTAPDAAFDSF<br>DIGYWEWDDDGEAIVLTVPGSCRSYDLTGLK<br>PGTEYHVYIAGVKGGQWSFPLSAIFTT |
| P233FR9P1001-H3-1_v6 | 129 | LPAPKNLVVSRVTEDSARLSWTAPDAAFDSF<br>AIGYWEWDDDGEAIVLTVPGSCRSYDLTGLK<br>PGTEYHVYIAGVKGGQWSFPLSAIFTT |
| P233FR9P1001-H3-1_v7 | 130 | LPAPKNLVVSRVTEDSARLSWTAPDAAFDSF<br>GIGYWEWDDDGEAIVLTVPGSCRSYDLTGLK<br>PGTEYHVYIAGVKGGQWSFPLSAIFTT |
| P233FR9P1001-H3-1_v8 | 131 | LPAPKNLVVSRVTEDSARLSWTAPDAAFDSF<br>VIGYWEWDDDGEAIVLTVPGSCRSYDLTGLK<br>PGTEYHVYIAGVKGGQWSFPLSAIFTT |
| P233FR9P1001-H3-1_v9 | 132 | LPAPKNLVVSRVTEDSARLSWTAPDAAFDSF<br>LIGYWEWDDDGEAIVLTVPGSCRSYDLTGLK<br>PGTEYHVYIAGVKGGQWSFPLSAIFTT |
| P233FR9P1001-H3-1_v10 | 133 | LPAPKNLVVSRVTEDSARLSWTAPDAAFDSF<br>IIGYWEWDDDGEAIVLTVPGSCRSYDLTGLK<br>PGTEYHVYIAGVKGGQWSFPLSAIFTT |

TABLE 16-continued

| Clone ID | SEQ ID NO: | Sequence |
|---|---|---|
| P233FR9P1001-H3-1_v11 | 134 | LPAPKNLVVSRVTEDSARLSWTAPDAAFDSF FIGYWEWDDDGEAIVLTVPGSCRSYDLTGLK PGTEYHVYIAGVKGGQWSFPLSAIFTT |
| P233FR9P1001-H3-1_v12 | 135 | LPAPKNLVVSRVTEDSARLSWTAPDAAFDSF WIGYWEWDDDGEAIVLTVPGSCRSYDLTGLK PGTEYHVYIAGVKGGQWSFPLSAIFTT |
| P233FR9P1001-H3-1_v13 | 136 | LPAPKNLVVSRVTEDSARLSWTAPDAAFDSF NIGYWEWDDDGEAIVLTVPGSCRSYDLTGLK PGTEYHVYIAGVKGGQWSFPLSAIFTT |
| P233FR9P1001-H3-1_v14 | 137 | LPAPKNLVVSRVTEDSARLSWTAPDAAFDSF QIGYWEWDDDGEAIVLTVPGSCRSYDLTGLK PGTEYHVYIAGVKGGQWSFPLSAIFTT |
| P233FR9P1001-H3-1_v15 | 138 | LPAPKNLVVSRVTEDSARLSWTAPDAAFDSF SIGYWEWDDDGEAIVLTVPGSCRSYDLTGLK PGTEYHVYIAGVKGGQWSFPLSAIFTT |
| P233FR9P1001-H3-1_v16 | 139 | LPAPKNLVVSRVTEDSARLSWTAPDAAFDSF TIGYWEWDDDGEAIVLTVPGSCRSYDLTGLK PGTEYHVYIAGVKGGQWSFPLSAIFTT |
| P233FR9P1001-H3-1_v17 | 140 | LPAPKNLVVSRVTEDSARLSWTAPDAAFDSF YIGYWEWDDDGEAIVLTVPGSCRSYDLTGLK PGTEYHVYIAGVKGGQWSFPLSAIFTT |

Example 9: Detection of PSMA Expression on Tumor Cells Using Anti PSMA FN3 Domain Conjugated to Fluorescent Dye This example shows the detection of PSMA present on cells with anti PSMA FN3 domain conjugated to a fluorescent dye. C-terminally His-tagged anti PSMA FN3 domain P233FR9_H10 (SEQ ID NO:49) with a free cysteine at amino acid 53 was conjugated to R-phycoerythrin (PE) (Prozyme catalog # PB31). The PE was activated using sulfo-SMCC (Pierce catalog #22122) for 60 min, and activated PE was separated from free sulfo-SMCC by gel filtration chromatography using SEPHADEX™ G25 and PBS/EDTA buffer. The FN3 domain was reduced using TCEP (Sigma, cat. #646547) for 30 min. The reduced FN3 domain was separated from free TCEP by gel filtration chromatography using SEPHADEX™ G25 and PBS/EDTA buffer. The activated PE was covalently coupled to the reduced FN3 domain for 90 min followed by quenching with N-Ethylmaleimide (Sigma catalog #04260) for 20 min. The "PE-conjugated FN3 domain" was purified by size-exclusion chromatography (SEC) using a Tosoh TSKgel G3000SW column in 100 mM sodium phosphate, 100 mM sodium sulfate, 0.05% sodium azide, pH 6.5 on an AKTA explorer FPLC (General Electric).

The PE-conjugated FN3 domain was tested for sensitivity and specificity using PSMA positive and negative cell lines by flow cytometry and CellSearch Circulating Tumor Cell (CTC) assay. The following prostate cell lines were purchased from ATCC and used to validate the specificity of the anti-PSMA FN3 domain: LNCaP (high PSMA expression), 22Rv1 (low PSMA expression) and PC3 (no PSMA expression).

Detection of PSMA on Cell Lines by Flow Cytometry

Figure 6:
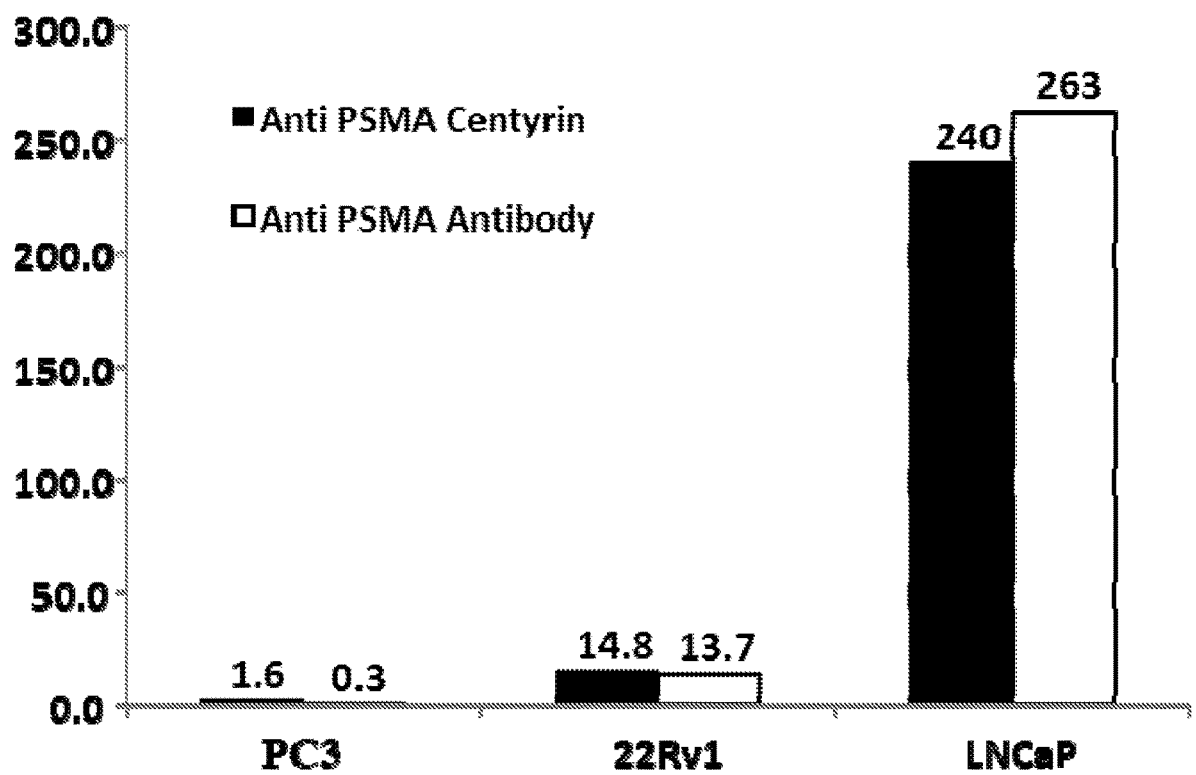
FIG. 6.

Prostate cell lines were harvested using standard cell culture procedures. The cells (~30,000) were stained in 0.1 ml of PBS containing 1% bovine serum albumin (BSA) with PE-conjugated FN3 domain for 20 minutes. Anti PSMA antibody-PE conjugate from Biolegend (clone LNI-17 catalog #342504) was used as a positive control. After the incubation, 3 ml of PBS/BSA buffer was added and unbound PE conjugate was removed by centrifugation at 800 g for 5 minutes. The supernatant was aspirated and the cells were resuspended in 0.3 ml of PBS/BSA. The samples were analyzed by BD Biosciences FACSCalibur. The mean fluorescent intensity (MFI) of PSMA staining from each cell line was determined and compared to MFI with anti PSMA antibody. The MFI is directly related to PSMA expression level with higher MFI from high PSMA expressing cell line. FIG. 6 shows the MFI values from different cell lines detected with anti PSMA PE-conjugated FN3 domain in comparison to MFI values with anti PSMA antibody-PE.

The results show that anti-PSMA PE-conjugated FN3 domain binds to PSMA positive cell lines and does not bind nonspecifically to PSMA negative cells. The MFI is higher with high PSMA expressing cell line (LNCaP) compared to low MFI with low PSMA expressing cell line (22Rv1) as expected. The MFI with PSMA negative cell line (PC3) is close to the background signal. In addition, the performance of FN3 domain-PE in binding to different cell lines is similar to anti-PSMA antibody-PE, as similar MFI values were obtained with both FN3 domain and antibody conjugates. This example shows that anti PSMA PE-conjugated FN3 domain shows sensitivity and specificity in the detection of PSMA on tumor cells.

Detection of PSMA by Circulating Tumor Cell Assay

The above results were further confirmed by testing anti-PSMA PE-conjugated FN3 domain in a CELL-SEARCH assay to detect and enumerate circulating tumor cells (CTCs) from 7.5 ml of blood. Circulating tumor cell enumeration using the CELLSEARCH system (Janssen Diagnostics, Raritan, N.J., USA) was carried out according to the manufacturer's protocol and training. The CellSearch assay uses anti-EpCAM conjugated to ferrofluid magnetic particles to capture and anti-cytokeratin specific to cytokeratins 8, 18 and 19 conjugated to fluorescein to visualize CTCs. The CELLSEARCH assay uses AutoPrep for sample preparation and CELLTRACKS Analyzer II® (CTA II) for the analysis. The CTA II is a four color semi-automated fluorescent microscope and uses 3 colors to identify and enumerate CTCs. The fourth color on CTA II is available to phenotype CTCs with additional markers of interest. In this example, tissue cultured tumor cells were spiked into normal blood to mimic CTCs in blood. Approximately 500 tumor cells (LNCaP, 22Rv1, PC3 or SKBR3 cells) were spiked into 7.5 ml of normal donor blood collected in a CellSave tube (Janssen Diagnostics). The breast cancer cell line (SKBR3) was also used as PSMA negative cell line. The samples were processed on the AutoPrep using CELLSEARCH CXC kit and anti PSMA PE-conjugated FN3 domain as a marker. The AutoPrep sample preparation system enriches tumor cells by capturing tumor cells using anti EpCAM ferrofluid. The CTC enriched samples were stained with a nucleic acid dye (DAPI) to identify nucleated cells, anti-cytokeratin antibody conjugated to fluorescein isothiocyanate (FITC) to identify tumor cells, and anti-leukocyte antibody conjugated to allophycocyanin (APC) to identify leukocytes. The sample was processed to a final volume of 0.32 ml and was transferred to a sample chamber while inside the MagNest® cell presentation device. The MagNest® device presents the magnetically labeled cells for analysis by the CELLTRACKS Analyzer II®. The samples were analyzed using CTAII to enumerate CTCs and detect PSMA on CTCs. The analyzer automatically analyzes samples and presents candidate tumor cells which are positive for DAPI and cytokeratin as thumbnail images for the review. The results from tumor cells stained with anti PSMA PE-conjugated FN3 domain in CELLSEARCH assay are shown in FIG. 7.

Figure 7A:
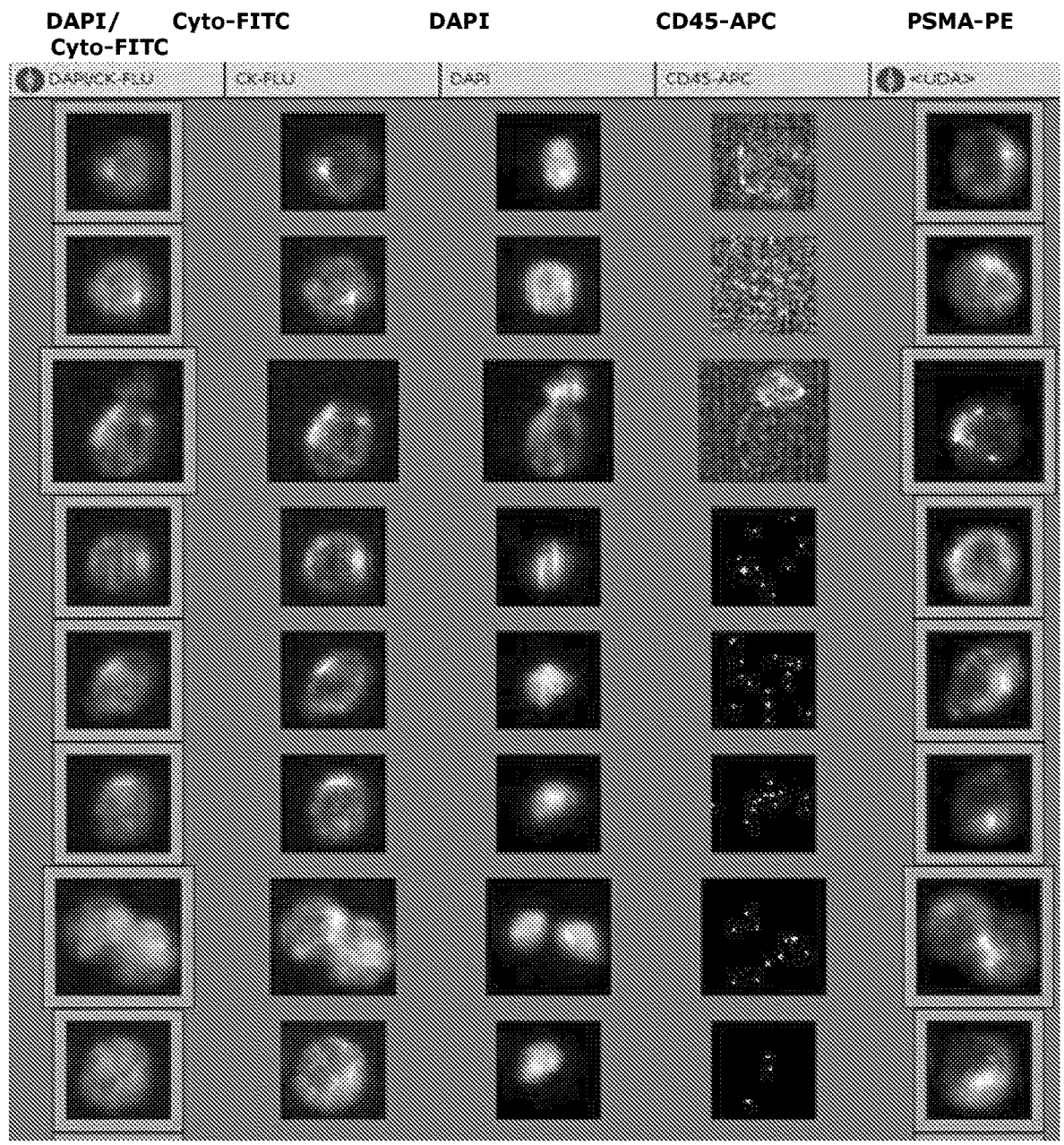
FIGS. 7A, 7B, 7C and 7D.
Figure 7B:
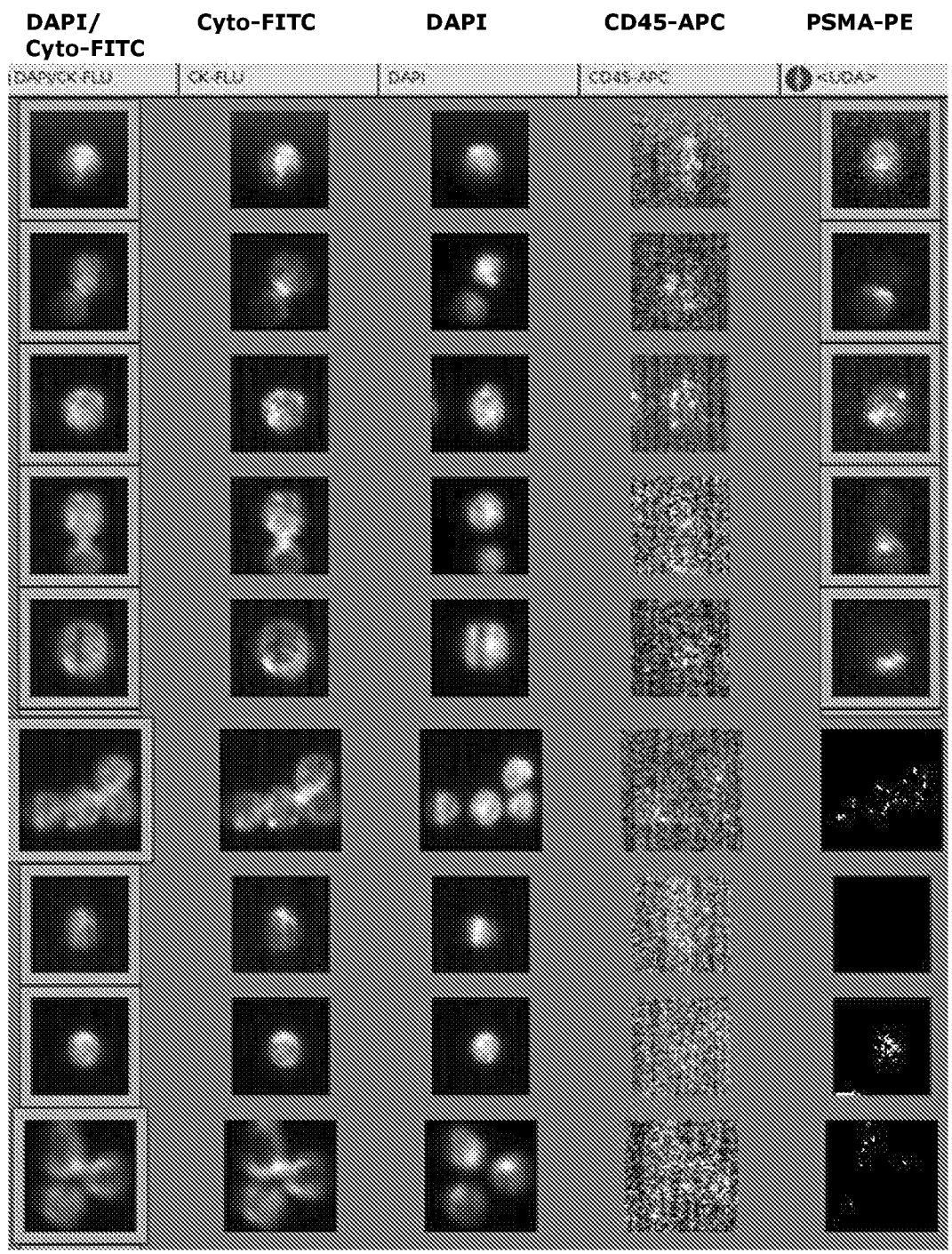
Figure 7C:
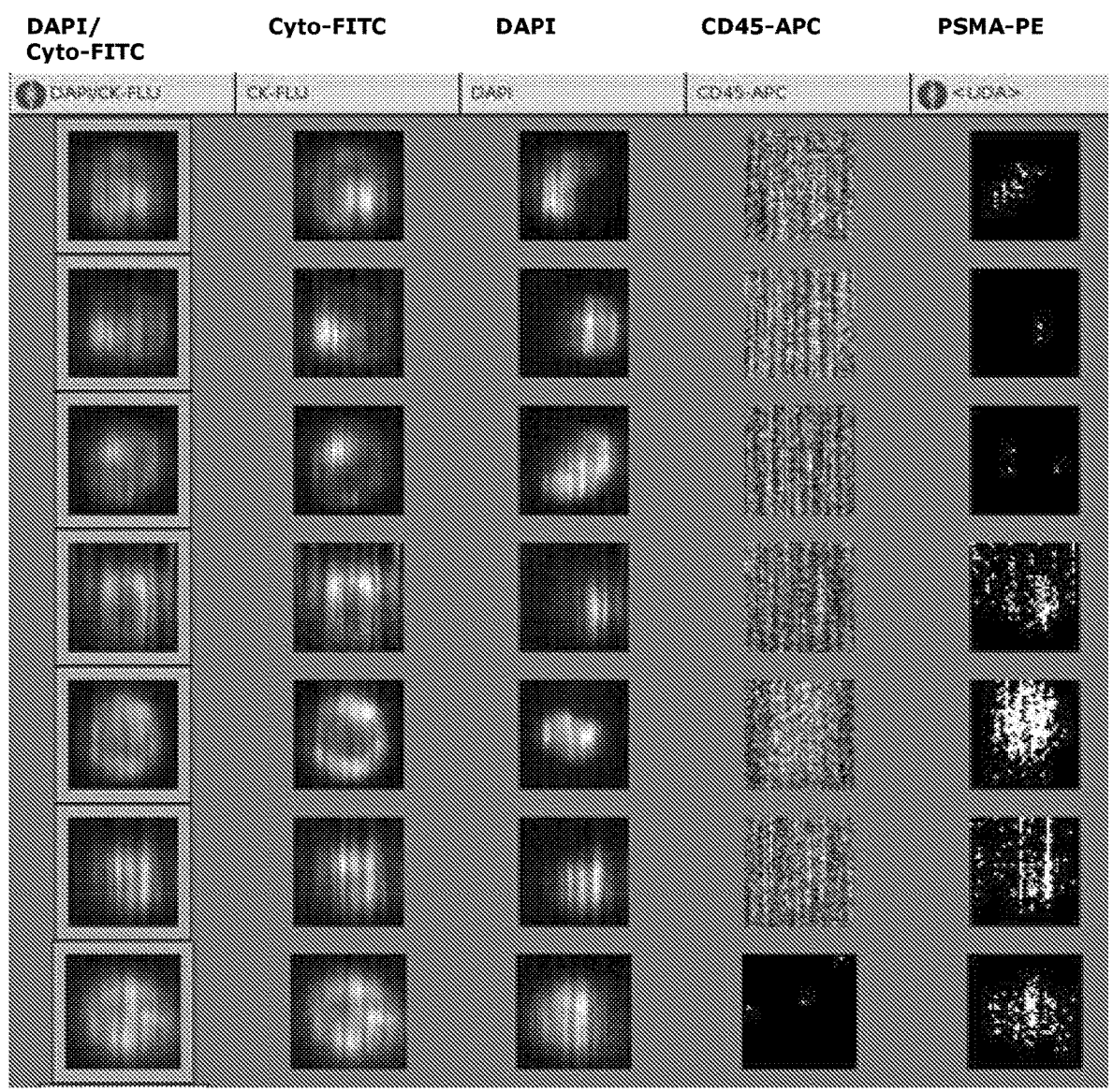
Figure 7D:
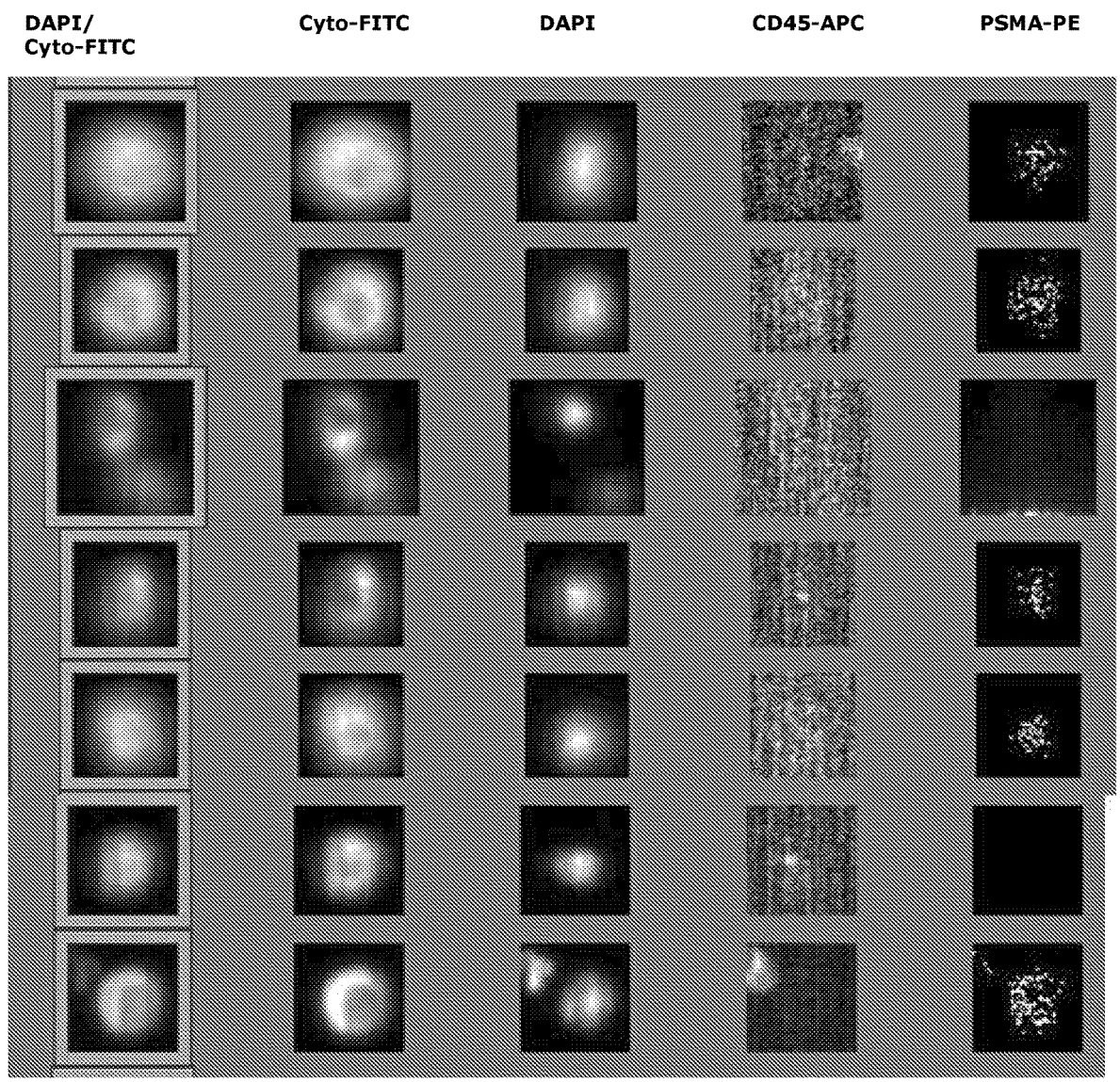

FIG. 7A shows the expression of PSMA on LNCaP tumor cells and 100% of these cells are positive for PSMA. Low PSMA expressing cell line (22Rv1) is 26% positive for PSMA (FIG. 7B). On the other hand, PSMA negative cell lines (PC3-9 and SKBR3) are negative for PSMA (FIGS. 7C and 7D). These results are consistent with flow cytometry results. This example shows that anti PSMA FN3 domain can be used to detect PSMA expression on CTCs and further confirms the sensitivity and specificity of anti PSMA FN3 domain.

Example 10: Crystal Structure of an Anti-CD3 Fab

The crystal structure of the SP34 Fab was determined at 2.1 Å resolution. It revealed the complete amino acid sequence and identified the possible mouse germlines from which the SP34 mAb was derived. The structure was used to guide human framework adaptation.
Materials SP34 mAb, mouse IgG3/lambda isotype, was purchased from BD Biosciences Pharmingen (San Diego, Calif.), Cat. No. 556611. According to the technical data sheet, it was purified from tissue culture supernatant by affinity chromatography and stored at 4° C. The Fab fragment was produced by papain digestion of mAb (Pierce, Cat #44985, Thermofisher) and was separated from Fc using Nab Protein A Plus Spin column (Pierce, Cat #44985, Thermofisher) according to manufacturer's protocol. The Fab was further purified on a MonoS column (GE Healthcare) equilibrated with 20 mM MES, pH 6.5 (buffer A). Elution was performed with buffer A in 13-28% gradient of 1 M NaCl in 50 column volumes. Fractions corresponding to the main peak were pooled, concentrated to 9.2 mg/mL and used for crystallization.
Crystallization Crystallization was carried out by the vapor diffusion method at 20° C. using an Oryx4 robot (Douglas Instruments) and a Mosquito robot (TTP Labtech). The experiments were composed of equal volumes of protein and reservoir solution in a sitting drop format in 96-well Corning 3550 plates. The initial screening was performed with the PEGs kit (Qiagen) and in-house screens IH1 and IH2. MMS optimization using the Fab seeds obtained after initial screening from IH2 screen produced a number of crystals under various conditions. The Fab crystal used for X-ray analysis was obtained from 12% PEG 3350, 0.2 M K/Na tartrate (pH 7.4), 3% isopropanol and 3% dioxane (no buffer). Crystal data are given in Table 17.

| Crystal data | |
|---|---|
| Space group | P21 |
| Unit cell axes | 55.14, 141.23, 61.29 |
| Unit cell angles (°) | 90, 99.02, 90 |
| Molecules/asym.unit | 2 |
| Vm (Å3/Da) | 2.48 |
| Solvent content (%) | 50 |
| X-ray data | |
| Resolution (Å) | 30-2.1 (2.15-2.10)* |
| No. measured reflections | 179,420 (11,506) |
| No. unique reflections | 53,483 (3,667) |
| Completeness (%) | 98.9 (92.5) |
| Redundancy | 3.4 (3.1) |
| R-merge | 0.038 (0.393) |
| <I/σ> | 18.7 (3.8) |
| B-factor (Wilson) (Å2) | 45.4 |
| Refinement | |
| Resolution (Å) | 15-2.1 |
| No. refls used in refinement | 52,212 |
| No. all atoms | 6,886 |
| No water molecules | 219 |
| R-factor (%) | 20.5 |
| R-free (%) | 26.2 |
| RMSD bond lengths (Å) | 0.008 |
| RMSD bond angles (°) | 1.2 |
| RMSD B-factor main-chain (Å2) | 2.7 |
| Mean B-factor (Å2) | 53.7 |

*Numbers in parentheses are for the highest resolution shell.

X-Ray Data Collection and Structure Determination

For X-ray data collection, one crystal was soaked for a few seconds in the mother liquor supplemented with 20% glycerol and flash frozen in liquid nitrogen. Diffraction data were collected at the Advanced Photon Source (Argonne, IL) IMCA beamline using a Pilatus CCD detector. Diffraction intensities were detected over a 180° crystal rotation with 0.5 sec exposures per half-degree image and were processed with the program XDS [Kabsch W. 2010. XDS. Acta Crystallogr. D66:125-132.]. X-ray data statistics are given in Table 17.

The structure was solved by molecular replacement using a Fab model constructed from mouse anti-Thomsen-Friedenreich Antigen antibody Jaa-F11 (PDB 3gnm), which is a IgG3/kappa isotype. All crystallographic calculations were performed with the CCP4 suite of programs [1994, Acta Crystallogr. D50:760-763.]. Model adjustments were carried out using the program COOT [Emsley P, and Cowtan K. 2004. Acta Crystallogr. D60:2126-2132.]. The refinement statistics are given in Table 17.

Germline information guided sequence determination for SP34. X-ray data allowed identification of several somatic mutations, as well as the entire sequence of CDR-H3, which is not part of the germline. Ambiguities of assigning D/N, E/Q, T/V were resolved, where possible, on the basis of H-bond networks and atomic B-factors, which in some cases can differentiate between atoms C, N and O.

Somatic mutations were identified in positions 40, 97 and 98 of VL and in positions 35, 55, 56, 57 and 80 of VH.

Five disulfides were observed in the Fab structure as expected: 22-90 and 137-196 in the light chain, 22-98 and 152-207 in the heavy chain, and an interchain disulfide 214(L)-140(H).

Interaction Between Fabs in the Crystal

In the crystal, Fab molecules pack head-to-tail, so that the CDRs of one Fab bind the C-terminal portion of the heavy chain of the other Fab. The C-terminus fits the deep crevice between VL and VH in a dead-end mode. The terminal carboxyl group of S230 forms hydrogen bonds to N35 and R50 of VH and W98 of VL. This leaves no room for an extra residue and indicates that the papain cleavage of mAb occurred between S230 and T231 of the hinge region.

Putative Paratope

The conformation of the CDRs in the present structure and the mode of the C-terminus recognition described above allowed selection of residues that are most likely involved in antigen binding. These are the following:
CDR-L1: Y34; CDR-L2: none; CDR-L3: W93;
CDR-H1: T31, Y32, A33; CDR-H2: R50, R52, Y55, N56;
CDR-H3: N103, G105, S107, Y108, S110

The majority of interactions likely occur at VH with major contributions from CDR-H2 and CDR-H3.

The sequence of SP34 is shown in FIG. 8 (SEQ ID NO:160 and 161), with residues 231-455 derived from IGHG3_MOUSE (mouse IgG3, isoform 2).

Example 11: Human Framework Adaptation of Anti-CD3 Antibody SP34

Anti-CD3 murine antibody SP34 was humanized by the Human Framework Adaptation method (Fransson, et al, JMB, 2010). Four different heavy chains were combined with three different light chains to produce 12 humanized variants.

SP34 Humanization and Affinity Maturation

Selection of Human Germlines

SP34 was humanized using the Human Framework Adaptation (HFA) method [16]. A matrix of four human heavy and three light v region sequences were selected for testing. Selection of human germlines was based solely on the overall sequence similarity to SP34 in the framework region (FR). Neither the CDR sequences, nor their length or canonical structures, were considered in this selection.

The closest matches for the heavy chain are human GLs IGHV3-72 and IGHV3-73. Another GL, IGHV3-23 was selected because of its high frequency of occurrence in the human B-cell repertoire.

The closest matches for the light chain are human lambda GLs IGLV7-43 (aka 7a), IGLV7-46 (aka 7b) and IGLV1-51 (aka 1b). IGLV7-46 is virtually identical to IGLV7-43, but has an advantage of Ala at position 2, i.e. as in SP34.

Selected J-regions are the following: IGHJ1 for the heavy chain; IGLJ3 for the lambda light chain.

Back Mutations

Figure 9:
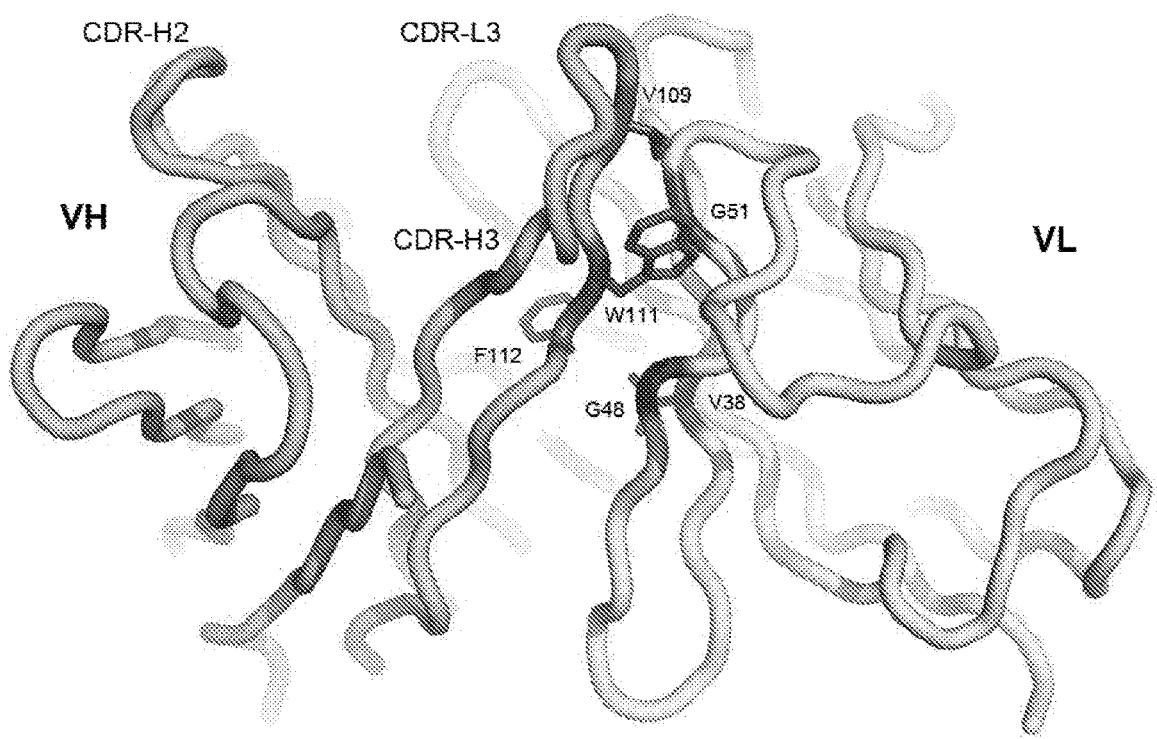
FIG. 9.
Figure 11:
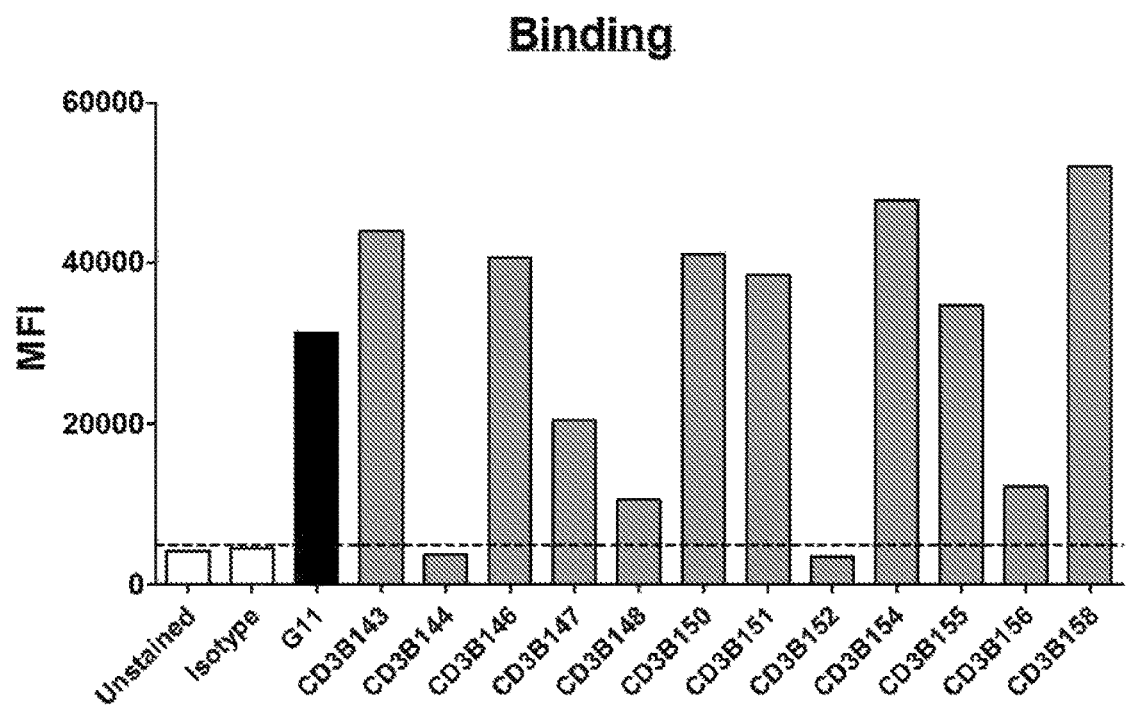
FIG. 11.
Figure 12:
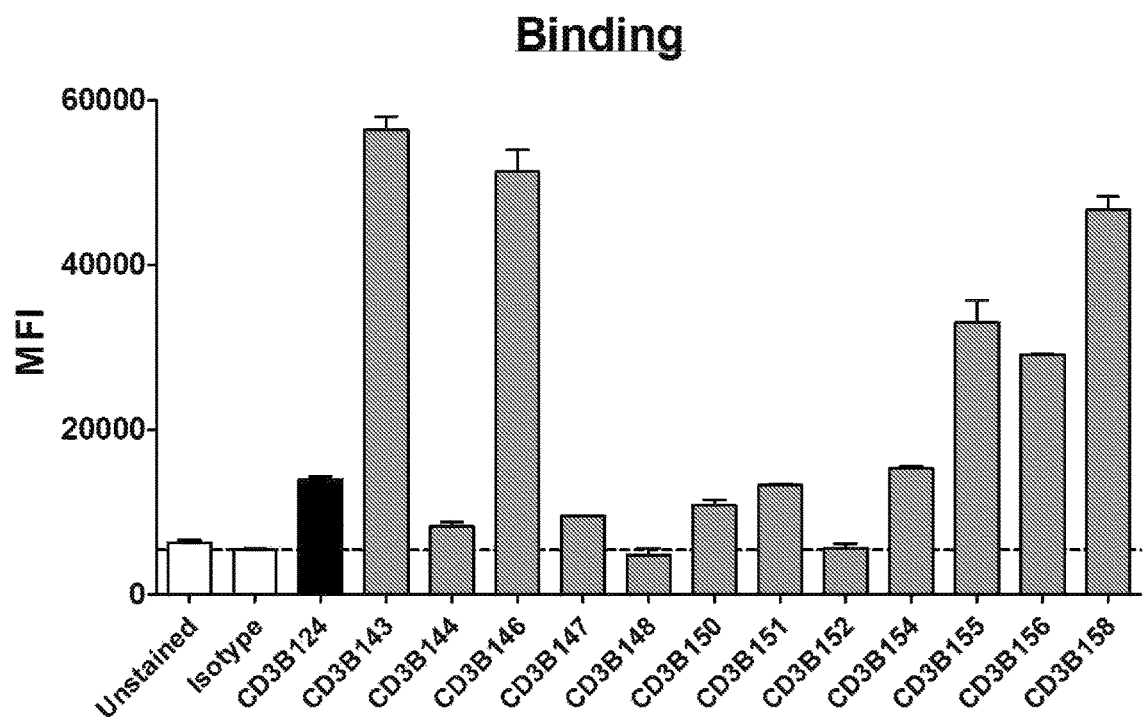
FIG. 12.

Based on the crystal structure of SP34, a model of the HFA variants was built. The model revealed several FR positions in VL with potential clashes, most notably positions Val38, Gly48 and Gly51 (FIG. 9). Mouse residues must be retained at all three positions (aka 'back mutations') in order to preserve the conformation of CDR-H3. These mutations were added into the maturation plan.

The Asn at position 57 of the heavy chain does not have good side chain density in the structure. It also sits in the middle of CDR-H2 and points away from the typical binding site. Based upon this analysis, it may not contribute to binding significantly. In addition, the backbone geometry sits in a region most favorable for a Gly residue in the Ramachadran plot. Thus it was truncated to Gly in the maturation plan to allow necessary flexibility and potentially improve stability (by reducing non-glycine related local structural strain) while not impacting binding.

There were several other considerations made in the affinity maturation design. First, human GLs IGLV7-46 and IGLV7-43 introduce a Trp at position 59 with an unwanted oxidation potential. Two other GLs have Gly at this position, which corresponds to the mouse sequence. Therefore, Gly59 was preserved in both IGLV7-46 and IGLV7-43 variants. Finally, Ala at position 49 of VH is essential. Also, the residue at position 99 (Val in SP34) may impact antigen binding. To test these positions, back mutations were introduced in some variants (FIG. 10).

HFA Matrix

The HFA matrix is composed of four variants of VH and three variants of VL (FIG. 10). For the purpose of HFA, AbM CDR definition is used (short CDR-H2, long CDR-L1).

The Variants for VH:

```
CD3H141 (SEQ ID NO: 163):
IGHV3-72*01 with mouse CDRs + Gly49Ala
EVQLVESGGGLVQPGGSLRLSCAASGFTFNTYAMNWVRQAPGKGLEWVA

RIRSKYNNYATYYAASVKGRFTISRDDSKNSLYLQMNSLKTEDTAVYYC

ARHGNFGNSYVSWFAYWGQGTLVTVSS

CD3H142 (SEQ ID NO: 164):
IGHV3-23*01 with mouse CDRs + Ser49Ala
EVQLLESGGGLVQPGGSLRLSCAASGFTFNTYAMNWVRQAPGKGLEWVA

RIRSKYNNYATYYADSVKGRFTISRDNSKNTLYLQMNSLRAEDTAVYYC

AKHGNFGNSYVSWFAYWGQGTLVTVSS

CD3H143 (SEQ ID NO: 165):
IGHV3-23*01 with mouse CDRs + Ser49Ala, Ala99Val
EVQLLESGGGLVQPGGSLRLSCAASGFTFNTYAMNWVRQAPGKGLEWVA

RIRSKYNNYATYYADSVKGRFTISRDNSKNTLYLQMNSLRAEDTAVYYC

VKHGNFGNSYVSWFAYWGQGTLVTVSS

CD3H144 (SEQ ID NO: 166):
IGHV3-73*01 with mouse CDRs + Asn57Gly
EVQLVESGGGLVQPGGSLKLSCAASGFTFNTYAMNWVRQASGKGLEWVG

RIRSKYNGYATYYAASVKGRFTISRDDSKNTAYLQMNSLKTEDTAVYYCT

RHGNFGNSYVSWFAYWGQGTLVTVSS
```

The Variants for VL:

```
CD3L63 (SEQ ID NO: 167): IGLV7-46*01
with mouse CDRs + F38V, A48G, Y51G, W59G
QAVVTQEPSLTVSPGGTVTLTCRSSTGAVTTSNYANWVQQKPGQAPRG

LIGGTNKRAPGTPARFSGSLLGGKAALTLSGAQPEDEAEYYCALWYSN

LWVFGGGTKLTVL

CD3L64 (SEQ ID NO: 168):
IGLV1-51*01 with mouse CDRs + Y38V, L48G, Y51G
QSVLTQPPSVSAAPGQKVTISCRSSTGAVTTSNYANWVQQLPGTAPKG

LIGGTNKRAPGIPDRFSGSKSGTSATLGITGLQTGDEADYYCALWYSN

LWVFGGGTKLTVL
```

-continued

```
CD3L66 (SEQ ID NO: 169): IGLV7-43*01 with mouse
CDRs + F38V, A48G, Y51G, W59G
QTVVTQEPSLTVSPGGTVTLTCRSSTGAVTTSNYANWVQQKPGQA

PRGLIGGTNKRAPGTPARFSGSLLGGKAALTLSGVQPEDEAEYYCAL

WYSNLWVFGGGTKLTVL
```

Table 18 Matrix of CD3 Heavy and Light chains (All were prepared with IgG1-AA Fc containing L234A, L235A, and F405L)

TABLE 18

| | CD3L63 (LV7-46/ W59G) SEQ ID NO: 167 | CD3L64 (LV1-51) SEQ ID NO: 168 | CD3L66 (LV7-43/ W59G) SEQ ID NO: 169 |
|---|---|---|---|
| CD3H141 (HV3-72 + G49A) SEQ ID NO: 163 | CD3B143 | CD3B144 | CD3B146 |
| CD3H142 (HV3-23 + S49A) SEQ ID NO: 164 | CD3B147 | CD3B148 | CD3B150 |
| CD3H143 (HV3-23 + S49A, A99V) SEQ ID NO: 165 | CD3B151 | CD3B152 | CD3B154 |
| CD3H144 (VH3-73 with G49) SEQ ID NO: 166 | CD3B155 | CD3B156 | CD3B158 |

Amino acid sequences were back-translated to DNA and cDNA was prepared using gene synthesis techniques (U.S. Pat. Nos. 6,670,127; 6,521,427). Heavy chain (HC) v regions were subcloned onto human IgG1-AA Fc containing L234A, L235A, and F405L mutations using an in-house expression vector with the CMV promoter using standard molecular biology techniques. Light chain (LC) variable regions were subcloned onto a human Lambda (λ) constant regions using an in-house expression vector with the CMV promoter using standard molecular biology techniques. Resulting plasmids were transfected into Expi293F cells (Invitrogen) and mAbs were expressed. Purification was by standard methods using a Protein A column (hiTrap MAb-Select SuRe column). After elution, the pools were dialyzed into D-PBS, pH 7.2.

TABLE 19

The VH and VL sequences of the antibodies are shown below:

| mAb | HC | VH Amino Acid sequence | SEQ ID NO: | LC | VL Amino Acid sequence | SEQ ID NO: |
|---|---|---|---|---|---|---|
| CD3B143 | CD3H141 | EVQLVESGGGLVQPGGSLRLSCAASGFTFNTYAMNWVRQAPGKGLEWVARIRSKYNNYATYYAASVKGRFTISRDDSKNSLYLQMNSLKTEDTAVYYCARHGNFGNSYVSWFAYWGQGTLVTVSS | 163 | CD3L63 | QAVVTQEPSLTVSPGGTVTLTCRSSTGAVTTSNYANWVQQKPGQAPRGLIGGTNKRAPGTPARFSGSLLGGKAALTLSGAQPEDEAEYYCALWYSNLWVFGGGTKLTVL | 167 |
| CD3B144 | CD3H141 | EVQLVESGGGLVQPGGSLRLSCAASGFTFNTYAMNWVRQAPGKGLEWVARIRSKYNNYATYYAASVKGRFTISRDDSKNSLYLQMNSLKTEDTAVYYCARHGNFGNSYVSWFAYWGQGTLVTVSS | 163 | CD3L64 | QSVLTQPPSVSAAPGQKVTISCRSSTGAVTTSNYANWVQQLPGTAPKGLIGGTNKRAPGIPDRFSGSKSGTSATLGITGLQTGDEADYYCALWYSNLWVFGGGTKLTVL | 168 |
| CD3B146 | CD3H141 | EVQLVESGGGLVQPGGSLRLSCAASGFTFNTYAMNWVRQAPGKGLEWVARIRSKYNNYATYYAASVKGRFTISRDDSKNSLYLQMNSLKTEDTAVYYCARHGNFGNSYVSWFAYWGQGTLVTVSS | 163 | CD3L66 | QTVVTQEPSLTVSPGGTVTLTCRSSTGAVTTSNYANWVQQKPGQAPRGLIGGTNKRAPGTPARFSGSLLGGKAALTLSGVQPEDEAEYYCALWYSNLWVFGGGTKLTVL | 169 |
| CD3B147 | CD3H142 | EVQLLESGGGLVQPGGSLRLSCAASGFTFNTYAMNWVRQAPGKGLEWVARIRSKYNNYATYYADSVKGRFTISRDNSKNTLYLQMNSLRAEDTAVYYCAKHGNFGNSYVSWFAYWGQGTLVTVSS | 164 | CD3L63 | QAVVTQEPSLTVSPGGTVTLTCRSSTGAVTTSNYANWVQQKPGQAPRGLIGGTNKRAPGTPARFSGSLLGGKAALTLSGAQPEDEAEYYCALWYSNLWVFGGGTKLTVL | 167 |

TABLE 19-continued

The VH and VL sequences of the antibodies are shown below:

| mAb | HC | VH Amino Acid sequence | SEQ ID NO: | LC | VL Amino Acid sequence | SEQ ID NO: |
|---|---|---|---|---|---|---|
| CD3B148 | CD3H142 | EVQLLESGGGLVQPGGSLRLSCAASGFTFNTYAMNWVRQAPGKGLEWVARIRSKYNNYATYYADSVKGRFTISRDNSKNTLYLQMNSLRAEDTAVYYCAKHGNFGNSYVSWFAYWGQGTLVTVSS | 164 | CD3L64 | QSVLTQPPSVSAAPGQKVTISCRSSTGAVTTSNYANWVQQLPGTAPKGLIGGTNKRAPGIPDRFSGSKSGTSATLGITGLQTGDEADYYCALWYSNLWVFGGGTKLTVL | 168 |
| CD3B150 | CD3H142 | EVQLLESGGGLVQPGGSLRLSCAASGFTFNTYAMNWVRQAPGKGLEWVARIRSKYNNYATYYADSVKGRFTISRDNSKNTLYLQMNSLRAEDTAVYYCAKHGNFGNSYVSWFAYWGQGTLVTVSS | 164 | CD3L66 | QTVVTQEPSLTVSPGGTVTLTCRSSTGAVTTSNYANWVQQKPGQAPRGLIGGTNKRAPGTPARFSGSLLGGKAALTLSGVQPEDEAEYYCALWYSNLWVFGGGTKLTVL | 169 |
| CD3B151 | CD3H143 | EVQLLESGGGLVQPGGSLRLSCAASGFTFNTYAMNWVRQAPGKGLEWVARIRSKYNNYATYYADSVKGRFTISRDNSKNTLYLQMNSLRAEDTAVYYCVKHGNFGNSYVSWFAYWGQGTLVTVSS | 165 | CD3L63 | QAVVTQEPSLTVSPGGTVTLTCRSSTGAVTTSNYANWVQQKPGQAPRGLIGGTNKRAPGTPARFSGSLLGGKAALTLSGAQPEDEAEYYCALWYSNLWVFGGGTKLTVL | 167 |
| CD3B152 | CD3H143 | EVQLLESGGGLVQPGGSLRLSCAASGFTFNTYANNWVRQAPGKGLEWVARIRSKYNNYATYYADSVKGRFTISRDNSKNTLYLQMNSLRAEDTAVYYCVKHGNFGNSYVSWFAYWGQGTLVTVSS | 165 | CD3L64 | QSVLTQPPSVSAAPGQKVTISCRSSTGAVTTSNYANWVQQLPGTAPKGLIGGTNKRAPGIPDRFSGSKSGTSATLGITGLQTGDEADYYCALWYSNLWVFGGGTKLTVL | 168 |
| CD3B154 | CD3H143 | EVQLLESGGGLVQPGGSLRLSCAASGFTFNTYAMNWVRQAPGKGLEWVARIRSKYNNYATYYADSVKGRFTISRDNSKNTLYLQMNSLRAEDTAVYYCVKHGNFGNSYVSWFAYWGQGTLVTVSS | 165 | CD3L66 | QTVVTQEPSLTVSPGGTVTLTCRSSTGAVTTSNYANWVQQKPGQAPRGLIGGTNKRAPGTPARFSGSLLGGKAALTLSGVQPEDEAEYYCALWYSNLWVFGGGTKLTVL | 169 |
| CD3B155 | CD3H144 | EVQLVESGGGLVQPGGSLKLSCAASGFTFNTYAMNWVRQASGKGLEWVGRIRSKYNGYATYYAASVKGRFTISRDDSKNTAYLQMNSLKTEDTAVYYCTRHGNFGNSYVSWFAYWGQGTLVTVSS | 166 | CD3L63 | QTVVTQEPSLTVSPGGTVTLTCRSSTGAVTTSNYANWVQQKPGQAPRGLIGGTNKRAPGTPARFSGSLLGGKAALTLSGAQPEDEAEYYCALWYSNLWVFGGGTKLTVL | 167 |
| CD3B156 | CD3H144 | EVQLVESGGGLVQPGGSLKLSCAASGFTFNTYAMNWVRQASGKGLEWVGRIRSKYNGYATYYAASVKGRFTISRDDSKNTAYLQMNSLKTEDTAVYYCTRHGNFGNSYVSWFAYWGQGTLVTVSS | 166 | CD3L64 | QSVLTQPPSVSAAPGQKVTISCRSSTGAVTTSNYANWVQQLPGTAPKGLIGGTNKRAPGIPDRFSGSKSGTSATLGITGLQTGDEADYYCALWYSNLWVFGGGTKLTVL | 168 |
| CD3B158 | CD3H144 | EVQLVESGGGLVQPGGSLKLSCAASGFTFNTYAMNWVRQASGKGLEWVGRIRSKYNGYAT | 166 | CD3L66 | QTVVTQEPSLTVSPGGTVTLTCRSSTGAVTTSNYANWVQQKPGQAPRGLIGGTNKR | 169 |

TABLE 19-continued

The VH and VL sequences of the antibodies are shown below:

| mAb | HC | VH Amino Acid sequence | SEQ ID NO: | LC | VL Amino Acid sequence | SEQ ID NO: |
|---|---|---|---|---|---|---|
| | | YYAASVKGRFTISRD DSKNTAYLQMNSLKT EDTAVYYCTRHGNFG NSYVSWFAYWGQGTL VTVSS | | | APGTPARFSGSLLG GKAALTLSGVQPED EAEYYCALWYSNLW VFGGGTKLTVL | |

A monospecific anti-CD3 antibody CDB143 was generated comprising the VH and VL regions having the VH of SEQ ID NO: 163 and the VL of SEQ ID NO: 167 and an IgG1 constant region with L234A, L235A, F405L substitution. A monospecific anti-CD3 antibody CDB144 was generated comprising the VH and VL regions having the VH of SEQ ID NO: 163 and the VL of SEQ ID NO: 168 and an IgG1 constant region with L234A, L235A, and F405L substitutions. A monospecific anti-CD3 antibody CDB146 was generated comprising the VH and VL regions having the VH of SEQ ID NO: 163 and the VL of SEQ ID NO: 169) and an IgG1 constant region with L234A, L235A, and F405L substitutions. A monospecific anti-CD3 antibody CDB147 was generated comprising the VH and VL regions having the VH of SEQ ID NO: 164 and the VL of SEQ ID NO: 167) and an IgG1 constant region with L234A, L235A, and F405L substitutions. A monospecific anti-CD3 antibody CDB148 was generated comprising the VH and VL regions having the VH of SEQ ID NO: 164 and the VL of SEQ ID NO: 168 and an IgG1 constant region with L234A, L235A, and F405L substitutions. A monospecific anti-CD3 antibody CDB150 was generated comprising the VH and VL regions having the VH of SEQ ID NO: 164 and the VL of SEQ ID NO: 169 and an IgG1 constant region with L234A, L235A, and F405L substitutions. A monospecific anti-CD3 antibody CDB151 was generated comprising the VH and VL regions having the VH of SEQ ID NO: 165 and the VL of SEQ ID NO: 167 and an IgG1 constant region with L234A, L235A, and F405L substitutions. A monospecific anti-CD3 antibody CDB152 was generated comprising the VH and VL regions having the VH of SEQ ID NO: 165 and the VL of SEQ ID NO: 168 and an IgG1 constant region with L234A, L235A, and F405L substitutions. A monospecific anti-CD3 antibody CDB 154 was generated comprising the VH and VL regions having the VH of SEQ ID NO: 165 and the VL of SEQ ID NO: 169 and an IgG1 constant region with L234A, L235A, and F405L substitutions. A monospecific anti-CD3 antibody CDB155 was generated comprising the VH and VL regions having the VH of SEQ ID NO: 166 and the VL of SEQ ID NO: 167 and an IgG1 constant region with L234A, L235A, and F405L substitutions. A monospecific anti-CD3 antibody CDB156 was generated comprising the VH and VL regions having the VH of SEQ ID NO: 166 and the VL of SEQ ID NO: 168 and an IgG1 constant region with L234A, L235A, and F405L substitutions. A monospecific anti-CD3 antibody CDB158 was generated comprising the VH and VL regions having the VH of SEQ ID NO: 166 and the VL of SEQ ID NO: 169 and an IgG1 constant region with L234A, L235A, and F405L substitutions.

Example 12: Endogenous Cell Binding of the Humanized Anti-CD3 Hits to Primary T Cells The resulting panel of anti-CD3 antibodies was tested for binding against cell-surface CD3ε on primary human T cells. To do this, binding of antibodies from expression supernatants was visualized using a polyclonal anti-human secondary antibody and analyzed by flow cytometry. Briefly, binding of anti-CD3 antibodies to cell-surface CD3ε was assessed by flow cytometry using primary Human T lymphocytes purified by negative selection (Biological Specialty, Colmar, USA). Expression supernatants or purified antibodies were normalized to 10 µg/ml in media or FACS buffer (BD BioSciences), respectively. $2\times10^5$ cells were aliquoted into wells of a 96 well round-bottomed plate (CoStar) for labeling. Antibodies in expression supernatant were added to cells and incubated for 45 min at 4° C. Following centrifugation at 1300 rpm for 3 min and removal of supernatant, 50 µL of anti-human IgG (H+L) Alexa Fluor 647 secondary antibody (Life technologies Inc.) was incubated with the cells at a final concentration of 10 µg/mL for 30 min at 4° C. away from direct light. Following washing and resuspension in 30 µL FACs buffer (BD BioSciences). Sample collection was performed on an Intellicyt HTFC system using ForeCyt software. Viable single cells were gated prior to analysis of binding using the green or red fixable live/dead dyes (Life Technologies Inc.) and forward/side scatter area and height parameters, respectively. Graphs were generated in GraphPad Prism version 5 using mean fluorescence intensity values.

Figure 13:
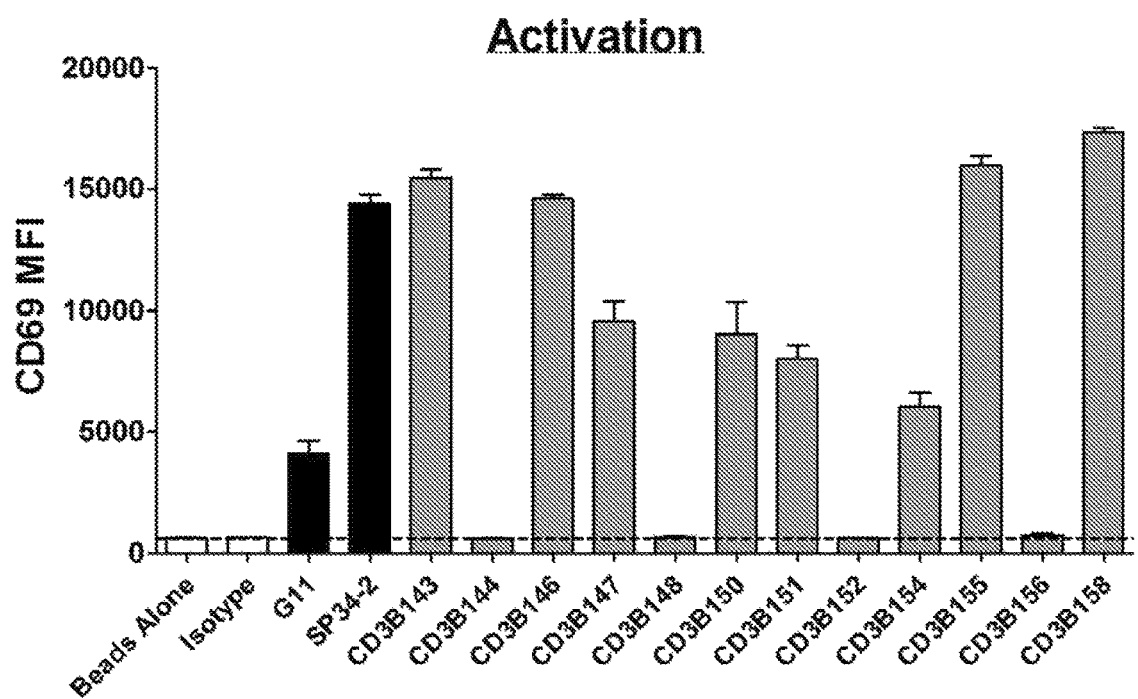
FIG. 13.

Although a titration series was run, an intermediate concentration is presented in FIG. 13 for clarity. Two in-house phage-derived antibodies with the same Fc region as the therapeutic antibodies were used as controls: G11 (HC SEQ ID NO: 176, LC SEQ ID NO: 177), a non-cyno cross-reactive, agonistic antibody was used as a positive control and CD3B94 (HC-SEQ ID NO: 178, LC-SEQ ID NO:179) a non-binder/non-agonistic antibody was used to assess non-specific binding. The commercial SP34 antibody was not used as a comparator in this assay since it is a mouse antibody and the use of a different secondary detection reagent would have prohibited direct comparison with the variants tested.

The data demonstrates an array of binding potential within the panel of humanized anti-CD3 hits, with two antibodies (CD3B144, CD3B152) showing complete loss of binding to human T cells. The remaining antibodies showed a range of binding potential that could be broadly split into strong and weak binders using G11 binding as an arbitrary threshold. Using these parameters, seven strong binders and seven weak binders were identified from the panel of variants (FIG. 13).

Figure 14:
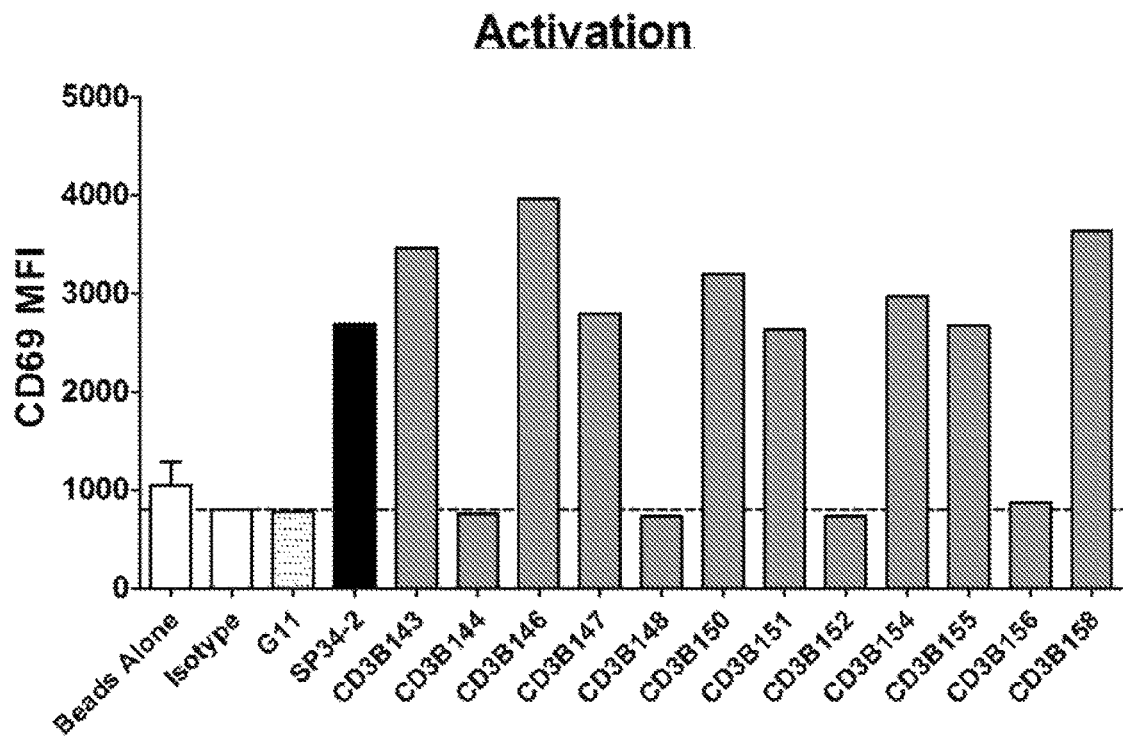
FIG. 14.

Binding analysis of the anti-CD3 hits to primary cynomolgusCD4+ T cells was then tested in order to assess the retention of cross-reactivity. Purified CD4+ T cells from the peripheral blood of cynomolgus monkeys (Zen Bio, Triangle Research Park, USA were used). Assay protocols were similar to those described above. Since G11 does not cross-react with cynomolgusCD3ε, CD3B124, an in-house chimeric SP34-derived antibody having the VH and VL of SP34 with murine framework and a human IgG1 Fc was used as a positive control in this assay (FIG. 14). Interestingly, several variants showed decreased binding potential compared to that seen with human cells. This included the strong binders CD3B150, CD3B151 and CD3B154, in which binding was reduced, and several weak binders where binding could no longer be detected over background. This loss of binding was not related to a specific immunoglobulin chain, suggesting that the combination of heavy and light chains played a role in the loss of cross-reactivity. Together, these assays allowed the identification of variants that retained species cross-reactivity between human and cynomolgus CD3ε.

Example 13: Functional Analysis of the Humanized Anti-CD3 Hits in Primary T Cells Binding analysis demonstrated that the panel of humanized anti-CD3 hits showed a range of binding potential to human and cynomolgusT-cells. To investigate the capacity of each variant to induce activation in via CD3ε crosslinking, primary T-cells were cultured overnight in the presence of bead-conjugated antibody. The following day, cells were harvested and labeled with an anti-CD69 antibody to measure activation (FIG. 13). Humanized anti-CD3 antibodies were bound to protein A coated magnetic beads (SpheroTech, Lake forest, USA) by overnight incubation with antibody at 10 µg/mL. The following day, $2 \times 10^5$ primary human T cells were plated in round-bottomed cell culture plates in triplicate and $2 \times 10^5$ coated beads were added. Following overnight culture at 37° C., cells were harvested and labeled with anti-CD69 Alexa Fluor 488 antibody (clone FN50; Biolegend) to assess the up-regulation of this activation marker. Sample collection and analysis were performed as described above for binding. Several negative controls were run, including T-cells alone, T-cells with non-coated beads, and T-cells with isotype control (CD3B94)-coated beads. All of these showed similar mean fluorescence intensity values comparable to unstained T-cells indicating that background was low in this assay. Several positive controls were run for comparison, including OKT3 (U.S. Pat. No. 5,929,212) and commercially available SP34-2 antibody.

The humanized anti-CD3 hits were then tested for their capacity to activate primary cynomolgus CD4+ T cells (Zen Bio, Triangle Research Park, USA) in the same assay (FIG. 14). The FN50 anti-CD69 antibody has been described as being cross-reactive with non-human protein and could therefore be used to test activation of these cells.

The human and cynomolgus activation data correlated with the binding data in that the panel of hits displayed a range of activation potentials. A number of the strong binders showed the capacity to activate human T-cells to an equivalent or greater extent when compared to commercially available SP34-2. Several variants showed activation potential that was lower compared SP34-2, whereas some binders did not show evidence of CD69 stimulation. The inability to activate was only seen in the variants that showed no or weak binding and all strong binders showed some level of activation, suggesting a correlation between binding and activation potentials for both human (FIG. 15A) and cynomolgus (FIG. 15B).

Example 15. Preparation of the Multispecific Antigen-Binding Molecule in a Bispecific Format in IgG4 S228P, L234A, L235A Bispecific PSMA×CD3 multispecific antigen-binding molecules were generated by combining a CD3 mAb arm with and without FN3 domain fusion and a monospecific PSMA Fn3 domain FC fusion in in-vitro Fab arm exchange (as described in WO2011/131746). In order to produce a bispecific isolated multispecific antigen-binding molecules that bind the antigens CD3 and PSMA, the anti-PSMA FN3 domain (P233FR9-H10, SEQ ID 41) was produced as a fusion protein with an anti-CD3 mAb in multiple orientations to assess the effects of such orientations on the ability of these molecules to activate and target cytotoxic T-cells to PSMA expressing cell lines.
Expression of CD3 mAb B219

One of the monospecific CD3 antibodies, CDB146, was expressed as IgG4, having Fc substitutions S228P, F234A, L235A F405L and R409K (numbering according to EU index) in their Fc regions. The monospecific antibody was produced by transient transfection in HEK293 cells.

Figure 16:
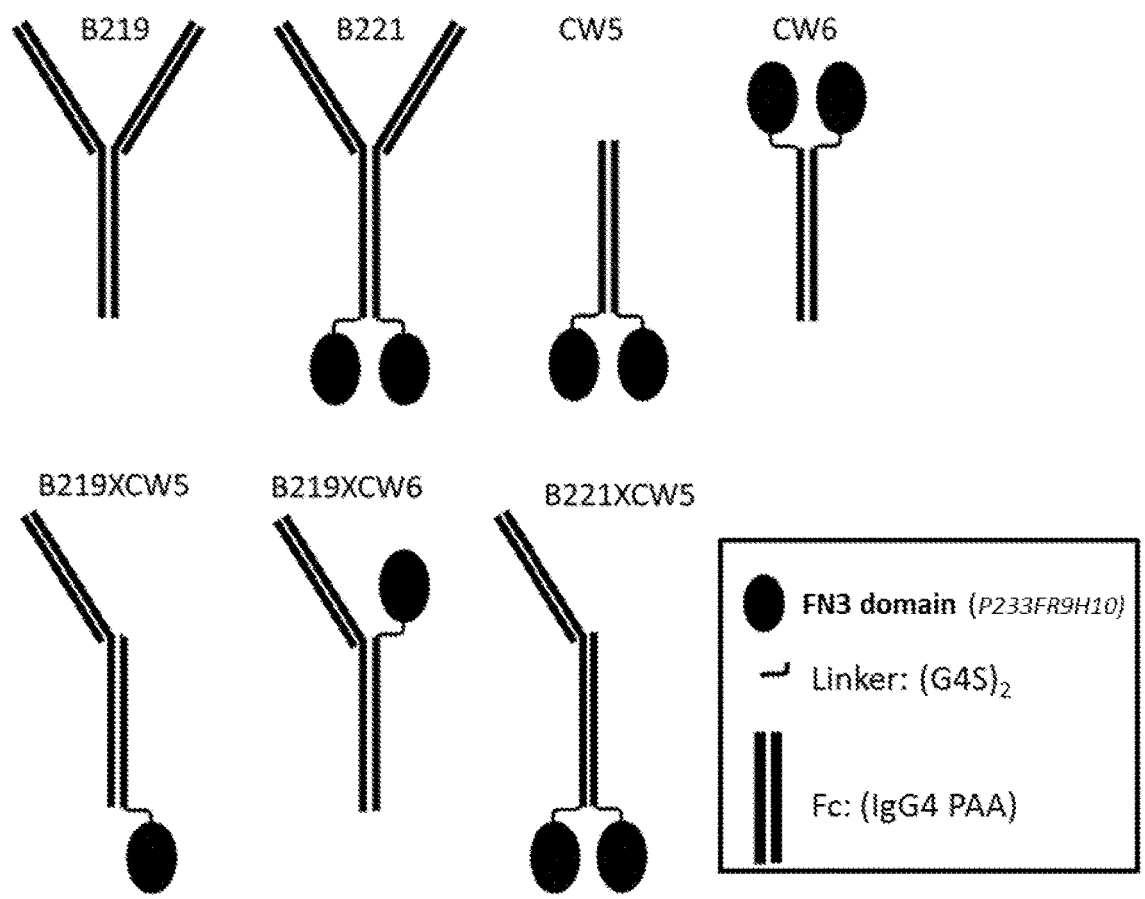
FIG. 16.

A monospecific anti-CD3 antibody B219 was generated comprising the VH and VL regions having the VH of SEQ ID NO: 163 and the VL of SEQ ID NO: 169 and an IgG4 constant region with S228P, L234A, L235A, F405L and R409K substitutions. The monospecific anti-CD3 antibody B219 comprises the light chain amino acid sequence of SEQ ID NO: 170 and the heavy chain amino acid sequence of SEQ ID NO: 171.
Design of PSMA FN3 Domain Fusions Constructs were designed to produce either monovalent CD3 interactions: B219 (SEQ ID NOs: 170,171) X CW5 (SEQ ID NO:172), B219 (SEQ ID NOs: 170,171) X CW6 (SEQ ID NO:173), B221 (SEQ ID NOs:170,174) X CW5 (SEQ ID NO:172) or bivalent CD3 interactions: B221 (SEQ ID NOs:170,174). Likewise molecules capable of monovalent PSMA interactions: B219 (SEQ ID NOs: 170,171) X CW6 (SEQ ID NO:173, B219 (SEQ ID NOs: 170,171)X CW5 (SEQ ID NO:172), or bivalent PSMA interactions: (B221 (SEQ ID NOs:170,174), B221 (SEQ ID NOs:170, 175) XCW5 (SEQ ID NO:172) were designed. A final variation was the location of the FN3 domain relative to the heavy chain, with both N-terminal and C-terminal fusions produced. A $(GGGGS)_2$ linker (SEQ ID NO:175) was incorporated between P233FR9-H10 and the heavy chain constant region in all molecules. A cartoon diagram of the designed isolated multispecific antigen-binding molecules that bind the antigens CD3 and PSMA is shown in FIG. 16.

TABLE 20

Location and valence of FN3 domain fusions

| Molecule | Fusion form to Fc or heavy chain | PSMA binding | CD3 binding | Heavy chain1 SEQ ID | FN3 domain FC fusion SEQ ID | Light Chain SEQ ID |
| --- | --- | --- | --- | --- | --- | --- |
| B219XCW5 | C-terminal | monovalent | monovalent | 171 | 172 | 170 |
| B219XCW6 | N-terminal | monovalent | monovalent | 171 | 173 | 170 |
| B221XCW5 | C-terminal | bivalent | monovalent | 174 | 172 | 170 |
| B221 | C-terminal | bivalent | bivalent | 174 | 174 | 170 |

Amino acid sequences were back-translated to DNA and cDNA was prepared using gene synthesis techniques (U.S. Pat. No. 6,670,127; 6,521,427) and proteins were expressed using an in-house expression vector with the CMV promoter using standard molecular biology techniques. Heavy chain (HC) v regions were subcloned onto human IgG4-AA Fc containing L234A, L235A, and F405L mutations using an in-house expression vector with the CMV promoter using standard molecular biology techniques. Light chain (LC) variable regions were subcloned onto a human Lambda (λ) constant regions using an in-house expression vector with the CMV promoter using standard molecular biology techniques. Resulting plasmids were transfected into Expi293F cells (Invitrogen) and mAbs were expressed. Purification was by standard methods using a Protein A column (hiTrap MAbSelect SuRe column). After elution, the pools were dialyzed into D-PBS, pH 7.2.

An anti-PSMA FN3 domain fusion CW5 was generated comprising the anti-PSMA FN3 domain P233FR9-H10 (SEQ ID NO:41) connected with a linker (SEQ ID NO: 175) to the C-terminus of an IgG4 constant region with S228P, L234A and L235A substitutions, the amino acid sequence of the fusion comprising SEQ ID NO: 172. An anti-PSMA FN3 domain fusion CW6 was generated comprising the anti-PSMA FN3 domain P233FR9-H10 (SEQ ID NO:41) connected with a linker (SEQ ID NO: 175) to the N-terminus of an IgG4 constant region with S228P, L234A and L235A substitutions, the amino acid sequence of the fusion comprising SEQ ID NO: 173. An isolated bispecific, anti-PSMA×CD3 antigen-binding molecule that binds the antigens CD3 and PSMA, B221, was generated comprising the anti-CD3 mAb B219 comprising the VH and VL regions having the VH of SEQ ID NO: 163 and the VL of SEQ ID NO: 169 and an IgG4 constant region with S228P, L234A, L235A, F405L and K409R substitutions fused at the C-terminus of the heavy chain by a linker (SEQ ID NO: 175) to the anti-PSMA isolated multispecific antigen-binding molecules that bind the antigens CD3 and PSMA P233FR9-H10 (SEQ ID NO:41), the amino acid sequence of the anti-PSMA×CD3 isolated multispecific antigen-binding molecules that bind the antigens CD3 and PSMA heavy chain comprising SEQ ID NO: 174 and the light chain comprising SEQ ID NO: 170.

Isolated multispecific antigen-binding molecules that bind the antigens CD3 and PSMA proteins B219XCW5, B219XCW6 and B221XCW5 were prepared by partial reduction and controlled Fab arm exchange using combinations of parent molecules as described in Table 17. Briefly, the parental molecules were mixed at about 1-20 mg/ml at a molar ratio of 1.08:1 B219/B221 to W5/W6, and 2-MEA (stock solution of 750 mM in PBS) was added to a final concentration of 75 mM. Reactions were incubated at 5 hr at 31° C., followed by dialysis into PBS. The protein was then collected, sterile filtered and purity and concentration measured by absorbance at 280 nm, cation exchange HPLC, size exclusion HPLC and SDS-PAGE.

A bispecific, anti-PSMA×CD3 isolated multispecific antigen-binding molecules that bind the antigens CD3 and PSMA B219XCW5 was generated comprising the CW5 anti-PSMA FN3 domain fusion arm comprising the amino acids sequence of SEQ ID NO: 172 paired with the B219 anti-CD3 heavy and light chains comprising the VL and VH amino acid sequences of SEQ ID NOs: 163 and 169 A bispecific, anti-PSMA×CD3 isolated multispecific antigen-binding molecules that bind the antigens CD3 and PSMA B219XCW6 was generated comprising the CW6 anti-PSMA FN3 domain fusion arm comprising the amino acids sequence of SEQ ID NO: 173 paired with the B219 anti-CD3 heavy and light chains comprising the amino acid sequences of SEQ ID NOs: 171 and 170. A bispecific, anti-PSMA×CD3 isolated multispecific antigen-binding molecule B221XCW5 was generated comprising the CW5 anti-PSMA FN3 domain fusion arm comprising the amino acid sequence of SEQ ID NO: 172 paired with the B221 anti-CD3× anti-PSMA FN3 domain heavy chain fusion comprising the amino acid sequence of SEQ ID NO: 174 and a light chain comprising the amino acid sequences of SEQ ID NO: 170

TABLE 21

| Molecule | | Amino Acid Sequence |
|---|---|---|
| B219XCW5 | Heavy chain 1 B219HC (SEQ ID NO: 171) | EVQLVESGGGLVQPGGSLRLSCAASGFTFNTYAMNWVRQ APGKGLEWVARIRSKYNNYATYYAASVKGRFTISRDDSK NSLYLQMNSLKTEDTAVYYCARHGNFGNSYVSWFAYWGQ GTLVTVSSASTKGPSVFPLAPCSRSTSESTAALGCLVKD YFPEPVTVSWNSGALTSGVHTFPAVLQSSGLYSLSSVVT VPSSSLGTKTYTCNVDHKPSNTKVDKRVESKYGPPCPPC PAPEAAGGPSVFLFPPKPKDTLMISRTPEVTCVVVDVSQ EDPEVQFNWYVDGVEVHNAKTKPREEQFNSTYRVVSVLT VLHQDWLNGKEYKCKVSNKGLPSSIEKTISKAKGQPREP QVYTLPPSQEEMTKNQVSLTCLVKGFYPSDIAVEWESNG QPENNYKTTPPVLDSDGSFLLYSKLTVDKSRWQEGNVFS CSVMHEALHNHYTQKSLSLSLGK |
| | Light Chain 1 B219 LC (SEQ ID NO: 170) | QTVVTQEPSLTVSPGGTVTLTCRSSTGAVTTSNYANWVQ QKPGQAPRGLIGGTNKRAPGTPARFSGSLLGGKAALTLS GVQPEDEAEYYCALWYSNLWVFGGGTKLTVLGQPKAAPS VTLFPPSSEELQANKATLVCLISDFYPGAVTVAWKADSS PVKAGVETTTPSKQSNNKYAASSYLSLTPEQWKSHRSYS CQVTHEGSTVEKTVAPTECS |
| | FN3 domain C-terminal FC fusion CW5 (SEQ ID NO: 172) | GSCPPCPAPEAAGGPSVFLFPPKPKDTLMISRTPEVTCV VVDVSQEDPEVQFNWYVDGVEVHNAKTKPREEQFNSTYR VVSVLTVLHQDWLNGKEYKCKVSNKGLPSSIEKTISKAK GQPREPQVYTLPPSQEEMTKNQVSLTCLVKGFYPSDIAV EWESNGQPENNYKTTPPVLDSDGSFFLYSRLTVDKSRWQ EGNVFSCSVMHEALHNHYTQKSLSLSLGKGGGGSGGGGS MLPAPKNLVVSRVTEDSARLSWTAPDAAFDSFAIGYWEW DDDGEAIVLTVPGSERSYDLTGLKPGTEYPVYIAGVKGG QWSFPLSAIFTT |

TABLE 21-continued

| Molecule | | Amino Acid Sequence |
|---|---|---|
| B219XCW6 | Heavy chain 1 B219HC (SEQ ID NO: 171) | EVQLVESGGGLVQPGGSLRLSCAASGFTFNTYAMNWVRQ APGKGLEWVARIRSKYNNYATYYAASVKGRFTISRDDSK NSLYLQMNSLKTEDTAVYYCARHGNFGNSYVSWFAYWGQ GTLVTVSSASTKGPSVFPLAPCSRSTSESTAALGCLVKD YFPEPVTVSWNSGALTSGVHTFPAVLQSSGLYSLSSVVT VPSSSLGTKTYTCNVDHKPSNTKVDKRVESKYGPPCPPC PAPEAAGGPSVFLFPPKPKDTLMISRTPEVTCVVVDVSQ EDPEVQFNWYVDGVEVHNAKTKPREEQFNSTYRVVSVLT VLHQDWLNGKEYKCKVSNKGLPSSIEKTISKAKGQPREP QVYTLPPSQEEMTKNQVSLTCLVKGFYPSDIAVEWESNG QPENNYKTTPPVLDSDGSFLLYSKLTVDKSRWQEGNVFS CSVMHEALHNHYTQKSLSLSLGK |
| | Light Chain 1 B219 LC (SEQ ID NO: 170) | QTVVTQEPSLTVSPGGTVTLTCRSSTGAVTTSNYANWVQ QKPGQAPRGLIGGTNKRAPGTPARFSGSLLGGKAALTLS GVQPEDEAEYYCALWYSNLWVFGGGTKLTVLGQPKAAPS VTLFPPSSEELQANKATLVCLISDFYPGAVTVAWKADSS PVKAGVETTTPSKQSNNKYAASSYLSLTPEQWKSHRSYS CQVTHEGSTVEKTVAPTECS |
| | FN3 domain N-terminal FC fusion CW6 (SEQ ID NO: 173) | MLPAPKNLVVSRVTEDSARLSWTAPDAAFDSFAIGYWEW DDDGEAIVLTVPGSERSYDLTGLKPGTEYPVYIAGVKGG QWSFPLSAIFTTGGGGSGGGGSCPPCPAPEAAGGPSVFL FPPKPKDTLMISRTPEVTCVVVDVSQEDPEVQFNWYVDG VEVHNAKTKPREEQFNSTYRVVSVLTVLHQDWLNGKEYK CKVSNKGLPSSIEKTISKAKGQPREPQVYTLPPSQEEMT KNQVSLTCLVKGFYPSDIAVEWESNGQPENNYKTTPPVL DSDGSFFLYSRLTVDKSRWQEGNVFSCSVMHEALHNHYT QKSLSLSLGK |
| B221XCW5 | Centryin C-terminal Heavy chain fusion B221 (SEQ ID NO: 174) | EVQLVESGGGLVQPGGSLRLSCAASGFTFNTYAMNWVRQ APGKGLEWVARIRSKYNNYATYYAASVKGRFTISRDDSK NSLYLQMNSLKTEDTAVYYCARHGNFGNSYVSWFAYWGQ GTLVTVSSASTKGPSVFPLAPCSRSTSESTAALGCLVKD YFPEPVTVSWNSGALTSGVHTFPAVLQSSGLYSLSSWT VPSSSLGTKTYTCNVDHKPSNTKVDKRVESKYGPPCPPC PAPEAAGGPSVFLFPPKPKDTLMISRTPEVTCVVVDVSQ EDPEVQFNWYVDGVEVHNAKTKPREEQFNSTYRVVSVLT VLHQDWLNGKEYKCKVSNKGLPSSIEKTISKAKGQPREP QVYTLPPSQEEMTKNQVSLTCLVKGFYPSDIAVEWESNG QPENNYKTTPPVLDSDGSFLLYSKLTVDKSRWQEGNVFS CSVMHEALHNHYTQKSLSLSLGKGGGGSGGGGSMLPAPK NLVVSRVTEDSARLSWTAPDAAFDSFAIGYWEWDDDGEA IVLTVPGSERSYDLTGLKPGTEYPVYIAGVKGGQWSFPL SAIFTT |
| | Light Chain 1 B219 LC (SEQ ID NO: 170) | QTVVTQEPSLTVSPGGTVTLTCRSSTGAVTTSNYANWVQ QKPGQAPRGLIGGTNKRAPGTPARFSGSLLGGKAALTLS GVQPEDEAEYYCALWYSNLWVFGGGTKLTVLGQPKAAPS VTLFPPSSEELQANKATLVCLISDFYPGAVTVAWKADSS PVKAGVETTTPSKQSNNKYAASSYLSLTPEQWKSHRSYS CQVTHEGSTVEKTVAPTECS |
| | FN3 domain N-terminal FC fusion CW6 (SEQ ID NO: 173) | MLPAPKNLVVSRVTEDSARLSWTAPDAAFDSFAIGYWEW DDDGEAIVLTVPGSERSYDLTGLKPGTEYPVYIAGVKGG QWSFPLSAIFTTGGGGSGGGGSCPPCPAPEAAGGPSVFL FPPKPKDTLMISRTPEVTCVVVDVSQEDPEVQFNWYVDG VEVHNAKTKPREEQFNSTYRVVSVLTVLHQDWLNGKEYK CKVSNKGLPSSIEKTISKAKGQPREPQVYTLPPSQEEMT KNQVSLTCLVKGFYPSDIAVEWESNGQPENNYKTTPPVL DSDGSFFLYSRLTVDKSRWQEGNVFSCSVMHEALHNHYT QKSLSLSLGK |

Example 16: Evaluation of Bispecific Isolated Multispecific Antigen-Binding Molecules that Bind the Antigens CD3 and PSMA in Functional Cell Killing Assay A 24 hour standard chromium release assay was used to determine isolated multispecific antigen-binding molecules that bind the antigens CD3 and PSMA function in killing PSMA positive LNCAP tumor targets (ATCC CRL-1740). Frozen normal donor pan-T cells (All Cells Cat #PB900-1F) were pre-activated with 1 µg/ml of OKT3 (U.S. Pat. No. 5,929,212) and 20 U/ml of IL2 (Peprotech Cat #200-02) for 12-24 hours. T cells were then washed and co-cultured with LNCAP tumor target cells in RPMI labeled with chromium (Perkin-Elmer, Cat #NEZ030S001MC) at a 5:1 effector to target ratio. Isolated multispecific antigen-binding molecules that bind the antigens CD3 and PSMA were added so that the final concentration in the well at the highest dose was 10 µg/ml and followed a 7-point titration curve using 1:20 dilutions and incubated for 18-24 hours. The culture supernatant was harvested and read on a gamma-counter. As a control for spontaneous release of chromium from target cells, targets were cultured with media only and supernatant was collected. Maximum release was determined by the addition of Triton-X-100 to lyse all targets. The counts per minute were collected using a gamma counter and used in the following formula to determine % cytotoxicity. All samples were run in triplicate.

The calculation for % Cytotoxicity=(experimental counts-spontaneous release) (maximum release-spontaneous release)×100%.

% cytotoxicity is calculated for each triplicate and plotted at a mean % cytotoxicity+SEM of the triplicates.

Figure 17:
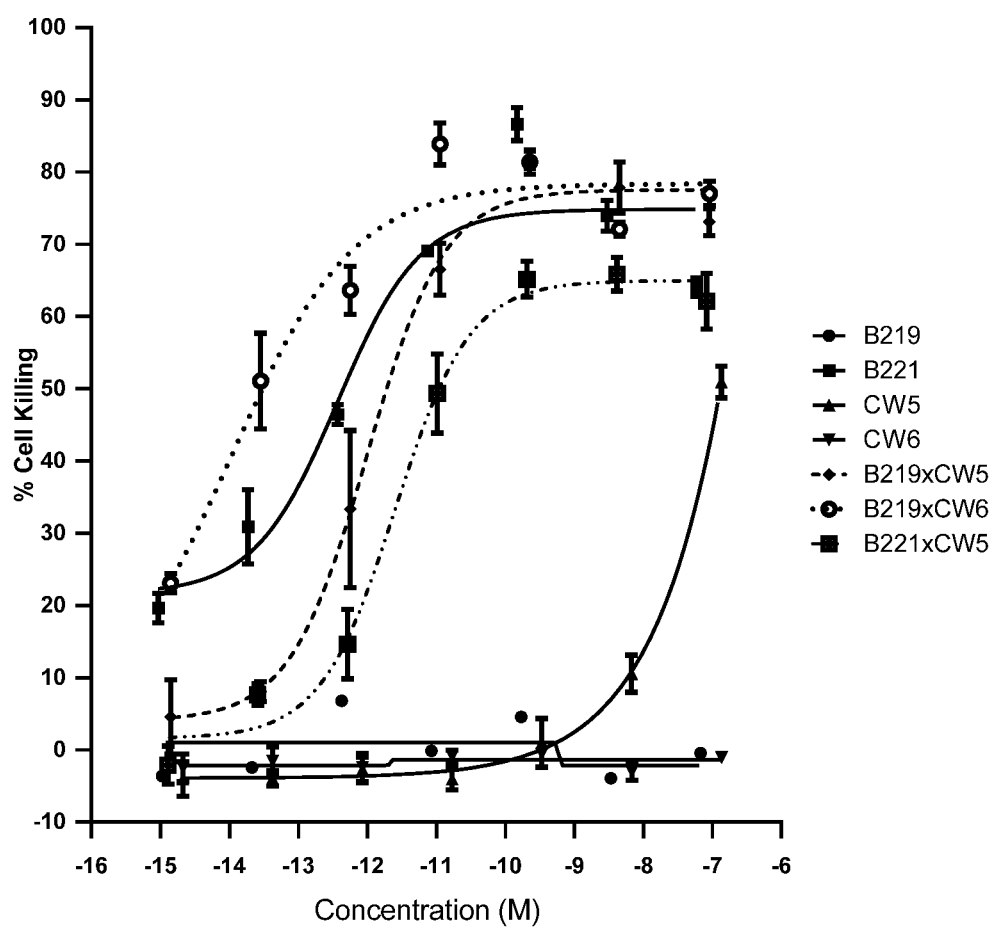
FIG. 17.

FIG. 17 shows a respresentative graph of two independent experiments. The data demonstrates that all CD3B219× PSMA isolated CD3×PSMA-bispecific antigen-binding molecule configurations resulted in tumor cell killing with B219XCW6 being the most potent followed by B221 and B219xCW5. Table 22 below indicates the EC50 for each isolated CD3×PSMA-bispecific antigen-binding molecule, as well as the 95% confidence range for these EC50s and R squared values.

TABLE 22

|  | EC50 | EC50 95% Confidence Range | R2 |
| --- | --- | --- | --- |
| B221 | 3.713E−13 | 7.105e−015 to 1.990e−011 | 0.916 |
| B219 × CW5 | 9.877E−13 | 3.393e−013 to 2.876e−012 | 0.9926 |
| B219 × CW6 | 1.066E−14 | 0.0 to 1.289e−009 | 0.9475 |
| B221 × CW5 | 2.526E−12 | 7.070e−013 to 9.031e−012 | 0.9908 |

Example 17: Anti-Tumor Efficacy of Mabtyrin, B219xCW6, in Tumorigenesis Prevention of HEK293-PSMA Xenografts in PBMC-Humanized NSG Mice Efficacy of B219xCW6 was evaluated by prevention of tumorigenesis (prophylactic model) of HEK293-PSMA human xenografts using inoculated human donor peripheral blood mononuclear cells (PBMC) in male NSG mice (NOD.Cg-Prkdcscid IL2rgtmlWjl/SzJ, Jackson Laboratories, Bar Harbor, Me.). Mice were injected intravenously (iv) in the lateral tail vein with 1×107 human PBMCs 7 days (day −7) prior to tumor cell implantation. Mice were implanted subcutaneously (sc) on day 0 with 1×107 HEK293-PSMA cells in the right hind flank. Beginning on the day of tumor implantation PBS (phosphate buffered saline) control and B219xCW6 were administered iv at 0.004 mg/kg, 0.04 mg/kg, 0.4 mg/kg (equivalent to 0.1 μg, 1 μg and 10 μg per 25 gram mouse, respectively), q2d-q3d for a total of 5 doses on days 0, 3, 5, 7 and 10.

Tumor volume was calculated using the formula: Tumor Volume (mm3)=(a×b2/2); where 'a' represents the length, and 'b' the width of the tumor as determined by caliper measurements], and monitored twice weekly throughout the study. Percent tumor growth inhibition (TGI) was defined as the difference between mean tumor volumes of the treated and control (PBS) groups, calculated as TGI=[((TVc−TVt)/TVc)*100] where TVc is the mean tumor volume of a given control group and TVt is the mean tumor volume of the treated group. As defined by NCI criteria, ≥60% TGI is considered biologically significant (Johnson J I, et al (2001) Br J Cancer 84(10):1424-31). Animals were removed from studies when a maximum tumor volume of 1500 mm3 was reached.

Engraftment of human PBMC eventually leads to graft versus host disease (GVHD) in the mice, where the engrafted donor T cells become activated and infiltrate the host tissues, leading to body weight loss, organ failure, and inevitably, death. To monitor the onset and severity of GVHD, body weight was recorded twice weekly and expressed in grams (g). Percent body weight change was calculated using the formula: Body weight change=[((Bt B0)/B0)*100] where Bt is the body weight on a given day of study and B0 is the body weight at the initiation of treatment. Animals with sustained body weight loss greater than 20% of the initial body weight were considered moribund and removed from the study.

Statistical significance was evaluated using a 1-way ANOVA with multiple comparisons using Dunnett's multiple comparisons test using Graph Pad Prism software (version 6). Additional statistical analyses for indicated studies can be found in the laboratory notebook.

All in vivo studies were performed in accordance with The Guide for the Care and Use of Laboratory Animals and approved by the Institutional Animal Care and Use Committee of Janssen R & D, Spring House, Pa.

Figure 18:
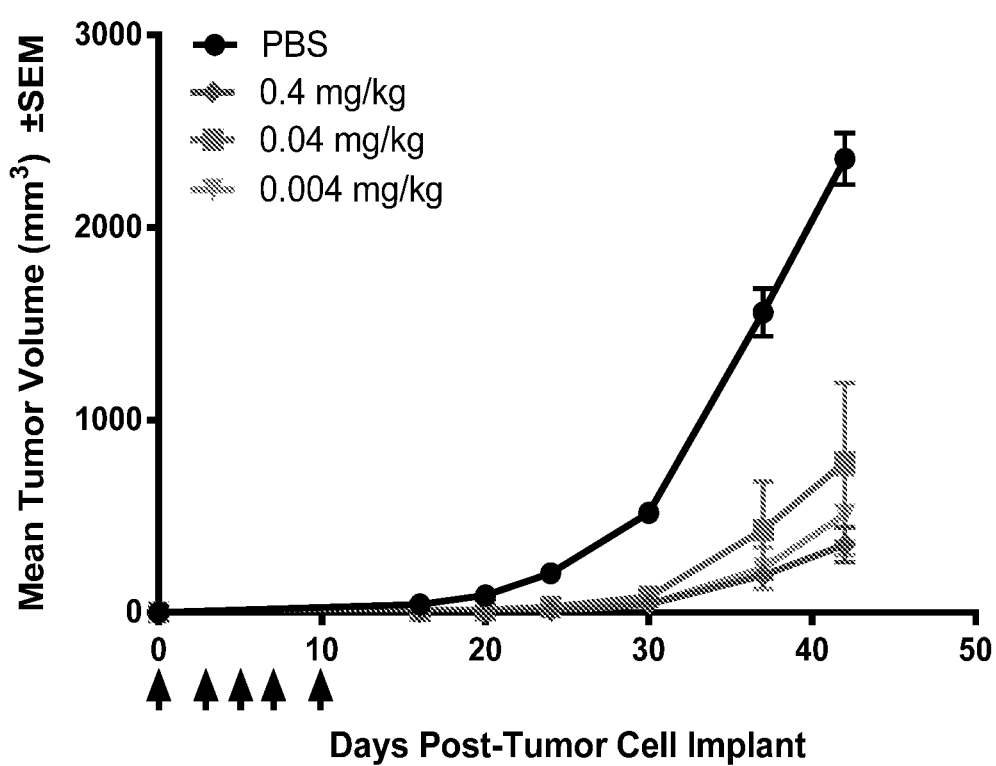
FIG. 18.

B219xCW6 Mabtyrin treatment effectively delayed tumorigenesis and inhibited tumor growth of implanted HEK293-PSMA cells (FIG. 18). Small but palpable HEK293-PSMA tumors were detectable in seven of eight mice in the PBS treated group on study day 16 (6 days post last therapeutic treatment), whereas there were no tumors in all eight mice of the 0.4 mg/kgCD3B250 treated group. Two out of eight mice had palpable tumors in the 0.04 mg/kg B219xCW6 treatment group and one out of eight mice had a small tumor in the 0.004 mg/kg B219xCW6 group. Tumor growth inhibition was assessed 32 days following cessation of treatment (day 42 post-tumor implantation), when there were still 7 or 8 animals per group. Tumor growth in the high dosed B219xCW6 (0.4 mg/kg, n=8) treated group was inhibited by 85% compared to PBS-treated controls ($p<0.001$). The mid dose of B219xCW6 (0.04 mg/kg) inhibited tumor growth in a statistically significant fashion (TGI=67%, n=7) vs. PBS control, ($p<0.0001$). Lastly, the lowest dose, 0.004 mg/kg, of B219xCW6 was also efficacious inhibiting HEK293-PSMA tumor growth by 78% ($p<0.0001$) compared to control PBS treated tumors.

Figure 19:
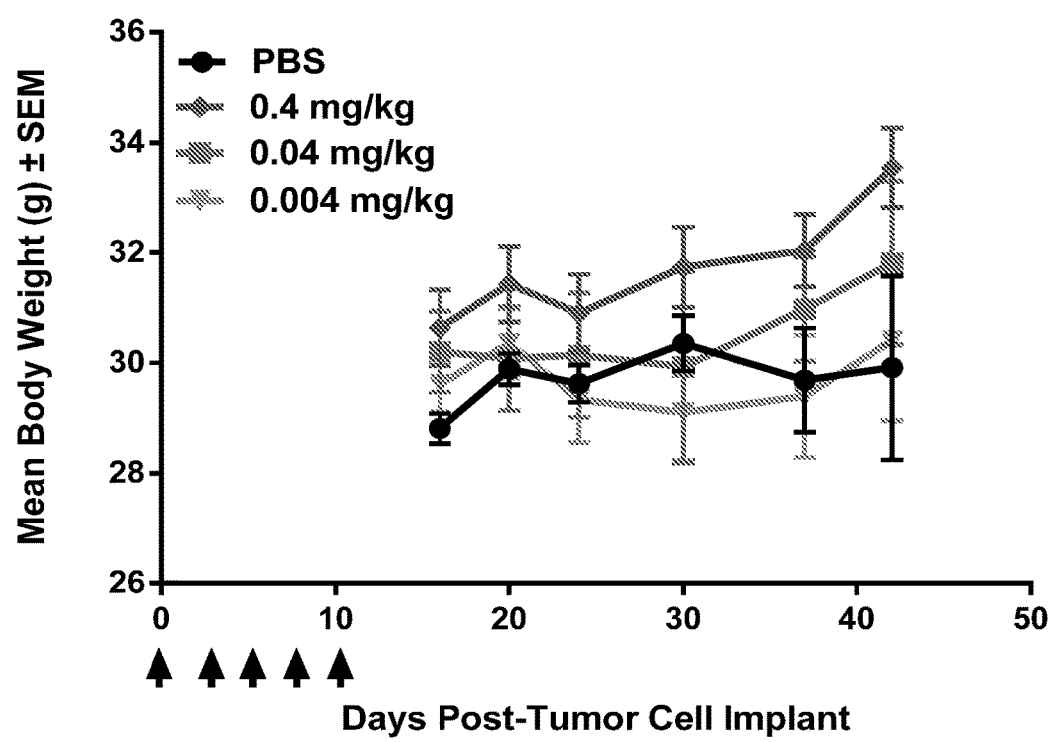
FIG. 19.

Animal groups receiving PBMCs eventually succumb to progressive GVHD, however body weight loss was slight in the current study (FIG. 19). Only one mouse in the 1 ug B219xCW6 group had significant body weight and succumbed to GVHD on day 30. By day 42, the majority of the tumors in the PBS treated group had exceeded the 1500 mm3 tumor volume endpoint, at which time the study was terminated.

SEQUENCE LISTING

```
SEQ ID No. 1 = Original TENCON ™ Sequence
LPAPKNLVVSEVTEDSLRLSWTAPDAAFDSFLIQYQESEKVGEAINLTVPGSERSY

DLTGLKPGTEYTVSIYGVKGGHRSNPLSAEFTT

SEQ ID No. 2 = TCL1 library
LPAPKNLVVSEVTEDSLRLSWTAPDAAFDSFLIQYQESEKVGEAINLTVPGSERSY DLTGLKPGTEYTVSIYGV(X) 7-12PLSAEFTT; wherein X1, X2, X3, X4, X5, X6, X7 is any amino acid; and X8, X9, X10, X11 and X12 are any amino acid or deleted
```

-continued

SEQ ID No. 3 = TCL2 library
LPAPKNLVVSEVTEDSLRLSWX$_1$X$_2$X$_3$X$_4$X$_5$X$_6$X$_7$X$_8$SFLIQYQESEKVGEAINLTVPG SERSYDLTGLKPGTEYTVSIYGVX$_9$X$_{10}$X$_{11}$X$_{12}$X$_{13}$SX$_{14}$X$_{15}$LSAEFTT; wherein X$_1$ is Ala, Arg, Asn, Asp, Glu, Gln, Gly, His, Ile, Leu, Lys, Phe, Pro, Ser, Thr, Trp, Tyr or Val; X$_2$ is Ala, Arg, Asn, Asp, Glu, Gln, Gly, His, Ile, Leu, Lys, Phe, Pro, Ser, Thr, Trp, Tyr or Val; X$_3$ Ala, Arg, Asn, Asp, Glu, Gln, Gly, His, Ile, Leu, Lys, Phe, Pro, Ser, Thr, Trp, Tyr or Val; X$_4$ is Ala, Arg, Asn, Asp, Glu, Gln, Gly, His, Ile, Leu, Lys, Phe, Pro, Ser, Thr, Trp, Tyr or Val; X$_5$ is Ala, Arg, Asn, Asp, Glu, Gln, Gly, His, Ile, Leu, Lys, Phe, Pro, Ser, Thr, Trp, Tyr or Val; X$_6$ is Ala, Arg, Asn, Asp, Glu, Gln, Gly, His, Ile, Leu, Lys, Phe, Pro, Ser, Thr, Trp, Tyr or Val; X$_7$ is Phe, Ile, Leu, Val or Tyr; X$_8$ is Asp, Glu or Thr; X$_9$ is Ala, Arg, Asn, Asp, Glu, Gln, Gly, His, Ile, Leu, Lys, Phe, Pro, Ser, Thr, Trp, Tyr or Val; X$_{10}$ is Ala, Arg, Asn, Asp, Glu, Gln, Gly, His, Ile, Leu, Lys, Phe, Pro, Ser, Thr, Trp, Tyr or Val; X$_{11}$ is Ala, Arg, Asn, Asp, Glu, Gln, Gly, His, Ile, Leu, Lys, Phe, Pro, Ser, Thr, Trp, Tyr or Val; X$_{12}$ is Ala, Arg, Asn, Asp, Glu, Gln, Gly, His, Ile, Leu, Lys, Phe, Pro, Ser, Thr, Trp, Tyr or Val; X$_{13}$ is Ala, Arg, Asn, Asp, Glu, Gln, Gly, His, Ile, Leu, Lys, Phe, Pro, Ser, Thr, Trp, Tyr or Val; X$_{14}$ is Ala, Arg, Asn, Asp, Glu, Gln, Gly, His, Ile, Leu, Lys, Phe, Pro, Ser, Thr, Trp, Tyr or Val; and X$_{15}$ is Ala, Arg, Asn, Asp, Glu, Gln, Gly, His, Ile, Leu, Lys, Phe, Pro, Ser, Thr, Trp, Tyr or Val.
SEQ ID No. 4 = Stabilized Tencon
LPAPKNLVVSRVTEDSARLSWTAPDAAFDSFLIQYQESEKVGEAIVLTVPGSERS

YDLTGLKPGTEYTVSIYGVKGGHRSNPLSAIFTT

SEQ ID No. 5 = TCL7 (FG and BC loops)
LPAPKNLVVSRVTEDSARLSWX$_1$X$_2$X$_3$X$_4$X$_5$X$_6$X$_7$X$_8$X$_9$FDSFLIQYQESEKVGEAIVL TVPGSERSYDLTGLKPGTEYTVSIYGVX$_{10}$X$_{11}$X$_{12}$X$_{13}$X$_{14}$X$_{15}$X$_{16}$X$_{17}$X$_{18}$X$_{19}$SNPLSAIF TT; wherein X$_1$, X$_2$, X$_3$, X$_4$, X$_5$, X$_6$, X$_{10}$, X$_{11}$, X$_{12}$, X$_{13}$, X$_{14}$, X$_{15}$ and X$_{16}$ are A, D, E, F, G, H, I, K, L, N, P, Q, R, S, T, V, W or Y; and X$_7$, X$_8$, X$_9$, X$_{17}$, X$_{18}$ and X$_{19}$, are A, D, E, F, G, H, I, K, L, N, P, Q, R, S, T, V, W, Y or deleted.
SEQ ID No. 6 = TCL9 (FG loop)
LPAPKNLVVSRVTEDSARLSWTAPDAAFDSFLIQYQESEKVGEAIVLTVPGSERS YDLTGLKPGTEYTVSIYGV X$_1$X$_2$X$_3$X$_4$X$_5$X$_6$X$_7$X$_8$X$_9$ X$_{10}$X$_{11}$X$_{12}$SNPLSAIFTT;

wherein X$_1$, X$_2$, X$_3$, X$_4$, X$_5$, X$_6$ and X$_7$, is A, D, E, F, G, H, I, K, L, N, P, Q, R, S, T, V, W or Y; and X$_8$, X$_9$, X$_{10}$, X$_{11}$ and X$_{12}$ is A, D, E, F, G, H, I, K, L, N, P, Q, R, S, T, V, W, Y or deleted.
SEQ ID No. 7 = TCL14 library
LPAPKNLVVSRVTEDSARLSWTAPDAAFDSFX$_1$IX$_2$YX$_3$EX$_4$X$_5$X$_6$X$_7$GEAIVLTVPG SERSYDLTGLKPGTEYX$_8$VX$_9$IX$_{10}$GVKGGX$_{11}$X$_{12}$SX$_{13}$PLSAIFTT; wherein X$_1$, X$_2$, X$_3$, X$_4$, X$_5$, X$_6$, X$_7$, X$_8$, X$_9$, X$_{10}$, X$_{11}$, X$_{12}$ and X$_{13}$ are A, C, D, E, F, G, H, I, K, L, M, N, P, Q, R, S, T, V, W or Y
SEQ ID No. 8 = TCL24 Library
TCL24 Library (SEQ ID NO: 8)
LPAPKNLVVSRVTEDSARLSWTAPDAAFDSFX$_1$IX$_2$YX$_3$EX$_4$X$_5$X$_6$X$_7$GEAIX$_8$LX$_9$VP GSERSYDLTGLKPGTEYX$_{10}$VX$_{11}$IX$_{12}$GVKGGX$_{13}$X$_{14}$SX$_{15}$PLX$_{16}$AX$_{17}$FTT; wherein X$_1$, X$_2$, X$_3$, X$_4$, X$_5$, X$_6$, X$_{10}$, X$_{11}$, X$_{12}$, X$_{13}$, X$_{14}$, X$_{15}$, X$_{16}$ and X$_{17}$ are A, D, E, F, G, H, I, K, L, N, P, Q, R, S, T, V, Y or W.
SEQ ID No. 9 = Sloning-FOR
GTGACACGGCGGTTAGAAC SEQ ID No. 10 = Sloning-REV
GCCTTTGGGAAGCTTCTAAG SEQ ID No. 11 = POP2250
CGGCGGTTAGAACGCGGCTACAATTAATAC SEQ ID No. 12 = DigLigRev
CATGATTACGCCAAGCTCAGAA SEQ ID No. 13 = BC9
GTGACACGGCGGTTAGAACGCGGCTACAATTAATACATAACCCCATCCCCCT

GTTGACAATTAATCATCGGCTCGTATAATGTGTGGAATTGTGAGCGGATAAC

AATTTCACACAGGAAACAGGATCTACCATGCTGCCGGCGCCGAAAAACCTGG

TTGTTTCTGAAGTTACCGAAGACTCTCTGCGTCTGTCTTGGNNNNNNNNNNNN

NNNNNNNNNNNNNNNNNTTYGACTCTTTCCTGATCCAGTACCAGGAATCTGAAA

AAGTTGGTGAAGCGATCAACCTGACCGTTCCGGGTTCTGAACGTTCTTACGAC

-continued

CTGACCGGTCTGAAACCGGGTACCGAATACACCGTTTCTATCTACGGTGTTCT

TAGAAGCTTCCCAAAGGC

SEQ ID No. 14 = BC8
GTGACACGGCGGTTAGAACGCGGCTACAATTAATACATAACCCCATCCCCCT

GTTGACAATTAATCATCGGCTCGTATAATGTGTGGAATTGTGAGCGGATAAC

AATTTCACACAGGAAACAGGATCTACCATGCTGCCGGCGCCGAAAAACCTGG

TTGTTTCTGAAGTTACCGAAGACTCTCTGCGTCTGTCTTGGNNNNNNNNNNN

NNNNNNNNNNNNTTYGACTCTTTCCTGATCCAGTACCAGGAATCTGAAAAAG

TTGGTGAAGCGATCAACCTGACCGTTCCGGGTTCTGAACGTTCTTACGACCTG

ACCGGTCTGAAACCGGGTACCGAATACACCGTTTCTATCTACGGTGTTCTTAG

AAGCTTCCCAAAGGC

SEQ ID No. 15 = BC7
GTGACACGGCGGTTAGAACGCGGCTACAATTAATACATAACCCCATCCCCCT

GTTGACAATTAATCATCGGCTCGTATAATGTGTGGAATTGTGAGCGGATAAC

AATTTCACACAGGAAACAGGATCTACCATGCTGCCGGCGCCGAAAAACCTGG

TTGTTTCTGAAGTTACCGAAGACTCTCTGCGTCTGTCTTGGNNNNNNNNNNN

NNNNNNNNNNTTYGACTCTTTCCTGATCCAGTACCAGGAATCTGAAAAAGTTG

GTGAAGCGATCAACCTGACCGTTCCGGGTTCTGAACGTTCTTACGACCTGACC

GGTCTGAAACCGGGTACCGAATACACCGTTTCTATCTACGGTGTTCTTAGAAG

CTTCCCAAAGGC

SEQ ID No. 16 = BC6
GTGACACGGCGGTTAGAACGCGGCTACAATTAATACATAACCCCATCCCCCT

GTTGACAATTAATCATCGGCTCGTATAATGTGTGGAATTGTGAGCGGATAAC

AATTTCACACAGGAAACAGGATCTACCATGCTGCCGGCGCCGAAAAACCTGG

TTGTTTCTGAAGTTACCGAAGACTCTCTGCGTCTGTCTTGGNNNNNNNNNNN

NNNNNNTTYGACTCTTTCCTGATCCAGTACCAGGAATCTGAAAAAGTTGGTG

AAGCGATCAACCTGACCGTTCCGGGTTCTGAACGTTCTTACGACCTGACCGGT

CTGAAACCGGGTACCGAATACACCGTTTCTATCTACGGTGTTCTTAGAAGCTT

CCCAAAGGC

SEQ ID No. 17 = 130mer-L17A
CGGCGGTTAGAACGCGGCTACAATTAATACATAACCCCATCCCCCTGTTGAC

AATTAATCATCGGCTCGTATAATGTGTGGAATTGTGAGCGGATAACAATTTCA

CACAGGAAACAGGATCTACCATGCTG

SEQ ID No. 18 = POP222ext
CGG CGG TTA GAA CGC GGC TAC AAT TAA TAC

SEQ ID No. 19 = LS1114
CCA AGA CAG ACG GGC AGA GTC TTC GGT AAC GCG AGA AAC AAC CAG

GTT TTT CGG CGC CGG CAG CAT GGT AGA TCC TGT TTC

SEQ ID No. 20 = LS1115
CCG AAG ACT CTG CCC GTC TGT CTT GG

SEQ ID No. 21 = LS1117
CAG TGG TCT CAC GGA TTC CTG GTA CTG GAT CAG GAA AGA GTC GAA

SEQ ID No. 22 = SDG10
CATGCGGTCTCTTCCGAAAAAGTTGGTGAAGCGATCGTCCTGACCGTTCCGG

GT

SEQ ID No. 23 = SDG24
GGTGGTGAAGATCGCAGACAGCGGGTTAG

SEQ ID No. 24 = POP2222
CGGCGGTTAGAACGCGGCTAC

SEQ ID No. 25 = SDG28
AAGATCAGTTGCGGCCGCTAGACTAGAACCGCTGCCACCGCCGGTGGTGAAG

ATCGCAGAC

SEQ ID No. 26 = FG12
GTGACACGGCGGTTAGAACGCGGCTACAATTAATACATAACCCCATCCCCCT

GTTGACAATTAATCATCGGCTCGTATAATGTGTGGAATTGTGAGCGGATAAC

AATTTCACACAGGAAACAGGATCTACCATGCTGCCGGCGCCGAAAAACCTGG

TTGTTTCTCGCGTTACCGAAGACTCTGCGCGTCTGTCTTGGACCGCGCCGGAC

GCGGCGTTCGACTCTTTCCTGATCCAGTACCAGGAATCTGAAAAAGTTGGTG

AAGCGATCGTGCTGACCGTTCCGGGTTCTGAACGTTCTTACGACCTGACCGGT

CTGAAACCGGGTACCGAATACACCGTTTCTATCTACGGTGTTNNNNNNNNNN

NNNNNNNNNNNNNNNNNNNNNNNNTCTAACCCGCTGTCTGCGATCTTCA

CCACCGGCGGTCACCATCACCATCACCATGGCAGCGGTTCTAGTCTAGCGGC

CGCAACTGATCTTGGC

SEQ ID No. 27 = FG11
GTGACACGGCGGTTAGAACGCGGCTACAATTAATACATAACCCCATCCCCCT

GTTGACAATTAATCATCGGCTCGTATAATGTGTGGAATTGTGAGCGGATAAC

AATTTCACACAGGAAACAGGATCTACCATGCTGCCGGCGCCGAAAAACCTGG

TTGTTTCTCGCGTTACCGAAGACTCTGCGCGTCTGTCTTGGACCGCGCCGGAC

GCGGCGTTCGACTCTTTCCTGATCCAGTACCAGGAATCTGAAAAAGTTGGTG

AAGCGATCGTGCTGACCGTTCCGGGTTCTGAACGTTCTTACGACCTGACCGGT

CTGAAACCGGGTACCGAATACACCGTTTCTATCTACGGTGTTNNNNNNNNNN

NNNNNNNNNNNNNNNNNNNNNNNTCTAACCCGCTGTCTGCGATCTTCACCAC

CGGCGGTCACCATCACCATCACCATGGCAGCGGTTCTAGTCTAGCGGCCGCA

ACTGATCTTGGC

SEQ ID No. 28 = FG10
GTGACACGGCGGTTAGAACGCGGCTACAATTAATACATAACCCCATCCCCCT

GTTGACAATTAATCATCGGCTCGTATAATGTGTGGAATTGTGAGCGGATAAC

AATTTCACACAGGAAACAGGATCTACCATGCTGCCGGCGCCGAAAAACCTGG

TTGTTTCTCGCGTTACCGAAGACTCTGCGCGTCTGTCTTGGACCGCGCCGGAC

GCGGCGTTCGACTCTTTCCTGATCCAGTACCAGGAATCTGAAAAAGTTGGTG

AAGCGATCGTGCTGACCGTTCCGGGTTCTGAACGTTCTTACGACCTGACCGGT

CTGAAACCGGGTACCGAATACACCGTTTCTATCTACGGTGTTNNNNNNNNNN

NNNNNNNNNNNNNNNNNNNNNTCTAACCCGCTGTCTGCGATCTTCACCACCGG

CGGTCACCATCACCATCACCATGGCAGCGGTTCTAGTCTAGCGGCCGCAACT

GATCTTGGC

SEQ ID No. 29 = FG9
GTGACACGGCGGTTAGAACGCGGCTACAATTAATACATAACCCCATCCCCCT

GTTGACAATTAATCATCGGCTCGTATAATGTGTGGAATTGTGAGCGGATAAC

AATTTCACACAGGAAACAGGATCTACCATGCTGCCGGCGCCGAAAAACCTGG

```
                                     -continued
TTGTTTCTCGCGTTACCGAAGACTCTGCGCGTCTGTCTTGGACCGCGCCGGAC

GCGGCGTTCGACTCTTTCCTGATCCAGTACCAGGAATCTGAAAAAGTTGGTG

AAGCGATCGTGCTGACCGTTCCGGGTTCTGAACGTTCTTACGACCTGACCGGT

CTGAAACCGGGTACCGAATACACCGTTTCTATCTACGGTGTTNNNNNNNNNN

NNNNNNNNNNNNNNNNNTCTAACCCGCTGTCTGCGATCTTCACCACCGGCGG

TCACCATCACCATCACCATGGCAGCGGTTCTAGTCTAGCGGCCGCAACTGAT

CTTGGC

SEQ ID No. 30 = FG8
GTGACACGGCGGTTAGAACGCGGCTACAATTAATACATAACCCCATCCCCCT

GTTGACAATTAATCATCGGCTCGTATAATGTGTGGAATTGTGAGCGGATAAC

AATTTCACACAGGAAACAGGATCTACCATGCTGCCGGCGCCGAAAAACCTGG

TTGTTTCTCGCGTTACCGAAGACTCTGCGCGTCTGTCTTGGACCGCGCCGGAC

GCGGCGTTCGACTCTTTCCTGATCCAGTACCAGGAATCTGAAAAAGTTGGTG

AAGCGATCGTGCTGACCGTTCCGGGTTCTGAACGTTCTTACGACCTGACCGGT

CTGAAACCGGGTACCGAATACACCGTTTCTATCTACGGTGTTNNNNNNNNNN

NNNNNNNNNNNNNNTCTAACCCGCTGTCTGCGATCTTCACCACCGGCGGTCA

CCATCACCATCACCATGGCAGCGGTTCTAGTCTAGCGGCCGCAACTGATCTTG

GC

SEQ ID No. 31 = FG7
GTGACACGGCGGTTAGAACGCGGCTACAATTAATACATAACCCCATCCCCCT

GTTGACAATTAATCATCGGCTCGTATAATGTGTGGAATTGTGAGCGGATAAC

AATTTCACACAGGAAACAGGATCTACCATGCTGCCGGCGCCGAAAAACCTGG

TTGTTTCTCGCGTTACCGAAGACTCTGCGCGTCTGTCTTGGACCGCGCCGGAC

GCGGCGTTCGACTCTTTCCTGATCCAGTACCAGGAATCTGAAAAAGTTGGTG

AAGCGATCGTGCTGACCGTTCCGGGTTCTGAACGTTCTTACGACCTGACCGGT

CTGAAACCGGGTACCGAATACACCGTTTCTATCTACGGTGTTNNNNNNNNNN

NNNNNNNNNNNNTCTAACCCGCTGTCTGCGATCTTCACCACCGGCGGTCACCA

TCACCATCACCATGGCAGCGGTTCTAGTCTAGCGGCCGCAACTGATCTTGGC

SEQ ID No. 32 = PSMW1 (N'-AviTag-HisTag-GS-Cyno PSMA_ECD)
KSSSEATNITPKHNMKAFLDELKAENIKKFLHNFTQIPHLAGTEQNFQLAKQIQSQ

WKEFGLDSVELTHYDVLLSYPNKTHPNYISIINEDGNEIFNTSLFEPPPAGYENVS

DIVPPFSAFSPQGMPEGDLVYVNYARTEDFFKLERDMKINCSGKIVIARYGKVFR

GNKVKNAQLAGATGVILYSDPDDYFAPGVKSYPDGWNLPGGGVQRGNILNLNG

AGDPLTPGYPANEYAYRRGMAEAVGLPSIPVHPIGYYDAQKLLEKMGGSASPDS

SWRGSLKVPYNVGPGFTGNFSTQKVKMHIHSTSEVTRIYNVIGTLRGAVEPDRY

VILGGHRDSWVFGGIDPQSGAAVVHEIVRSFGMLKKEGWRPRRTILFASWDAEE

FGLLGSTEWAEENSRLLQERGVAYINADSSIEGNYTLRVDCTPLMYSLVYNLTKE

LESPDEGFEGKSLYESWTKKSPSPEFSGMPRISKLGSGNDFEVFFQRLGIASGRAR

YTKNWETNKFSSYPLYHSVYETYELVEKFYDPMFKYHLTVAQVRGGMVFELAN

SVVLPFDCRDYAVVLRKYADKIYNISMKHPQEMKTYSVSFDSLFSAVKNFTEIAS

KFSERLRDFDKSNPILLRMMNDQLMFLERAFIDPLGLPDRPFYRHVIYAPSSHNK

YAGESFPGIYDALFDIESKVDPSQAWGEVKRQISIATFTVQAAAETLSEVA
```

SEQ ID No. 33 = PSMW8 (N'-AviTag-HisTag-GS-Chimp PSMA_ECD)
KSSNEATNITPKHNMKAFLDELKAENIKKFLYNFTQIPHLAGTEQNFQLAKQIQS

QWKEFGLDSVELAHYDVLLSYPNKTHPNYISIINEDGNEIFNTSLFEPPPPGYENV

LDIVPPFSAFSPQGMPEGDLVYVNYARTEDFFKLERDMKINCSGKIVIARYGKVF

RGNKVKNAQLAGAKGVILYSDPADYFAPGVKSYPDGWNLPGGGVQRGNILNLN

GAGDPLTPGYPANEYAYRHGIAEAVGLPSIPVHPIGYYDAQKLLEKMGGSAPPDS

SWRGSLKVPYNVGPGFTGNFSTQKVKMHIHSTNEVTRIYNVIGTLRGAVEPDRY

VILGGHRDSWVFGGIDPQSGAAVVHEIVRSFGTLKKEGWRPRRTILFASWDAEEF

GLLGSTEWAEENSRLLQERGVAYINADSSIEGNYTLRVDCTPLMYSLVYNLTKEL

KSPDEGFEGKSLYESWTKKSPSPEFSGMPRISKLGSGNDFEVFFQRLGIASGRARY

TKNWETNKFSGYPLYHSVYETYELVEKFYDPMFKYHLTVAQVRGGMVFELANS

IVLPFDCRDYAVVLRKYADKIYNISMKHPQEMKTYSVSFDSLFSAVKNFTEIASK

FTERLQDFDKSNPILLRMMNDQLMFLERAFIDPLGLPDRPFYRHVIYAPSSHNKY

AGESFPGIYDALFDIESKVDPSKAWGDVKRQISVAAFTVQAAAETLSEVA

SEQ ID NO. 34 hexahistidine tag
HHHHHH

SEQ ID No. 35 = P258AR6P1071_G03
LPAPKNLVVSRVTEDSARLSWDIDEQRDWFDSFLIQYQESEKVGEAIVLTVPGSE

RSYDLTGLKPGTEYTVSIYGVYHVYRSNPLSAIFTT

SEQ ID No. 36 = P258AR6P1070_A05
LPAPKNLVVSRVTEDSARLSWTIDEQRDWFDSFLIQYQESEKVGEAIVLTVPGSE

RSYDLTGLKPGTEYTVSIYGVYHVYRSNPLSAIFTT

SEQ ID No. 37 = P258AR6P1071_F04
LPAPKNLVVSRVTEDSARLSWVIDEQRDWFDSFLIQYQESEKVGEAIVLTVPGSE

RSYDLTGLKPGTEYTVSIYGVYHVYRSNPLSAIFTT

SEQ ID No. 38 = P258AR6P1070_F09
LPAPKNLVVSRVTEDSARLSWTIDEQRDWFESFLIQYQESEKVGEAIVLTVPGSE

RSYDLTGLKPGTEYTVSIYGVYHVYRSNPLSAIFTT

SEQ ID No. 39 = P258AR6P1071_D02
LPAPKNLVVSRVTEDSARLSWAIDEQRDWFESFLIQYQESEKVGEAIVLTVPGSE

RSYDLTGLKPGTEYTVSIYGVYHVYRSNPLSAIFTT

SEQ ID No. 40 = P229CR5P819_H11
LPAPKNLVVSRVTEDSARLSWDIDEQRDWFDSFLIQYQESEKVGEAIVLTVPGSE

RSYDLTGLKPGTEYTVSIYGVYHVYRSSNPLSAIFTT

SEQ ID No. 41 = P233FR9_H10
LPAPKNLVVSRVTEDSARLSWTAPDAAFDSFAIGYWEWDDDGEAIVLTVPGSER

SYDLTGLKPGTEYPVYIAGVKGGQWSFPLSAIFTT

SEQ ID No. 42 = P233FR9P1001_B5-5
LPAPKNLVVSRVTEDSARLSWTAPDAAFDSFTIGYWEWDDDGEAIVLTVPGSER

SYDLTGLKPGTEYPVYIAGVKGGQWSFPLSAIFTT

SEQ ID No. 43 = P233FR9P1001_H3-1
LPAPKNLVVSRVTEDSARLSWTAPDAAFDSFPIGYWEWDDDGEAIVLTVPGSER

SYDLTGLKPGTEYHVYIAGVKGGQWSFPLSAIFTT

SEQ ID No. 44 = P233FR9P1001_D9
LPAPKNLVVSRVTEDSARLSWTAPDAAFDSFPIGYWEWDDDGEAIVLTVPGSER

SYDLTGLKPGTEYWVYIAGVKGGQWSFPLSAIFTT

SEQ ID No. 45 = P234CR9_A07

LPAPKNLVVSRVTEDSARLSWGEQFTIFDSFLIQYQESEKVGEAIVLTVPGSERSY

DLTGLKPGTEYTVSIYGASGYEWFHAFGSSNPLSAIFTT

SEQ ID No. 46 = P234CR9_H01
LPAPKNLVVSRVTEDSARLSWEWWVIPGDFDSFLIQYQESEKVGEAIVLTVPGSE

RSYDLTGLKPGTEYTVSIYGVVNSGQWNDTSNPLSAIFTT

SEQ ID No. 47 = P233FR9_H10 (cterm cys)
LPAPKNLVVSRVTEDSARLSWTAPDAAFDSFAIGYWEWDDDGEAIVLTVPGSER

SYDLTGLKPGTEYPVYIAGVKGGQWSFPLSAIFTTC

SEQ ID No. 48 = P233FR9_H10 (K62C)
LPAPKNLVVSRVTEDSARLSWTAPDAAFDSFAIGYWEWDDDGEAIVLTVPGSER

SYDLTGLCPGTEYPVYIAGVKGGQWSFPLSAIFTT

SEQ ID No. 49 = P233FR9_H10 (E53C)
LPAPKNLVVSRVTEDSARLSWTAPDAAFDSFAIGYWEWDDDGEAIVLTVPGSCR

SYDLTGLKPGTEYPVYIAGVKGGQWSFPLSAIFTT

SEQ ID No. 50 = P233FR9_H10 (R11C)
LPAPKNLVVSCVTEDSARLSWTAPDAAFDSFAIGYWEWDDDGEAIVLTVPGSER

SYDLTGLKPGTEYPVYIAGVKGGQWSFPLSAIFTT

SEQ ID No. 51 = untargeted FN3 domain (K62C)
LPAPKNLVVSEVTEDSARLSWTAPDAAFDSFLIQYQESEKVGEAIVLTVPGSERS

YDLTGLCPGTEYTVSIYGVKGGHRSNPLSAIFTTGGHHHHHH

SEQ ID No. 52 = Sortase A
MSHHHHHHSSGENLYFQSKPHIDNYLHDKDKDEKIEQYDKNVKEQASKDKKQQ

AKPQIPKDKSKVAGYIEIPDADIKEPVYPGPATREQLNRGVSFAEENESLDDQNISI

AGHTFIDRPNYQFTNLKAAKKGSMVYFKVGNETRKYKMTSIRNVKPTAVEVLD

EQKGKDKQLTLITCDDYNEETGVWETRKIFVATEVK

SEQ ID No. 53 = tagless Sortase A
SKPHIDNYLHDKDKDEKIEQYDKNVKEQASKDKKQQAKPQIPKDKSKVAGYIEI

PDADIKEPVYPGPATREQLNRGVSFAEENESLDDQNISIAGHTFIDRPNYQFTNLK

AAKKGSMVYFKVGNETRKYKMTSIRNVKPTAVEVLDEQKGKDKQLTLITCDDY

NEETGVWETRKIFVATEVK

SEQ ID NO: 54 TEV protease cleavage site
ENLYFQS

SEQ ID NO: 55 FG loop of Tencon
KGGHRSN

SEQ ID NO: 56 BC loop
DIDEQRDW

SEQ ID NO: 57 BC loop
TIDEQRDW

SEQ ID NO: 58 BC loop
VIDEQRDW

SEQ ID NO: 59 BC loop
AIDEQRDW

SEQ ID NO: 60 BC loop
EWWVIPGD

SEQ ID NO: 61 BC loop
GEQFTI

SEQ ID NO: 62 BC loop
TAPDAA

SEQ ID NO: 63 C loop
FDSFLIQYQE

SEQ ID NO: 64 C loop
FESFLIQYQE

SEQ ID NO: 65 C loop
FDSFAIGYWE

SEQ ID NO: 66 C loop
FDSFPIGYWE

SEQ ID NO: 67 C loop
FDSFTIGYWE

SEQ ID NO: 68 CD loop
SEKVGE

SEQ ID NO: 69 CD loop
WDDDGE

SEQ ID NO: 70 F loop
TEYTVSIYGV

SEQ ID NO: 71 F loop
TEYTVSIYG

SEQ ID NO: 72 F loop
TEYPVYIAGV

SEQ ID NO: 73 F loop
TEYWVYIAGV

SEQ ID NO: 74 F loop
TEYHVYIAGV

SEQ ID NOs: 75-140 are above in the tables
SEQ ID NO: 141 full length cynoPSMA
MWNLLHETDSAVATARRPRWLCAGALVLAGGFFLLGFLFGWFIKSSSEATNITP

KHNMKAFLDELKAENIKKFLHNFTQIPHLAGTEQNFQLAKQIQSQWKEFGLDSV

ELTHYDVLLSYPNKTHPNYISIINEDGNEIFNTSLFEPPPAGYENVSDIVPPFSAFSP

QGMPEGDLVYVNYARTEDFFKLERDMKINCSGKIVIARYGKVFRGNKVKNAQL

AGATGVILYSDPDDYFAPGVKSYPDGWNLPGGGVQRGNILNLNGAGDPLTPGYP

ANEYAYRRGMAEAVGLPSIPVHPIGYYDAQKLLEKMGGSASPDSSWRGSLKVP

YNVGPGFTGNFSTQKVKMHIHSTSEVTRIYNVIGTLRGAVEPDRYVILGGHRDS

WVFGGIDPQSGAAVVHEIVRSFGMLKKEGWRPRRTILFASWDAEEFGLLGSTEW

AEENSRLLQERGVAYINADSSIEGNYTLRVDCTPLMYSLVYNLTKELESPDEGFE

GKSLYESWTKKSPSPEFSGMPRISKLGSGNDFEVFFQRLGIASGRARYTKNWETN

KFSSYPLYHSVYETYELVEKFYDPMFKYHLTVAQVRGGMVFELANSVVLPFDCR

DYAVVLRKYADKIYNISMKHPQEMKTYSVSFDSLFSAVKNFTEIASKFSERLRDF

DKSNPILLRMMNDQLMFLERAFIDPLGLPDRPFYRHVIYAPSSHNKY

>142 linker
AEAAAKEAAAKEAAAKEAAAKEAAAKAAA

>143 human PSMA ECD
KSSNEATNITPKHNMKAFLDELKAENIKKFLYNFTQIPHLAGTEQNFQLAKQIQS

QWKEFGLDSVELAHYDVLLSYPNKTHPNYISIINEDGNEIFNTSLFEPPPPGYENV

SDIVPPFSAFSPQGMPEGDLVYVNYARTEDFFKLERDMKINCSGKIVIARYGKVF

RGNKVKNAQLAGAKGVILYSDPADYFAPGVKSYPDGWNLPGGGVQRGNILNLN

GAGDPLTPGYPANEYAYRRGIAEAVGLPSIPVHPIGYYDAQKLLEKMGGSAPPDS

SWRGSLKVPYNVGPGFTGNFSTQKVKMHIHSTNEVTRIYNVIGTLRGAVEPDRY

VILGGHRDSWVFGGIDPQSGAAVVHEIVRSFGTLKKEGWRPRRTILFASWDAEEF

GLLGSTEWAEENSRLLQERGVAYINADSSIEGNYTLRVDCTPLMYSLVHNLTKEL

-continued

KSPDEGFEGKSLYESWTKKSPSPEFSGMPRISKLGSGNDFEVFFQRLGIASGRARY

TKNWETNKFSGYPLYHSVYETYELVEKFYDPMFKYHLTVAQVRGGMVFELANS

IVLPFDCRDYAVVLRKYADKIYSISMKHPQEMKTYSVSFDSLFSAVKNFTEIASKF

SERLQDFDKSNPIVLRMMNDQLMFLERAFIDPLGLPDRPFYRHVIYAPSSHNKYA

GESFPGIYDALFDIESKVDPSKAWGEVKRQIYVAAFTVQAAAETLSEVA

>144 human FL PSMA with signal sequence
MWNLLHETDSAVATARRPRWLCAGALVLAGGFFLLGFLFGWFIKSSNEATNITP

KHNMKAFLDELKAENIKKFLYNFTQIPHLAGTEQNFQLAKQIQSQWKEFGLDSV

ELAHYDVLLSYPNKTHPNYISIINEDGNEIFNTSLFEPPPPGYENVSDIVPPFSAFSP

QGMPEGDLVYVNYARTEDFFKLERDMKINCSGKIVIARYGKVFRGNKVKNAQL

AGAKGVILYSDPADYFAPGVKSYPDGWNLPGGGVQRGNILNLNGAGDPLTPGY

PANEYAYRRGIAEAVGLPSIPVHPIGYYDAQKLLEKMGGSAPPDSSWRGSLKVP

YNVGPGFTGNFSTQKVKMHIHSTNEVTRIYNVIGTLRGAVEPDRYVILGGHRDS

WVFGGIDPQSGAAVVHEIVRSFGTLKKEGWRPRRTILFASWDAEEFGLLGSTEW

AEENSRLLQERGVAYINADSSIEGNYTLRVDCTPLMYSLVHNLTKELKSPDEGFE

GKSLYESWTKKSPSPEFSGMPRISKLGSGNDFEVFFQRLGIASGRARYTKNWETN

KFSGYPLYHSVYETYELVEKFYDPMFKYHLTVAQVRGGMVFELANSIVLPFDCR

DYAVVLRKYADKIYSISMKHPQEMKTYSVSFDSLFSAVKNFTEIASKFSERLQDF

DKSNPIVLRMMNDQLMFLERAFIDPLGLPDRPFYRHVIYAPSSHNKYAGESFPGI

YDALFDIESKVDPSKAWGEVKRQIYVAAFTVQAAAETLSEVA

>145 3rd FN3 domain of tenascin C
DAPSQIEVKDVTDTTALITWFKPLAEIDGIELTYGIKDVPGDRTTIDLTEDENQYSI

GNLKPDTEYEVSLISRRGDMSSNPAKETFTT

>146 Fibcon
LDAPTDLQVTNVTDTSITVSWTPPSATITGYRITYTPSNGPGEPKELTVPPSSTSVT

ITGLTPGVEYVVSLYALKDNQESPPLVGTQTT

>147 10$^{th}$ FN3 domain of fibronectin
VSDVPRDLEVVAATPTSLLISWDAPAVTVRYYRITYGETGGNSPVQEFTVPGSKS

TATISGLKPGVDYTITVYAVTGRGDSPASSKPISINYRT

>148
GSGS

>149
GGGSGGGS

>150
GGGGSGGGGSGGGGSGGGGSGGGGS

>151
APAP

>152
APAPAPAPAP

>153
APAPAPAPAPAPAPAPAP

>154
APAPAPAPAPAPAPAPAPAPAPAPAPAPAPAPAPAP

>155 Albumin variant
DAHKSEVAHRFKDLGEENFKALVLIAFAQYLQQSPFEDHVKLVNEVTEFAKTCV

ADESAENCDKSLHTLFGDKLCTVATLRETYGEMADCCAKQEPERNECFLQHKD

-continued

DNPNLPRLVRPEVDVMCTAFHDNEETFLKKYLYEIARRHPYFYAPELLFFAKRY

KAAFTECCQAADKAACLLPKLDELRDEGKASSAKQRLKCASLQKFGERAFKAW

AVARLSQRFPKAEFAEVSKLVTDLTKVHTECCHGDLLECADDRADLAKYICENQ

DSISSKLKECCEKPLLEKSHCIAEVENDEMPADLPSLAADFVESKDVCKNYAEAK

DVFLGMFLYEYARRHPDYSVVLLLRLAKTYETTLEKCCAAADPHECYAKVFDE

FKPLVEEPQNLIKQNCELFEQLGEYKFQNALLVRYTKKVPQVSTPTLVEVSRNLG

KVGSKCCKHPEAKRMPCAEDYLSVVLNQLCVLHEKTPVSDRVTKCCTESLVNR

RPCFSALEVDETYVPKEFNAETFTFHADICTLSEKERQIKKQTALVELVKHKPKA

TKEQLKAVMDDFAAFVEKCCKADDKETCFAEEGKKLVAASQAALGL

>156 cDNA H10
CTGCCAGCCCCGAAGAATTTGGTCGTTTCCCGTGTCACTGAGGACTCTGCACG

TCTGAGCTGGACCGCACCGGACGCGGCGTTCGACAGCTTTGCAATCGGCTAC

TGGGAGTGGGATGATGACGGCGAGGCCATTGTGCTGACCGTTCCGGGTAGCG

AGCGCAGCTACGATCTGACCGGTCTGAAGCCGGGTACGGAATATCCGGTGTA

TATTGCGGGCGTGAAGGGTGGCCAGTGGAGCTTCCCGCTGAGCGCGATCTTT

ACCACC

>157 cDNA P258AR6P1071_D02
CTGCCGGCTCCGAAAAACCTGGTCGTTTCCCGTGTCACTGAAGATTCTGCACG

CTTGAGCTGGGCGATCGACGAGCAGCGTGACTGGTTTGAGAGCTTCCTGATT

CAGTATCAAGAATCGGAAAAAGTTGGCGAGGCCATCGTGCTGACCGTTCCGG

GTAGCGAGCGCAGCTATGATCTGACGGGTCTGAAGCCAGGCACCGAGTATAC

GGTGAGCATTTACGGTGTCTACCATGTGTACCGTAGCAATCCGCTGAGCGCG

ATCTTCACCACC

>158 cDNA
P233FR9P1001_H3-1
CTGCCAGCCCCGAAAAACTTAGTTGTCTCCCGCGTGACCGAAGATTCTGCTCG

TCTGAGCTGGACTGCACCGGACGCGGCGTTCGACAGCTTTCCGATTGGCTACT

GGGAGTGGGATGATGACGGTGAAGCGATCGTGCTGACCGTTCCGGGTAGCGA

GCGTAGCTATGACCTGACGGGTTTGAAACCTGGTACCGAGTATCACGTTTAC

ATTGCGGGCGTCAAGGGTGGCCAGTGGTCGTTCCCGCTGAGCGCAATCTTTA

CGACC

>159 PSMA epitope
KKSPSPEFSGMPRISK

>160 PSMA epitope
NWETNKF

>161 SP34 Light Chain
QAVVTQESALTTSPGETVTLTCRSSTGAVTTSNYANWVQEKPDHLFTGLIGGTN

KRAPGVPARFSGSLIGDKAALTITGAQTEDEAIYFCALWYSNLWVFGGGTKLTV

LGQPKSSPSVTLFPPSSEELETNKATLVCTITDFYPGVVTVDWKVDGTPVTQGME

TTQPSKQSNNKYMASSYLTLTARAWERHSSYSCQVTHEGHTVEKSLSRADCS

>162 SP34 Heavy Chain
EVKLLESGGGLVQPKGSLKLSCAASGFTFNTYAMNWVRQAPGKGLEWVARIRS

KYNNYATYYADSVKDRFTISRDDSQSILYLQMNNLKTEDTAMYYCVRHGNFGN

SYVSWFAYWGQGTLVTVSAATTTAPSVYPLVPGCSDTSGSSVTLGCLVKGYFPE

PVTVKWNYGALSSGVRTVSSVLQSAFYSLSSLVTVPSSTWPSQTVICNVAHPASK

-continued

TELIKRIEPRIPKPSTPPGSSCPPGNILGGPSVFIFPPKPKDALMISLTPKVTCVVVDV

SEDDPDVHVSWFVDNKEVHTAWTQPREAQYNSTFRVVSALPIQHQDWMRGKE

FKCKVNNKALPAPIERTISKPKGRAQTPQVYTIPPPREQMSKKKVSLTCLVTNFFS

EAISVEWERNGELEQDYKNTPPILDSDGTYFLYSKLTVDTDSWLQGEIFTCSVVH

EALHNHHTQKNLSRSPGK

>163 CD3H141
EVQLVESGGGLVQPGGSLRLSCAASGFTFNTYAMNWVRQAPGKGLEWVARIRS

KYNNYATYYAASVKGRFTISRDDSKNSLYLQMNSLKTEDTAVYYCARHGNFGN

SYVSWFAYWGQGTLVTVSS

>164 CD3H142
EVQLLESGGGLVQPGGSLRLSCAASGFTFNTYAMNWVRQAPGKGLEWVARIRS

KYNNYATYYADSVKGRFTISRDNSKNTLYLQMNSLRAEDTAVYYCAKHGNFGN

SYVSWFAYWGQGTLVTVSS

>165 CD3H143
EVQLLESGGGLVQPGGSLRLSCAASGFTFNTYAMNWVRQAPGKGLEWVARIRS

KYNNYATYYADSVKGRFTISRDNSKNTLYLQMNSLRAEDTAVYYCVKHGNFGN

SYVSWFAYWGQGTLVTVSS

>166 CD3H144
EVQLVESGGGLVQPGGSLKLSCAASGFTFNTYAMNWVRQASGKGLEWVGRIRS

KYNGYATYYAASVKGRFTISRDDSKNTAYLQMNSLKTEDTAVYYCTRHGNFGN

SYVSWFAYWGQGTLVTVSS

>167 CD3L63
QAVVTQEPSLTVSPGGTVTLTCRSSTGAVTTSNYANWVQQKPGQAPRGLIGGTN

KRAPGTPARFSGSLLGGKAALTLSGAQPEDEAEYYCALWYSNLWVFGGGTKLT

VL

>168 CD3L64
QSVLTQPPSVSAAPGQKVTISCRSSTGAVTTSNYANWVQQLPGTAPKGLIGGTNK

RAPGIPDRFSGSKSGTSATLGITGLQTGDEADYYCALWYSNLWVFGGGTKLTVL

>169 CD3L66
QTVVTQEPSLTVSPGGTVTLTCRSSTGAVTTSNYANWVQQKPGQAPRGLIGGTN

KRAPGTPARFSGSLLGGKAALTLSGVQPEDEAEYYCALWYSNLWVFGGGTKLT

VL

>170. B219 Light Chain
QTVVTQEPSLTVSPGGTVTLTCRSSTGAVTTSNYANWVQQKPGQAPRGLIGGTN

KRAPGTPARFSGSLLGGKAALTLSGVQPEDEAEYYCALWYSNLWVFGGGTKLT

VLGQPKAAPSVTLFPPSSEELQANKATLVCLISDFYPGAVTVAWKADSSPVKAG

VETTTPSKQSNNKYAASSYLSLTPEQWKSHRSYSCQVTHEGSTVEKTVAPTECS

>171. B219 Heavy chain
EVQLVESGGGLVQPGGSLRLSCAASGFTFNTYAMNWVRQAPGKGLEWVARIRS

KYNNYATYYAASVKGRFTISRDDSKNSLYLQMNSLKTEDTAVYYCARHGNFGN

SYVSWFAYWGQGTLVTVSSASTKGPSVFPLAPCSRSTSESTAALGCLVKDYFPEP

VTVSWNSGALTSGVHTFPAVLQSSGLYSLSSVVTVPSSSLGTKTYTCNVDHKPSN

TKVDKRVESKYGPPCPPCPAPEAAGGPSVFLFPPKPKDTLMISRTPEVTCVVVDV

SQEDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCLVKGFY

PSDIAVEWESNGQPENNYKTTPPVLDSDGSFLLYSKLTVDKSRWQEGNVFSCSV

MHEALHNHYTQKSLSLSLGK

>172. CW5 C-terminal FN3 domain FC fusion
GSCPPCPAPEAAGGPSVFLFPPKPKDTLMISRTPEVTCVVVDVSQEDPEVQFNWY

VDGVEVHNAKTKPREEQFNSTYRVVSVLTVLHQDWLNGKEYKCKVSNKGLPSS

IEKTISKAKGQPREPQVYTLPPSQEEMTKNQVSLTCLVKGFYPSDIAVEWESNGQ

PENNYKTTPPVLDSDGSFFLYSRLTVDKSRWQEGNVFSCSVMHEALHNHYTQKS

LSLSLGKGGGGSGGGGSMLPAPKNLVVSRVTEDSARLSWTAPDAAFDSFAIGYW

EWDDDGEAIVLTVPGSERSYDLTGLKPGTEYPVYIAGVKGGQWSFPLSAIFTT

>173. CW6 N-terminal FN3 domain FC fusion
MLPAPKNLVVSRVTEDSARLSWTAPDAAFDSFAIGYWEWDDDGEAIVLTVPGSE

RSYDLTGLKPGTEYPVYIAGVKGGQWSFPLSAIFTTGGGGSGGGGSCPPCPAPEA

AGGPSVFLFPPKPKDTLMISRTPEVTCVVVDVSQEDPEVQFNWYVDGVEVHNAK

TKPREEQFNSTYRVVSVLTVLHQDWLNGKEYKCKVSNKGLPSSIEKTISKAKGQ

PREPQVYTLPPSQEEMTKNQVSLTCLVKGFYPSDIAVEWESNGQPENNYKTTPPV

LDSDGSFFLYSRLTVDKSRWQEGNVFSCSVMHEALHNHYTQKSLSLSLGK

>174. B221 Heavy Chain
EVQLVESGGGLVQPGGSLRLSCAASGFTFNTYAMNWVRQAPGKGLEWVARIRS

KYNNYATYYAASVKGRFTISRDDSKNSLYLQMNSLKTEDTAVYYCARHGNFGN

SYVSWFAYWGQGTLVTVSSASTKGPSVFPLAPCSRSTSESTAALGCLVKDYFPEP

VTVSWNSGALTSGVHTFPAVLQSSGLYSLSSVVTVPSSSLGTKTYTCNVDHKPSN

TKVDKRVESKYGPPCPPCPAPEAAGGPSVFLFPPKPKDTLMISRTPEVTCVVVDV

SQEDPEVQFNWYVDGVEVHNAKTKPREEQFNSTYRVVSVLTVLHQDWLNGKE

YKCKVSNKGLPSSIEKTISKAKGQPREPQVYTLPPSQEEMTKNQVSLTCLVKGFY

PSDIAVEWESNGQPENNYKTTPPVLDSDGSFLLYSKLTVDKSRWQEGNVFSCSV

MHEALHNHYTQKSLSLSLGKGGGGSGGGGSMLPAPKNLVVSRVTEDSARLSWT

APDAAFDSFAIGYWEWDDDGEAIVLTVPGSERSYDLTGLKPGTEYPVYIAGVKG

GQWSFPLSAIFTT

>175
GGGGSGGGGS

>176 G11 mAb heavy chain
EVQLLESGGG LVQPGGSLRL SCAASGFTFS SYGMSWVRQA PGKGLEWVSG

INGGGGSKYY ADSVKGRFTI SRDNSKNTLY LQMNSLRAED TAVYYCAKTS

AQRFDYWGQG TLVTVSSAST KGPSVFPLAP SSKSTSGGTA ALGCLVKDYF

PEPVTVSWNS GALTSGVHTF PAVLQSSGLY SLSSVVTVPS SSLGTQTYIC

NVNHKPSNTK VDKKVEPKSC DKTHTCPPCP APELLGGPSV FLFPPKPKDT

LMISRTPEVT CVVVDVSHED PEVKFNWYVD GVEVHNAKTK

PREEQYNSTY RVVSVLTVLH QDWLNGKEYK CKVSNKALPA PIEKTISKAK

GQPREPQVYT LPPSRDELTK NQVSLTCLVK GFYPSDIAVE WESNGQPENN

YKTTPPVLDS DGSFFLYSKL TVDKSRWQQG NVFSCSVMHE ALHNHYTQKS

LSLSPGK

>177 G11 mAb light chain
DIQMTQSPSS LSASVGDRVT ITCRASQSIS SYLNWYQQKP GKAPKLLIYA

ASSLQSGVPS RFSGSGSGTD FTLTISSLQP EDFATYYCQQ SYSLPLTFGQ

GTKVEIKRTV AAPSVFIFPP SDEQLKSGTA SVVCLLNNFY PREAKVQWKV

DNALQSGNSQ ESVTEQDSKD STYSLSSTLT LSKADYEKHK VYACEVTHQG

LSSPVTKSFN RGEC

>178 CD3B94 mAb heavy chain
QVQLVQSGAE VKKPGSSVKV SCKASGGTFS SYAISWVRQA PGQGLEWMGG

IIPIFGTANY AQKFQGRVTI TADESTSTAY MELSSLRSED TAVYYCARDP

ARLYSYYFDY WGQGTLVTVS SASTKGPSVF PLAPSSKSTS

GGTAALGCLV KDYFPEPVTV SWNSGALTSG VHTFPAVLQS SGLYSLSSVV

TVPSSSLGTQ TYICNVNHKP SNTKVDKKVE PKSCDKTHTC

PPCPAPEAAG GPSVFLFPPK PKDTLMISRT PEVTCVVVDV

SHEDPEVKFN WYVDGVEVHN AKTKPREEQY NSTYRVVSVL TVLHQDWLNG

KEYKCKVSNK ALPAPIEKTI SKAKGQPREP QVYTLPPSRD ELTKNQVSLT

CLVKGFYPSD IAVEWESNGQ PENNYKTTPP VLDSDGSFLL YSKLTVDKSR

WQQGNVFSCS VMHEALHNHY TQKSLSLSPG K

>179 CD3B94 mAb light chain
DIQMTQSPSS LSASVGDRVT ITCRASQSISSYLNWYQQKPGKAPKLLIYA

ASSLQSGVPSRFSGSGSGTDFTLTISSLQP

EDFATYYCQQSYSTPLTFGQGTKVEIKRTVAAPSVFIFPPSDEQLKSGTASVVCLL

NNFYPREAKVQWKV DNALQSGNSQESVTEQDSKD

STYSLSSTLTLSKADYEKHKVYACEVTHQG LSSPVTKSFN

---

What is claimed:

1. An isolated CD3×PSMA-bispecific antigen-binding molecule comprising:
   a. an FN3 domain comprising the amino acid sequence of SEQ ID NO: 41;
   b. an antibody light chain (LC) comprising the amino acid sequence of SEQ ID NO: 170; and
   c. an antibody heavy chain (HC) comprising the amino acid sequence of SEQ ID NO: 171, wherein the FN3 domain forms a first antigen-binding site that specifically binds human PSMA, and the HC and the LC pair form a second antigen-binding site that immunospecifically binds CD3, or a bispecific antigen-binding fragment thereof.

2. An isolated CD3×PSMA-bispecific antigen-binding molecule or bispecific antigen-binding fragment thereof, comprising:
   a. an FN3 domain comprising the amino acid sequence of SEQ ID NO: 41 modified to include a cysteine residue in at least one residue position corresponding to residue positions 11, 53 and 62 of SEQ ID NO: 41, or at a C-terminus of SEQ ID NO: 41;
   b. an antibody light chain (LC) comprising the amino acid sequence of SEQ ID NO: 170; and
   c. an antibody heavy chain (HC) comprising the amino acid sequence of SEQ ID NO: 171, wherein the FN3 domain forms a first antigen-binding site that specifically binds human PSMA, and the HC and the LC pair form a second antigen-binding site that immunospecifically binds CD3.

3. The isolated CD3×PSMA-bispecific antigen-binding molecule or bispecific antigen-binding fragment thereof of claim 1, wherein the CD3×PSMA-bispecific antigen-binding molecule or bispecific antigen-binding fragment thereof comprises an immunoglobulin molecule of an IgG1, IgG2, IgG3, or IgG4 isotype.

4. The isolated CD3×PSMA-bispecific antigen-binding molecule or bispecific antigen-binding fragment thereof of claim 3, wherein the CD3×PSMA-bispecific antigen-binding molecule or bispecific antigen-binding fragment thereof comprises an immunoglobulin molecule of an IgG4 isotype.

5. The isolated CD3×PSMA-bispecific antigen-binding molecule or bispecific antigen-binding fragment thereof of claim 1, further comprising a methionine at the N-terminus of the FN3 domain.

6. A pharmaceutical composition comprising the isolated CD3×PSMA-bispecific antigen-binding molecule or bispecific antigen-binding fragment thereof of claim 1 and a pharmaceutically acceptable carrier.

7. A kit comprising the isolated CD3×PSMA-bispecific antigen-binding molecule or bispecific antigen-binding fragment thereof of claim 1 and packaging for the same.

8. An isolated CD3×PSMA-bispecific antigen-binding molecule or bispecific antigen-binding fragment thereof comprising:
   a. an FN3 domain comprising the amino acid sequence of SEQ ID NO: 173;
   b. an antibody light chain (LC) comprising the amino acid sequence of SEQ ID NO: 170; and
   c. an antibody heavy chain (HC) comprising the amino acid sequence of SEQ ID NO: 171, wherein the FN3 domain forms a first antigen-binding site that specifically binds human PSMA, and the HC and the LC pair form a second antigen-binding site that immunospecifically binds CD3.

* * * * *

SEQUENCE LISTING

<160> NUMBER OF SEQ ID NOS: 179

<210> SEQ ID NO 1
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Glu Phe Thr Thr
                85

<210> SEQ ID NO 2
<211> LENGTH: 94
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<221> NAME/KEY: MOD_RES
<222> LOCATION: (75)..(86)
<223> OTHER INFORMATION: Any amino acid
<220> FEATURE:
<221> NAME/KEY: MISC_FEATURE
<222> LOCATION: (75)..(86)
<223> OTHER INFORMATION: This region may encompass 7-12 residues

<400> SEQUENCE: 2

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Xaa Xaa Xaa Xaa Xaa Xaa
65                  70                  75                  80

Xaa Xaa Xaa Xaa Xaa Xaa Pro Leu Ser Ala Glu Phe Thr Thr
                85                  90

<210> SEQ ID NO 3
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (22)..(27)
<223> OTHER INFORMATION: Ala, Arg, Asn, Asp, Glu, Gln, Gly, His, Ile,
      Leu, Lys, Phe, Pro, Ser, Thr, Trp, Tyr or Val
<220> FEATURE:
<221> NAME/KEY: MOD_RES
<222> LOCATION: (28)..(28)
<223> OTHER INFORMATION: Phe, Ile, Leu, Val or Tyr
<220> FEATURE:
<221> NAME/KEY: MOD_RES
<222> LOCATION: (29)..(29)
<223> OTHER INFORMATION: Asp, Glu or Thr
<220> FEATURE:
<221> NAME/KEY: MOD_RES
<222> LOCATION: (75)..(79)
<223> OTHER INFORMATION: Ala, Arg, Asn, Asp, Glu, Gln, Gly, His, Ile,
      Leu, Lys, Phe, Pro, Ser, Thr, Trp, Tyr or Val
<220> FEATURE:
<221> NAME/KEY: MOD_RES
<222> LOCATION: (81)..(82)
<223> OTHER INFORMATION: Ala, Arg, Asn, Asp, Glu, Gln, Gly, His, Ile,
      Leu, Lys, Phe, Pro, Ser, Thr, Trp, Tyr or Val

<400> SEQUENCE: 3

Leu Pro Ala Pro Lys Asn Leu Val Val Ser Glu Val Thr Glu Asp Ser
1               5                   10                  15

Leu Arg Leu Ser Trp Xaa Xaa Xaa Xaa Xaa Xaa Xaa Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Xaa Xaa Xaa Xaa Xaa Ser
```

```
                65                  70                  75                  80

Xaa Xaa Leu Ser Ala Glu Phe Thr Thr
                85

<210> SEQ ID NO 4
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Ile Phe Thr Thr
                85

<210> SEQ ID NO 5
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (22)..(30)
<223> OTHER INFORMATION: Ala, Asp, Glu, Phe, Gly, His, Ile, Lys, Leu,
      Asn, Pro, Gln, Arg, Ser, Thr, Val, Trp or Tyr
<220> FEATURE:
<221> NAME/KEY: MISC_FEATURE
<222> LOCATION: (22)..(30)
<223> OTHER INFORMATION: This region may encompass 6-9 residues
<220> FEATURE:
<221> NAME/KEY: MOD_RES
<222> LOCATION: (78)..(87)
<223> OTHER INFORMATION: Ala, Asp, Glu, Phe, Gly, His, Ile, Lys, Leu,
      Asn, Pro, Gln, Arg, Ser, Thr, Val, Trp or Tyr
<220> FEATURE:
<221> NAME/KEY: MISC_FEATURE
<222> LOCATION: (78)..(87)
<223> OTHER INFORMATION: This region may encompass 7-9 residues

<400> SEQUENCE: 5

Leu Pro Ala Pro Lys Asn Leu Val Val Ser Arg Val Thr Glu Asp Ser
1               5                   10                  15

Ala Arg Leu Ser Trp Xaa Xaa Xaa Xaa Xaa Xaa Xaa Xaa Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
    50                  55                  60

Lys Pro Gly Thr Glu Tyr Thr Val Ser Ile Tyr Gly Val Xaa Xaa Xaa
65                  70                  75                  80

Xaa Xaa Xaa Xaa Xaa Xaa Xaa Ser Asn Pro Leu Ser Ala Ile Phe Thr
```

Thr

```
<210> SEQ ID NO 6
<211> LENGTH: 96
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (75)..(86)
<223> OTHER INFORMATION: Ala, Asp, Glu, Phe, Gly, His, Ile, Lys, Leu,
      Asn, Pro, Gln, Arg, Ser, Thr, Val, Trp or Tyr
<220> FEATURE:
<221> NAME/KEY: MOD_RES
<222> LOCATION: (75)..(86)
<223> OTHER INFORMATION: This region may encompass 7-12 residues

<400> SEQUENCE: 6
```

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Xaa Xaa Xaa Xaa Xaa
65                  70                  75                  80

Xaa Xaa Xaa Xaa Xaa Xaa Ser Asn Pro Leu Ser Ala Ile Phe Thr Thr
                85                  90                  95

```
<210> SEQ ID NO 7
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (32)..(32)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (34)..(34)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (36)..(36)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (38)..(41)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (68)..(68)
<223> OTHER INFORMATION: Ala, Cys, Asp, Glu, Phe, Gly, His, Ile, Lys,
      Leu, Asn, Pro, Gln, Arg, Ser, Thr, Val, Trp, Tyr or Met
<220> FEATURE:
<221> NAME/KEY: MOD_RES
<222> LOCATION: (70)..(70)
<223> OTHER INFORMATION: Ala, Cys, Asp, Glu, Phe, Gly, His, Ile, Lys,
```

```
            Leu, Asn, Pro, Gln, Arg, Ser, Thr, Val, Trp, Tyr or Met
<220> FEATURE:
<221> NAME/KEY: MOD_RES
<222> LOCATION: (72)..(72)
<223> OTHER INFORMATION: Ala, Cys, Asp, Glu, Phe, Gly, His, Ile, Lys,
            Leu, Asn, Pro, Gln, Arg, Ser, Thr, Val, Trp, Tyr or Met
<220> FEATURE:
<221> NAME/KEY: MOD_RES
<222> LOCATION: (78)..(79)
<223> OTHER INFORMATION: Ala, Cys, Asp, Glu, Phe, Gly, His, Ile, Lys,
            Leu, Asn, Pro, Gln, Arg, Ser, Thr, Val, Trp, Tyr or Met
<220> FEATURE:
<221> NAME/KEY: MOD_RES
<222> LOCATION: (81)..(81)
<223> OTHER INFORMATION: Ala, Cys, Asp, Glu, Phe, Gly, His, Ile, Lys,
            Leu, Asn, Pro, Gln, Arg, Ser, Thr, Val, Trp, Tyr or Met

<400> SEQUENCE: 7

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Xaa
            20                  25                  30

Ile Xaa Tyr Xaa Glu Xaa Xaa Xaa Xaa Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Xaa Val Xaa Ile Xaa Gly Val Lys Gly Xaa Xaa Ser
65                  70                  75                  80

Xaa Pro Leu Ser Ala Ile Phe Thr Thr
                85

<210> SEQ ID NO 8
<211> LENGTH: 89
<212> TYPE: PRT
<213> ORGANISM: Artificial Sequence
<220> FEATURE:
<223> OTHER INFORMATION: Description of Artificial Sequence: Synthetic
            polypeptide
<220> FEATURE:
<221> NAME/KEY: MOD_RES
<222> LOCATION: (32)..(32)
<223> OTHER INFORMATION: Ala, Asp, Glu, Phe, Gly, His, Ile, Lys, Leu,
            Asn, Pro, Gln, Arg, Ser, Thr, Val, Tyr or Trp
<220> FEATURE:
<221> NAME/KEY: MOD_RES
<222> LOCATION: (34)..(34)
<223> OTHER INFORMATION: Ala, Asp, Glu, Phe, Gly, His, Ile, Lys, Leu,
            Asn, Pro, Gln, Arg, Ser, Thr, Val, Tyr or Trp
<220> FEATURE:
<221> NAME/KEY: MOD_RES
<222> LOCATION: (36)..(36)
<223> OTHER INFORMATION: Ala, Asp, Glu, Phe, Gly, His, Ile, Lys, Leu,
            Asn, Pro, Gln, Arg, Ser, Thr, Val, Tyr or Trp
<220> FEATURE:
<221> NAME/KEY: MOD_RES
<222> LOCATION: (38)..(41)
<223> OTHER INFORMATION: Ala, Asp, Glu, Phe, Gly, His, Ile, Lys, Leu,
            Asn, Pro, Gln, Arg, Ser, Thr, Val, Tyr or Trp
<220> FEATURE:
<221> NAME/KEY: MOD_RES
<222> LOCATION: (46)..(46)
<223> OTHER INFORMATION: Ala, Asp, Glu, Phe, Gly, His, Ile, Lys, Leu,
            Asn, Pro, Gln, Arg, Ser, Thr, Val, Tyr or Trp
<220> FEATURE:
<221> NAME/KEY: MOD_RES
<222> LOCATION: (48)..(48)
<223> OTHER INFORMATION: Ala, Asp, Glu, Phe, Gly, His, Ile, Lys, Leu,
            Asn, Pro, Gln, Arg, Ser, Thr, Val, Tyr or Trp
<220> FEATURE:
<221> NAME/KEY: MOD_RES
<222> LOCATION: (68)..(68)
<223> OTHER INFORMATION: Ala, Asp, Glu, Phe, Gly, His, Ile, Lys, Leu,
```

```
      Asn, Pro, Gln, Arg, Ser, Thr, Val, Tyr or Trp
<220> FEATURE:
<221> NAME/KEY: MOD_RES
<222> LOCATION: (70)..(70)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (72)..(72)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (78)..(79)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (81)..(81)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (84)..(84)
<223> OTHER INFORMATION: Ala, Asp, Glu, Phe, Gly, His, Ile, Lys, Leu,
      Asn, Pro, Gln, Arg, Ser, Thr, Val, Tyr or Trp
<220> FEATURE:
<221> NAME/KEY: MOD_RES
<222> LOCATION: (86)..(86)
<223> OTHER INFORMATION: Ala, Asp, Glu, Phe, Gly, His, Ile, Lys, Leu,
      Asn, Pro, Gln, Arg, Ser, Thr, Val, Tyr or Trp

<400> SEQUENCE: 8

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Xaa
            20                  25                  30

Ile Xaa Tyr Xaa Glu Xaa Xaa Xaa Xaa Gly Glu Ala Ile Xaa Leu Xaa
        35                  40                  45

Val Pro Gly Ser Glu Arg Ser Tyr Asp Leu Thr Gly Leu Lys Pro Gly
50                  55                  60

Thr Glu Tyr Xaa Val Xaa Ile Xaa Gly Val Lys Gly Gly Xaa Xaa Ser
65                  70                  75                  80

Xaa Pro Leu Xaa Ala Xaa Phe Thr Thr
                85

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gtgacacggc ggttagaac                                              19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gcctttggga agcttctaag                                             20
```

```
<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cggcggttag aacgcggcta caattaatac                                           30

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
catgattacg ccaagctcag aa                                                   22

<210> SEQ ID NO 13
<211> LENGTH: 385
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (198)..(224)
<223> OTHER INFORMATION: a, c, t, g, unknown or other

<400> SEQUENCE: 13
gtgacacggc ggttagaacg cggctacaat taatacataa ccccatcccc ctgttgacaa          60
ttaatcatcg gctcgtataa tgtgtggaat tgtgagcgga taacaatttc acacaggaaa         120
caggatctac catgctgccg gcgccgaaaa acctggttgt ttctgaagtt accgaagact         180
ctctgcgtct gtcttggnnn nnnnnnnnn nnnnnnnnn nnnnttygac tctttcctga          240
tccagtacca ggaatctgaa aaagttggtg aagcgatcaa cctgaccgtt ccgggttctg         300
aacgttctta cgacctgacc ggtctgaaac cgggtaccga atacaccgtt tctatctacg         360
gtgttcttag aagcttccca aaggc                                              385

<210> SEQ ID NO 14
<211> LENGTH: 382
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (198)..(221)
<223> OTHER INFORMATION: a, c, t, g, unknown or other

<400> SEQUENCE: 14
gtgacacggc ggttagaacg cggctacaat taatacataa ccccatcccc ctgttgacaa          60
ttaatcatcg gctcgtataa tgtgtggaat tgtgagcgga taacaatttc acacaggaaa         120
caggatctac catgctgccg gcgccgaaaa acctggttgt ttctgaagtt accgaagact         180
ctctgcgtct gtcttggnnn nnnnnnnnn nnnnnnnnn nttygactct tcctgatcc           240 agtaccagga atctgaaaaa gttggtgaag cgatcaacct gaccgttccg ggttctgaac         300
```
gttcttacga cctgaccggt ctgaaaccgg gtaccgaata caccgtttct atctacggtg      360
ttcttagaag cttcccaaag gc                                              382

<210> SEQ ID NO 15
<211> LENGTH: 379
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (198)..(218)
<223> OTHER INFORMATION: a, c, t, g, unknown or other

<400> SEQUENCE: 15
gtgacacggc ggttagaacg cggctacaat taatacataa ccccatcccc ctgttgacaa      60
ttaatcatcg gctcgtataa tgtgtggaat tgtgagcgga taacaatttc acacaggaaa     120
caggatctac catgctgccg gcgccgaaaa acctggttgt ttctgaagtt accgaagact     180
ctctgcgtct gtcttggnnn nnnnnnnnn nnnnnnnntt ygactctttc ctgatccagt      240
accaggaatc tgaaaaagtt ggtgaagcga tcaacctgac cgttccgggt tctgaacgtt     300
cttacgacct gaccggtctg aaaccgggta ccgaatacac cgtttctatc tacggtgttc     360
ttagaagctt cccaaaggc                                                 379

<210> SEQ ID NO 16
<211> LENGTH: 376
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (198)..(215)
<223> OTHER INFORMATION: a, c, t, g, unknown or other

<400> SEQUENCE: 16
gtgacacggc ggttagaacg cggctacaat taatacataa ccccatcccc ctgttgacaa      60
ttaatcatcg gctcgtataa tgtgtggaat tgtgagcgga taacaatttc acacaggaaa     120
caggatctac catgctgccg gcgccgaaaa acctggttgt ttctgaagtt accgaagact     180
ctctgcgtct gtcttggnnn nnnnnnnnn nnnnttyga ctctttcctg atccagtacc       240
aggaatctga aaaagttggt gaagcgatca acctgaccgt tccgggttct gaacgttctt     300
acgacctgac cggtctgaaa ccgggtaccg aatacaccgt ttctatctac ggtgttctta    360
gaagcttccc aaaggc                                                    376

<210> SEQ ID NO 17
<211> LENGTH: 131
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
cggcggttag aacgcggcta caattaatac ataaccccat cccctgttg acaattaatc       60 atcggctcgt ataatgtgtg gaattgtgag cggataacaa tttcacacag gaaacaggat    120
ctaccatgct g                                                         131

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cggcggttag aacgcggcta caattaatac                                     30

<210> SEQ ID NO 19
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ccaagacaga cgggcagagt cttcggtaac gcgagaaaca accaggtttt tcggcgccgg    60
cagcatggta gatcctgttt c                                              81

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
ccgaagactc tgcccgtctg tcttgg                                         26

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
cagtggtctc acggattcct ggtactggat caggaaagag tcgaa                    45

<210> SEQ ID NO 22
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
catgcggtct cttccgaaaa agttggtgaa gcgatcgtcc tgaccgttcc gggt          54

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ggtggtgaag atcgcagaca gcgggttag                                      29

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 24
cggcggttag aacgcggcta c                                              21

<210> SEQ ID NO 25
<211> LENGTH: 61
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 25
aagatcagtt gcggccgcta gactagaacc gctgccaccg ccggtggtga agatcgcaga    60
c                                                                    61

<210> SEQ ID NO 26
<211> LENGTH: 485
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<221> NAME/KEY: modified_base
<222> LOCATION: (357)..(392)
<223> OTHER INFORMATION: a, c, t, g, unknown or other

<400> SEQUENCE: 26
gtgacacggc ggttagaacg cggctacaat taatacataa ccccatcccc ctgttgacaa    60
ttaatcatcg gctcgtataa tgtgtggaat tgtgagcgga taacaatttc acacaggaaa   120
caggatctac catgctgccg gcgccgaaaa acctggttgt ttctcgcgtt accgaagact   180
ctgcgcgtct gtcttggacc gcgccggacg cggcgttcga ctctttcctg atccagtacc   240
aggaatctga aaaagttggt gaagcgatcg tgctgaccgt tccgggttct gaacgttctt   300
acgacctgac cggtctgaaa ccgggtaccg aatacaccgt ttctatctac ggtgttnnnn   360 nnnnnnnnn nnnnnnnnnn nnnnnnnnnn nntctaaccc gctgtctgcg atcttcacca   420
ccggcggtca ccatcaccat caccatggca gcggttctag tctagcggcc gcaactgatc   480
ttggc                                                              485

<210> SEQ ID NO 27
<211> LENGTH: 482
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<221> NAME/KEY: modified_base
<222> LOCATION: (357)..(389)
<223> OTHER INFORMATION: a, c, t, g, unknown or other

<400> SEQUENCE: 27
gtgacacggc ggttagaacg cggctacaat taatacataa ccccatcccc ctgttgacaa    60

| | |
|---|---|
| ttaatcatcg gctcgtataa tgtgtggaat tgtgagcgga taacaatttc acacaggaaa | 120 |
| caggatctac catgctgccg gcgccgaaaa acctggttgt ttctcgcgtt accgaagact | 180 |
| ctgcgcgtct gtcttggacc gcgccggacg cggcgttcga ctctttcctg atccagtacc | 240 |
| aggaatctga aaaagttggt gaagcgatcg tgctgaccgt tccgggttct gaacgttctt | 300 |
| acgacctgac cggtctgaaa ccgggtaccg aatacaccgt ttctatctac ggtgttnnnn | 360 |
| nnnnnnnnnn nnnnnnnnnn nnnnnnnnnt ctaacccgct gtctgcgatc ttcaccaccg | 420 |
| gcggtcacca tcaccatcac catggcagcg gttctagtct agcggccgca actgatcttg | 480 |
| gc | 482 |

<210> SEQ ID NO 28
<211> LENGTH: 479
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (357)..(386)
<223> OTHER INFORMATION: a, c, t, g, unknown or other

<400> SEQUENCE: 28

| | |
|---|---|
| gtgacacggc ggttagaacg cggctacaat taatacataa ccccatcccc ctgttgacaa | 60 |
| ttaatcatcg gctcgtataa tgtgtggaat tgtgagcgga taacaatttc acacaggaaa | 120 |
| caggatctac catgctgccg gcgccgaaaa acctggttgt ttctcgcgtt accgaagact | 180 |
| ctgcgcgtct gtcttggacc gcgccggacg cggcgttcga ctctttcctg atccagtacc | 240 |
| aggaatctga aaaagttggt gaagcgatcg tgctgaccgt tccgggttct gaacgttctt | 300 |
| acgacctgac cggtctgaaa ccgggtaccg aatacaccgt ttctatctac ggtgttnnnn | 360 |
| nnnnnnnnnn nnnnnnnnnn nnnnntcta acccgctgtc tgcgatcttc accaccggcg | 420 |
| gtcaccatca ccatcaccat ggcagcggtt ctagtctagc ggccgcaact gatcttggc | 479 |

<210> SEQ ID NO 29
<211> LENGTH: 476
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (357)..(383)
<223> OTHER INFORMATION: a, c, t, g, unknown or other

<400> SEQUENCE: 29

| | |
|---|---|
| gtgacacggc ggttagaacg cggctacaat taatacataa ccccatcccc ctgttgacaa | 60 |
| ttaatcatcg gctcgtataa tgtgtggaat tgtgagcgga taacaatttc acacaggaaa | 120 |
| caggatctac catgctgccg gcgccgaaaa acctggttgt ttctcgcgtt accgaagact | 180 |
| ctgcgcgtct gtcttggacc gcgccggacg cggcgttcga ctctttcctg atccagtacc | 240 |
| aggaatctga aaaagttggt gaagcgatcg tgctgaccgt tccgggttct gaacgttctt | 300 |
| acgacctgac cggtctgaaa ccgggtaccg aatacaccgt ttctatctac ggtgttnnnn | 360 |
| nnnnnnnnnn nnnnnnnnnn nnntctaacc cgctgtctgc gatcttcacc accgcggtc | 420 |
| accatcacca tcaccatggc agcggttcta gtctagcggc cgcaactgat cttggc | 476 |

-continued

<210> SEQ ID NO 30
<211> LENGTH: 473
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (357)..(380)
<223> OTHER INFORMATION: a, c, t, g, unknown or other

<400> SEQUENCE: 30

```
gtgacacggc ggttagaacg cggctacaat taatacataa ccccatcccc ctgttgacaa    60
ttaatcatcg gctcgtataa tgtgtggaat tgtgagcgga taacaatttc acacaggaaa   120
caggatctac catgctgccg gcgccgaaaa acctggttgt ttctcgcgtt accgaagact   180
ctgcgcgtct gtcttggacc gcgccggacg cggcgttcga ctctttcctg atccagtacc   240
aggaatctga aaaagttggt gaagcgatcg tgctgaccgt tccgggttct gaacgttctt   300
acgacctgac cggtctgaaa ccgggtaccg aatacaccgt ttctatctac ggtgttnnnn   360
nnnnnnnnnn nnnnnnnnnn tctaacccgc tgtctgcgat cttcaccacc ggcggtcacc   420
atcaccatca ccatggcagc ggttctagtc tagcggccgc aactgatctt ggc          473
```

<210> SEQ ID NO 31
<211> LENGTH: 470
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (357)..(377)
<223> OTHER INFORMATION: a, c, t, g, unknown or other

<400> SEQUENCE: 31

```
gtgacacggc ggttagaacg cggctacaat taatacataa ccccatcccc ctgttgacaa    60
ttaatcatcg gctcgtataa tgtgtggaat tgtgagcgga taacaatttc acacaggaaa   120
caggatctac catgctgccg gcgccgaaaa acctggttgt ttctcgcgtt accgaagact   180
ctgcgcgtct gtcttggacc gcgccggacg cggcgttcga ctctttcctg atccagtacc   240
aggaatctga aaaagttggt gaagcgatcg tgctgaccgt tccgggttct gaacgttctt   300
acgacctgac cggtctgaaa ccgggtaccg aatacaccgt ttctatctac ggtgttnnnn   360
nnnnnnnnnn nnnnnntct aaccgctgt ctgcgatctt caccaccggc ggtcaccatc   420
accatcacca tggcagcggt tctagtctag cggccgcaac tgatcttggc              470
```

<210> SEQ ID NO 32
<211> LENGTH: 707
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Lys Ser Ser Ser Glu Ala Thr Asn Ile Thr Pro Lys His Asn Met Lys
1               5                   10                  15

Ala Phe Leu Asp Glu Leu Lys Ala Glu Asn Ile Lys Lys Phe Leu His
            20                  25                  30

Asn Phe Thr Gln Ile Pro His Leu Ala Gly Thr Glu Gln Asn Phe Gln
```

```
              35                  40                  45
Leu Ala Lys Gln Ile Gln Ser Gln Trp Lys Glu Phe Gly Leu Asp Ser
 50                  55                  60

Val Glu Leu Thr His Tyr Asp Val Leu Ser Tyr Pro Asn Lys Thr
 65              70                  75                  80

His Pro Asn Tyr Ile Ser Ile Ile Asn Glu Asp Gly Asn Glu Ile Phe
                     85                  90                  95

Asn Thr Ser Leu Phe Glu Pro Pro Ala Gly Tyr Glu Asn Val Ser
                100                 105                 110

Asp Ile Val Pro Pro Phe Ser Ala Phe Ser Pro Gln Gly Met Pro Glu
            115                 120                 125

Gly Asp Leu Val Tyr Val Asn Tyr Ala Arg Thr Glu Asp Phe Phe Lys
        130                 135                 140

Leu Glu Arg Asp Met Lys Ile Asn Cys Ser Gly Lys Ile Val Ile Ala
145                 150                 155                 160

Arg Tyr Gly Lys Val Phe Arg Gly Asn Lys Val Lys Asn Ala Gln Leu
                165                 170                 175

Ala Gly Ala Thr Gly Val Ile Leu Tyr Ser Asp Pro Asp Asp Tyr Phe
                180                 185                 190

Ala Pro Gly Val Lys Ser Tyr Pro Asp Gly Trp Asn Leu Pro Gly Gly
            195                 200                 205

Gly Val Gln Arg Gly Asn Ile Leu Asn Leu Asn Gly Ala Gly Asp Pro
        210                 215                 220

Leu Thr Pro Gly Tyr Pro Ala Asn Glu Tyr Ala Tyr Arg Arg Gly Met
225                 230                 235                 240

Ala Glu Ala Val Gly Leu Pro Ser Ile Pro Val His Pro Ile Gly Tyr
                245                 250                 255

Tyr Asp Ala Gln Lys Leu Leu Glu Lys Met Gly Gly Ser Ala Ser Pro
                260                 265                 270

Asp Ser Ser Trp Arg Gly Ser Leu Lys Val Pro Tyr Asn Val Gly Pro
            275                 280                 285

Gly Phe Thr Gly Asn Phe Ser Thr Gln Lys Val Lys Met His Ile His
        290                 295                 300

Ser Thr Ser Glu Val Thr Arg Ile Tyr Asn Val Ile Gly Thr Leu Arg
305                 310                 315                 320

Gly Ala Val Glu Pro Asp Arg Tyr Val Ile Leu Gly His Arg Asp
                325                 330                 335

Ser Trp Val Phe Gly Gly Ile Asp Pro Gln Ser Gly Ala Ala Val Val
            340                 345                 350

His Glu Ile Val Arg Ser Phe Gly Met Leu Lys Lys Glu Gly Trp Arg
        355                 360                 365

Pro Arg Arg Thr Ile Leu Phe Ala Ser Trp Asp Ala Glu Glu Phe Gly
        370                 375                 380

Leu Leu Gly Ser Thr Glu Trp Ala Glu Glu Asn Ser Arg Leu Leu Gln
385                 390                 395                 400

Glu Arg Gly Val Ala Tyr Ile Asn Ala Asp Ser Ser Ile Glu Gly Asn
                405                 410                 415

Tyr Thr Leu Arg Val Asp Cys Thr Pro Leu Met Tyr Ser Leu Val Tyr
                420                 425                 430

Asn Leu Thr Lys Glu Leu Glu Ser Pro Asp Glu Gly Phe Glu Gly Lys
            435                 440                 445

Ser Leu Tyr Glu Ser Trp Thr Lys Lys Ser Pro Ser Pro Glu Phe Ser
        450                 455                 460
```

Gly Met Pro Arg Ile Ser Lys Leu Gly Ser Gly Asn Asp Phe Glu Val
465                 470                 475                 480

Phe Phe Gln Arg Leu Gly Ile Ala Ser Gly Arg Ala Arg Tyr Thr Lys
                485                 490                 495

Asn Trp Glu Thr Asn Lys Phe Ser Ser Tyr Pro Leu Tyr His Ser Val
            500                 505                 510

Tyr Glu Thr Tyr Glu Leu Val Glu Lys Phe Tyr Asp Pro Met Phe Lys
        515                 520                 525

Tyr His Leu Thr Val Ala Gln Val Arg Gly Gly Met Val Phe Glu Leu
    530                 535                 540

Ala Asn Ser Val Val Leu Pro Phe Asp Cys Arg Asp Tyr Ala Val Val
545                 550                 555                 560

Leu Arg Lys Tyr Ala Asp Lys Ile Tyr Asn Ile Ser Met Lys His Pro
                565                 570                 575

Gln Glu Met Lys Thr Tyr Ser Val Ser Phe Asp Ser Leu Phe Ser Ala
            580                 585                 590

Val Lys Asn Phe Thr Glu Ile Ala Ser Lys Phe Ser Glu Arg Leu Arg
        595                 600                 605

Asp Phe Asp Lys Ser Asn Pro Ile Leu Leu Arg Met Met Asn Asp Gln
    610                 615                 620

Leu Met Phe Leu Glu Arg Ala Phe Ile Asp Pro Leu Gly Leu Pro Asp
625                 630                 635                 640

Arg Pro Phe Tyr Arg His Val Ile Tyr Ala Pro Ser Ser His Asn Lys
                645                 650                 655

Tyr Ala Gly Glu Ser Phe Pro Gly Ile Tyr Asp Ala Leu Phe Asp Ile
            660                 665                 670

Glu Ser Lys Val Asp Pro Ser Gln Ala Trp Gly Glu Val Lys Arg Gln
        675                 680                 685

Ile Ser Ile Ala Thr Phe Thr Val Gln Ala Ala Glu Thr Leu Ser
    690                 695                 700

Glu Val Ala
705

<210> SEQ ID NO 33
<211> LENGTH: 707
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Lys Ser Ser Asn Glu Ala Thr Asn Ile Thr Pro Lys His Asn Met Lys
1               5                   10                  15

Ala Phe Leu Asp Glu Leu Lys Ala Glu Asn Ile Lys Lys Phe Leu Tyr
            20                  25                  30

Asn Phe Thr Gln Ile Pro His Leu Ala Gly Thr Glu Gln Asn Phe Gln
        35                  40                  45

Leu Ala Lys Gln Ile Gln Ser Gln Trp Lys Glu Phe Gly Leu Asp Ser
    50                  55                  60

Val Glu Leu Ala His Tyr Asp Val Leu Leu Ser Tyr Pro Asn Lys Thr
65                  70                  75                  80

His Pro Asn Tyr Ile Ser Ile Ile Asn Glu Asp Gly Asn Glu Ile Phe
                85                  90                  95

Asn Thr Ser Leu Phe Glu Pro Pro Pro Pro Gly Tyr Glu Asn Val Leu

```
                100             105             110
Asp Ile Val Pro Pro Phe Ser Ala Phe Ser Pro Gln Gly Met Pro Glu
            115                 120             125
Gly Asp Leu Val Tyr Val Asn Tyr Ala Arg Thr Glu Asp Phe Phe Lys
130                             135             140
Leu Glu Arg Asp Met Lys Ile Asn Cys Ser Gly Lys Ile Val Ile Ala
145                 150                 155                 160
Arg Tyr Gly Lys Val Phe Arg Gly Asn Lys Val Lys Asn Ala Gln Leu
                165                 170                 175
Ala Gly Ala Lys Gly Val Ile Leu Tyr Ser Asp Pro Ala Asp Tyr Phe
            180                 185                 190
Ala Pro Gly Val Lys Ser Tyr Pro Asp Gly Trp Asn Leu Pro Gly Gly
        195                 200                 205
Gly Val Gln Arg Gly Asn Ile Leu Asn Leu Asn Gly Ala Gly Asp Pro
    210                 215                 220
Leu Thr Pro Gly Tyr Pro Ala Asn Glu Tyr Ala Tyr Arg His Gly Ile
225                 230                 235                 240
Ala Glu Ala Val Gly Leu Pro Ser Ile Pro Val His Pro Ile Gly Tyr
                245                 250                 255
Tyr Asp Ala Gln Lys Leu Leu Glu Lys Met Gly Gly Ser Ala Pro Pro
            260                 265                 270
Asp Ser Ser Trp Arg Gly Ser Leu Lys Val Pro Tyr Asn Val Gly Pro
        275                 280                 285
Gly Phe Thr Gly Asn Phe Ser Thr Gln Lys Val Lys Met His Ile His
    290                 295                 300
Ser Thr Asn Glu Val Thr Arg Ile Tyr Asn Val Ile Gly Thr Leu Arg
305                 310                 315                 320
Gly Ala Val Glu Pro Asp Arg Tyr Val Ile Leu Gly Gly His Arg Asp
                325                 330                 335
Ser Trp Val Phe Gly Gly Ile Asp Pro Gln Ser Gly Ala Ala Val Val
            340                 345                 350
His Glu Ile Val Arg Ser Phe Gly Thr Leu Lys Lys Glu Gly Trp Arg
        355                 360                 365
Pro Arg Arg Thr Ile Leu Phe Ala Ser Trp Asp Ala Glu Glu Phe Gly
    370                 375                 380
Leu Leu Gly Ser Thr Glu Trp Ala Glu Glu Asn Ser Arg Leu Leu Gln
385                 390                 395                 400
Glu Arg Gly Val Ala Tyr Ile Asn Ala Asp Ser Ser Ile Glu Gly Asn
                405                 410                 415
Tyr Thr Leu Arg Val Asp Cys Thr Pro Leu Met Tyr Ser Leu Val Tyr
            420                 425                 430
Asn Leu Thr Lys Glu Leu Lys Ser Pro Asp Glu Gly Phe Glu Gly Lys
        435                 440                 445
Ser Leu Tyr Glu Ser Trp Thr Lys Lys Ser Pro Ser Pro Glu Phe Ser
    450                 455                 460
Gly Met Pro Arg Ile Ser Lys Leu Gly Ser Gly Asn Asp Phe Glu Val
465                 470                 475                 480
Phe Phe Gln Arg Leu Gly Ile Ala Ser Gly Arg Ala Arg Tyr Thr Lys
                485                 490                 495
Asn Trp Glu Thr Asn Lys Phe Ser Gly Tyr Pro Leu Tyr His Ser Val
            500                 505                 510
Tyr Glu Thr Tyr Glu Leu Val Glu Lys Phe Tyr Asp Pro Met Phe Lys
        515                 520                 525
```

```
Tyr His Leu Thr Val Ala Gln Val Arg Gly Gly Met Val Phe Glu Leu
            530                 535                 540
Ala Asn Ser Ile Val Leu Pro Phe Asp Cys Arg Asp Tyr Ala Val Val
545                 550                 555                 560
Leu Arg Lys Tyr Ala Asp Lys Ile Tyr Asn Ile Ser Met Lys His Pro
                565                 570                 575
Gln Glu Met Lys Thr Tyr Ser Val Ser Phe Asp Ser Leu Phe Ser Ala
            580                 585                 590
Val Lys Asn Phe Thr Glu Ile Ala Ser Lys Phe Thr Glu Arg Leu Gln
        595                 600                 605
Asp Phe Asp Lys Ser Asn Pro Ile Leu Leu Arg Met Met Asn Asp Gln
    610                 615                 620
Leu Met Phe Leu Glu Arg Ala Phe Ile Asp Pro Leu Gly Leu Pro Asp
625                 630                 635                 640
Arg Pro Phe Tyr Arg His Val Ile Tyr Ala Pro Ser Ser His Asn Lys
                645                 650                 655
Tyr Ala Gly Glu Ser Phe Pro Gly Ile Tyr Asp Ala Leu Phe Asp Ile
            660                 665                 670
Glu Ser Lys Val Asp Pro Ser Lys Ala Trp Gly Asp Val Lys Arg Gln
        675                 680                 685
Ile Ser Val Ala Ala Phe Thr Val Gln Ala Ala Glu Thr Leu Ser
    690                 695                 700
Glu Val Ala
705

<210> SEQ ID NO 34

<400> SEQUENCE: 34

000

<210> SEQ ID NO 35
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Leu Pro Ala Pro Lys Asn Leu Val Val Ser Arg Val Thr Glu Asp Ser
1               5                   10                  15
Ala Arg Leu Ser Trp Asp Ile Asp Glu Gln Arg Asp Trp Phe Asp Ser
            20                  25                  30
Phe Leu Ile Gln Tyr Gln Glu Ser Glu Lys Val Gly Glu Ala Ile Val
        35                  40                  45
Leu Thr Val Pro Gly Ser Glu Arg Ser Tyr Asp Leu Thr Gly Leu Lys
    50                  55                  60
Pro Gly Thr Glu Tyr Thr Val Ser Ile Tyr Gly Val Tyr His Val Tyr
65                  70                  75                  80
Arg Ser Asn Pro Leu Ser Ala Ile Phe Thr Thr
                85                  90

<210> SEQ ID NO 36
<211> LENGTH: 91
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 36

Leu Pro Ala Pro Lys Asn Leu Val Val Ser Arg Val Thr Glu Asp Ser
1               5                   10                  15

Ala Arg Leu Ser Trp Thr Ile Asp Glu Gln Arg Asp Trp Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Asn Pro Leu Ser Ala Ile Phe Thr Thr
                85                  90

<210> SEQ ID NO 37
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Leu Pro Ala Pro Lys Asn Leu Val Val Ser Arg Val Thr Glu Asp Ser
1               5                   10                  15

Ala Arg Leu Ser Trp Val Ile Asp Glu Gln Arg Asp Trp Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Asn Pro Leu Ser Ala Ile Phe Thr Thr
                85                  90

<210> SEQ ID NO 38
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Leu Pro Ala Pro Lys Asn Leu Val Val Ser Arg Val Thr Glu Asp Ser
1               5                   10                  15

Ala Arg Leu Ser Trp Thr Ile Asp Glu Gln Arg Asp Trp Phe Glu Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Asn Pro Leu Ser Ala Ile Phe Thr Thr

```
                        85                  90

<210> SEQ ID NO 39
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Leu Pro Ala Pro Lys Asn Leu Val Val Ser Arg Val Thr Glu Asp Ser
1               5                   10                  15

Ala Arg Leu Ser Trp Ala Ile Asp Glu Gln Arg Asp Trp Phe Glu Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Asn Pro Leu Ser Ala Ile Phe Thr Thr
                85                  90

<210> SEQ ID NO 40
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Leu Pro Ala Pro Lys Asn Leu Val Val Ser Arg Val Thr Glu Asp Ser
1               5                   10                  15

Ala Arg Leu Ser Trp Asp Ile Asp Glu Gln Arg Asp Trp Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Glu Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Ser Asn Pro Leu Ser Ala Ile Phe Thr Thr
                85                  90

<210> SEQ ID NO 41
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Gly Glu Ala Ile Val Leu Thr
        35                  40                  45
```

Val Pro Gly Ser Glu Arg Ser Tyr Asp Leu Thr Gly Leu Lys Pro Gly
         50                  55                  60

Thr Glu Tyr Pro Val Tyr Ile Ala Gly Val Lys Gly Gly Gln Trp Ser
 65                  70                  75                  80

Phe Pro Leu Ser Ala Ile Phe Thr Thr
                 85

<210> SEQ ID NO 42
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Thr
                 20                  25                  30

Ile Gly Tyr Trp Glu Trp Asp Asp Gly Glu Ala Ile Val Leu Thr
             35                  40                  45

Val Pro Gly Ser Glu Arg Ser Tyr Asp Leu Thr Gly Leu Lys Pro Gly
         50                  55                  60

Thr Glu Tyr Pro Val Tyr Ile Ala Gly Val Lys Gly Gly Gln Trp Ser
 65                  70                  75                  80

Phe Pro Leu Ser Ala Ile Phe Thr Thr
                 85

<210> SEQ ID NO 43
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Pro
                 20                  25                  30

Ile Gly Tyr Trp Glu Trp Asp Asp Gly Glu Ala Ile Val Leu Thr
             35                  40                  45

Val Pro Gly Ser Glu Arg Ser Tyr Asp Leu Thr Gly Leu Lys Pro Gly
         50                  55                  60

Thr Glu Tyr His Val Tyr Ile Ala Gly Val Lys Gly Gly Gln Trp Ser
 65                  70                  75                  80

Phe Pro Leu Ser Ala Ile Phe Thr Thr
                 85

<210> SEQ ID NO 44
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Pro
            20                  25                  30

Ile Gly Tyr Trp Glu Trp Asp Asp Gly Glu Ala Ile Val Leu Thr
            35              40                  45

Val Pro Gly Ser Glu Arg Ser Tyr Asp Leu Thr Gly Leu Lys Pro Gly
50                  55                  60

Thr Glu Tyr Trp Val Tyr Ile Ala Gly Val Lys Gly Gly Gln Trp Ser
65                  70                  75                  80

Phe Pro Leu Ser Ala Ile Phe Thr Thr
                85
```

<210> SEQ ID NO 45
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

```
Leu Pro Ala Pro Lys Asn Leu Val Val Ser Arg Val Thr Glu Asp Ser
1               5                   10                  15

Ala Arg Leu Ser Trp Gly Glu Gln Phe Thr Ile Phe Asp Ser Phe Leu
            20                  25                  30

Ile Gln Tyr Gln Glu Ser Glu Lys Val Gly Glu Ala Ile Val Leu Thr
            35              40                  45

Val Pro Gly Ser Glu Arg Ser Tyr Asp Leu Thr Gly Leu Lys Pro Gly
50                  55                  60

Thr Glu Tyr Thr Val Ser Ile Tyr Gly Ala Ser Gly Tyr Glu Trp Phe
65                  70                  75                  80

His Ala Phe Gly Ser Ser Asn Pro Leu Ser Ala Ile Phe Thr Thr
                85                  90                  95
```

<210> SEQ ID NO 46
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

```
Leu Pro Ala Pro Lys Asn Leu Val Val Ser Arg Val Thr Glu Asp Ser
1               5                   10                  15

Ala Arg Leu Ser Trp Glu Trp Trp Val Ile Pro Gly Asp Phe Asp Ser
            20                  25                  30

Phe Leu Ile Gln Tyr Gln Glu Ser Glu Lys Val Gly Glu Ala Ile Val
            35              40                  45

Leu Thr Val Pro Gly Ser Glu Arg Ser Tyr Asp Leu Thr Gly Leu Lys
50                  55                  60

Pro Gly Thr Glu Tyr Thr Val Ser Ile Tyr Gly Val Val Asn Ser Gly
65                  70                  75                  80

Gln Trp Asn Asp Thr Ser Asn Pro Leu Ser Ala Ile Phe Thr Thr
                85                  90                  95
```

<210> SEQ ID NO 47
<211> LENGTH: 90

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Pro Val Tyr Ile Ala Gly Val Lys Gly Gly Gln Trp Ser
65                  70                  75                  80

Phe Pro Leu Ser Ala Ile Phe Thr Thr Cys
                85                  90

<210> SEQ ID NO 48
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Gly Glu Ala Ile Val Leu Thr
        35                  40                  45

Val Pro Gly Ser Glu Arg Ser Tyr Asp Leu Thr Gly Leu Cys Pro Gly
    50                  55                  60

Thr Glu Tyr Pro Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 49
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Pro Val Tyr Ile Ala Gly Val Lys Gly Gly Gln Trp Ser

```
                65                  70                  75                  80
Phe Pro Leu Ser Ala Ile Phe Thr Thr
                85

<210> SEQ ID NO 50
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Leu Pro Ala Pro Lys Asn Leu Val Val Ser Cys Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Pro Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 51
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Leu Pro Ala Pro Lys Asn Leu Val Val Ser Glu Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Cys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Ile Phe Thr Thr Gly Gly His His His His
                85                  90                  95

His

<210> SEQ ID NO 52
<211> LENGTH: 199
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Met Ser His His His His His His Ser Ser Gly Glu Asn Leu Tyr Phe
1               5                   10                  15
```

```
Gln Ser Lys Pro His Ile Asp Asn Tyr Leu His Asp Lys Asp Lys Asp
            20                  25                  30

Glu Lys Ile Glu Gln Tyr Asp Lys Asn Val Lys Glu Gln Ala Ser Lys
        35                  40                  45

Asp Lys Lys Gln Gln Ala Lys Pro Gln Ile Pro Lys Asp Lys Ser Lys
    50                  55                  60

Val Ala Gly Tyr Ile Glu Ile Pro Asp Ala Asp Ile Lys Glu Pro Val
65                  70                  75                  80

Tyr Pro Gly Pro Ala Thr Arg Glu Gln Leu Asn Arg Gly Val Ser Phe
                85                  90                  95

Ala Glu Glu Asn Glu Ser Leu Asp Asp Gln Asn Ile Ser Ile Ala Gly
            100                 105                 110

His Thr Phe Ile Asp Arg Pro Asn Tyr Gln Phe Thr Asn Leu Lys Ala
            115                 120                 125

Ala Lys Lys Gly Ser Met Val Tyr Phe Lys Val Gly Asn Glu Thr Arg
        130                 135                 140

Lys Tyr Lys Met Thr Ser Ile Arg Asn Val Lys Pro Thr Ala Val Glu
145                 150                 155                 160

Val Leu Asp Glu Gln Lys Gly Lys Asp Lys Gln Leu Thr Leu Ile Thr
                165                 170                 175

Cys Asp Asp Tyr Asn Glu Glu Thr Gly Val Trp Glu Thr Arg Lys Ile
            180                 185                 190

Phe Val Ala Thr Glu Val Lys
        195

<210> SEQ ID NO 53
<211> LENGTH: 182
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Ser Lys Pro His Ile Asp Asn Tyr Leu His Asp Lys Asp Lys Asp Glu
1               5                   10                  15

Lys Ile Glu Gln Tyr Asp Lys Asn Val Lys Glu Gln Ala Ser Lys Asp
            20                  25                  30

Lys Lys Gln Gln Ala Lys Pro Gln Ile Pro Lys Asp Lys Ser Lys Val
        35                  40                  45

Ala Gly Tyr Ile Glu Ile Pro Asp Ala Asp Ile Lys Glu Pro Val Tyr
    50                  55                  60

Pro Gly Pro Ala Thr Arg Glu Gln Leu Asn Arg Gly Val Ser Phe Ala
65                  70                  75                  80

Glu Glu Asn Glu Ser Leu Asp Asp Gln Asn Ile Ser Ile Ala Gly His
                85                  90                  95

Thr Phe Ile Asp Arg Pro Asn Tyr Gln Phe Thr Asn Leu Lys Ala Ala
            100                 105                 110

Lys Lys Gly Ser Met Val Tyr Phe Lys Val Gly Asn Glu Thr Arg Lys
        115                 120                 125

Tyr Lys Met Thr Ser Ile Arg Asn Val Lys Pro Thr Ala Val Glu Val
    130                 135                 140

Leu Asp Glu Gln Lys Gly Lys Asp Lys Gln Leu Thr Leu Ile Thr Cys
145                 150                 155                 160

Asp Asp Tyr Asn Glu Glu Thr Gly Val Trp Glu Thr Arg Lys Ile Phe
                165                 170                 175
```

```
Val Ala Thr Glu Val Lys
            180

<210> SEQ ID NO 54
<211> LENGTH: 7
<212> TYPE: PRT
<213> ORGANISM: Unknown
<220> FEATURE:
<223> OTHER INFORMATION: Description of Unknown: TEV protease cleavage
      site peptide

<400> SEQUENCE: 54

Glu Asn Leu Tyr Phe Gln Ser
1               5

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Lys Gly Gly His Arg Ser Asn
1               5

<210> SEQ ID NO 56
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Asp Ile Asp Glu Gln Arg Asp Trp
1               5

<210> SEQ ID NO 57
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Thr Ile Asp Glu Gln Arg Asp Trp
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Val Ile Asp Glu Gln Arg Asp Trp
1               5

<210> SEQ ID NO 59
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 59

Ala Ile Asp Glu Gln Arg Asp Trp
1               5

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Trp Trp Val Ile Pro Gly Asp
1               5

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Glu Gln Phe Thr Ile
1               5

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Thr Ala Pro Asp Ala Ala
1               5

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Phe Asp Ser Phe Leu Ile Gln Tyr Gln Glu
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Phe Glu Ser Phe Leu Ile Gln Tyr Gln Glu
1               5                   10
```

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Phe Asp Ser Phe Ala Ile Gly Tyr Trp Glu
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Phe Asp Ser Phe Pro Ile Gly Tyr Trp Glu
1               5                   10

<210> SEQ ID NO 67
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Phe Asp Ser Phe Thr Ile Gly Tyr Trp Glu
1               5                   10

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser Glu Lys Val Gly Glu
1               5

<210> SEQ ID NO 69
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Trp Asp Asp Asp Gly Glu
1               5

<210> SEQ ID NO 70
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 70

Thr Glu Tyr Thr Val Ser Ile Tyr Gly Val
1               5                   10

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Thr Glu Tyr Thr Val Ser Ile Tyr Gly
1               5

<210> SEQ ID NO 72
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Thr Glu Tyr Pro Val Tyr Ile Ala Gly Val
1               5                   10

<210> SEQ ID NO 73
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Thr Glu Tyr Trp Val Tyr Ile Ala Gly Val
1               5                   10

<210> SEQ ID NO 74
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Thr Glu Tyr His Val Tyr Ile Ala Gly Val
1               5                   10

<210> SEQ ID NO 75
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Leu Pro Ala Pro Lys Asn Leu Val Val Ser Arg Val Thr Glu Asp Ser
1               5                   10                  15

Ala Arg Leu Ser Trp Ala Ala Asp Glu Gln Arg Asp Trp Phe Glu Ser
            20                  25                  30

Phe Leu Ile Gln Tyr Gln Glu Ser Glu Lys Val Gly Glu Ala Ile Val
```

```
                35                  40                  45

Leu Thr Val Pro Gly Ser Cys Arg Ser Tyr Asp Leu Thr Gly Leu Lys
 50                  55                  60

Pro Gly Thr Glu Tyr Thr Val Ser Ile Tyr Gly Val Tyr His Val Tyr
 65                  70                  75                  80

Arg Ser Asn Pro Leu Ser Ala Ile Phe Thr Thr
                 85                  90

<210> SEQ ID NO 76
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Leu Pro Ala Pro Lys Asn Leu Val Val Ser Arg Val Thr Glu Asp Ser
 1               5                  10                  15

Ala Arg Leu Ser Trp Ala Ile Ala Glu Gln Arg Asp Trp Phe Glu Ser
                 20                  25                  30

Phe Leu Ile Gln Tyr Gln Glu Ser Glu Lys Val Gly Glu Ala Ile Val
                 35                  40                  45

Leu Thr Val Pro Gly Ser Cys Arg Ser Tyr Asp Leu Thr Gly Leu Lys
 50                  55                  60

Pro Gly Thr Glu Tyr Thr Val Ser Ile Tyr Gly Val Tyr His Val Tyr
 65                  70                  75                  80

Arg Ser Asn Pro Leu Ser Ala Ile Phe Thr Thr
                 85                  90

<210> SEQ ID NO 77
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Leu Pro Ala Pro Lys Asn Leu Val Val Ser Arg Val Thr Glu Asp Ser
 1               5                  10                  15

Ala Arg Leu Ser Trp Ala Ile Asp Ala Gln Arg Asp Trp Phe Glu Ser
                 20                  25                  30

Phe Leu Ile Gln Tyr Gln Glu Ser Glu Lys Val Gly Glu Ala Ile Val
                 35                  40                  45

Leu Thr Val Pro Gly Ser Cys Arg Ser Tyr Asp Leu Thr Gly Leu Lys
 50                  55                  60

Pro Gly Thr Glu Tyr Thr Val Ser Ile Tyr Gly Val Tyr His Val Tyr
 65                  70                  75                  80

Arg Ser Asn Pro Leu Ser Ala Ile Phe Thr Thr
                 85                  90

<210> SEQ ID NO 78
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78
```

Leu Pro Ala Pro Lys Asn Leu Val Val Ser Arg Val Thr Glu Asp Ser
1               5                   10                  15

Ala Arg Leu Ser Trp Ala Ile Asp Glu Ala Arg Asp Trp Phe Glu Ser
                20                  25                  30

Phe Leu Ile Gln Tyr Gln Glu Ser Glu Lys Val Gly Glu Ala Ile Val
            35                  40                  45

Leu Thr Val Pro Gly Ser Cys Arg Ser Tyr Asp Leu Thr Gly Leu Lys
        50                  55                  60

Pro Gly Thr Glu Tyr Thr Val Ser Ile Tyr Gly Val Tyr His Val Tyr
65                  70                  75                  80

Arg Ser Asn Pro Leu Ser Ala Ile Phe Thr Thr
                85                  90

<210> SEQ ID NO 79
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Leu Pro Ala Pro Lys Asn Leu Val Val Ser Arg Val Thr Glu Asp Ser
1               5                   10                  15

Ala Arg Leu Ser Trp Ala Ile Asp Glu Gln Ala Asp Trp Phe Glu Ser
                20                  25                  30

Phe Leu Ile Gln Tyr Gln Glu Ser Glu Lys Val Gly Glu Ala Ile Val
            35                  40                  45

Leu Thr Val Pro Gly Ser Cys Arg Ser Tyr Asp Leu Thr Gly Leu Lys
        50                  55                  60

Pro Gly Thr Glu Tyr Thr Val Ser Ile Tyr Gly Val Tyr His Val Tyr
65                  70                  75                  80

Arg Ser Asn Pro Leu Ser Ala Ile Phe Thr Thr
                85                  90

<210> SEQ ID NO 80
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Leu Pro Ala Pro Lys Asn Leu Val Val Ser Arg Val Thr Glu Asp Ser
1               5                   10                  15

Ala Arg Leu Ser Trp Ala Ile Asp Glu Gln Arg Ala Trp Phe Glu Ser
                20                  25                  30

Phe Leu Ile Gln Tyr Gln Glu Ser Glu Lys Val Gly Glu Ala Ile Val
            35                  40                  45

Leu Thr Val Pro Gly Ser Cys Arg Ser Tyr Asp Leu Thr Gly Leu Lys
        50                  55                  60

Pro Gly Thr Glu Tyr Thr Val Ser Ile Tyr Gly Val Tyr His Val Tyr
65                  70                  75                  80

Arg Ser Asn Pro Leu Ser Ala Ile Phe Thr Thr
                85                  90

<210> SEQ ID NO 81

```
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Leu Pro Ala Pro Lys Asn Leu Val Val Ser Arg Val Thr Glu Asp Ser
1               5                   10                  15

Ala Arg Leu Ser Trp Ala Ile Asp Glu Gln Arg Asp Ala Phe Glu Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Asn Pro Leu Ser Ala Ile Phe Thr Thr
                85                  90

<210> SEQ ID NO 82
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Leu Pro Ala Pro Lys Asn Leu Val Val Ser Arg Val Thr Glu Asp Ser
1               5                   10                  15

Ala Arg Leu Ser Trp Ala Ile Asp Glu Gln Arg Asp Trp Phe Glu Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Ala His Val Tyr
65                  70                  75                  80

Arg Ser Asn Pro Leu Ser Ala Ile Phe Thr Thr
                85                  90

<210> SEQ ID NO 83
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Leu Pro Ala Pro Lys Asn Leu Val Val Ser Arg Val Thr Glu Asp Ser
1               5                   10                  15

Ala Arg Leu Ser Trp Ala Ile Asp Glu Gln Arg Asp Trp Phe Glu Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60
```

```
Pro Gly Thr Glu Tyr Thr Val Ser Ile Tyr Gly Val Tyr Ala Val Tyr
65                  70                  75                  80

Arg Ser Asn Pro Leu Ser Ala Ile Phe Thr Thr
                85                  90
```

<210> SEQ ID NO 84
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

```
Leu Pro Ala Pro Lys Asn Leu Val Val Ser Arg Val Thr Glu Asp Ser
1               5                   10                  15

Ala Arg Leu Ser Trp Ala Ile Asp Glu Gln Arg Asp Trp Phe Glu Ser
                20                  25                  30

Phe Leu Ile Gln Tyr Gln Glu Ser Glu Lys Val Gly Glu Ala Ile Val
            35                  40                  45

Leu Thr Val Pro Gly Ser Cys Arg Ser Tyr Asp Leu Thr Gly Leu Lys
        50                  55                  60

Pro Gly Thr Glu Tyr Thr Val Ser Ile Tyr Gly Val Tyr His Ala Tyr
65                  70                  75                  80

Arg Ser Asn Pro Leu Ser Ala Ile Phe Thr Thr
                85                  90
```

<210> SEQ ID NO 85
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

```
Leu Pro Ala Pro Lys Asn Leu Val Val Ser Arg Val Thr Glu Asp Ser
1               5                   10                  15

Ala Arg Leu Ser Trp Ala Ile Asp Glu Gln Arg Asp Trp Phe Glu Ser
                20                  25                  30

Phe Leu Ile Gln Tyr Gln Glu Ser Glu Lys Val Gly Glu Ala Ile Val
            35                  40                  45

Leu Thr Val Pro Gly Ser Cys Arg Ser Tyr Asp Leu Thr Gly Leu Lys
        50                  55                  60

Pro Gly Thr Glu Tyr Thr Val Ser Ile Tyr Gly Val Tyr His Val Ala
65                  70                  75                  80

Arg Ser Asn Pro Leu Ser Ala Ile Phe Thr Thr
                85                  90
```

<210> SEQ ID NO 86
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

```
Leu Pro Ala Pro Lys Asn Leu Val Val Ser Arg Val Thr Glu Asp Ser
1               5                   10                  15

Ala Arg Leu Ser Trp Ala Ile Asp Glu Gln Arg Asp Trp Phe Glu Ser
```

```
                    20                  25                  30

Phe Leu Ile Gln Tyr Gln Glu Ser Glu Lys Val Gly Glu Ala Ile Val
            35                  40                  45

Leu Thr Val Pro Gly Ser Cys Arg Ser Tyr Asp Leu Thr Gly Leu Lys
        50                  55                  60

Pro Gly Thr Glu Tyr Thr Val Ser Ile Tyr Gly Val Tyr His Val Tyr
65                  70                  75                  80

Ala Ser Asn Pro Leu Ser Ala Ile Phe Thr Thr
                85                  90

<210> SEQ ID NO 87
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Leu Pro Ala Pro Lys Asn Leu Val Val Ser Arg Val Thr Glu Asp Ser
1               5                   10                  15

Ala Arg Leu Ser Trp Ala Ile Asp Glu Gln Arg Asp Trp Phe Ala Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Asn Pro Leu Ser Ala Ile Phe Thr Thr
                85                  90

<210> SEQ ID NO 88
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Leu Pro Ala Pro Lys Asn Leu Val Val Ser Arg Val Thr Glu Asp Ser
1               5                   10                  15

Ala Arg Leu Ser Trp Asp Ile Asp Glu Gln Arg Asp Trp Phe Glu Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Asn Pro Leu Ser Ala Ile Phe Thr Thr
                85                  90

<210> SEQ ID NO 89
<211> LENGTH: 91
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 89

Leu Pro Ala Pro Lys Asn Leu Val Val Ser Arg Val Thr Glu Asp Ser
1               5                   10                  15

Ala Arg Leu Ser Trp Ala Ile Asp Glu Gln Arg Asp Trp Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Asn Pro Leu Ser Ala Ile Phe Thr Thr
                85                  90

<210> SEQ ID NO 90
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Leu Pro Ala Pro Lys Asn Leu Val Val Ser Arg Val Thr Glu Asp Ser
1               5                   10                  15

Ala Arg Leu Ser Trp Ala Ile Asp Glu Gln Arg Asp Trp Phe Glu Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Ser Asn Pro Leu Ser Ala Ile Phe Thr Thr
                85                  90

<210> SEQ ID NO 91
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Leu Pro Ala Pro Lys Asn Leu Val Val Ser Arg Val Thr Glu Asp Ser
1               5                   10                  15

Ala Arg Leu Ser Trp Asp Ile Asp Glu Gln Arg Asp Trp Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Asn Pro Leu Ser Ala Ile Phe Thr Thr
                85                  90

<210> SEQ ID NO 92
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Leu Pro Ala Pro Lys Asn Leu Val Val Ser Arg Val Thr Glu Asp Ser
1               5                   10                  15

Ala Arg Leu Ser Trp Asp Ile Asp Glu Gln Arg Asp Trp Phe Glu Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Ser Asn Pro Leu Ser Ala Ile Phe Thr Thr
                85                  90

<210> SEQ ID NO 93
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Leu Pro Ala Pro Lys Asn Leu Val Val Ser Arg Val Thr Glu Asp Ser
1               5                   10                  15

Ala Arg Leu Ser Trp Ala Ile Asp Glu Gln Arg Asp Trp Phe Asp Ser
            20                  25                  30

Phe Leu Ile Gln Tyr Gln Glu Ser Glu Lys Val Gly Glu Ala Ile Val
        35                  40                  45

Leu Thr Val Pro Gly Ser Cys Arg Ser Tyr Asp Leu Thr Gly Leu Lys
    50                  55                  60

Pro Gly Thr Glu Tyr Thr Val Ser Ile Tyr Gly Val Tyr His Val Tyr
65                  70                  75                  80

Arg Ser Ser Asn Pro Leu Ser Ala Ile Phe Thr Thr
                85                  90

<210> SEQ ID NO 94
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Asp Gly Glu Ala Ile Val Leu Thr
        35                  40                  45

```
Val Pro Gly Ser Cys Arg Ser Tyr Asp Leu Thr Gly Leu Lys Pro Gly
    50                  55                  60

Thr Glu Tyr Arg Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 95
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Lys Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 96
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Glu Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 97
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Leu Pro Ala Pro Lys Asn Leu Val Val Ser Arg Val Thr Glu Asp Ser
```

```
                1               5                  10                  15
Ala Arg Leu Ser Trp Thr Ala Pro Asp Ala Ala Phe Asp Ser Phe Ala
                20                  25                  30

Ile Gly Tyr Trp Glu Trp Asp Asp Gly Glu Ala Ile Val Leu Thr
            35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85
```

<210> SEQ ID NO 98
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
                20                  25                  30

Ile Gly Tyr Trp Glu Trp Asp Asp Gly Glu Ala Ile Val Leu Thr
            35                  40                  45

Val Pro Gly Ser Cys Arg Ser Tyr Asp Leu Thr Gly Leu Lys Pro Gly
    50                  55                  60

Thr Glu Tyr Asp Val Tyr Ile Ala Gly Val Lys Gly Gly Gln Trp Ser
65                  70                  75                  80

Phe Pro Leu Ser Ala Ile Phe Thr Thr
                85
```

<210> SEQ ID NO 99
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

```
Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
                20                  25                  30

Ile Gly Tyr Trp Glu Trp Asp Asp Gly Glu Ala Ile Val Leu Thr
            35                  40                  45

Val Pro Gly Ser Cys Arg Ser Tyr Asp Leu Thr Gly Leu Lys Pro Gly
    50                  55                  60

Thr Glu Tyr Ala Val Tyr Ile Ala Gly Val Lys Gly Gly Gln Trp Ser
65                  70                  75                  80

Phe Pro Leu Ser Ala Ile Phe Thr Thr
                85
```

<210> SEQ ID NO 100
<211> LENGTH: 89
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 100

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Gly Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 101
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Val Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 102
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Leu Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 103
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Ile Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 104
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Phe Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 105
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

-continued

Ile Gly Tyr Trp Glu Trp Asp Asp Gly Glu Ala Ile Val Leu Thr
            35                  40                  45

Val Pro Gly Ser Cys Arg Ser Tyr Asp Leu Thr Gly Leu Lys Pro Gly
 50                  55                  60

Thr Glu Tyr Trp Val Tyr Ile Ala Gly Val Lys Gly Gln Trp Ser
 65                  70                  75                  80

Phe Pro Leu Ser Ala Ile Phe Thr Thr
                    85

<210> SEQ ID NO 106
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Ala
                20                  25                  30

Ile Gly Tyr Trp Glu Trp Asp Asp Gly Glu Ala Ile Val Leu Thr
            35                  40                  45

Val Pro Gly Ser Cys Arg Ser Tyr Asp Leu Thr Gly Leu Lys Pro Gly
 50                  55                  60

Thr Glu Tyr Asn Val Tyr Ile Ala Gly Val Lys Gly Gln Trp Ser
 65                  70                  75                  80

Phe Pro Leu Ser Ala Ile Phe Thr Thr
                    85

<210> SEQ ID NO 107
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Ala
                20                  25                  30

Ile Gly Tyr Trp Glu Trp Asp Asp Gly Glu Ala Ile Val Leu Thr
            35                  40                  45

Val Pro Gly Ser Cys Arg Ser Tyr Asp Leu Thr Gly Leu Lys Pro Gly
 50                  55                  60

Thr Glu Tyr Gln Val Tyr Ile Ala Gly Val Lys Gly Gln Trp Ser
 65                  70                  75                  80

Phe Pro Leu Ser Ala Ile Phe Thr Thr
                    85

<210> SEQ ID NO 108
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Ser Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 109
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Thr Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 110
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Tyr Val Tyr Ile Ala Gly Val Lys Gly Gly Gln Trp Ser
65                  70                  75                  80

Phe Pro Leu Ser Ala Ile Phe Thr Thr
                85

```
<210> SEQ ID NO 111
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
                20                  25                  30

Ile Ala Tyr Trp Glu Trp Asp Asp Gly Ala Ile Val Leu Thr
            35                  40                  45

Val Pro Gly Ser Cys Arg Ser Tyr Asp Leu Thr Gly Leu Lys Pro Gly
        50                  55                  60

Thr Glu Tyr Pro Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 112
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
                20                  25                  30

Ile Ser Tyr Trp Glu Trp Asp Asp Gly Ala Ile Val Leu Thr
            35                  40                  45

Val Pro Gly Ser Cys Arg Ser Tyr Asp Leu Thr Gly Leu Lys Pro Gly
        50                  55                  60

Thr Glu Tyr Pro Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 113
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
                20                  25                  30

Ile Gly Tyr Trp Glu Trp Asp Thr Asp Gly Glu Ala Ile Val Leu Thr
            35                  40                  45

Val Pro Gly Ser Cys Arg Ser Tyr Asp Leu Thr Gly Leu Lys Pro Gly
        50                  55                  60
```

Thr Glu Tyr Pro Val Tyr Ile Ala Gly Val Lys Gly Gln Trp Ser
 65                  70                  75                  80

Phe Pro Leu Ser Ala Ile Phe Thr Thr
                 85

<210> SEQ ID NO 114
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
                20                  25                  30

Ile Gly Tyr Trp Glu Trp Asp Ser Asp Gly Glu Ala Ile Val Leu Thr
            35                  40                  45

Val Pro Gly Ser Cys Arg Ser Tyr Asp Leu Thr Gly Leu Lys Pro Gly
        50                  55                  60

Thr Glu Tyr Pro Val Tyr Ile Ala Gly Val Lys Gly Gln Trp Ser
 65                  70                  75                  80

Phe Pro Leu Ser Ala Ile Phe Thr Thr
                 85

<210> SEQ ID NO 115
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
                20                  25                  30

Ile Gly Tyr Tyr Glu Trp Asp Asp Gly Glu Ala Ile Val Leu Thr
            35                  40                  45

Val Pro Gly Ser Cys Arg Ser Tyr Asp Leu Thr Gly Leu Lys Pro Gly
        50                  55                  60

Thr Glu Tyr Pro Val Tyr Ile Ala Gly Val Lys Gly Gln Trp Ser
 65                  70                  75                  80

Phe Pro Leu Ser Ala Ile Phe Thr Thr
                 85

<210> SEQ ID NO 116
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 116

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Phe Glu Trp Asp Asp Gly Glu Ala Ile Val Leu Thr
            35                  40                  45

Val Pro Gly Ser Cys Arg Ser Tyr Asp Leu Thr Gly Leu Lys Pro Gly
 50                  55                  60

Thr Glu Tyr Pro Val Tyr Ile Ala Gly Val Lys Gly Gly Gln Trp Ser
 65                  70                  75                  80

Phe Pro Leu Ser Ala Ile Phe Thr Thr
                85

<210> SEQ ID NO 117
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Ala
            20                  25                  30

Ile Gly Tyr Leu Glu Trp Asp Asp Gly Glu Ala Ile Val Leu Thr
            35                  40                  45

Val Pro Gly Ser Cys Arg Ser Tyr Asp Leu Thr Gly Leu Lys Pro Gly
 50                  55                  60

Thr Glu Tyr Pro Val Tyr Ile Ala Gly Val Lys Gly Gly Gln Trp Ser
 65                  70                  75                  80

Phe Pro Leu Ser Ala Ile Phe Thr Thr
                85

<210> SEQ ID NO 118
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Ala
            20                  25                  30

Ile Gly Tyr Trp Glu Tyr Asp Asp Gly Glu Ala Ile Val Leu Thr
            35                  40                  45

Val Pro Gly Ser Cys Arg Ser Tyr Asp Leu Thr Gly Leu Lys Pro Gly
 50                  55                  60

Thr Glu Tyr Pro Val Tyr Ile Ala Gly Val Lys Gly Gly Gln Trp Ser
 65                  70                  75                  80

Phe Pro Leu Ser Ala Ile Phe Thr Thr
                85

<210> SEQ ID NO 119
<211> LENGTH: 89
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 119

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Phe Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Pro Val Tyr Ile Ala Gly Val Lys Gly Gln Trp Ser
65                  70                  75                  80

Phe Pro Leu Ser Ala Ile Phe Thr Thr
                85

<210> SEQ ID NO 120
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Leu Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Pro Val Tyr Ile Ala Gly Val Lys Gly Gln Trp Ser
65                  70                  75                  80

Phe Pro Leu Ser Ala Ile Phe Thr Thr
                85

<210> SEQ ID NO 121
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Pro Val Tyr Ile Ala Gly Val Lys Gly Gln Tyr Ser
65                  70                  75                  80

Phe Pro Leu Ser Ala Ile Phe Thr Thr

<210> SEQ ID NO 122
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Pro Val Tyr Ile Ala Gly Val Lys Gly Gly Gln Phe Ser
65                  70                  75                  80

Phe Pro Leu Ser Ala Ile Phe Thr Thr
                85

<210> SEQ ID NO 123
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr Pro Val Tyr Ile Ala Gly Val Lys Gly Gly Gln Leu Ser
65                  70                  75                  80

Phe Pro Leu Ser Ala Ile Phe Thr Thr
                85

<210> SEQ ID NO 124
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Arg
            20                  25                  30

Ile Gly Tyr Trp Glu Trp Asp Asp Gly Glu Ala Ile Val Leu Thr
        35                  40                  45

```
Val Pro Gly Ser Cys Arg Ser Tyr Asp Leu Thr Gly Leu Lys Pro Gly
         50                  55                  60

Thr Glu Tyr His Val Tyr Ile Ala Gly Val Lys Gly Gly Gln Trp Ser
 65                  70                  75                  80

Phe Pro Leu Ser Ala Ile Phe Thr Thr
                 85
```

<210> SEQ ID NO 125
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

```
Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Lys
             20                  25                  30

Ile Gly Tyr Trp Glu Trp Asp Asp Gly Glu Ala Ile Val Leu Thr
             35                  40                  45

Val Pro Gly Ser Cys Arg Ser Tyr Asp Leu Thr Gly Leu Lys Pro Gly
         50                  55                  60

Thr Glu Tyr His Val Tyr Ile Ala Gly Val Lys Gly Gly Gln Trp Ser
 65                  70                  75                  80

Phe Pro Leu Ser Ala Ile Phe Thr Thr
                 85
```

<210> SEQ ID NO 126
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

```
Leu Pro Ala Pro Lys Asn Leu Val Val Ser Arg Val Thr Glu Asp Ser
 1               5                  10                  15

Ala Arg Leu Ser Trp Thr Ala Pro Asp Ala Ala Phe Asp Ser Phe Glu
             20                  25                  30

Ile Gly Tyr Trp Glu Trp Asp Asp Gly Glu Ala Ile Val Leu Thr
             35                  40                  45

Val Pro Gly Ser Cys Arg Ser Tyr Asp Leu Thr Gly Leu Lys Pro Gly
         50                  55                  60

Thr Glu Tyr His Val Tyr Ile Ala Gly Val Lys Gly Gly Gln Trp Ser
 65                  70                  75                  80

Phe Pro Leu Ser Ala Ile Phe Thr Thr
                 85
```

<210> SEQ ID NO 127
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe His
            20                  25                  30

Ile Gly Tyr Trp Glu Trp Asp Asp Gly Glu Ala Ile Val Leu Thr
            35                  40                  45

Val Pro Gly Ser Cys Arg Ser Tyr Asp Leu Thr Gly Leu Lys Pro Gly
        50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 128
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 128

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asp
            20                  25                  30

Ile Gly Tyr Trp Glu Trp Asp Asp Gly Glu Ala Ile Val Leu Thr
            35                  40                  45

Val Pro Gly Ser Cys Arg Ser Tyr Asp Leu Thr Gly Leu Lys Pro Gly
        50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 129
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ala
            20                  25                  30

Ile Gly Tyr Trp Glu Trp Asp Asp Gly Glu Ala Ile Val Leu Thr
            35                  40                  45

Val Pro Gly Ser Cys Arg Ser Tyr Asp Leu Thr Gly Leu Lys Pro Gly
        50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 130
<211> LENGTH: 89

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gly
                20                  25                  30

Ile Gly Tyr Trp Glu Trp Asp Asp Gly Glu Ala Ile Val Leu Thr
            35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 131
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 131

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Val
                20                  25                  30

Ile Gly Tyr Trp Glu Trp Asp Asp Gly Glu Ala Ile Val Leu Thr
            35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 132
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 132

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
                20                  25                  30

Ile Gly Tyr Trp Glu Trp Asp Asp Gly Glu Ala Ile Val Leu Thr
            35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser

```
                65                  70                  75                  80
Phe Pro Leu Ser Ala Ile Phe Thr Thr
                85

<210> SEQ ID NO 133
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ile
            20                  25                  30

Ile Gly Tyr Trp Glu Trp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 134
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Phe
            20                  25                  30

Ile Gly Tyr Trp Glu Trp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 135
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Trp
            20                  25                  30
```

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 136
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Asn
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 137
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Gln
            20                  25                  30

Ile Gly Tyr Trp Glu Trp Asp Asp Asp Gly Glu Ala Ile Val Leu Thr
        35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65                  70                  75                  80

Phe Pro Leu Ser Ala Ile Phe Thr Thr
                85

<210> SEQ ID NO 138
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Ser
                20                  25                  30

Ile Gly Tyr Trp Glu Trp Asp Asp Gly Glu Ala Ile Val Leu Thr
            35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65              70                  75                  80

Phe Pro Leu Ser Ala Ile Phe Thr Thr
                85

<210> SEQ ID NO 139
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Thr
                20                  25                  30

Ile Gly Tyr Trp Glu Trp Asp Asp Gly Glu Ala Ile Val Leu Thr
            35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65              70                  75                  80

Phe Pro Leu Ser Ala Ile Phe Thr Thr
                85

<210> SEQ ID NO 140
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Tyr
                20                  25                  30

Ile Gly Tyr Trp Glu Trp Asp Asp Gly Glu Ala Ile Val Leu Thr
            35                  40                  45

Val Pro Gly Ser Cys Arg Ser Tyr Asp Leu Thr Gly Leu Lys Pro Gly
    50                  55                  60

Thr Glu Tyr His Val Tyr Ile Ala Gly Val Lys Gly Gly Gln Trp Ser
65              70                  75                  80

Phe Pro Leu Ser Ala Ile Phe Thr Thr
                85

<210> SEQ ID NO 141
<211> LENGTH: 700
<212> TYPE: PRT
<213> ORGANISM: Macaca fascicularis

<400> SEQUENCE: 141

Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Ser Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu His Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Thr His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Ala Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Thr Gly
    210                 215                 220

Val Ile Leu Tyr Ser Asp Pro Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Met Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Ser Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Ser Glu Val
            340                 345                 350

Thr Arg Ile Tyr Asn Val Ile Gly Thr Leu Arg Gly Ala Val Glu Pro
        355                 360                 365

Asp Arg Tyr Val Ile Leu Gly Gly His Arg Asp Ser Trp Val Phe Gly
    370                 375                 380

```
Gly Ile Asp Pro Gln Ser Gly Ala Ala Val Val His Glu Ile Val Arg
385                 390                 395                 400

Ser Phe Gly Met Leu Lys Lys Glu Gly Trp Arg Pro Arg Arg Thr Ile
            405                 410                 415

Leu Phe Ala Ser Trp Asp Ala Glu Glu Phe Gly Leu Leu Gly Ser Thr
            420                 425                 430

Glu Trp Ala Glu Glu Asn Ser Arg Leu Leu Gln Glu Arg Gly Val Ala
            435                 440                 445

Tyr Ile Asn Ala Asp Ser Ser Ile Glu Gly Asn Tyr Thr Leu Arg Val
450                 455                 460

Asp Cys Thr Pro Leu Met Tyr Ser Leu Val Tyr Asn Leu Thr Lys Glu
465                 470                 475                 480

Leu Glu Ser Pro Asp Glu Gly Phe Glu Gly Lys Ser Leu Tyr Glu Ser
            485                 490                 495

Trp Thr Lys Lys Ser Pro Ser Pro Glu Phe Ser Gly Met Pro Arg Ile
            500                 505                 510

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
530                 535                 540

Lys Phe Ser Ser Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
            565                 570                 575

Ala Gln Val Arg Gly Gly Met Val Phe Glu Leu Ala Asn Ser Val Val
            580                 585                 590

Leu Pro Phe Asp Cys Arg Asp Tyr Ala Val Val Leu Arg Lys Tyr Ala
            595                 600                 605

Asp Lys Ile Tyr Asn Ile Ser Met Lys His Pro Gln Glu Met Lys Thr
610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Arg Asp Phe Asp Lys Ser
            645                 650                 655

Asn Pro Ile Leu Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr
            690                 695                 700

<210> SEQ ID NO 142
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Ala Glu Ala Ala Ala Lys Glu Ala Ala Lys Glu Ala Ala Lys Ala Ala Lys
1               5                   10                  15

Glu Ala Ala Ala Lys Glu Ala Ala Ala Lys Ala Ala Ala
                20                  25
```

```
<210> SEQ ID NO 143
<211> LENGTH: 707
<212> TYPE: PRT
<213> ORGANISM: Homo sapiens

<400> SEQUENCE: 143

Lys Ser Ser Asn Glu Ala Thr Asn Ile Thr Pro Lys His Asn Met Lys
1               5                   10                  15

Ala Phe Leu Asp Glu Leu Lys Ala Glu Asn Ile Lys Lys Phe Leu Tyr
            20                  25                  30

Asn Phe Thr Gln Ile Pro His Leu Ala Gly Thr Glu Gln Asn Phe Gln
        35                  40                  45

Leu Ala Lys Gln Ile Gln Ser Gln Trp Lys Glu Phe Gly Leu Asp Ser
    50                  55                  60

Val Glu Leu Ala His Tyr Asp Val Leu Leu Ser Tyr Pro Asn Lys Thr
65                  70                  75                  80

His Pro Asn Tyr Ile Ser Ile Ile Asn Glu Asp Gly Asn Glu Ile Phe
                85                  90                  95

Asn Thr Ser Leu Phe Glu Pro Pro Pro Gly Tyr Glu Asn Val Ser
            100                 105                 110

Asp Ile Val Pro Pro Phe Ser Ala Phe Ser Pro Gln Gly Met Pro Glu
        115                 120                 125

Gly Asp Leu Val Tyr Val Asn Tyr Ala Arg Thr Glu Asp Phe Phe Lys
    130                 135                 140

Leu Glu Arg Asp Met Lys Ile Asn Cys Ser Gly Lys Ile Val Ile Ala
145                 150                 155                 160

Arg Tyr Gly Lys Val Phe Arg Gly Asn Lys Val Lys Asn Ala Gln Leu
                165                 170                 175

Ala Gly Ala Lys Gly Val Ile Leu Tyr Ser Asp Pro Ala Asp Tyr Phe
            180                 185                 190

Ala Pro Gly Val Lys Ser Tyr Pro Asp Gly Trp Asn Leu Pro Gly Gly
        195                 200                 205

Gly Val Gln Arg Gly Asn Ile Leu Asn Leu Asn Gly Ala Gly Asp Pro
    210                 215                 220

Leu Thr Pro Gly Tyr Pro Ala Asn Glu Tyr Ala Tyr Arg Arg Gly Ile
225                 230                 235                 240

Ala Glu Ala Val Gly Leu Pro Ser Ile Pro Val His Pro Ile Gly Tyr
                245                 250                 255

Tyr Asp Ala Gln Lys Leu Leu Glu Lys Met Gly Gly Ser Ala Pro Pro
            260                 265                 270

Asp Ser Ser Trp Arg Gly Ser Leu Lys Val Pro Tyr Asn Val Gly Pro
        275                 280                 285

Gly Phe Thr Gly Asn Phe Ser Thr Gln Lys Val Lys Met His Ile His
    290                 295                 300

Ser Thr Asn Glu Val Thr Arg Ile Tyr Asn Val Ile Gly Thr Leu Arg
305                 310                 315                 320

Gly Ala Val Glu Pro Asp Arg Tyr Val Ile Leu Gly Gly His Arg Asp
                325                 330                 335

Ser Trp Val Phe Gly Gly Ile Asp Pro Gln Ser Gly Ala Ala Val Val
            340                 345                 350

His Glu Ile Val Arg Ser Phe Gly Thr Leu Lys Lys Glu Gly Trp Arg
        355                 360                 365

Pro Arg Arg Thr Ile Leu Phe Ala Ser Trp Asp Ala Glu Glu Phe Gly
    370                 375                 380
```

-continued

```
Leu Leu Gly Ser Thr Glu Trp Ala Glu Asn Ser Arg Leu Leu Gln
385                 390                 395                 400

Glu Arg Gly Val Ala Tyr Ile Asn Ala Asp Ser Ser Ile Glu Gly Asn
            405                 410                 415

Tyr Thr Leu Arg Val Asp Cys Thr Pro Leu Met Tyr Ser Leu Val His
            420                 425                 430

Asn Leu Thr Lys Glu Leu Lys Ser Pro Asp Glu Gly Phe Glu Gly Lys
            435                 440                 445

Ser Leu Tyr Glu Ser Trp Thr Lys Lys Ser Pro Ser Pro Glu Phe Ser
        450                 455                 460

Gly Met Pro Arg Ile Ser Lys Leu Gly Ser Gly Asn Asp Phe Glu Val
465                 470                 475                 480

Phe Phe Gln Arg Leu Gly Ile Ala Ser Gly Arg Ala Arg Tyr Thr Lys
                485                 490                 495

Asn Trp Glu Thr Asn Lys Phe Ser Gly Tyr Pro Leu Tyr His Ser Val
            500                 505                 510

Tyr Glu Thr Tyr Glu Leu Val Glu Lys Phe Tyr Asp Pro Met Phe Lys
        515                 520                 525

Tyr His Leu Thr Val Ala Gln Val Arg Gly Gly Met Val Phe Glu Leu
    530                 535                 540

Ala Asn Ser Ile Val Leu Pro Phe Asp Cys Arg Asp Tyr Ala Val Val
545                 550                 555                 560

Leu Arg Lys Tyr Ala Asp Lys Ile Tyr Ser Ile Ser Met Lys His Pro
                565                 570                 575

Gln Glu Met Lys Thr Tyr Ser Val Ser Phe Asp Ser Leu Phe Ser Ala
            580                 585                 590

Val Lys Asn Phe Thr Glu Ile Ala Ser Lys Phe Ser Glu Arg Leu Gln
        595                 600                 605

Asp Phe Asp Lys Ser Asn Pro Ile Val Leu Arg Met Met Asn Asp Gln
    610                 615                 620

Leu Met Phe Leu Glu Arg Ala Phe Ile Asp Pro Leu Gly Leu Pro Asp
625                 630                 635                 640

Arg Pro Phe Tyr Arg His Val Ile Tyr Ala Pro Ser Ser His Asn Lys
                645                 650                 655

Tyr Ala Gly Glu Ser Phe Pro Gly Ile Tyr Asp Ala Leu Phe Asp Ile
            660                 665                 670

Glu Ser Lys Val Asp Pro Ser Lys Ala Trp Gly Glu Val Lys Arg Gln
        675                 680                 685

Ile Tyr Val Ala Ala Phe Thr Val Gln Ala Ala Glu Thr Leu Ser
    690                 695                 700

Glu Val Ala
705
```

<210> SEQ ID NO 144
<211> LENGTH: 750
<212> TYPE: PRT
<213> ORGANISM: Homo sapiens

<400> SEQUENCE: 144

```
Met Trp Asn Leu Leu His Glu Thr Asp Ser Ala Val Ala Thr Ala Arg
1               5                   10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45
```

```
Ala Thr Asn Ile Thr Pro Lys His Asn Met Lys Ala Phe Leu Asp Glu
 50                  55                  60

Leu Lys Ala Glu Asn Ile Lys Lys Phe Leu Tyr Asn Phe Thr Gln Ile
 65                  70                  75                  80

Pro His Leu Ala Gly Thr Glu Gln Asn Phe Gln Leu Ala Lys Gln Ile
                 85                  90                  95

Gln Ser Gln Trp Lys Glu Phe Gly Leu Asp Ser Val Glu Leu Ala His
             100                 105                 110

Tyr Asp Val Leu Leu Ser Tyr Pro Asn Lys Thr His Pro Asn Tyr Ile
         115                 120                 125

Ser Ile Ile Asn Glu Asp Gly Asn Glu Ile Phe Asn Thr Ser Leu Phe
     130                 135                 140

Glu Pro Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                 165                 170                 175

Val Asn Tyr Ala Arg Thr Glu Asp Phe Phe Lys Leu Glu Arg Asp Met
             180                 185                 190

Lys Ile Asn Cys Ser Gly Lys Ile Val Ile Ala Arg Tyr Gly Lys Val
         195                 200                 205

Phe Arg Gly Asn Lys Val Lys Asn Ala Gln Leu Ala Gly Ala Lys Gly
     210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                 245                 250                 255

Asn Ile Leu Asn Leu Asn Gly Ala Gly Asp Pro Leu Thr Pro Gly Tyr
             260                 265                 270

Pro Ala Asn Glu Tyr Ala Tyr Arg Arg Gly Ile Ala Glu Ala Val Gly
         275                 280                 285

Leu Pro Ser Ile Pro Val His Pro Ile Gly Tyr Tyr Asp Ala Gln Lys
     290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                 325                 330                 335

Phe Ser Thr Gln Lys Val Lys Met His Ile His Ser Thr Asn Glu Val
             340                 345                 350

Thr Arg Ile Tyr Asn Val Ile Gly Thr Leu Arg Gly Ala Val Glu Pro
         355                 360                 365

Asp Arg Tyr Val Ile Leu Gly Gly His Arg Asp Ser Trp Val Phe Gly
     370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                 405                 410                 415

Leu Phe Ala Ser Trp Asp Ala Glu Glu Phe Gly Leu Leu Gly Ser Thr
             420                 425                 430

Glu Trp Ala Glu Glu Asn Ser Arg Leu Leu Gln Glu Arg Gly Val Ala
         435                 440                 445

Tyr Ile Asn Ala Asp Ser Ser Ile Glu Gly Asn Tyr Thr Leu Arg Val
     450                 455                 460
```

```
Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
            485                 490                 495

Trp Thr Lys Lys Ser Pro Ser Pro Glu Phe Ser Gly Met Pro Arg Ile
                500                 505                 510

Ser Lys Leu Gly Ser Gly Asn Asp Phe Glu Val Phe Gln Arg Leu
        515                 520                 525

Gly Ile Ala Ser Gly Arg Ala Arg Tyr Thr Lys Asn Trp Glu Thr Asn
            530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
            580                 585                 590

Leu Pro Phe Asp Cys Arg Asp Tyr Ala Val Val Leu Arg Lys Tyr Ala
        595                 600                 605

Asp Lys Ile Tyr Ser Ile Ser Met Lys His Pro Gln Glu Met Lys Thr
610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
            660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
            690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750

<210> SEQ ID NO 145
<211> LENGTH: 88
<212> TYPE: PRT
<213> ORGANISM: Unknown
<220> FEATURE:
<223> OTHER INFORMATION: Description of Unknown:
      3rd FN3 domain of tenascin C polypeptide

<400> SEQUENCE: 145

Asp Ala Pro Ser Gln Ile Glu Val Lys Asp Val Thr Asp Thr Thr Ala
1               5                   10                  15

Leu Ile Thr Trp Phe Lys Pro Leu Ala Glu Ile Asp Gly Ile Glu Leu
            20                  25                  30

Thr Tyr Gly Ile Lys Asp Val Pro Gly Asp Arg Thr Thr Ile Asp Leu
        35                  40                  45

Thr Glu Asp Glu Asn Gln Tyr Ser Ile Gly Asn Leu Lys Pro Asp Thr
    50                  55                  60

Glu Tyr Glu Val Ser Leu Ile Ser Arg Arg Gly Asp Met Ser Ser Asn
65                  70                  75                  80
```

```
Pro Ala Lys Glu Thr Phe Thr Thr
                85

<210> SEQ ID NO 146
<211> LENGTH: 89
<212> TYPE: PRT
<213> ORGANISM: Unknown
<220> FEATURE:
<223> OTHER INFORMATION: Description of Unknown:
      Fibcon polypeptide

<400> SEQUENCE: 146

Leu Asp Ala Pro Thr Asp Leu Gln Val Thr Asn Val Thr Asp Thr Ser
1               5                   10                  15

Ile Thr Val Ser Trp Thr Pro Pro Ser Ala Thr Ile Thr Gly Tyr Arg
            20                  25                  30

Ile Thr Tyr Thr Pro Ser Asn Gly Pro Gly Glu Pro Lys Glu Leu Thr
        35                  40                  45

Val Pro Pro Ser Ser Thr Ser Val Thr Ile Thr Gly Leu Thr Pro Gly
    50                  55                  60

Val Glu Tyr Val Val Ser Leu Tyr Ala Leu Lys Asp Asn Gln Glu Ser
65                  70                  75                  80

Pro Pro Leu Val Gly Thr Gln Thr Thr
                85

<210> SEQ ID NO 147
<211> LENGTH: 94
<212> TYPE: PRT
<213> ORGANISM: Unknown
<220> FEATURE:
<223> OTHER INFORMATION: Description of Unknown:
      10th FN3 domain of fibronectin polypeptide

<400> SEQUENCE: 147

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 148
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Ser Gly Ser
1

<210> SEQ ID NO 149
<211> LENGTH: 8
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gly Gly Gly Ser Gly Gly Gly Ser
1               5

<210> SEQ ID NO 150
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Gly Gly Gly Gly Ser Gly Gly Gly Ser Gly Gly Gly Gly Ser Gly
1               5                  10                  15

Gly Gly Ser Gly Gly Gly Gly Ser
            20                  25

<210> SEQ ID NO 151
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ala Pro Ala Pro
1

<210> SEQ ID NO 152
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ala Pro Ala Pro Ala Pro Ala Pro Ala Pro
1               5                   10

<210> SEQ ID NO 153
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Ala Pro Ala Pro Ala Pro Ala Pro Ala Pro Ala Pro Ala Pro Ala Pro
1               5                  10                  15

Ala Pro Ala Pro
            20

<210> SEQ ID NO 154
<211> LENGTH: 40
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 154

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro Ala Pro Ala Pro Ala Pro
        35                  40

<210> SEQ ID NO 155
<211> LENGTH: 585
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 155

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Ser Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
            325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
            485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
            565                 570                 575

Ala Ala Ser Gln Ala Ala Leu Gly Leu
            580                 585

<210> SEQ ID NO 156
<211> LENGTH: 267
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 156
ctgccagccc cgaagaattt ggtcgtttcc cgtgtcactg aggactctgc acgtctgagc      60
tggaccgcac cggacgcggc gttcgacagc tttgcaatcg ctactggga gtgggatgat     120 gacggcgagg ccattgtgct gaccgttccg ggtagcgagc gcagctacga tctgaccggt     180
ctgaagccgg gtacggaata tccggtgtat attgcgggcg tgaagggtgg ccagtggagc     240
ttcccgctga gcgcgatctt taccacc                                          267

<210> SEQ ID NO 157
<211> LENGTH: 273
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 157

```
ctgccggctc cgaaaaacct ggtcgtttcc cgtgtcactg aagattctgc acgcttgagc     60
tgggcgatcg acgagcagcg tgactggttt gagagcttcc tgattcagta tcaagaatcg    120
gaaaaagttg gcgaggccat cgtgctgacc gttccgggta gcgagcgcag ctatgatctg    180
acgggtctga agccaggcac cgagtatacg gtgagcattt acggtgtcta ccatgtgtac    240
cgtagcaatc cgctgagcgc gatcttcacc acc                                 273
```

<210> SEQ ID NO 158
<211> LENGTH: 267
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 158

```
ctgccagccc cgaaaaactt agttgtctcc cgcgtgaccg aagattctgc tcgtctgagc     60
tggactgcac cggacgcggc gttcgacagc tttccgattg gctactggga gtgggatgat    120
gacggtgaag cgatcgtgct gaccgttccg ggtagcgagc gtagctatga cctgacgggt    180
ttgaaacctg gtaccgagta tcacgtttac attgcgggcg tcaagggtgg ccagtggtcg    240
ttcccgctga gcgcaatctt tacgacc                                        267
```

<210> SEQ ID NO 159
<211> LENGTH: 16
<212> TYPE: PRT
<213> ORGANISM: Unknown
<220> FEATURE:
<223> OTHER INFORMATION: Description of Unknown:
      PSMA epitope peptide

<400> SEQUENCE: 159

```
Lys Lys Ser Pro Ser Pro Glu Phe Ser Gly Met Pro Arg Ile Ser Lys
1               5                   10                  15
```

<210> SEQ ID NO 160
<211> LENGTH: 7
<212> TYPE: PRT
<213> ORGANISM: Unknown
<220> FEATURE:
<223> OTHER INFORMATION: Description of Unknown:
      PSMA epitope peptide

<400> SEQUENCE: 160

```
Asn Trp Glu Thr Asn Lys Phe
1               5
```

<210> SEQ ID NO 161
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65              70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu Gly Gln Pro
            100                 105                 110

Lys Ser Ser Pro Ser Val Thr Leu Phe Pro Pro Ser Ser Glu Glu Leu
            115                 120                 125

Glu Thr Asn Lys Ala Thr Leu Val Cys Thr Ile Thr Asp Phe Tyr Pro
    130                 135                 140

Gly Val Val Thr Val Asp Trp Lys Val Asp Gly Thr Pro Val Thr Gln
145                 150                 155                 160

Gly Met Glu Thr Thr Gln Pro Ser Lys Gln Ser Asn Asn Lys Tyr Met
                165                 170                 175

Ala Ser Ser Tyr Leu Thr Leu Thr Ala Arg Ala Trp Glu Arg His Ser
            180                 185                 190

Ser Tyr Ser Cys Gln Val Thr His Glu Gly His Thr Val Glu Lys Ser
        195                 200                 205

Leu Ser Arg Ala Asp Cys Ser
    210                 215
```

<210> SEQ ID NO 162
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

```
Glu Val Lys Leu Leu Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65              70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala Ala Thr Thr
            115                 120                 125

Thr Ala Pro Ser Val Tyr Pro Leu Val Pro Gly Cys Ser Asp Thr Ser
```

-continued

```
                130                 135                 140
Gly Ser Ser Val Thr Leu Gly Cys Leu Val Lys Gly Tyr Phe Pro Glu
145                 150                 155                 160

Pro Val Thr Val Lys Trp Asn Tyr Gly Ala Leu Ser Ser Gly Val Arg
                165                 170                 175

Thr Val Ser Ser Val Leu Gln Ser Ala Phe Tyr Ser Leu Ser Ser Leu
            180                 185                 190

Val Thr Val Pro Ser Ser Thr Trp Pro Ser Gln Thr Val Ile Cys Asn
                195                 200                 205

Val Ala His Pro Ala Ser Lys Thr Glu Leu Ile Lys Arg Ile Glu Pro
210                 215                 220

Arg Ile Pro Lys Pro Ser Thr Pro Pro Gly Ser Ser Cys Pro Pro Gly
225                 230                 235                 240

Asn Ile Leu Gly Gly Pro Ser Val Phe Ile Phe Pro Pro Lys Pro Lys
                245                 250                 255

Asp Ala Leu Met Ile Ser Leu Thr Pro Lys Val Thr Cys Val Val Val
                260                 265                 270

Asp Val Ser Glu Asp Asp Pro Asp Val His Val Ser Trp Phe Val Asp
            275                 280                 285

Asn Lys Glu Val His Thr Ala Trp Thr Gln Pro Arg Glu Ala Gln Tyr
        290                 295                 300

Asn Ser Thr Phe Arg Val Val Ser Ala Leu Pro Ile Gln His Gln Asp
305                 310                 315                 320

Trp Met Arg Gly Lys Glu Phe Lys Cys Lys Val Asn Asn Lys Ala Leu
                325                 330                 335

Pro Ala Pro Ile Glu Arg Thr Ile Ser Lys Pro Lys Gly Arg Ala Gln
                340                 345                 350

Thr Pro Gln Val Tyr Thr Ile Pro Pro Arg Glu Gln Met Ser Lys
            355                 360                 365

Lys Lys Val Ser Leu Thr Cys Leu Val Thr Asn Phe Phe Ser Glu Ala
370                 375                 380

Ile Ser Val Glu Trp Glu Arg Asn Gly Glu Leu Glu Gln Asp Tyr Lys
385                 390                 395                 400

Asn Thr Pro Pro Ile Leu Asp Ser Asp Gly Thr Tyr Phe Leu Tyr Ser
                405                 410                 415

Lys Leu Thr Val Asp Thr Asp Ser Trp Leu Gln Gly Glu Ile Phe Thr
                420                 425                 430

Cys Ser Val Val His Glu Ala Leu His Asn His Thr Gln Lys Asn
            435                 440                 445

Leu Ser Arg Ser Pro Gly Lys
450                 455

<210> SEQ ID NO 163
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 163

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30
```

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Ala
 50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 164
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 164

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Ala Val Tyr
                85                  90                  95

Tyr Cys Ala Lys His Gly Asn Phe Gly Asn Ser Tyr Val Ser Trp Phe
            100                 105                 110

Ala Tyr Trp Gly Gln Gly Thr Leu Val Thr Val Ser Ser
            115                 120                 125

<210> SEQ ID NO 165
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Glu Val Gln Leu Leu Glu Ser Gly Gly Gly Leu Val Gln Pro Gly Gly
 1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
            35                  40                  45

Ala Arg Ile Arg Ser Lys Tyr Asn Asn Tyr Ala Thr Tyr Tyr Ala Asp
 50                  55                  60

Ser Val Lys Gly Arg Phe Thr Ile Ser Arg Asp Asn Ser Lys Asn Thr
 65                  70                  75                  80

-continued

Leu Tyr Leu Gln Met Asn Ser Leu Arg Ala Glu Asp Thr Ala Val Tyr
                85                  90                  95

Tyr Cys Val Lys His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 166
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Ser Gly Lys Gly Leu Glu Trp Val
        35                  40                  45

Gly Arg Ile Arg Ser Lys Tyr Asn Gly Tyr Ala Thr Tyr Tyr Ala Ala
    50                  55                  60

Ser Val Lys Gly Arg Phe Thr Ile Ser Arg Asp Asp Ser Lys Asn Thr
65                  70                  75                  80

Ala Tyr Leu Gln Met Asn Ser Leu Lys Thr Glu Asp Thr Ala Val Tyr
                85                  90                  95

Tyr Cys Thr Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125

<210> SEQ ID NO 167
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 168
<211> LENGTH: 109

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 168

Gln Ser Val Leu Thr Gln Pro Pro Ser Val Ser Ala Ala Pro Gly Gln
1               5                   10                  15

Lys Val Thr Ile Ser Cys Arg Ser Ser Thr Gly Ala Val Thr Thr Ser
            20                  25                  30

Asn Tyr Ala Asn Trp Val Gln Gln Leu Pro Gly Thr Ala Pro Lys Gly
        35                  40                  45

Leu Ile Gly Gly Thr Asn Lys Arg Ala Pro Gly Ile Pro Asp Arg Phe
    50                  55                  60

Ser Gly Ser Lys Ser Gly Thr Ser Ala Thr Leu Gly Ile Thr Gly Leu
65                  70                  75                  80

Gln Thr Gly Asp Glu Ala Asp Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 169
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105

<210> SEQ ID NO 170
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Gln Thr Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
```

```
                35                  40                  45
Leu Ile Gly Gly Thr Asn Lys Arg Ala Pro Gly Thr Pro Ala Arg Phe
 50                  55                  60

Ser Gly Ser Leu Leu Gly Gly Lys Ala Ala Leu Thr Leu Ser Gly Val
 65                  70                  75                  80

Gln Pro Glu Asp Glu Ala Glu Tyr Tyr Cys Ala Leu Trp Tyr Ser Asn
                 85                  90                  95

Leu Trp Val Phe Gly Gly Gly Thr Lys Leu Thr Val Leu Gly Gln Pro
            100                 105                 110

Lys Ala Ala Pro Ser Val Thr Leu Phe Pro Pro Ser Ser Glu Glu Leu
        115                 120                 125

Gln Ala Asn Lys Ala Thr Leu Val Cys Leu Ile Ser Asp Phe Tyr Pro
    130                 135                 140

Gly Ala Val Thr Val Ala Trp Lys Ala Asp Ser Ser Pro Val Lys Ala
145                 150                 155                 160

Gly Val Glu Thr Thr Thr Pro Ser Lys Gln Ser Asn Asn Lys Tyr Ala
                165                 170                 175

Ala Ser Ser Tyr Leu Ser Leu Thr Pro Glu Gln Trp Lys Ser His Arg
            180                 185                 190

Ser Tyr Ser Cys Gln Val Thr His Glu Gly Ser Thr Val Glu Lys Thr
        195                 200                 205

Val Ala Pro Thr Glu Cys Ser
    210                 215

<210> SEQ ID NO 171
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 171

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asn Thr Tyr
             20                  25                  30

Ala Met Asn Trp Val Arg Gln Ala Pro Gly Lys Gly Leu Glu Trp Val
         35                  40                  45

Ala Arg Ile Arg Ser Lys Tyr Asn Asn Tyr Ala Thr Tyr Tyr Ala Ala
 50                  55                  60

Ser Val Lys Gly Arg Phe Thr Ile Ser Arg Asp Asp Ser Lys Asn Ser
 65                  70                  75                  80

Leu Tyr Leu Gln Met Asn Ser Leu Lys Thr Glu Asp Thr Ala Val Tyr
                 85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175
```

```
Thr Phe Pro Ala Val Leu Gln Ser Ser Gly Leu Tyr Ser Leu Ser Ser
            180                 185                 190

Val Val Thr Val Pro Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Leu Leu Tyr Ser Lys Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450

<210> SEQ ID NO 172
<211> LENGTH: 324
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 172

Gly Ser Cys Pro Pro Cys Pro Ala Pro Glu Ala Ala Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser Gln Glu Asp Pro
        35                  40                  45

Glu Val Gln Phe Asn Trp Tyr Val Asp Gly Val Glu Val His Asn Ala
    50                  55                  60

Lys Thr Lys Pro Arg Glu Glu Gln Phe Asn Ser Thr Tyr Arg Val Val
65                  70                  75                  80
```

Ser Val Leu Thr Val Leu His Gln Asp Trp Leu Asn Gly Lys Glu Tyr
            85                  90                  95

Lys Cys Lys Val Ser Asn Lys Gly Leu Pro Ser Ser Ile Glu Lys Thr
            100                 105                 110

Ile Ser Lys Ala Lys Gly Gln Pro Arg Glu Pro Gln Val Tyr Thr Leu
            115                 120                 125

Pro Pro Ser Gln Glu Glu Met Thr Lys Asn Gln Val Ser Leu Thr Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
            165                 170                 175

Ser Asp Gly Ser Phe Phe Leu Tyr Ser Arg Leu Thr Val Asp Lys Ser
            180                 185                 190

Arg Trp Gln Glu Gly Asn Val Phe Ser Cys Ser Val Met His Glu Ala
            195                 200                 205

Leu His Asn His Tyr Thr Gln Lys Ser Leu Ser Leu Ser Leu Gly Lys
            210                 215                 220

Gly Gly Gly Gly Ser Gly Gly Gly Ser Met Leu Pro Ala Pro Lys
225                 230                 235                 240

Asn Leu Val Val Ser Arg Val Thr Glu Asp Ser Ala Arg Leu Ser Trp
            245                 250                 255

Thr Ala Pro Asp Ala Ala Phe Asp Ser Phe Ala Ile Gly Tyr Trp Glu
            260                 265                 270

Trp Asp Asp Gly Glu Ala Ile Val Leu Thr Val Pro Gly Ser Glu
            275                 280                 285

Arg Ser Tyr Asp Leu Thr Gly Leu Lys Pro Gly Thr Glu Tyr Pro Val
            290                 295                 300

Tyr Ile Ala Gly Val Lys Gly Gly Gln Trp Ser Phe Pro Leu Ser Ala
305                 310                 315                 320

Ile Phe Thr Thr

<210> SEQ ID NO 173
<211> LENGTH: 322
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 173

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Gly Tyr Trp Glu Trp Asp Asp Gly Glu Ala Ile Val Leu
            35                  40                  45

Thr Val Pro Gly Ser Glu Arg Ser Tyr Asp Leu Thr Gly Leu Lys Pro
50                  55                  60

Gly Thr Glu Tyr Pro Val Tyr Ile Ala Gly Val Lys Gly Gly Gln Trp
65                  70                  75                  80

Ser Phe Pro Leu Ser Ala Ile Phe Thr Thr Gly Gly Gly Gly Ser Gly
            85                  90                  95

Gly Gly Gly Ser Cys Pro Pro Cys Pro Ala Pro Glu Ala Ala Gly Gly
            100                 105                 110

```
Pro Ser Val Phe Leu Phe Pro Pro Lys Pro Lys Asp Thr Leu Met Ile
            115                 120                 125

Ser Arg Thr Pro Glu Val Thr Cys Val Val Val Asp Val Ser Gln Glu
        130                 135                 140

Asp Pro Glu Val Gln Phe Asn Trp Tyr Val Asp Gly Val Glu Val His
145                 150                 155                 160

Asn Ala Lys Thr Lys Pro Arg Glu Glu Gln Phe Asn Ser Thr Tyr Arg
                165                 170                 175

Val Val Ser Val Leu Thr Val Leu His Gln Asp Trp Leu Asn Gly Lys
            180                 185                 190

Glu Tyr Lys Cys Lys Val Ser Asn Lys Gly Leu Pro Ser Ser Ile Glu
        195                 200                 205

Lys Thr Ile Ser Lys Ala Lys Gly Gln Pro Arg Glu Pro Gln Val Tyr
    210                 215                 220

Thr Leu Pro Pro Ser Gln Glu Glu Met Thr Lys Asn Gln Val Ser Leu
225                 230                 235                 240

Thr Cys Leu Val Lys Gly Phe Tyr Pro Ser Asp Ile Ala Val Glu Trp
                245                 250                 255

Glu Ser Asn Gly Gln Pro Glu Asn Asn Tyr Lys Thr Thr Pro Pro Val
            260                 265                 270

Leu Asp Ser Asp Gly Ser Phe Phe Leu Tyr Ser Arg Leu Thr Val Asp
        275                 280                 285

Lys Ser Arg Trp Gln Glu Gly Asn Val Phe Ser Cys Ser Val Met His
    290                 295                 300

Glu Ala Leu His Asn His Tyr Thr Gln Lys Ser Leu Ser Leu Ser Leu
305                 310                 315                 320

Gly Lys

<210> SEQ ID NO 174
<211> LENGTH: 552
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 174

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Ala
    50                  55                  60

Ser Val Lys Gly Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Ala Arg His Gly Asn Phe Gly Asn Ser Tyr Val Ser Trp Phe
            100                 105                 110

Ala Tyr Trp Gly Gln Gly Thr Leu Val Thr Val Ser Ser Ala Ser Thr
        115                 120                 125

Lys Gly Pro Ser Val Phe Pro Leu Ala Pro Cys Ser Arg Ser Thr Ser
    130                 135                 140
```

```
Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
        195                 200                 205

Asn Val Asp His Lys Pro Ser Asn Thr Lys Val Asp Lys Arg Val Glu
    210                 215                 220

Ser Lys Tyr Gly Pro Pro Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
        275                 280                 285

Val His Asn Ala Lys Thr Lys Pro Arg Glu Glu Gln Phe Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Leu Leu Tyr Ser Lys Leu Thr
                405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly Lys Gly Gly Gly Ser Gly Gly Gly Ser Met Leu
    450                 455                 460

Pro Ala Pro Lys Asn Leu Val Val Ser Arg Val Thr Glu Asp Ser Ala
465                 470                 475                 480

Arg Leu Ser Trp Thr Ala Pro Asp Ala Ala Phe Asp Ser Phe Ala Ile
                485                 490                 495

Gly Tyr Trp Glu Trp Asp Asp Gly Glu Ala Ile Val Leu Thr Val
            500                 505                 510

Pro Gly Ser Glu Arg Ser Tyr Asp Leu Thr Gly Leu Lys Pro Gly Thr
        515                 520                 525

Glu Tyr Pro Val Tyr Ile Ala Gly Val Lys Gly Gln Trp Ser Phe
    530                 535                 540

Pro Leu Ser Ala Ile Phe Thr Thr
545                 550
```

<210> SEQ ID NO 175
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 175

Gly Gly Gly Gly Ser Gly Gly Gly Gly Ser
1               5                   10

<210> SEQ ID NO 176
<211> LENGTH: 447
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 176

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Gly Ile Asn Gly Gly Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Ser Ala Gln Arg Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

```
Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 177
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Leu Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys
    210

<210> SEQ ID NO 178
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Ala Arg Leu Tyr Ser Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val

```
                    340                 345                 350
Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Leu Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
        450

<210> SEQ ID NO 179
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 179

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn
    210
```